United States Patent
Liu et al.

(10) Patent No.: US 11,942,224 B2
(45) Date of Patent: **\*Mar. 26, 2024**

(54) SYSTEM AND METHOD FOR IDENTIFYING TRANSDIAGNOSTIC FEATURES SHARED ACROSS MENTAL HEALTH DISORDERS

(71) Applicant: Blackthorn Therapeutics, Inc., San Francisco, CA (US)

(72) Inventors: Yuelu Liu, San Francisco, CA (US); Monika Sharma Mellem, San Francisco, CA (US); Parvez Ahammad, San Francisco, CA (US); Humberto Andres Gonzalez Cabezas, San Francisco, CA (US); Matthew Kollada, San Francisco, CA (US)

(73) Assignee: NEUMORA THERAPEUTICS, INC., Brisbane, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/646,756

(22) Filed: Jan. 3, 2022

(65) Prior Publication Data

US 2022/0139560 A1 May 5, 2022

Related U.S. Application Data

(63) Continuation of application No. 17/270,730, filed as application No. PCT/US2019/048762 on Aug. 29, 2019, now Pat. No. 11,244,762.

(Continued)

(51) Int. Cl.
*G16H 50/30* (2018.01)
*A61B 5/00* (2006.01)
(Continued)

(52) U.S. Cl.
CPC .......... *G16H 50/30* (2018.01); *A61B 5/0042* (2013.01); *A61B 5/055* (2013.01); *A61B 5/16* (2013.01);
(Continued)

(58) Field of Classification Search
CPC ......... A61B 5/0042; A61B 5/055; A61B 5/16; A61B 5/7267; G06N 20/00; G16H 10/20; G16H 50/20; G16H 50/70
See application file for complete search history.

(56) References Cited

U.S. PATENT DOCUMENTS 9,510,756 B2  12/2016 Grady et al.
2008/0012855 A1  1/2008 Bi
(Continued)

FOREIGN PATENT DOCUMENTS

AU  2003204909 B2  1/2004
CA  2715825 A1  8/2009
(Continued)

OTHER PUBLICATIONS

EESR in Application No. EP 19853733.4, mailed May 20, 2022, 9 pp.
(Continued)

*Primary Examiner* — Sheetal R Paulson
(74) *Attorney, Agent, or Firm* — NIXON PEABODY LLP

(57) ABSTRACT

A system for evaluating mental health of patients includes a memory and a control system. The memory contains executable code storing instructions for performing a method. The control system is coupled to the memory and includes one or more processors. The control system is configured to execute the machine executable code to cause the control system to perform the method: A selection of answers associated with a patient is received. The selection of answers corresponds to each question in a series of questions
(Continued)

from mental health questionnaires. Unprocessed MRI data are received. The unprocessed MRI data correspond to a set of MRI images of a biological structure associated with the patient. The unprocessed MRI data is processed to output a set of MRI features. Using a machine learning model, the selection of answers and the set of MRI features are processed to output a mental health indication of the patient.

20 Claims, 76 Drawing Sheets

Related U.S. Application Data

(60) Provisional application No. 62/725,994, filed on Aug. 31, 2018.

(51) Int. Cl.
    *A61B 5/055*     (2006.01)
    *A61B 5/16*     (2006.01)
    *G06F 18/21*     (2023.01)
    *G06F 18/214*     (2023.01)
    *G06N 20/00*     (2019.01)
    *G16H 10/20*     (2018.01)
    *G16H 30/20*     (2018.01)
    *G16H 30/40*     (2018.01)
    *G16H 50/20*     (2018.01)
    *G16H 50/70*     (2018.01)
    *G16H 20/70*     (2018.01)

(52) U.S. Cl.
    CPC ........ *A61B 5/7267* (2013.01); *G06F 18/2148* (2023.01); *G06F 18/2178* (2023.01); *G06F 18/2193* (2023.01); *G06N 20/00* (2019.01); *G16H 10/20* (2018.01); *G16H 30/20* (2018.01); *G16H 30/40* (2018.01); *G16H 50/20* (2018.01); *G16H 50/70* (2018.01); *A61B 2576/026* (2013.01); *G06V 2201/031* (2022.01); *G16H 20/70* (2018.01)

(56) References Cited

U.S. PATENT DOCUMENTS

| 2009/0240522 | A1* | 9/2009 | Handal ................ G16H 50/20 |
| | | | 705/2 |
| 2016/0110524 | A1 | 4/2016 | Short et al. |
| 2018/0310870 | A1* | 11/2018 | Givon ................. G06T 7/0014 |
| 2021/0319899 | A1 | 10/2021 | Liu et al. |
| 2021/0358594 | A1 | 11/2021 | Mellem et al. |
| 2022/0172822 | A1 | 6/2022 | Mellem et al. |

FOREIGN PATENT DOCUMENTS

| WO | 2009/103156 A1 | 8/2009 |
| WO | 2018029679 A1 | 2/2018 |
| WO | 2018074996 A1 | 4/2018 |
| WO | 2020047224 A1 | 3/2020 |
| WO | 2020047253 A1 | 3/2020 |

OTHER PUBLICATIONS

International Search Report and Written Opinion of International Searching Authority for Application No. PCT/US2019/048809, dated Jan. 7, 2020 (10 pages).
Liu Jin et al.: "Classification of Schizophrenia Based on Individual Hierarchical Brain Networks Constructed Structural MRI Images", Transactions on Nanobioscience, IEEE Service Center, Piscataway, NY, US, vol. 16, No. 7, Oct. 1, 2017 (Oct. 1, 2017), pp. 600-608.
International Search Report and Written Opinion of International Searching Authority for Application No. PCT/US2019/048762, dated Jan. 9, 2020 (11 pages).
Multiple Community Authors, "Feature Selection", scikit-learn Project on github, Mar. 18, 2015 (Mar. 18, 2015), pp. 1-4 Accessed Jun. 28, 2023 from the Internet: https://github.com/scikit-learn/scikit-learn/blob/b1b43c1372e3cb60e197d4786292ce80caa4534b/doc/modules/feature_selection.rst.
Communication pursuant to Article 94(3) EPC in Application No. EP 19853733.4, dated Apr. 4, 2023, 6 pp.

* cited by examiner

Bipolar, mood

Proportions in behav_sMRI_fMRI_QC_ElasticNet_bipollarii_mood

SANS, factor blunt affect

Proportions in behav_sMRI_fMRI_QC_ElasticNet_sans_factor_bluntaffect

HAMD q7

Proportions in behav_sMRI_fMRI_QC_ElasticNet_hamd7

SANS, factor anhedonia

Proportions in behav_sMRI_fMRI_QC_ElasticNet_sans_factor_anhedonia

SANS, factor attention

Proportions in behav_sMRI_fMRI_QC_ElasticNet_sans_factor_attention

SANS, global attention

Proportions in behav_sMRI_fMRI_QC_ElasticNet_sans_global_attention

SANS, factor alogia

Proportions in behav_sMRI_fMRI_QC_ElasticNet_sans_factor_alogia

SANS, global alogia

Proportions in behav_sMRI_fMRI_QC_ElasticNet_sans_global_alogia

SYSTEM AND METHOD FOR IDENTIFYING TRANSDIAGNOSTIC FEATURES SHARED ACROSS MENTAL HEALTH DISORDERS

CROSS-REFERENCE TO RELATED APPLICATION

This application is a continuation of U.S. application Ser. No. 17/270,730, filed on Feb. 23, 2021, which is the National Phase of International Application PCT/US2019/048762, filed on Aug. 29, 2019, which designated the United States, which claims priority to and the benefit of U.S. Provisional Patent No. 62/725,994, filed on Aug. 31, 2018, each of which is hereby incorporated by reference herein in its entirety.

TECHNICAL FIELD

The present disclosure relates to transdiagnostic feature selection, and more specifically, to the use of machine learning to identify shared transdiagnostic features.

BACKGROUND

The field of psychiatry has long relied on making diagnoses and recommending treatment for disorders based solely on clinical phenomenology. For example, the Diagnostic and Statistical Manual of Mental Disorders (DSM) is a standard for diagnosing psychiatric disorders in the United States. It provides a symptom-based taxonomy which serves to help clinicians classify various clusters of symptoms and abnormal behaviors into distinct categories of disorders.

However, categorizing mental disorders as discrete entities each having its own distinct cluster of symptoms has its inadequacies. This approach hampers prognostic assessment, treatment, and drug development. Therefore, one objective of the present disclosure is to use a data-driven method to find highly-predictive biomarkers for several measures of depressed mood, anxiety, anhedonia and related negative symptoms.

SUMMARY

Aspects of the present disclosure include a system for evaluating a patient for mental health issues. The system includes a display device, a user interface, a memory, and a control system. The memory contains machine readable medium. The machine readable medium includes machine executable code storing instructions for performing a method. The control system is coupled to the memory, and includes one or more processors. The control system is configured to execute the machine executable code to cause the control system to perform the method: On the display device, a series of questions from mental health questionnaires is displayed. The series of questions includes text and answers for each question. From the user interface, a selection of answers of each of the series of questions is received from a patient. Unprocessed MRI data are received. The unprocessed MRI data correspond to a set of MRI images of a biological structure associated with the patient. Using a machine learning model, the selection of answers and the unprocessed MRI data are processed to output a mental health indication of the patient.

In some aspects, the unprocessed MRI data corresponds to MRI data for a brain of the patient. In some aspects, the unprocessed MRI data includes at least one of: functional MRI data, resting-state functional MRI data, structural MRI data, and any combination thereof. In some aspects, the control system is further configured to preprocess the unprocessed MRI data to identify a plurality of features.

In some aspects, the mental health indication is categorical. For example, the mental health indication includes a determination that the processed selection of answers and the processed MRI data includes indications of at least one of: a neuropsychiatric disorder, schizophrenia, a bi-polar disorder, and any combination thereof.

In some aspects, outputting the mental health indication further comprises determining that the processed selection of answers and the processed MRI data identifies features corresponding to a mental disorder.

In some aspects, the machine learning model is at least one of: a generalized linear model, a regression model, a logistical regression model, a supervised regression method, random forest, LASSO, a supervised machine-learning model, and an elastic net.

In some aspects, the machine learning model was generated by receiving labeled training data for a plurality of individuals. The labeled training data indicates whether each of the plurality of individuals has one or more mental health disorders. The labeled training data includes MRI data recorded for each of the plurality of individuals. The labeled training data further includes a selection of answers to the series of questions for each of the plurality of individuals. A plurality of features is determined from the labeled training data. An initial machine learning model is trained in a supervised manner. The initial machine learning model is trained based on the plurality of features. Importance measures for each of the plurality of features extracted based on the training of the initial machine learning model. A plurality of subset machine learning models is generated based on the extracted importance measures for the plurality of features. A classification performance of the generated plurality of subset machine learning models is evaluated At least one of the subset machine learning models is selected as the machine learning model.

In some aspects, the machine learning model is trained on clinical scales data corresponding to the plurality of individuals. In some aspects, the machine learning model is trained on fMRI full connectivity data corresponding to the plurality of individuals. In some aspects, the machine learning model is trained on sMRI data corresponding to the plurality of individuals. The sMRI data includes cortical volume data, cortical thickness data, and cortical surface area data.

In some aspects, the machine learning model is trained on input data corresponding to the plurality of individuals. For each individual, the input data can include various types of data. As an example, the input data includes clinical scales data and fMRI data. As another example, the input data includes clinical scales data and sMRI data. As a further example, the input data includes fMRI data and sMRI data. As yet another example, the input data includes fMRI data, clinical scales data, and sMRI data.

Additional aspects of the present disclosure include a system for evaluating mental health of patients. The system includes a memory, and a control system. The memory contains machine readable medium. The machine readable medium includes machine executable code storing instructions for performing a method. The control system is coupled to the memory, and includes one or more processors. The control system is configured to execute the machine executable code to cause the control system to perform the method: A selection of answers associated with a patient is received. The selection of answers corresponds to each question in a series of questions from mental health questionnaires. Unprocessed MRI data are received. The unprocessed MRI data correspond to a set of MRI images of a biological structure associated with the patient. The unprocessed MRI data is processed to output a set of MRI features. Using a machine learning model, the selection of answers and the set of MRI features are processed to output a mental health indication of the patient.

Further aspects of the present disclosure include a machine learning training system. The machine learning training system includes at least one nontransitory processor-readable storage medium and at least one processor communicatively coupled to the at least one nontransitory processor-readable storage medium. The at least one nontransitory processor-readable storage medium stores at least one of processor-executable instructions or data. The at least one processor, in operation, is configured to receive labeled training data. The labeled training data includes data for a plurality of individuals, which indicate whether each of the individuals has one or more of a plurality of mental health disorders. The labeled training data further includes a selection of answers to mental health questionnaires for each of the individuals, and MRI data recorded for each of the plurality of individuals. The answers and MRI data are processed to output a plurality of features. An initial machine learning model is trained in a supervised manner based at least in part on the received labeled training data. An importance measure for each of the plurality of features is extracted from the trained initial machine learning model. A plurality of subset machine learning models is generated based at least in part on the extracted importance measures for the plurality of features. A classification performance of the generated plurality of subset machine learning models are evaluated. At least one of the subset machine learning models is selected as a diagnostic classifier. The features of the diagnostic classifier are stored in the at least one nontransitory processor-readable storage medium for subsequent use as a screening tool.

In some aspects, the machine learning system further includes using the features of the diagnostic classifier as a screening tool to assess at least one of intermediate or end-point outcomes in at least one clinical trial testing for treatment responses.

In some aspects, the selected subset machine learning model includes a portion of the plurality of features. The portion selected from features includes an importance measure above a threshold value.

In some aspects, each of the subset machine learning models includes a different selection of the portion of the plurality of features. In some aspects, at least twenty features of the plurality of features have an importance measure above the threshold value. For example, the portion of the plurality of features includes at least ten features and less than twenty features.

In some aspects, the diagnostic classifier is operative to determine whether an individual is healthy or has a general mental health issue. In some aspects, the diagnostic classifier is operative to determine whether an individual is healthy or has a specific mental health disorder. In some aspects, the diagnostic classifier is operative to determine whether an individual has a first specific mental health disorder or a second specific mental health disorder. In some aspects, the diagnostic classifier is operative to determine whether an individual is at risk of developing a mental health disorder.

In some aspects, the labeled training data includes, for each individual, an indication of at least one of the following: whether the individual is healthy, whether the individual has a general mental health issue, whether the individual has one or more specific mental health disorders, whether the individual is at risk of developing a general mental health issue, whether the individual is at risk of developing one or more specific mental health disorders, and any combination thereof. In some aspects, the labeled training data further comprises at least one of: functional measurement data or physiological measurement data.

In some aspects, the selected subset machine learning model includes at least a subset of the following features: "I have more fun doing activities with other people than by myself"; "I have trouble concentrating"; "I have frequent mood changes without understanding why"; "I try to do well at everything I do"; "I need to think for a long time before I make a decision"; "I need a lot of self-control to keep myself out of trouble"; "I am often restless and can't sit still"; "I am very affected when one of my friends seems upset"; "My mood changes more than I think I should"; and "I do not get enough emotional support from other people."

In some aspects, the selected subset machine learning model includes at least a subset of the following features: "I like to please other people as much as I can"; "There are often times when I am so restless that it is impossible for me to sit still"; "My mood often changes, from happiness to sadness, without my knowing why"; "Although there are things that I enjoy doing by myself, I usually seem to have more fun when I do things with other people"; "I am more sentimental than most people"; "I love to excel at everything I do"; "People consider me a rather freewheeling and spontaneous person"; "I feel that I never really get all that I need from people"; "In unfamiliar surroundings, I am often so assertive and sociable that I surprise myself"; "I like to think about things for a long time before I make a decision"; "Sometimes ideas and insights come to me so fast that I cannot express them all"; "I have many hobbies"; "I like to keep my problems to myself"; "It is difficult for me to keep the same interests for a long time because my attention often shifts to something else"; "How often do you have trouble wrapping up the final details of a project, once the challenging parts have been done"; "I like to go slow in starting work, even if it is easy to do"; and "Usually I am more worried than most people that something might go wrong in the future."

In some aspects, in operation, the at least one processor trains the initial machine learning model using k-fold cross validation with logistic regression. In some aspects, each of the subset machine learning models includes a different combination of the features of the initial machine learning model. In some aspects, each of the subset machine learning models includes a different number of the features of the initial machine learning model determined by the importance measures.

Still further aspects of the present disclosure include a system for evaluating mental health of patients. The system includes a memory and a control system. The memory contains machine readable medium. The machine readable medium includes machine executable code storing instructions for performing a method. The control system is coupled to the memory, and includes one or more processors. The control system is configured to execute the machine executable code to cause the control system to perform the method: Unprocessed MRI data are received. The unprocessed MRI data correspond to a set of MRI images of a biological structure of a patient. Using a machine learning model, the unprocessed MRI data are processed to output a mental health indication of the patient.

The above summary is not intended to represent each embodiment or every aspect of the present disclosure. Rather, the foregoing summary merely provides an example of some of the novel aspects and features set forth herein. The above features and advantages, and other features and advantages of the present disclosure, will be readily apparent from the following detailed description of representative embodiments and modes for carrying out the present disclosure, when taken in connection with the accompanying drawings and the appended claims.

BRIEF DESCRIPTION OF THE DRAWINGS

The foregoing and other advantages of the present disclosure will become apparent upon reading the following detailed description and upon reference to the drawings.

Figure 1A:
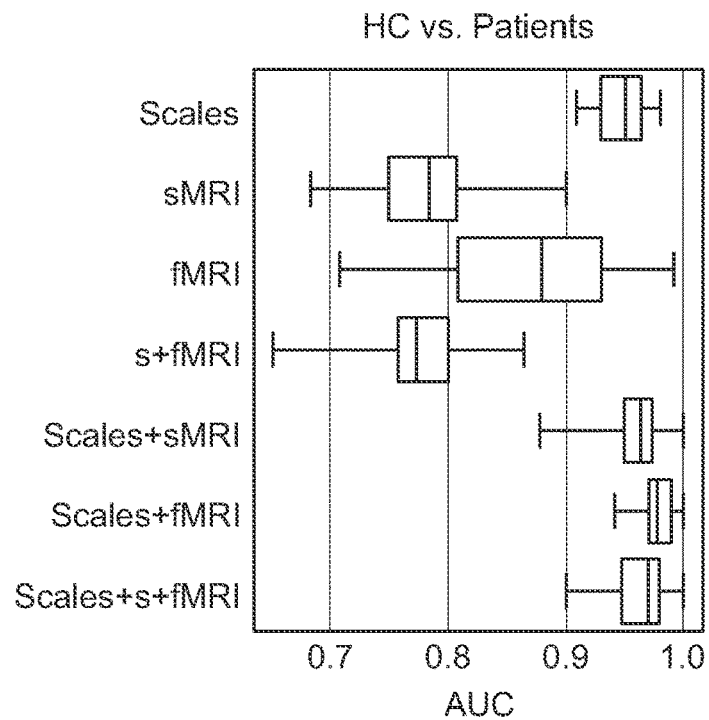
FIGS. 1A-1D illustrate boxplots of the maximum AUC's during sequential model selection, according to some implementations of the present disclosure.
Figure 1B:
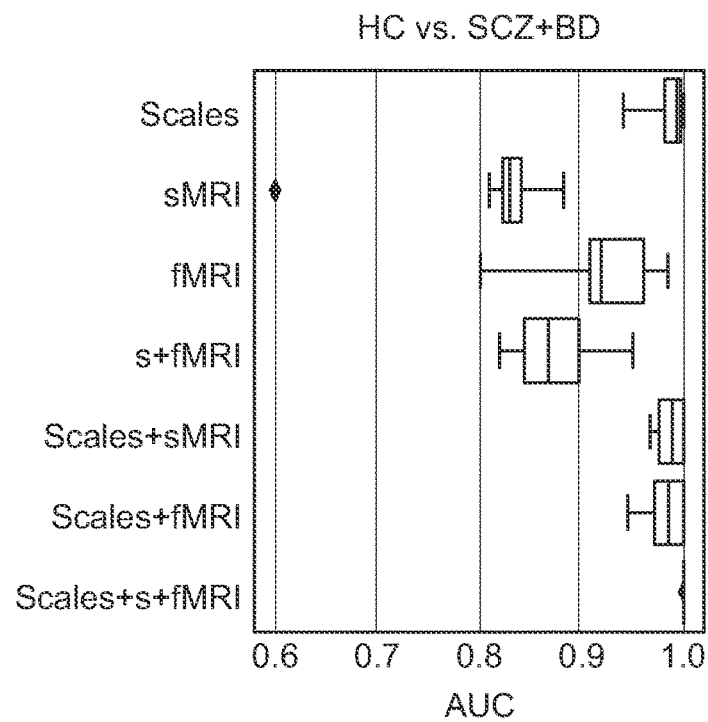
Figure 1C:
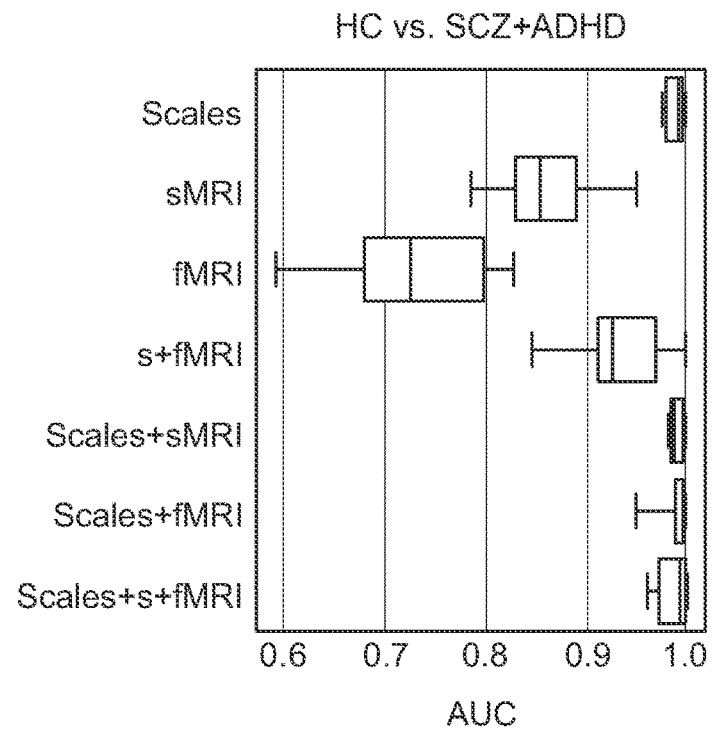
Figure 1D:
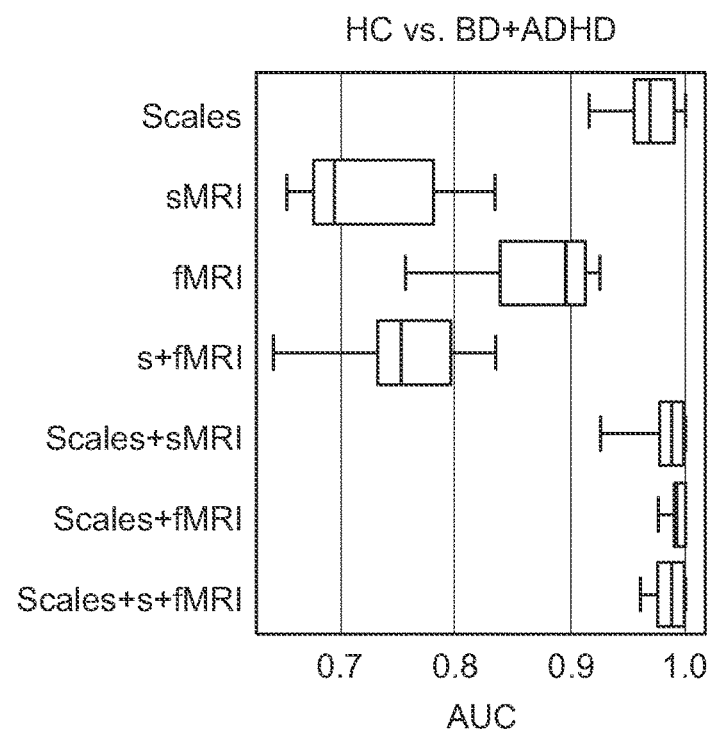

While the present disclosure is susceptible to various modifications and alternative forms, specific embodiments have been shown by way of example in the drawings and will be described in detail herein. It should be understood, however, that the present disclosure is not intended to be limited to the particular forms disclosed. Rather, the present disclosure is to cover all modifications, equivalents, and alternatives falling within the spirit and scope of the present disclosure as defined by the appended claims.

DETAILED DESCRIPTION

The present disclosure is described with reference to the attached figures, where like reference numerals are used throughout the figures to designate similar or equivalent elements. The figures are not drawn to scale, and are provided merely to illustrate the instant disclosure. Several aspects of the disclosure are described below with reference to example applications for illustration. It should be understood that numerous specific details, relationships, and methods are set forth to provide a full understanding of the disclosure. One having ordinary skill in the relevant art, however, will readily recognize that the disclosure can be practiced without one or more of the specific details, or with other methods. In other instances, well-known structures or operations are not shown in detail to avoid obscuring the disclosure. The present disclosure is not limited by the illustrated ordering of acts or events, as some acts may occur in different orders and/or concurrently with other acts or events. Furthermore, not all illustrated acts or events are required to implement a methodology in accordance with the present disclosure.

Aspects of the present disclosure can be implemented using one or more suitable processing device, such as general-purpose computer systems, microprocessors, digital signal processors, micro-controllers, application-specific integrated circuits (ASIC), programmable logic devices (PLD), field-programmable logic devices (FPLD), field-programmable gate arrays (FPGA), mobile devices such as a mobile telephone or personal digital assistants (PDA), a local server, a remote server, wearable computers, tablet computers, or the like.

Memory storage devices of the one or more processing devices can include a machine-readable medium on which is stored one or more sets of instructions (e.g., software) embodying any one or more of the methodologies or functions described herein. The instructions can further be transmitted or received over a network via a network transmitter receiver. While the machine-readable medium can be a single medium, the term "machine-readable medium" should be taken to include a single medium or multiple media (e.g., a centralized or distributed database, and/or associated caches and servers) that store the one or more sets of instructions. The term "machine-readable medium" can also be taken to include any medium that is capable of storing, encoding, or carrying a set of instructions for execution by the machine and that cause the machine to perform any one or more of the methodologies of the various embodiments, or that is capable of storing, encoding, or carrying data structures utilized by or associated with such a set of instructions. The term "machine-readable medium" can accordingly be taken to include, but not be limited to, solid-state memories, optical media, and magnetic media. A variety of different types of memory storage devices, such as a random access memory (RAM) or a read-only memory (ROM) in the system or a floppy disk, hard disk, CD ROM, DVD ROM, flash, or other computer-readable medium that is read from and/or written to by a magnetic, optical, or other reading and/or writing system that is coupled to the processing device, can be used for the memory or memories.

Overview

The Diagnostic and Statistical Manual of Mental Disorders (DSM) is a standard for diagnosing psychiatric disorders in the United States. Yet, evidence has long suggested that symptoms in psychiatric disorders do not follow boundaries between DSM categories, implicating an underlying latent transdiagnostic dimensional structure. While abnormal feature dimensions associated with the latent symptom dimensions can be identified within a single DSM category, the transdiagnostic dimensional structure shared across psychiatric disorders largely remains unknown.

Thus, the field of psychiatry can rely on making diagnoses and recommending treatment for disorders based solely on clinical phenomenology. However, this approach hampers prognostic assessment, treatment, and drug development. As with many other areas of medicine, defining mental illness based on a combination of symptoms and biological underpinnings could allow for a richer understanding and potentially better management of these disorders.

Moreover, dimensionality and comorbidity are pervasive in terms of symptoms across different DSM categories. Such dimensionality is manifested as heterogeneity in symptom clusters within disease categories defined by the DSM as well as overlaps across DSM categories. For instance, in the area of anxiety and mood disorders, more than 50% of individuals are diagnosed of having more than one category of disorders according to the DSM at a given time. Similarly, about 50% of bipolar disorder patients exhibit schizophrenic-like psychotic symptoms during illness episodes. The presence of such psychotic symptoms can be mood-incongruent and can occur outside of illness episodes, hence creating challenges in correctly categorizing and treating such patients. Overall, a latent trans-diagnostic dimensional structure may exist spanning multiple disorders. The DSM's symptom-based taxonomy may not provide an accurate account of such latent structure of psychopathology.

Furthermore, clinical symptoms such as depressed mood, anxiety, and anhedonia span multiple diagnostic categories, so one approach to linking them with their biological bases would be examination of symptom severity trans-diagnostically at suitable physiological levels. This approach of stratifying mental disorders by symptom dimension across current diagnostic categories could sidestep the main issue that categorical boundaries present. Evidence suggests symptom dimensions that span multiple psychiatric disorders and can be tied to biological bases.

This issue may be addressed by identifying the underlying structures of psychopathology on multiple levels including symptom, behavior, physiology, imaging, and genetics. Data-driven methods based on symptom and behavior have largely focused on classifying and subtyping patients within a single diagnostic category. While such a focus on re-partitioning a single diagnostic category is useful, it is likely to be limited given the observed symptom overlaps across DSM categories. On the other hand, genetic risk for psychiatric disorders is pleiotropic and shared across broad dimensions of disorders, such as SCZ, BD, and ADHD. Yet, the genetic risk identified for psychiatric disorder is generally characterized by polygenic inheritance, hence the effect size from a given risk allele is likely to be small. Based on neuroimaging (e.g., sMRI), shared abnormalities in certain brain regions underlying common psychiatric disorders were identified. Functional MRI (fMRI) found altered functional connectivity patterns shared across multiple categories of disorders such as SCZ, BD, and MDD.

Though valuable, the search for psychiatric biomarkers has thus largely been limited to those that permit diagnostic classification and generally limited to one type, mode, or category of biomarker. Certain clinical phenotypes described at the symptom or neurobiological levels may span multiple diagnoses. Therefore, exploration of transdiagnostic biomarkers that probe these levels of expression could expand our understanding beyond categorical definitions of disorders and towards disorders that vary along symptom dimensions.

Therefore, the present disclosure contemplates that there exist distinct subtypes within various mental health disorders (e.g., MDD, PTSD, and panic disorder) based on, for example, orthogonal symptom dimensions shared across the DSM diagnoses and their corresponding biomarkers. The corresponding biomarkers can include biomarkers identifiable in neuroimaging as discussed further herein and other modalities (including advantageously combining modalities). While these important shared abnormal features associated with the latent transdiagnostic symptom and behavior dimensions can be identified, the robustness of the identified features in terms of their ability to reliably classify patients according to the symptom and behavior dimensions are tested and discussed herein.

According to some implementations of the present disclosure, using the Consortium for Neuropsychiatric Phenomics ("CNP") dataset, a set of phenotypic features shared across schizophrenia ("SCZ"), bipolar disorder ("BD"), and attention deficit/hyperactivity disorder ("ADHD") from self-reported clinical instruments is identified. For example, the set of phenotypic features are identified according to four (4) transdiagnostic classifiers: (1) Healthy vs. All Patients, (2) Healthy vs. SCZ & BD, (3) Healthy vs. SCZ & ADHD, and (4) Healthy vs. BD & ADHD.

These phenotypic features can robustly distinguish patient groups from healthy controls, and outperformed classifiers trained on morphological and connectivity measures based on structural and functional magnetic resonance imaging. In addition, these phenotypic features encompass a wide range of domains, including personality and traits, positive and negative effects, cognition, sensory processing, and social processing. As an example, a highest proportion of shared phenotypic features consists of personality traits and temperaments defined in the Temperament and Character Inventory pertaining to harm avoidance, novelty seeking, persistence, and reward dependence. Thus, the present disclosure provides a robust data-driven approach to identify transdiagnostic features shared across various patient populations.

Cross-cutting symptom subtypes were identified in patients with major depressive disorder (MDD), panic disorder, posttraumatic stress disorder (PTSD) or in healthy controls (HC) and mapped onto measures of cognitive, physiological, and functional outcome measures. Reward responsivity, the lack of which is related to anhedonia, is tied to deficits in fMRI connectivity in a transdiagnostic sample of SZ, MDD, BD, and psychosis risk subjects. Derived symptom dimensions correlated with various network-based fMRI connectivity measures in a community sample including representation of multiple psychopathological categories. In some examples, ventral striatal connectivity can predict future depressive order.

Genetic risk variants correlate highly across MDD, SZ, BD, and attention deficit and hyperactivity disorder (ADHD), suggesting that examining symptoms in this transdiagnostic group could be highly informative. Thus, the present disclosure capitalizes on the Consortium for Neuropsychiatric Phenomics (CNP) dataset which includes three of these patient groups (SZ, BD, ADHD, and additionally healthy controls) and a rich set of clinical symptom evaluations and neuroimaging data for investigating biomarkers of symptom severity. One objective of the present disclosure is predicting severity for a subset of symptoms assessed in the dataset. In some examples, those datasets related to mood and emotional dysregulation are selected, for example, depression/depressed mood, anhedonia, anxiety, and other negative symptoms.

While performing correlations is the dominant approach to examine variation along a symptom dimension, the framework of machine learning overcomes some shortcomings of correlative approaches as it allows us to create models and test predictive value and generalizability of those models on held out or new samples. Additionally, multivariate modeling allows a concurrent examination of phenotypes across the multiple levels of expression of mental illness—levels of cognitive behaviors, symptoms, brain measures, etc.—which may improve predictive ability. According to some implementations of the present disclosure, an exemplary method is disclosed for sorting and evaluating features by importance in order to improve biomarker development.

Further, the present disclosure provides for predictive models of depression, anxiety, anhedonia, and other negative symptoms. Different types of machine learning ("ML") models are utilized. Using the CNP dataset, predictability of the models is analyzed. The analysis further includes a comparison of single v. multimodal features. This dataset includes data from clinical scales, resting-state functional-MRI scans, and structural-MRI scans for patients with schizophrenia, bipolar disorder, ADHD, and healthy controls. Thus, the present disclosure provides a custom, data-driven method of identifying subsets of the most predictive features. The present disclosure allows a comparison in an unbiased manner, via different permutations of input feature set and ML model choice. For example, the predictability is analyzed and compared using multi-modal biomarkers and single modality biomarkers. A subset of features that maximized predictability is identified from a set that is several orders of magnitude larger than the subset. As an example, such subset includes edge-level fMRI connectivity features, clinical scale features, and sMRI features. Thus, the present disclosure provides for predicting transdiagnostic symptoms related to depression, anxiety, anhedonia, and other negative symptoms.

Nonetheless, selection of the optimal features for exploring predictive models/biomarkers can be difficult in the face of high-dimensional, multi-modal data. An importance-weighted, forward selection approach is taken as a data-driven way to identify the optimal feature subset to include in regression model-building. Finding an optimal subset helps in high-dimensional cases where the number of features (p) is greater than the number of samples (n) to minimize overfitting of the models. It also reduces noise from uninformative input variables without requiring the modeler to judge whether a variable is signal or noise.

The importance-weighted, forward selection approach involves an initial rank-ordering step for ordering features by importance, a forward-selection search step for building a series of models utilizing subsets of ordered features selected from the first step, and an evaluation step for evaluating each of these models using these candidate subsets according to a pre-specified criterion to find the optimal model. Thus, this approach integrates feature selection into regression modeling. Additionally, different types of input features are evaluated (e.g., responses to clinical symptom and trait scales, structural MRI measures, functional MRI measures).

Two different linear regression algorithms that incorporate feature selection through regularization (Lasso, Elastic Net) and one non-linear algorithm (Random Forest) are also evaluated, in order to identify the best parameters and biomarkers for our selected set of symptom types. Thus, another exemplary method is disclosed herein to find highly-predictive biomarkers for several measures of depressed mood, anxiety, anhedonia and related negative symptoms and to compare the contribution of single versus multimodality feature sets and different algorithms to biomarker-building.

As such, another objective of the present disclosure is to better understand the features returned by the best biomarkers at a category level. In line with the objectives herein, the present disclosure is directed to, among others, that 1) multi-modal biomarkers that are more predictive than single modality biomarkers, 2) data-driven methods that identify a subset of features and maximize predictability from a much larger set, and 3) from among that subset, analyzing edge-level fMRI connectivity features, clinical scale features, and sMRI features. In addition, fMRI connectivity features can be broadly distributed across many resting-state networks for most symptom biomarkers (though in some instances, default-mode network connectivity can be more abnormal) and that a few clinical scales are more highly represented than others.

Exemplary Systems and Methodologies

Figure 28:
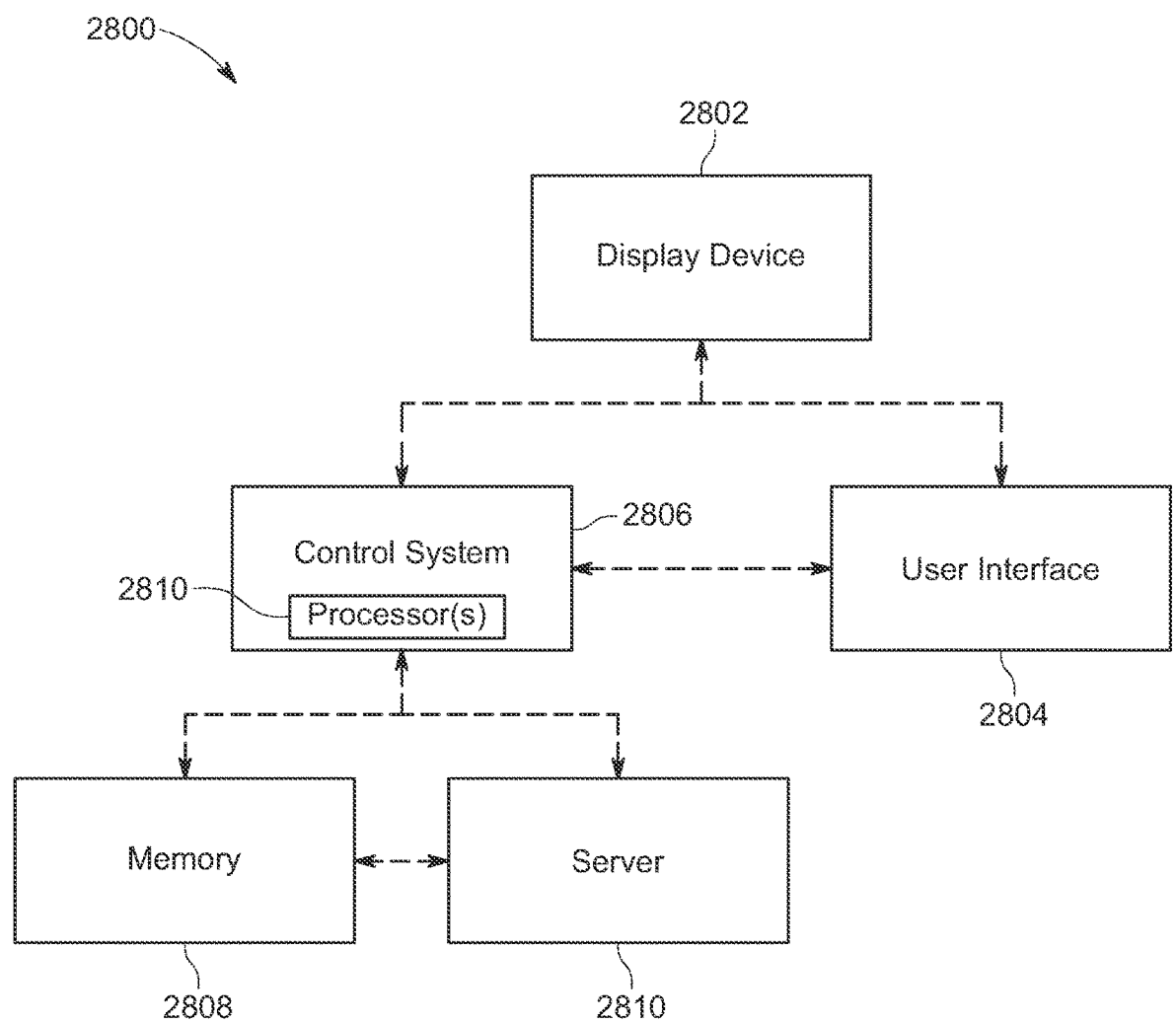
FIG. 28 illustrates an exemplary system for implementing various methodologies disclosed herein, according to some implementations of the present disclosure.

The present disclosure contemplates that a variety of systems can be used to perform various embodiments of the present disclosure. Referring now to FIG. 28, an exemplary system 2800 is shown, which can be configured to perform various methods of the present disclosure, including methods 2900, 3000, and 3300 of FIGS. 29, 30, and 33, respectively. In particular, system 2800 includes a display 2802, a user interface 2804, a control system 2806, and a memory 2808. In some examples, the system 2800 further includes one or more servers 2810.

The user interface 2804 is configured to receive input from a user. For example, the user interface 2804 can be a keyboard, a touchscreen, a mobile device, or any other device for receiving input, as known in the art. The user enters data on the user interface 2804 in response to prompts on the display 2802. For example, the display 2802 outputs a series of mental health questions, and the user inputs an answer to each question on the user interface 2804. In some examples, the user interface 2804 directly displays the input on display 2802 and relays the data to the control system 2806. In some examples, the data is then stored in the memory 2808.

The display 2802 is configured to receive data from the control system 2806 and the user interface 2804. For example, the display 2802 displays input received from the user interface 2804; in some examples, the data is first sent to the control system 2806, which then processes the data and instructs the display 2802 according to the processed data. In other examples, the display 2802 displays data received from the control system 2806. Exemplary data from the control system 2806 includes questions from a mental health questionnaire, answer boxes, answer options, answer data, or a mental health indicator. In some examples, the display 2802 is on a smart phone.

The present disclosure also contemplates that more than one display 2802 can be used in system 2800, as would be readily contemplated by a person skilled in the art. For example, one display can be viewable by a patient, while additional displays are visible to researchers and not to the patient. The multiple displays can output identical or different information, according to instructions by the control system 2806.

The control system 2806 can be communicatively coupled to the display 2802, the user interface 2804, and the memory 2808. Further, the control system 2806 can be communicatively coupled to the server 2810. For example, the communication can be wired or wireless. The control system 2806 is configured to perform any methods as contemplated according to FIGS. 29-30 (discussed further below). The control system 2806 can process and/or store input from the display 2802, the user interface 2804, and the memory 2808. In some examples, the methodologies disclosed herein can be implemented, via the control system 2806, on the server 2810. It is also contemplated that the server 2810 includes a plurality of servers, and can be remote or local. Optionally, the control system and/or the memory 2808 may be incorporated into the server 2810.

In some examples, system 2800 can be a unitary device, for example, a smart phone, which includes a display 2802, a user interface 2804, a control system 2806, and a memory 2808.

Figure 29:
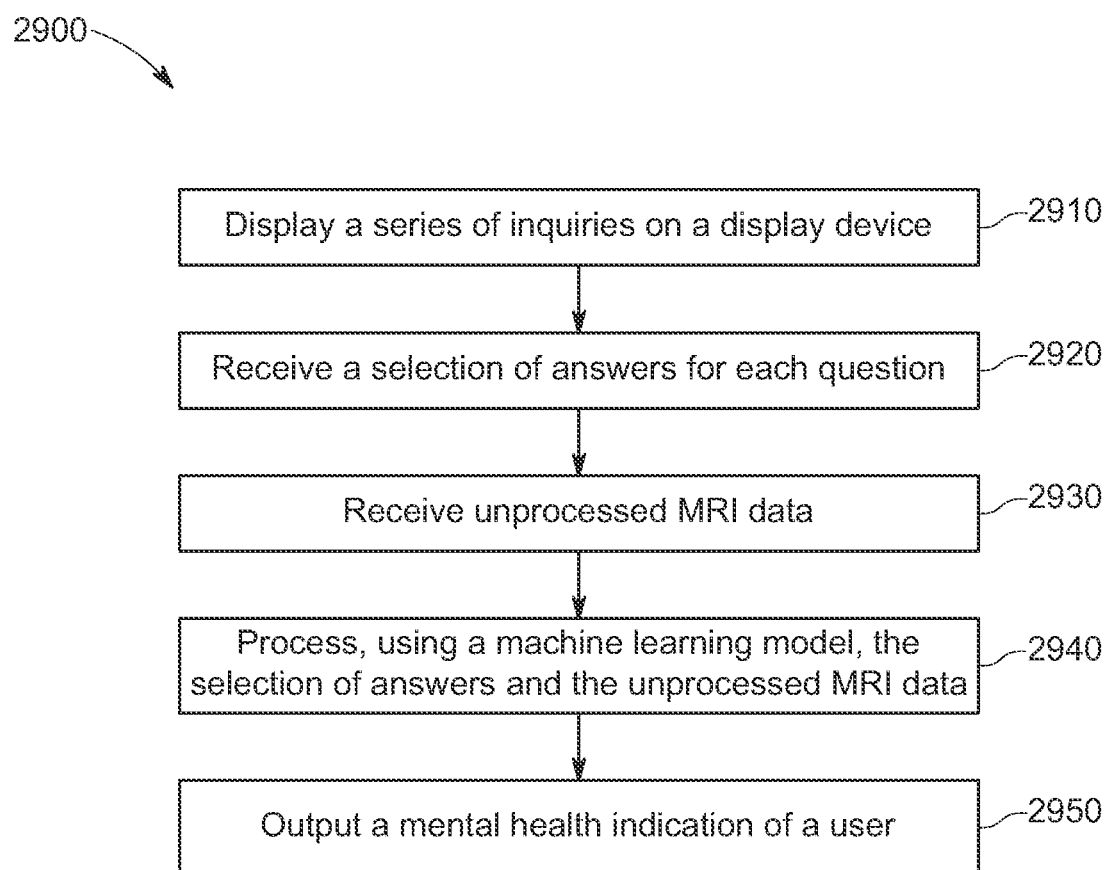
FIG. 29 illustrates an exemplary methodology for determining a symptom severity indicator for a patient, according to some implementations of the present disclosure.

Turning now to FIG. 29, an exemplary methodology 2900 is discussed for evaluating a patient for mental health issues. Additional details and alternate steps for methodology 2900 are discussed further with regards to FIGS. 1A-33 and the corresponding description.

Methodology 2900 begins at step 2910 which provides for displaying a series of questions. An exemplary series of questions includes questions from mental health questionnaires, and includes both text and answers for each question. In some examples, the series of questions are displayed on a display device (e.g., the display 2802 of FIG. 28).

In some aspects, the series of questions includes questions determined by a machine learning system (e.g., a machine learning algorithm) to be effective at screening patients. The questions determined by the machine learning system may be more effective than an initial and/or larger set of questions. For example, the machine learning system may be able to pick a number of most effective questions out of an initial set of questions. An exemplary set of most effective questions includes whether the patient agrees with each of the following statements in the past two weeks: "I have more fun doing activities with other people than by myself"; "I have trouble concentrating"; "I have frequent mood changes without understanding why"; "I try to do well at everything I do"; "I need to think for a long time before I make a decision"; "I need a lot of self-control to keep myself out of trouble"; "I am often restless and can't sit still"; "I am very affected when one of my friends seems upset"; "My mood changes more than I think I should"; and "I do not get enough emotional support from other people." An exemplary set of answers to each of those questions may include: "Strongly Disagree," "Disagree," "Neither agree nor disagree," "Agree," and "Strongly Agree."

Methodology 2900 then provides for, at step 2920, receiving answers for each of the series of questions (the questions provided for in step 2910). In some examples, the answers are received at a user interface (e.g., user interface 2804 of FIG. 28). In some examples, the answers include selection of a multiple choice question, a textual response, or any other user input as contemplated by one skilled in the art. In some examples, the answers are retrieved from a record entry corresponding to one patient in a database of patient records. This database can be stored in the memory 2808 of FIG. 28, for example. In some examples, the database can be stored in the sever 2810 of FIG. 28. In some examples, methodology 2900 begins directly at step 2920.

Step 2930 provides for receiving unprocessed MRI data. The unprocessed MRI data corresponds to a set of MRI images of a biological structure. In some examples, the biological structure is associated with the patient. In some examples, the MRI data corresponds to MRI data for a patient's brain (e.g., the same patient who provided answers at step 2920). The MRI data can include task-based fMRI data, rs-fMRI data, and/or sMRI data. In some examples, step 2930 receives other types of neuroimaging data instead of, or in addition to, the unprocessed MRI data. In additional examples of step 2930, methodology 2900 can provide for receiving clinical scales data. In some examples of step 2930, methodology 2900 provides for receiving processed MRI data.

Step 2940 then provides for processing, using a machine learning model, the selection of answers from step 2920 and the data received at step 2930 (e.g., the unprocessed MRI data). In some examples of methodology 2900, the data received at step 2930 is preprocessed to identify a plurality of features.

At step 2950, methodology 2900 provides for outputting a mental health indication of the patient. In some examples of the present disclosure, step 2850 performs processing of the answers and the received data as discussed further below with respect to methodology 3000 of FIG. 30 and methodology 3300 of FIG. 33. In some aspects, the mental health indication is categorical. For example, the mental health indication includes a determination that the processed selection of answers and the processed MRI data includes indications of at least one of: a neuropsychiatric disorder, schizophrenia, a bi-polar disorder, unhealthy generally (versus healthy control) and any combination thereof.

In some aspects, methodology 2900 further comprises determining that the processed selection of answers and the processed MRI data identifies features corresponding to a mental disorder.

Even though methodology 2900 is illustrated to include steps 2910-2950, the present disclosure also contemplates more or fewer steps. For example, real-time user input is optional for some implementations of the present disclosure. As such, additional aspects of the present disclosure include a system configured to perform a method, similar to methodology 2900 but not including real-time user input. For example, instead of first displaying a series of questions, this method begins with receiving a selection of answers associated with a patient.

As another example, questions and answers from a mental health questionnaire is optional for some implementations of the present disclosure. As such, additional aspects of the present disclosure include a system configured to perform a method, similar to methodology 2900 but not including a series of questions or a series of answers. For example, using a machine learning model, the unprocessed MRI data are processed to output a mental health indication of the patient, without reference to a selection of answers associated with a patient.

Figure 30:
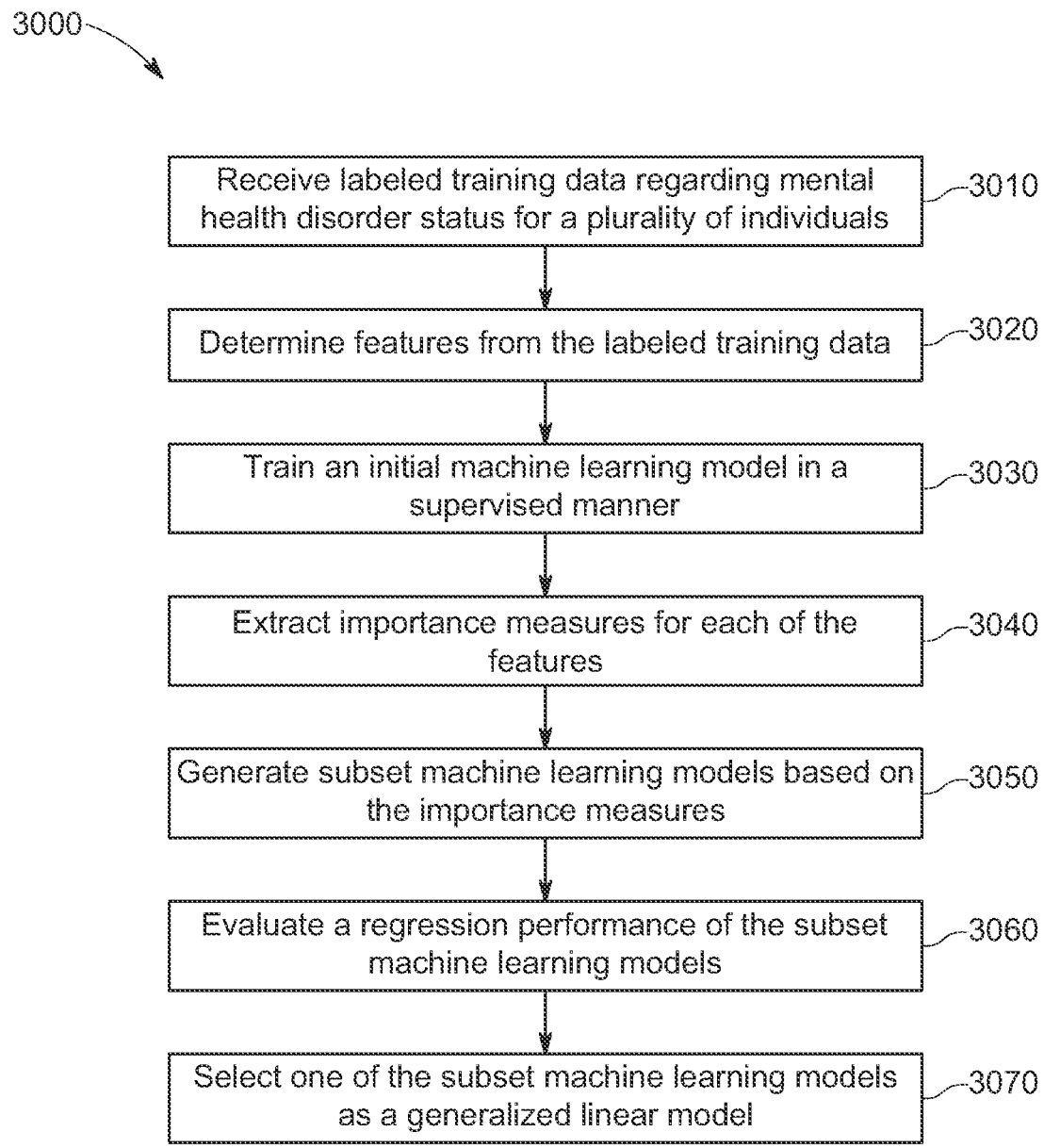
FIG. 30 illustrates an exemplary methodology for selecting a machine learning model as a generalized linear model, according to some implementations of the present disclosure.

Referring now to methodology 3000 of FIG. 30, an exemplary methodology is shown for selecting a machine learning model as a generalized linear model, according to various embodiments of the present disclosure. In some examples, the machine learning model is any of: a generalized linear model, a logistical regression model, a regression model, a supervised regression method, random forest model, LASSO model, and an elastic net model. In some examples, the machine learning model is any of the models and algorithms discussed further below. In one embodiment of method 3000, the present disclosure provides two regularized general linear model regression algorithms, LASSO and Elastic Net, and one non-linear regression model algorithm, Random Forest. Elastic Net in particular can be used when the number of predictor variables is much greater than the number of samples.

In step 3010, methodology 3000 provides for receiving labeled training data regarding mental health disorder status for a plurality of individuals. In some examples, the labeled training data identifies whether each of the individuals has one or more mental health disorders and the mental health indicator of their symptoms. The labeled training data includes, for each individual, a selection of answers to mental health questionnaires and includes MRI data. The MRI data can be task-based fMRI data, sMRI data, and/or rs-fMRI data. In some examples, the labeled training data includes other types of neuroimaging data for each individual. In some examples, the labeled training data includes, for each individual, an indication of any of: whether the individual is healthy, whether the individual has a general mental health issue, whether the individual has one or more specific mental health disorders, whether the individual is at risk of developing a general mental health issue, or whether the individual is at risk of developing one or more specific mental health disorders. In some examples, the labeled training data includes another functional and/or physiological measurement dataset, as known in the art.

In step 3020, methodology 3000 provides for determining features from the labeled training data of step 3010. The features are determined according to any methods, as known in the art.

In step 3030, methodology 3000 provides for training an initial machine learning model in a supervised manner, based on the features determined in step 3020. In some examples, training this initial machine learning model includes using k-fold cross-validation with LASSO and Elastic Net regression.

In some examples, training this initial machine learning model in step 3030 includes training the model on clinical scales data corresponding to the plurality of individuals. In some examples, training this initial machine learning model in step 3030 includes training the model on fMRI full connectivity data corresponding to the plurality of individuals. In some examples, training this initial machine learning model in step 3030 includes training the model on sMRI data corresponding to a plurality of individuals, the sMRI data including cortical volume data, cortical thickness data, and cortical surface area data.

In some examples, training this initial machine learning model in step 3030 includes training the model on input data corresponding to the plurality of individuals. For each individual, the input data includes a variety of combinations of data. As a first example, the input data includes clinical scales data and fMRI data. As a second example, the input data includes clinical scales data and sMRI data. As a third example, the input data comprises fMRI data and sMRI data.

As a fourth example, the input data comprises fMRI data, clinical scales data, and sMRI data. This particular combination of input data provides a high $r^2$ metric (calculated on an untouched evaluation set data to avoid biasing and overfitting our models) when using Elastic Net across the 5 different outcome variables.

In step 3040, methodology 3000 provides for extracting importance measures for each of the features. These importance measures are selected based on the trained initial machine learning model.

In step 3050, methodology 3000 provides for generating a plurality of subset machine learning models, based on the extracted importance measures of step 3040.

In step 3060, methodology 3000 provides for evaluating a regression performance of the generated subset machine learning models from step 3050. In some examples, each of the subset machine learning models includes a different selection of features. In some examples, the subset machine learning models include only features with an importance measure above a threshold value. In some examples, the features are ranked based on the importance measure. In some examples, each of the subset machine learning models includes a sequentially lower number of features than a following subset machine learning model, wherein the features are selected for each subset machine learning model based on a highest importance measure.

In step 3070, methodology 3000 provides for selecting one of the subset machine learning models as a generalized linear learning model. The selection is based on the regression performances as evaluated in step 3060. The selected subset machine learning model includes a portion of the plurality of features determined from step 3020. The portion of features is selected from features with an importance measure above a threshold value. In some examples, more than one subset machine learning model is selected.

In some examples of step 3070, the threshold value is set so that at least twenty features of the plurality of features determined in step 3020 have an importance measure above the threshold value. In some examples, the threshold value is set to select a portion of between ten and twenty features.

In some examples of step 3070, the features of the machine learning model are stored in a non-transitory processor-readable storage medium (e.g., memory 2808 of FIG. 28). The features can then be later used as a screening tool. In some examples, the screening tool can output a mental health indicator of a mental health condition. In some examples, the screening tool assesses intermediate and/or end-point outcomes in clinical trial testing for treatment responses.

Therefore, the selected machine learning model can then be used to process any of the input data as provided for in the present disclosure.

Figure 33:
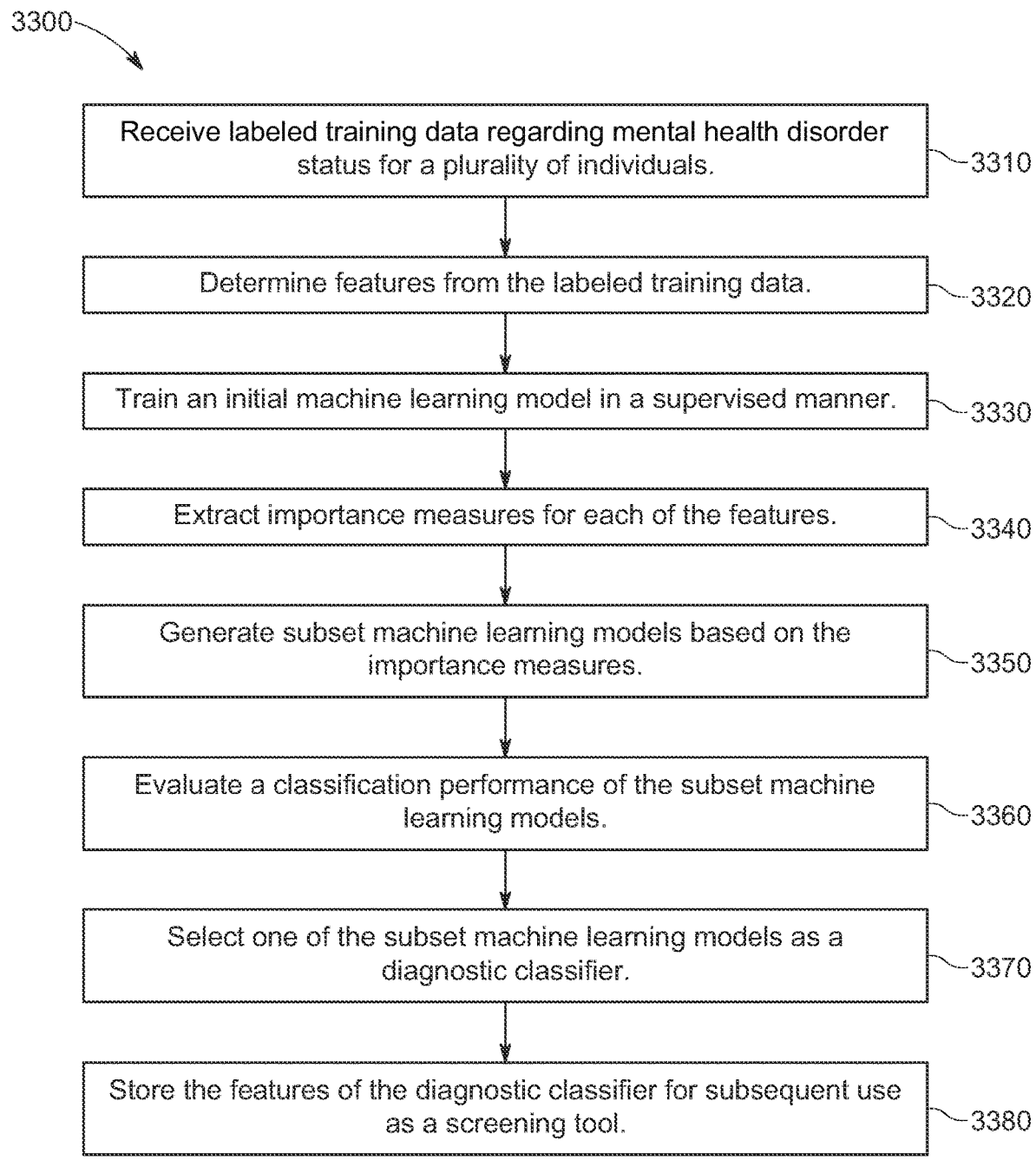
FIG. 33 illustrates an exemplary methodology for selecting a machine learning model as a diagnostic classifier, according to some implementations of the present disclosure.

Referring now to methodology 3300 of FIG. 33, an exemplary methodology is shown for selecting a machine learning model as a diagnostic classifier, according to various embodiments of the present disclosure. Methodology 3300 can be applied in place of, or in combination of, methodology 3000 of FIG. 30.

In step 3310, methodology 3300 provides for receiving labeled training data regarding mental health disorder status for a plurality of individuals. The labeled training data includes data for a plurality of individuals, which indicate whether each of the individuals has one or more of a plurality of mental health disorders. The labeled training data further includes a selection of answers to mental health questionnaires for each of the individuals, and MRI data recorded for each of the plurality of individuals.

In some aspects, the labeled training data of step 3310 includes, for each individual, an indication of whether the individual is healthy, whether the individual has a general mental health issue, whether the individual has one or more specific mental health disorders, whether the individual is at risk of developing a general mental health issue, whether the individual is at risk of developing one or more specific mental health disorders, or the like, or any combination thereof. In some aspects, the labeled training data of step 3310 further includes functional measurement data and/or physiological measurement data.

In step 3320, methodology 3300 provides for determining features from the labeled training data of step 3310. In some examples, the answers and MRI data of the received labeled training data are processed to output a plurality of features. The features are determined according to any methods, as known in the art.

In step 3330, methodology 3300 provides for training an initial machine learning model in a supervised manner, based at least in part on the received labeled training data. In some examples, the initial machine learning model is trained based on the features determined in step 3320. In some examples, training this initial machine learning model includes using k-fold cross validation with logistic regression (e.g., with LASSO and/or Elastic Net regression).

In step 3340, methodology 3300 provides for extracting importance measures for each of the plurality of features. These importance measures are selected based on the trained initial machine learning model.

In step 3350, methodology 3300 provides for generating a plurality of subset machine learning models, based on the extracted importance measures of step 3340. In some aspects, each of the subset machine learning models includes a different combination of the features of the initial machine learning model. In some aspects, each of the subset machine learning models includes a different number of the features of the initial machine learning model determined by the importance measures.

In step 3360, methodology 3300 provides for evaluating a classification performance of the generated subset machine learning models from step 3350.

In step 3370, methodology 3300 provides for selecting one of the subset machine learning models as a diagnostic classifier. The selection is based on the classification performances as evaluated in step 3360. The selected subset machine learning model includes a portion of the plurality of features determined from step 3320. The portion of features is selected from features with an importance measure above a threshold value. In some examples, more than one subset machine learning model is selected. It is also contemplated that the selected machine learning model can then be used to process any of the input data as provided for in the present disclosure.

In some aspects, the selected subset machine learning model of step 3370 includes a portion of the plurality of features. The portion selected from features includes an importance measure above a threshold value. In some aspects, each of the subset machine learning models includes a different selection of the portion of the plurality of features. In some aspects, at least twenty (2) features of the plurality of features have an importance measure above the threshold value. As an example, the portion of the plurality of features includes at least ten (10) features and less than twenty (20) features. As another example, the selected subset machine learning model includes M of the most important N features as determined by the importance measures, wherein M is an integer between 10 and 20 and N is an integer greater than 20.

In some aspects, the diagnostic classifier of step 3370 is operative to determine whether an individual is healthy or has a general mental health issue. In some aspects, the diagnostic classifier of step 3370 is operative to determine whether an individual is healthy or has a specific mental health disorder. In some aspects, the diagnostic classifier of step 3370 is operative to determine whether an individual has a first specific mental health disorder or a second specific mental health disorder. In some aspects, the diagnostic classifier of step 3370 is operative to determine whether an individual is at risk of developing a mental health disorder.

In some aspects, the selected subset machine learning model of step 3370 includes at least a subset of the following features, or any similar features as known in the art.
- "I have more fun doing activities with other people than by myself";
- "I have trouble concentrating";
- "I have frequent mood changes without understanding why";
- "I try to do well at everything I do";
- "I need to think for a long time before I make a decision";
- "I need a lot of self-control to keep myself out of trouble";
- "I am often restless and can't sit still";
- "I am very affected when one of my friends seems upset";
- "My mood changes more than I think I should"; and
- "I do not get enough emotional support from other people."

In some aspects, the selected subset machine learning model of step 3370 includes at least a subset of the following features, or any similar features as known in the art.
- "I like to please other people as much as I can";
- "There are often times when I am so restless that it is impossible for me to sit still";
- "My mood often changes, from happiness to sadness, without my knowing why";
- "Although there are things that I enjoy doing by myself, I usually seem to have more fun when I do things with other people";
- "I am more sentimental than most people";
- "I love to excel at everything I do";
- "People consider me a rather freewheeling and spontaneous person";
- "I feel that I never really get all that I need from people";
- "In unfamiliar surroundings, I am often so assertive and sociable that I surprise myself";
- "I like to think about things for a long time before I make a decision";
- "Sometimes ideas and insights come to me so fast that I cannot express them all";
- "I have many hobbies";
- "I like to keep my problems to myself";
- "It is difficult for me to keep the same interests for a long time because my attention often shifts to something else";
- "How often do you have trouble wrapping up the final details of a project, once the challenging parts have been done";
- "I like to go slow in starting work, even if it is easy to do"; and
- "Usually I am more worried than most people that something might go wrong in the future."

In step 3380, the features of the diagnostic classifier are stored for subsequent use as a screening tool. In some examples, the features are stored in at least one nontransitory processor-readable storage medium, such as the memory 2808 of FIG. 28.

In some aspects, the methodology 3300 further provides for includes using the features of the diagnostic classifier as a screening tool to assess at least one of intermediate or end-point outcomes in at least one clinical trial testing for treatment responses.

In some aspects, the methodology 3300 further provides for further includes using the features of the diagnostic classifier as a screening tool to assess at least one of intermediate or end-point outcomes in at least one clinical trial testing for treatment responses.

In some examples, the machine learning model of methodology 3300 can be implemented in a machine learning training system. Similar to the system 2800 of FIG. 28, the machine learning training system includes at least one nontransitory processor-readable storage medium and at least one processor communicatively coupled to the at least one nontransitory processor-readable storage medium. The at least one nontransitory processor-readable storage medium stores at least one of processor-executable instructions or data. The at least one processor, in operation, is configured to receive labeled training data of methodology 3300 of FIG. 33.

As discussed herein, conventional diagnostic biomarker approaches do not fully account for the heterogeneity of symptoms under the umbrella of a single diagnosis or the shared symptoms between multiple diagnoses. It must be noted that conventional clinical practice does not provide transdiagnostic, multimodal predictive models of mental health. Thus, based on the seven feature set input, such as the examples disclosed herein with regard to steps 3060 and 3070, various combinations of feature types are evaluated as inputs. For example, instead of only analyzing one type of biomarkers, the various combinations of input data include single and multimodal feature sets. The experimental data herein provides that the multimodal models perform better than those of single feature sets. Therefore, the models disclosed herein can be highly predictive based at least in part on their transdiagnostic and/or multimodal data input.

Experimental Application and Disclosed Models—Part I

An experimental methodology is disclosed further herein which provides additional examples of methodologies 2900-3000 and 3300, as would be readily apparent to one skilled in the art. The experimental methodology includes experimental results which verify additional aspects of the disclosed systems and methods; the experimental results further verify additional benefits of the present disclosure as compared against conventional systems and methods.

The CNP Dataset

The CNP dataset is utilized. The CNP dataset contains rich data sources from a variety of modalities. The disclosure herein is focused on identifying shared transdiagnostic features in the phenotype data in the form of clinical scales as well as neuroimaging data (including both structural MRI and resting-state functional MRI). The downloaded dataset in this disclosure included 272 subjects, of which 50 were diagnosed with schizophrenia (SCZ), 49 with bipolar disorder (BD), and 43 with attention deficit and hyperactivity disorder (ADHD). The remaining 130 subjects were agematched healthy controls (HC) recruited from the community. The diagnoses were given by following the Diagnostic and Statistical Manual of Mental Disorders, Fourth Edition (DSM-IV; cite DSM) and were based on the Structured Clinical Interview for DSM-IV (cite SCID). To better characterize ADHD related symptoms, the Adult ADHD Interview (cite) was further used as a supplement. Out of all subjects, 1 had incomplete phenotype data from the clinical scales used in this disclosure, 10 had missing structural MRI (sMRI) data, and 10 had missing resting-state functional MRI (fMRI) data. Fifty-five (55) subjects had an aliasing artifact in their sMRI data, whereas 22 subjects had errors in the structural-functional alignment step during MRI preprocessing. These subjects were excluded from the corresponding modeling analyses performed during the methods disclosed herein. The subject numbers and demographics information are given in Table 1. In Table 1, the demographic information is based on initial number of subjects. The number of subjects with sMRI data excludes subjects with aliasing artifacts. The number of subjects with fMRI data excludes subjects with misaligned structural-function imaging data.

TABLE 1

Demographic Information

| | HC | SCZ | BD | ADHD | Total |
|---|---|---|---|---|---|
| No of subjects | 130 | 50 | 49 | 43 | 262 |
| With complete phenotype data | 130 | 50 | 48 | 43 | 271 |
| With sMRI data | 98 | 30 | 44 | 34 | 206 |
| With fMRI data | 104 | 47 | 41 | 37 | 229 |
| Age | | | | | |
| Mean age | 31.26 | 36.46 | 35.15 | 33.09 | |
| SD age | 8.74 | 8.88 | 9.07 | 10.76 | |
| Range age | 21-50 | 22-49 | 21-50 | 21-50 | |
| Gender | | | | | |
| No. of female subjects | 62 | 12 | 21 | 22 | |
| Percent female subjects | 47.69% | 24.00% | 42.86% | 51.16% | |
| Race | | | | | |
| American Indian or Alaskan Native | 19.23% | 22.00% | 6.25% | 0% | |
| Asian | 15.38% | 2.00% | 0% | 2.33% | |
| Black/African American | 0.77% | 4.00% | 2.08% | 2.33% | |
| White | 78.46% | 66.00% | 77.08% | 88.37% | |
| More than one race | 0% | 2.00% | 14.58% | 6.98% | |
| Education | | | | | |
| No high school | 1.54% | 18.00% | 2.08% | 0% | |
| High school | 12.31% | 44.00% | 29.17% | 23.26% | |
| Some college | 20.77% | 18.00% | 25.00% | 30.23% | |
| Associate's degree | 7.69% | 4.00% | 6.25% | 6.98% | |
| Bachelor's degree | 50.00% | 10.00% | 29.17% | 32.56% | |
| Graduate degree | 6.92% | 0% | 4.17% | 2.33% | |
| Other | 0.77% | 4.00% | 4.17% | 4.65% | |

Phenotype Data

Subjects were administered a total of 20 questionnaires and scales to capture a wide range of phenotypical data including specific behavioral traits and symptom dimensions. These questionnaires/scales are either clinician-rated or self-reported. While the clinician-rated questionnaires only covered relevant patient groups, 13 self-reported clinical scales were given to all three patient groups as well as the heathy controls. Therefore, subjects' answers to each of the individual questions coming from these 13 self-reported scales are used as input features to the models. Specifically, the 13 self-reported scales used in the methods are: Chapman social anhedonia scale, Chapman physical anhedonia scale, Chapman perceptual aberrations scale, hypomanic personality scale, Hopkins symptom checklist, temperament and character inventory, adult ADHD self-report scale v1.1 screener, Barratt impulsiveness scale, Dickman functional and dysfunctional impulsivity scale, multidimensional personality questionnaire—control subscale, Eysenck's impulsivity inventory, scale for traits that increase risk for bipolar II disorder, and Golden and Meehl's Seven MMPI items selected by taxonomic method.

MRI Data Acquisition Parameters

MRI data were acquired on one of two 3T Siemens Trio scanners both housed at the University of California, Los Angeles. The sMRI data used in this disclosure are T1-weighted and were acquired using a magnetization-prepared rapid gradient-echo (MPRAGE) sequence with the following acquisition parameters: TR=1.9 s, TE=2.26 ms, FOV=250 mm, matrix=256×256, 176 1-mm thick slices oriented along the sagittal plane. The resting-state fMRI data contain a single run lasting 304 s. The scan was acquired using a T2*-weighted echoplanar imaging (EPI) sequence using the following parameters: 34 oblique slices, slice thickness=4 mm, TR=2 s, TE=30 ms, flip angle=90°, matrix size 64×64, FOV=192 mm. During the resting-state scan, subjects remained still and relaxed inside the scanner, and kept their eyes open. No specific stimulus or task was presented to them.

MRI Preprocessing—sMRI

Structural MRI preprocessing was implemented using Freesurfer's recon-all processing pipeline. Briefly, the T1-weighted structural image from each subject was intensity normalized and skull-stripped. The subcortical structures, white matter, and ventricles were segmented and labeled according to the algorithm. The pial and white matter surfaces were then extracted and tessellated, and cortical parcellation was obtained on the surfaces according to a gyral-based anatomical atlas which partitions each hemisphere into 34 regions.

MRI Preprocessing—Resting-State fMRI

Resting-state fMRI preprocessing was implemented in AFNI. Specifically, the first 3 volumes in the data were discarded to remove any transient magnetization effects in the data. Spikes in the resting-state fMRI data were then removed and all volumes were spatially registered with the $4^{th}$ volume to correct for any head motion. The T1w structural image was deobliqued and uniformized to remove shading artifacts before skull-stripping. The skull-stripped structural image was then spatially registered with motion corrected fMRI data. The fMRI data were further spatially smoothed using a 6-mm FWHM Gaussian kernel and converted to percent signal change. Separately, the Freesurfer-generated aparc+aseg image from sMRI preprocessing was also spatially registered with and resampled to have the same spatial resolution of the BOLD image.

Based on this, eroded white matter and ventricle masks were created, from which nuisance tissue regressors were built based on non-spatially smoothed fMRI data to model and remove variances that are not part of the BOLD signal. Specifically, the ANATICOR procedure is used where a locally averaged signal from the eroded white matter mask within a 25-mm radius spherical region of interest (ROI) centered at each gray matter voxel was used to create a voxel-wise local estimate of the white matter nuisance signal. This local estimate of the white matter nuisance signal, along with the estimated head motions and average signal from the ventricles were detrended with a $4^{th}$ order polynomial and then regressed out from the fMRI data. Finally, the clean resting-state fMRI data was spatially normalized to the MNI template and resampled to have 2 mm isocubic voxels.

Feature Extraction

Measures were extracted from 3 data modalities as features: phenotype data from clinical scales, measures derived from the sMRI data, and functional correlations based on resting-state fMRI data. For phenotype features from clinical scales, subjects' responses were directly used from a total of 578 questions from the above listed 13 self-reported clinical scales. Responses from non-True/False type questions were normalized to have a range of between 0 and 1 to match those from True/False type questions.

For sMRI features, the following were specifically used 1) the volume of subcortical structures generated by Freesurfer's subcortical volumetric segmentation, and 2) the area, thickness, and volume of cortical brain regions estimated from Freesurfer's surface-based analysis pipeline. For resting-state fMRI features, the brain is first parceled into 264 regions. Specifically, a 5-mm radius spherical ROI was seeded according to the MNI coordinates of each brain region specified in the atlas. Second, the clean resting-state BOLD time series from all voxels within a given 5-mm radius spherical ROI were averaged to create the representative time series for the brain region. Third, functional connectivity between ROIs was estimated via the Pearson's correlation coefficient between the average time series from all pairs of brain regions. This resulted in a 264-by-264 correlation matrix, from which 34,716 are unique correlations between two distinct ROIs and were used as input features to the models.

Model Fitting and Feature Importance Weighting

The primary goals of machine learning analyses in this disclosure are two-fold: 1) to establish robust transdiagnostic classifiers that can reliably separate patient groups from healthy controls, and more importantly 2) to identify important features commonly found across patient groups distinguishing them from healthy controls. To achieve the first goal, the logistic regression model as implemented in the scikit-learn toolbox is utilized. Specifically, 4 transdiagnostic problems based on the DSM diagnosis labels provided in the CNP dataset were addressed: HC vs. All Patients, HC vs. SCZ & BD, HC vs. SCZ & ADHD, HC vs. BD & ADHD. Separate logistic regression models were independently trained using each of the above extracted feature modalities (e.g., phenotype data, sMRI measures, and resting-state fMRI correlations) as inputs and their performances were evaluated in each of the transdiagnostic scenarios. Combinations of 2 and 3 feature modalities were also used as classifiers' inputs and their performances were evaluated in the same fashion.

Because the number of features extracted was relatively large compared to the sample size in CNP data, the elastic net regularization term is added in all of the logistic regression models to prevent overfitting. The elastic net regularization is a linear combination of the L1 and L2 regularization terms and has advantages over L1 and L2 regularization when dealing with high-dimensional data with small sample size and correlated features. The use of elastic net regularization in these models also enabled feature selection as the regularization induces sparse models via the grouping effect where all the important features will be retained and the unimportant ones set to zero. This allowed for the identification of predictive features that are shared across multiple patient categories.

The elastic net regularized logistic regression implemented in the scikit-learn toolbox contains two hyperparameters: the overall regularization strength and the mixing ratio between the L1 and L2 terms. The following procedure is adopted to determine the best regularization parameters. First, the input data were randomly partitioned into a development set and an evaluation set. The development set contains 80% of the data upon which a grid search with 3-fold cross validation procedure was implemented to determine the best hyperparameters. Then the model was trained on the entire development set using the best hyperparameters and was further tested on the remaining 20% of evaluation set which the model had never seen before to obtain testing performance.

All features were standardized to have zero mean and unit variance within the training data (the training folds in the 3-fold cross validation or the development set) and the mean and variance from the training data were used to standardize the corresponding test data (the testing fold or the evaluation set) to avoid information spill-over from test data to training data. The entire process was implemented 10 times on 10 different random partitions of the development and evaluation sets. The following metrics were used to quantify the model performances: area under the receiver operating characteristics curve (AUC), accuracy, sensitivity, and specificity. The mean and standard deviation of the above metrics over the 10 evaluation sets were reported.

From the above trained models, one can assess how predictive each feature is since the weights of the logistic regression model in the transdiagnostic classifiers represent the relationship between a given feature and the logarithm of the odds ratio of an observation being a patient. For each feature, its corresponding mean model weight is calculated and divided by the standard deviation across the 10 model implementations as the proxy for feature importance. Such a feature importance measure is analogous to the Cohen's d effect size measure and thus favored features with large weights and small standard deviations across the 10 model implementations. Features with large importance values from the transdiagnostic classifiers are potentially symptoms, traits, and neuropathological mechanisms shared across patient groups but are distinct from healthy controls.

Feature Importance-Guided Sequential Model Selection

Because the feature dimension of the input data is high compared to the sample size in the CNP dataset, the transdiagnostic classifiers using the full feature sets are likely to be subjected to a substantial amount of noise as well as features that are not predictive. The presence of those noisy features, especially when the sample size is small, might impede the ability of the models to achieve their best performances. To investigate whether improved classification performances can be achieved from a reduced set of most predictive features, the following feature importance-guided sequential model selection procedure is utilized.

Specifically, first the features in the transdiagnostic classifiers are rank ordered according to their feature importance measures. Next, a series of truncated models was built such that each model would only take the top k most predictive features as inputs to perform the same transdiagnostic classification problems. Let k range from the top 1 most predictive feature to all available features in steps of 1 for clinical phenotype features, sMRI features, and the combination of the two feature sets. For any feature or feature combinations involving fMRI correlations, because of the significantly increased feature dimension, the k's were chosen from a geometric sequence with a common ratio of 2 (e.g., 1, 2, 4, 8, 16, ... ).

Model performances were obtained for each truncated model and were evaluated as a function of the number of top features (k) included in each truncated model. To statistically test whether the models' performances are significantly above chance level, a random permutation test is performed where labels in the data (e.g., HC vs. Patients) were shuffled 100 times and models were trained on these label-shuffled data using exactly the same approach as described above. The performances from the 100 models were used to construct the empirical null distribution against which the model performance from the actual data was then compared.

For example, FIGS. 1A-1D illustrate boxplots of the maximum AUC's during sequential model selection (the models are discussed further with regard to FIGS. 28-30 and corresponding description). The box represents the 1st and 3rd quartiles of the AUC's across 10 model runs. The line represents the median and the whiskers represent the range of data.

Experimental Results

In total, classifiers were trained and tested on seven (7) sets of features by either using each individual feature modality (clinical scales, sMRI, and fMRI) or combinations of 2 or 3 feature modalities. The classifiers' performances using each of the seven (7) feature sets on the 4 transdiagnostic cases are reported in Table 2.

TABLE 2

Performance of models using the full sets of features

|  |  | Scales | sMRI | fMRI | s + fMRI | Scales + sMRI | Scales + fMRI | Scales + s + MRI |
|---|---|---|---|---|---|---|---|---|
| HC vs. Patients | AUC | 0.83 (0.04) | 0.56 (0.05) | 0.59 (0.04) | 0.57 (0.05) | 0.89 (0.07) | 0.86 (0.06) | 0.86 (0.05) |
|  | Accuracy | 0.77 (0.05) | 0.58 (0.08) | 0.60 (0.06) | 0.61 (0.07) | 0.91 (0.04) | 0.87 (0.05) | 0.86 (0.05) |
| HC vs. SCZ + BD | AUC | 0.90 (0.06) | 0.68 (0.09) | 0.65 (0.09) | 0.69 (0.08) | 0.90 (0.05) | 0.87 (0.06) | 0.89 (0.04) |
|  | Accuracy | 0.82 (0.05) | 0.68 (0.10) | 0.69 (0.08) | 0.74 (0.06) | 0.90 (0.05) | 0.88 (0.06) | 0.89 (0.04) |
| HC vs. SCZ + ADHD | AUC | 0.85 (0.06) | 0.61 (0.07) | 0.59 (0.08) | 0.60 (0.08) | 0.87 (0.06) | 0.79 (0.07) | 0.81 (0.07) |
|  | Accuracy | 0.77 (0.05) | 0.62 (0.07) | 0.59 (0.08) | 0.65 (0.06) | 0.89 (0.05) | 0.79 (0.07) | 0.81 (0.07) |
| HC vs. BD + ADHD | AUC | 0.87 (0.06) | 0.60 (0.06) | 0.54 (0.08) | 0.58 (0.09) | 0.92 (0.05) | 0.91 (0.05) | 0.88 (0.05) |
|  | Accuracy | 0.80 (0.07) | 0.60 (0.06) | 0.55 (0.08) | 0.58 (0.09) | 0.92 (0.05) | 0.91 (0.05) | 0.88 (0.05) |

Overall, classifiers trained on feature sets involving phenotypical data from clinical scales (e.g., scales and scales+MRI feature sets) outperformed those only trained on MRI features (sMRI, fMRI, and s+fMRI) for all 4 transdiagnostic cases. For classifiers using features involving clinical scales, the mean AUC ranged from 0.79 to 0.92 (mean accuracy: 0.77-0.92), whereas the mean AUC ranged from 0.54 to 0.69 (mean accuracy: 0.55-0.74) for MRI feature sets.

The importance of each feature in terms of its predictability of distinguishing HC from patient populations was estimated by the mean over standard deviation of the weights from 10 implementations of the above transdiagnostic classifiers. Based on this importance ranking of each individual feature, a set of truncated models were built sequentially by including only the top k (k ranging from 1 to all features) most predictive features in the models to identify the best subset of features producing the highest classification performance. The performance measures from the best truncated classification models are shown in FIGS. 1A-1D and Table 3, with the AUC from all transdiagnostic models being significantly above chance level as assessed via the random permutation test (all p's<0.05; see FIGS. 7A-7D—illustrating actual AUC's (shown as a small circle) versus the distribution of AUC's from classifiers trained and tested on randomly permuted class labels).

TABLE 3

Best model performance during sequential model selection

|  |  | Scales | sMRI | fMRI | s + fMRI | Scales + sMRI | Scales + fMRI | Scales + s + fMRI |
|---|---|---|---|---|---|---|---|---|
| HC vs. Patients | Maximum AUC | 0.95 (0.02) | 0.78 (0.06) | 0.87 (0.08) | 0.77 (0.06) | 0.96 (0.03) | 0.98 (0.02) | 0.96 (0.03) |
|  | Accuracy | 0.88 (0.04) | 0.71 (0.06) | 0.85 (0.07) | 0.77 (0.06) | 0.87 (0.05) | 0.92 (0.04) | 0.90 (0.04) |
|  | Sensitivity | 0.87 (0.08) | 0.81 (0.09) | 0.86 (0.09) | 0.77 (0.08) | 0.93 (0.07) | 0.91 (0.06) | 0.94 (0.05) |
|  | Specificity | 0.88 (0.04) | 0.60 (0.16) | 0.84 (0.18) | 0.76 (0.07) | 0.80 (0.15) | 0.92 (0.04) | 0.85 (0.09) |
|  | Median k ≠ 0 | 78 (5.50) | 124 (5.00) | 7539 (938.50) | 15569 (883.25) | 147 (29.00) | 32 (0.00) | 57 (2.75) |
| HC vs. SCZ + BD | Maximum AUC | 0.98 (0.02) | 0.82 (0.08) | 0.93 (0.05) | 0.88 (0.04) | 0.99 (0.01) | 0.98 (0.02) | 1.00 (0.00) |
|  | Accuracy | 0.92 (0.05) | 0.73 (0.04) | 0.87 (0.06) | 0.86 (0.04) | 0.94 (0.02) | 0.92 (0.07) | 0.87 (0.09) |
|  | Sensitivity | 0.94 (0.07) | 0.52 (0.15) | 0.82 (0.14) | 0.90 (0.07) | 0.95 (0.05) | 0.99 (0.02) | 0.72 (0.20) |
|  | Specificity | 0.90 (0.09) | 0.88 (0.06) | 0.91 (0.09) | 0.83 (0.07) | 0.93 (0.05) | 0.85 (0.13) | 1.00 (0.00) |
|  | Median k ≠ 0 | 126 (4.50) | 111 (4.25) | 7613 (1028.75) | 15325 (973.25) | 54 (4.50) | 233 (44.75) | 230 (9.50) |
| HC vs. SCZ + ADHD | Maximum AUC | 0.99 (0.01) | 0.86 (0.05) | 0.73 (0.07) | 0.93 (0.05) | 0.99 (0.01) | 0.99 (0.01) | 0.99 (0.01) |
|  | Accuracy | 0.93 (0.03) | 0.75 (0.06) | 0.68 (0.07) | 0.87 (0.08) | 0.81 (0.06) | 0.85 (0.07) | 0.87 (0.06) |
|  | Sensitivity | 0.91 (0.08) | 0.47 (0.15) | 0.65 (0.13) | 0.78 (0.20) | 0.52 (0.16) | 0.68 (0.18) | 0.72 (0.16) |
|  | Specificity | 0.95 (0.03) | 0.93 (0.02) | 0.70 (0.15) | 0.94 (0.07) | 1.00 (0.00) | 0.99 (0.04) | 0.99 (0.02) |
|  | Median k ≠ 0 | 90 (0.75) | 125 (10.75) | 13637 (1455.75) | 7216 (967.00) | 280 (13.75) | 422 (89.75) | 405 (91.75) |
| HC vs. BD + ADHD | Maximum AUC | 0.97 (0.03) | 0.73 (0.06) | 0.87 (0.05) | 0.75 (0.06) | 0.98 (0.02) | 0.99 (0.01) | 0.99 (0.01) |
|  | Accuracy | 0.93 (0.03) | 0.68 (0.06) | 0.80 (0.10) | 0.74 (0.06) | 0.87 (0.06) | 0.89 (0.07) | 0.90 (0.04) |
|  | Sensitivity | 0.89 (0.07) | 0.54 (0.17) | 0.65 (0.28) | 0.70 (0.11) | 0.74 (0.18) | 0.78 (0.18) | 0.89 (0.13) |
|  | Specificity | 0.96 (0.07) | 0.80 (0.09) | 0.91 (0.07) | 0.77 (0.08) | 0.96 (0.07) | 0.99 (0.03) | 0.90 (0.09) |
|  | Median k ≠ 0 | 94 (7.00) | 87 (8.75) | 7808 (667.25) | 15682 (576.25) | 95 (13.75) | 225 (19.75) | 206 (48.00) |

Figure 2A:
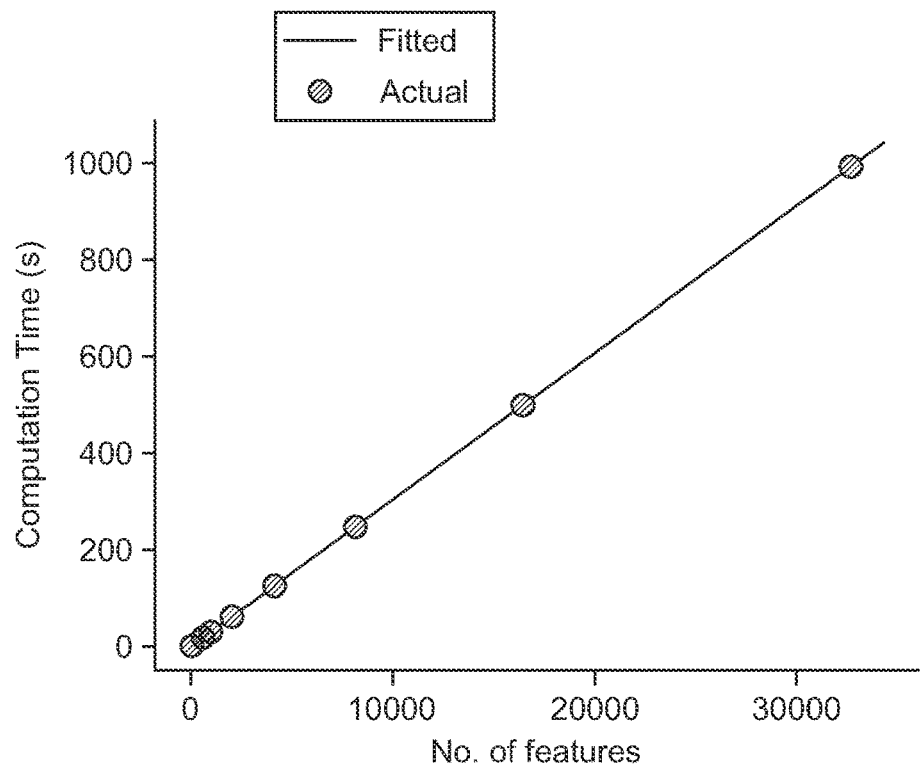
FIGS. 2A-2B illustrate time complexity of the importance-guided forward model selection procedure, according to some implementations of the present disclosure.
Figure 2B:
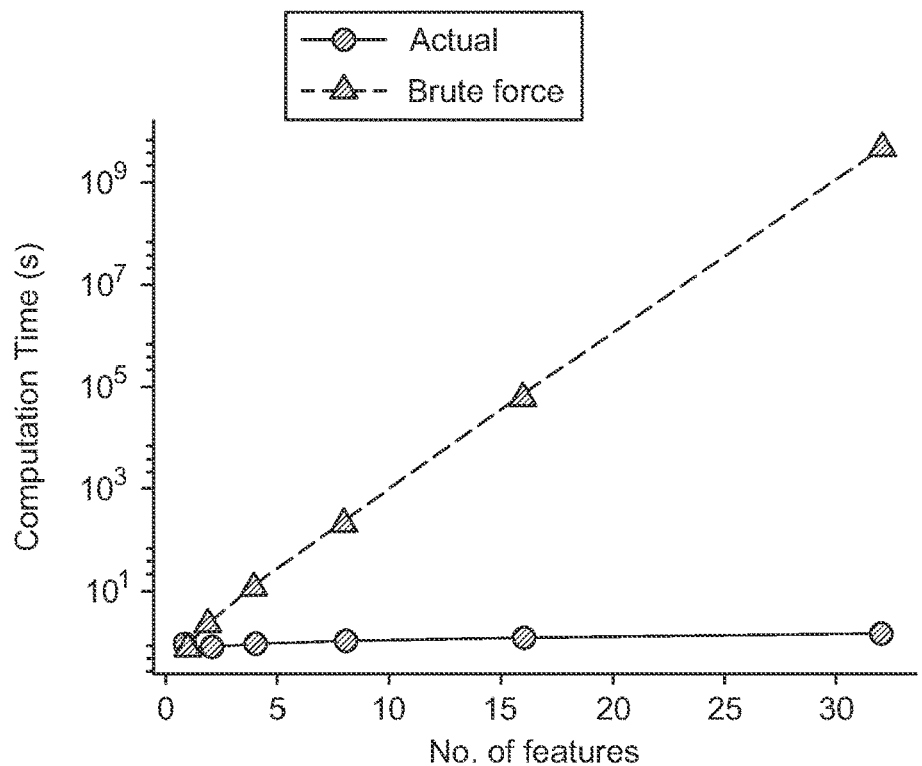
Figure 3A:
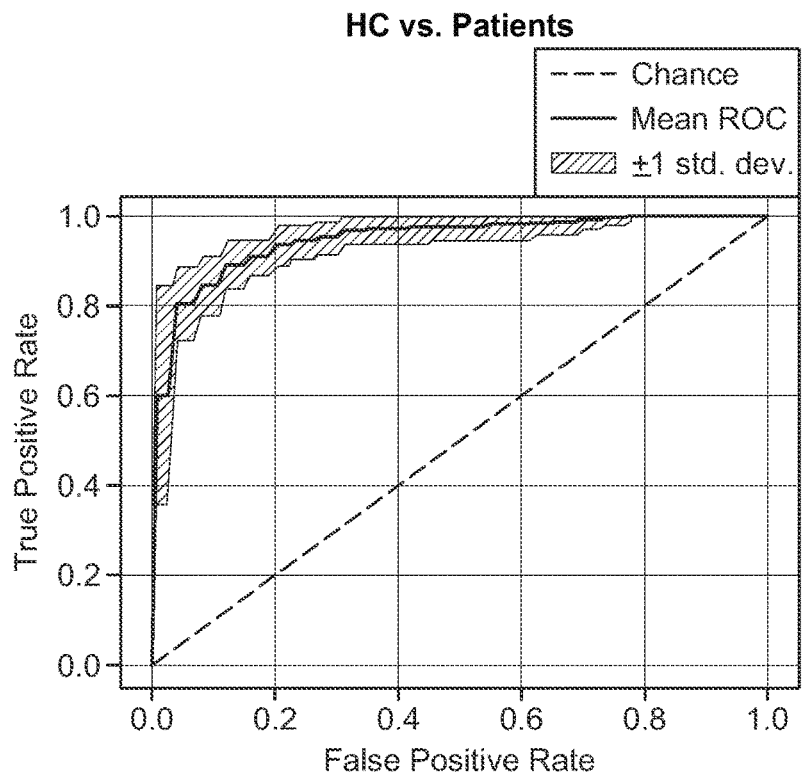
FIGS. 3A-3D illustrate ROC from the truncated models producing the best AUC using phenotype data as features, according to some implementations of the present disclosure.
Figure 3B:
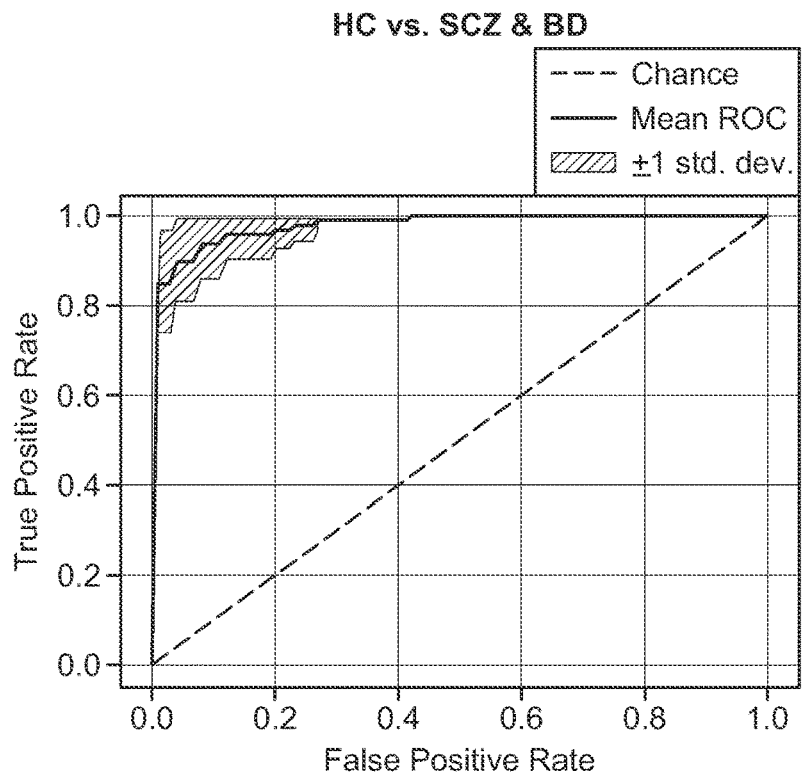
Figure 3C:
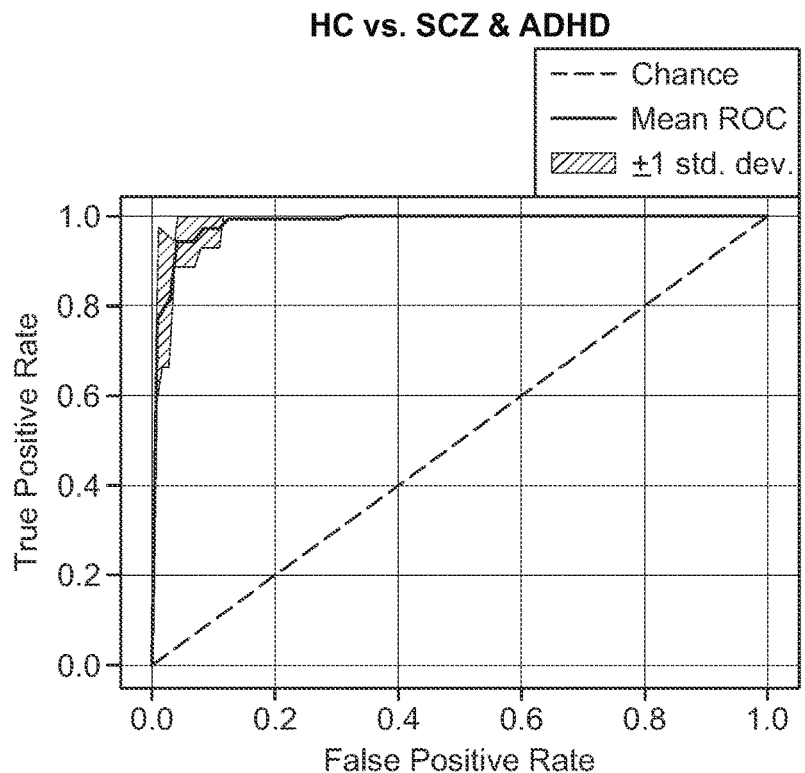
Figure 3D:
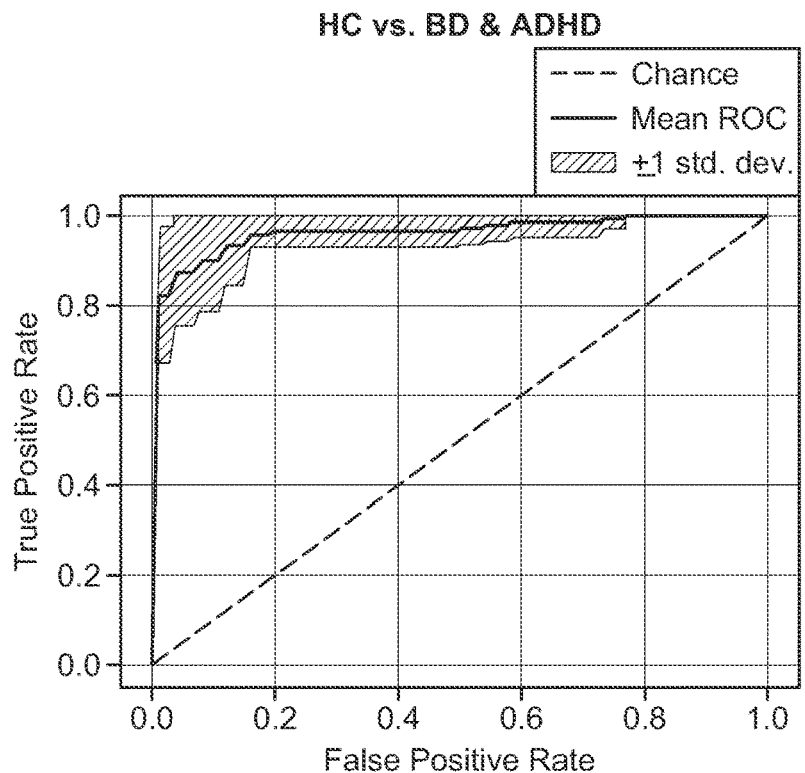

Referring now to FIGS. 2A and 2B, the time complexity of the importance-guided forward model selection procedure is illustrated. FIG. 2A shows that he computation time (median across three implementations) grew linearly as the number of features increases in importance-guided forward model selection procedure. The round dots represent the actual data points, whereas the solid line is the best fitted regression line (slope: 0.03; intercept: 0.80). FIG. 2B shows that reduced computation time was achieved via sequential model selection procedure (round dots with solid line) compared to the estimated time complexity of a brute force feature selection procedure where all combinations of features are evaluated (triangles with dashed line).

Referring again to FIG. 2A, the median computation time across three (3) implementations of the feature importance-guided sequential model selection procedure grew linearly as the number of input features increased. As shown in FIG. 2B, complexity is much reduced compared to the estimated time complexity from a brute force feature selection approach where all possible combinations of features were evaluated. The computation time of the brute force approach increased exponentially as the number of input features increased and quickly became intractable even for very small number of features (FIG. 2B).

More importantly, significantly improved performance was obtained from the best truncated classification models compared with the corresponding models using the full sets of features (all p's<0.05 as assessed by rank-sum tests; Table 4). The test results were obtained using Wilcoxon's rank-sum test.

TABLE 4

Test results comparing performances of the best truncated models against the full

|  |  | Scales | sMRI | fMRI | s + fMRI | Scales + sMRI | Scales + fMRI | Scales + s + fMRI |
|---|---|---|---|---|---|---|---|---|
| HC vs. Patients | Test statistic | 100 | 100 | 100 | 99.5 | 82.5 | 100 | 95 |
|  | p-value | 0.000182 | 0.000181 | 0.000183 | 0.000211 | 0.01537 | 0.000182 | 0.000769 |

TABLE 4-continued

Test results comparing performances of the best truncated models against the full

| | | Scales | sMRI | fMRI | s + fMRI | Scales + sMRI | Scales + fMRI | Scales + s + fMRI |
|---|---|---|---|---|---|---|---|---|
| HC vs. SCZ + BD | Test statistic | 94.5 | 91 | 100 | 99 | 100 | 94 | 100 |
| | p-value | 0.000853 | 0.002152 | 0.000182 | 0.000245 | 0.000172 | 0.000977 | 8.74E−05 |
| HC vs. SCZ + ADHD | Test statistic | 100 | 100 | 92 | 100 | 100 | 100 | 100 |
| | p-value | 0.000179 | 0.000183 | 0.001699 | 0.000182 | 0.000179 | 0.000162 | 0.00018 |
| HC vs. BD + ADHD | Test statistic | 96 | 94 | 100 | 96 | 88 | 95.5 | 100 |
| | p-value | 0.00058 | 0.001008 | 0.000182 | 0.000577 | 0.00451 | 0.00063 | 0.000176 |

Referring now to FIGS. 3A-3D, illustrating the ROC from the truncated models producing the best AUC using phenotype data as features. For all four (4) transdiagnostic cases, the truncated classification models using feature sets involving clinical scales had high performance with the mean AUC ranging from 0.95 to 1.00 (mean accuracy: 0.81-0.94). These models performed better compared to those using feature sets based solely on MRI, which had mean AUC ranging from 0.73-0.93 and mean accuracy ranging from 0.68-0.87. Among the truncated models using feature sets involving clinical scales, those using data only from clinical scales can already achieve very high performance with AUC ranging from 0.95 to 0.99 (see FIGS. 3A-3D). Combining MRI features with clinical scales do not seem to further improve the models' performance.

Turning now to FIGS. 6A-6D, AUC's are illustrated as a function of the number of top features included during sequential model selection. The dark trace represents the mean AUC across ten (10) iterations of the sequential model selection procedure and the shaded area represents the mean+/−1 standard deviation. As shown, the performances of all truncated models in terms of AUC increased initially as the number of top features k increased. Interestingly, after reaching the highest classification performance, adding more features caused the performance to deteriorate, suggesting that increasingly amount of noise are present in features deemed less predictive by the classification model.

The number of top features needed to produce the best truncated classification models for all four (4) transdiagnostic cases are listed in Table 3. The number of top features needed was relatively small for models involving clinical scales: 85-130 out of 578 features for models using only clinical scales; 58-312 out of 839 features for scales plus sMRI feature set; 32-512 out of 35294 features for scales plus fMRI; 64-512 out of 35555 features for scales plus sMRI and fMRI feature set. On the other hand, the number of top features needed to reach best performance for models involving fMRI was relatively large: 8192-16384 out of 34716 features for fMRI alone; 8192-16384 out of 34977 features for sMRI plus fMRI. For models using sMRI features alone, the model complexity was relatively low (89-136 out of 261 features).

Based on the above analyses, models using phenotype data from clinical instruments produced high classification performance while at the same time maintained a relatively low model complexity compared to models using MRI-only features. This suggests that the phenotypical data captured by the 13 self-reported instruments may contain a compact set of shared features that are common across the patient populations but are highly distinct from healthy controls. Examining these shared phenotypical features is further focused below.

Figure 4:
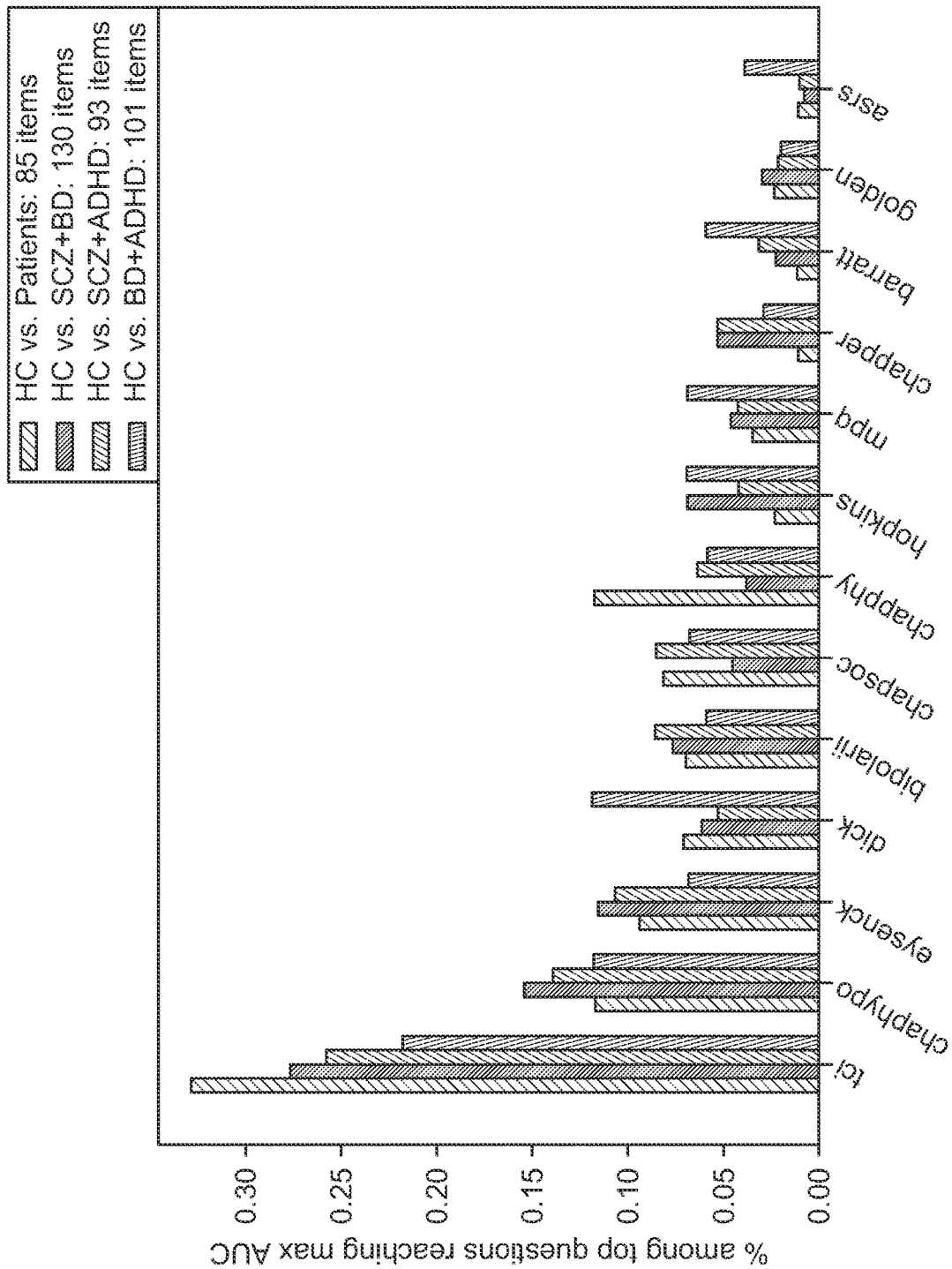
FIG. 4 illustrates percentage of questions from each of thirteen (13) questionnaires among the set of most predictive questions producing the highest AUC, according to some implementations of the present disclosure.
Figure 5A:
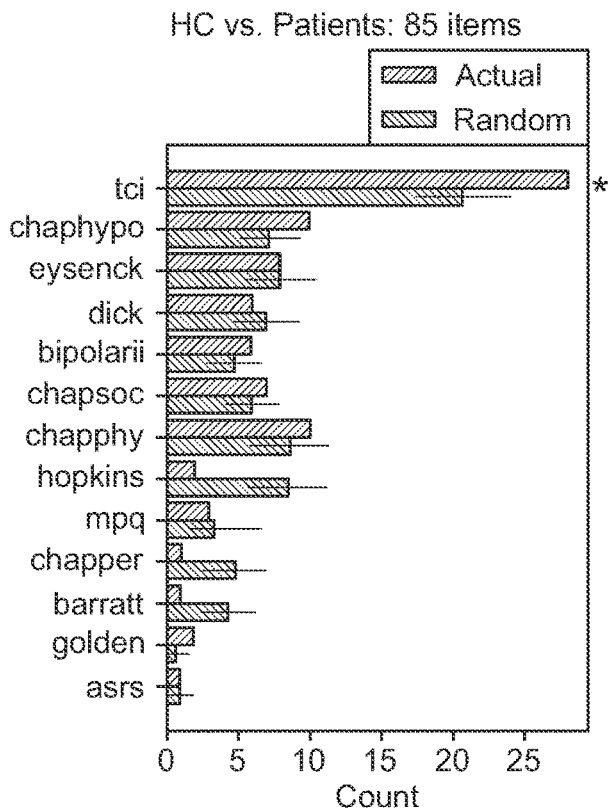
FIGS. 5A-5D illustrate comparing the count of items from each questionnaire among the actual set of most predictive questions with those from randomly ordered lists of questions, according to some implementations of the present disclosure.
Figure 5B:
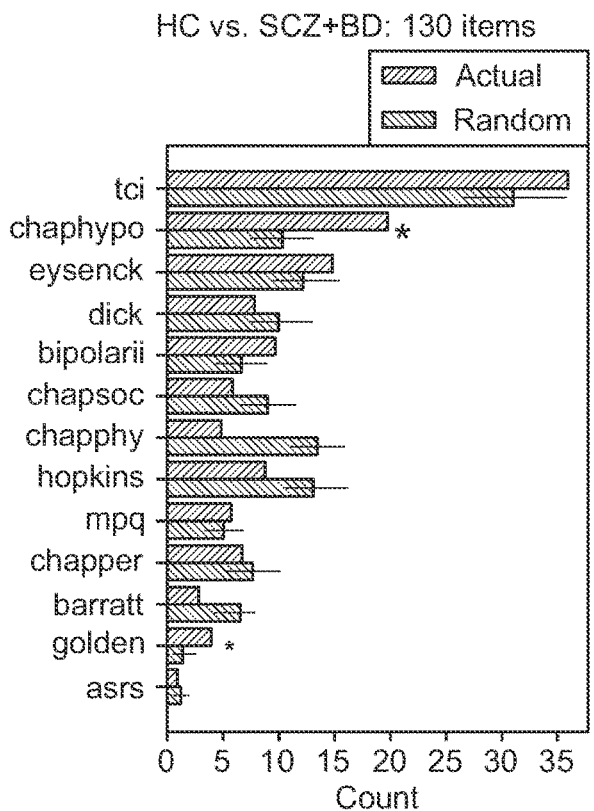
Figure 5C:
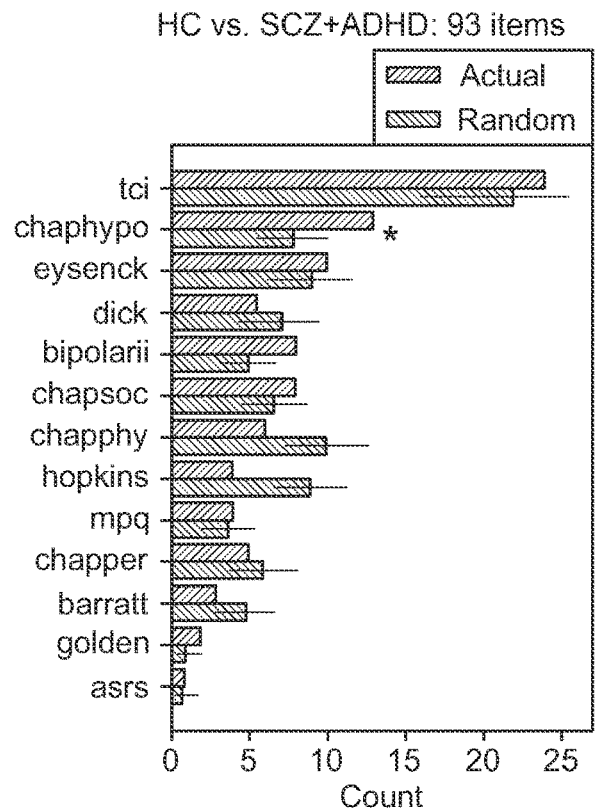
Figure 5D:
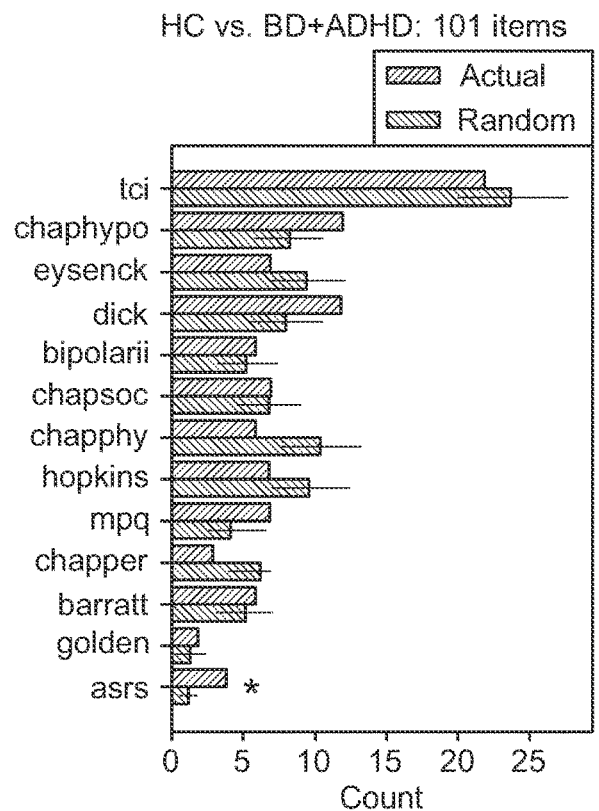
Figure 6A:
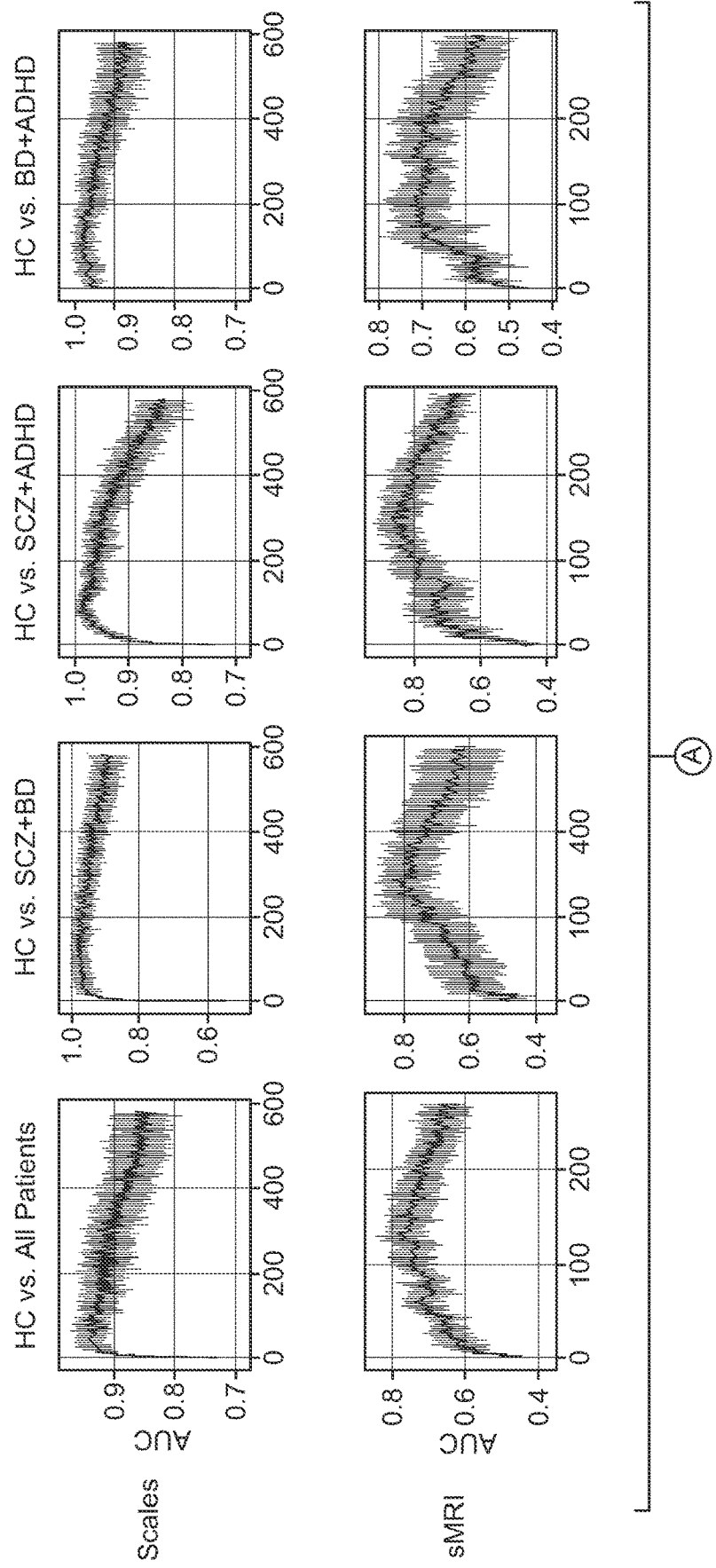
FIGS. 6A-6D illustrate AUC's as a function of the number of top features included during sequential model selection, according to some implementations of the present disclosure.
Figure 6B:
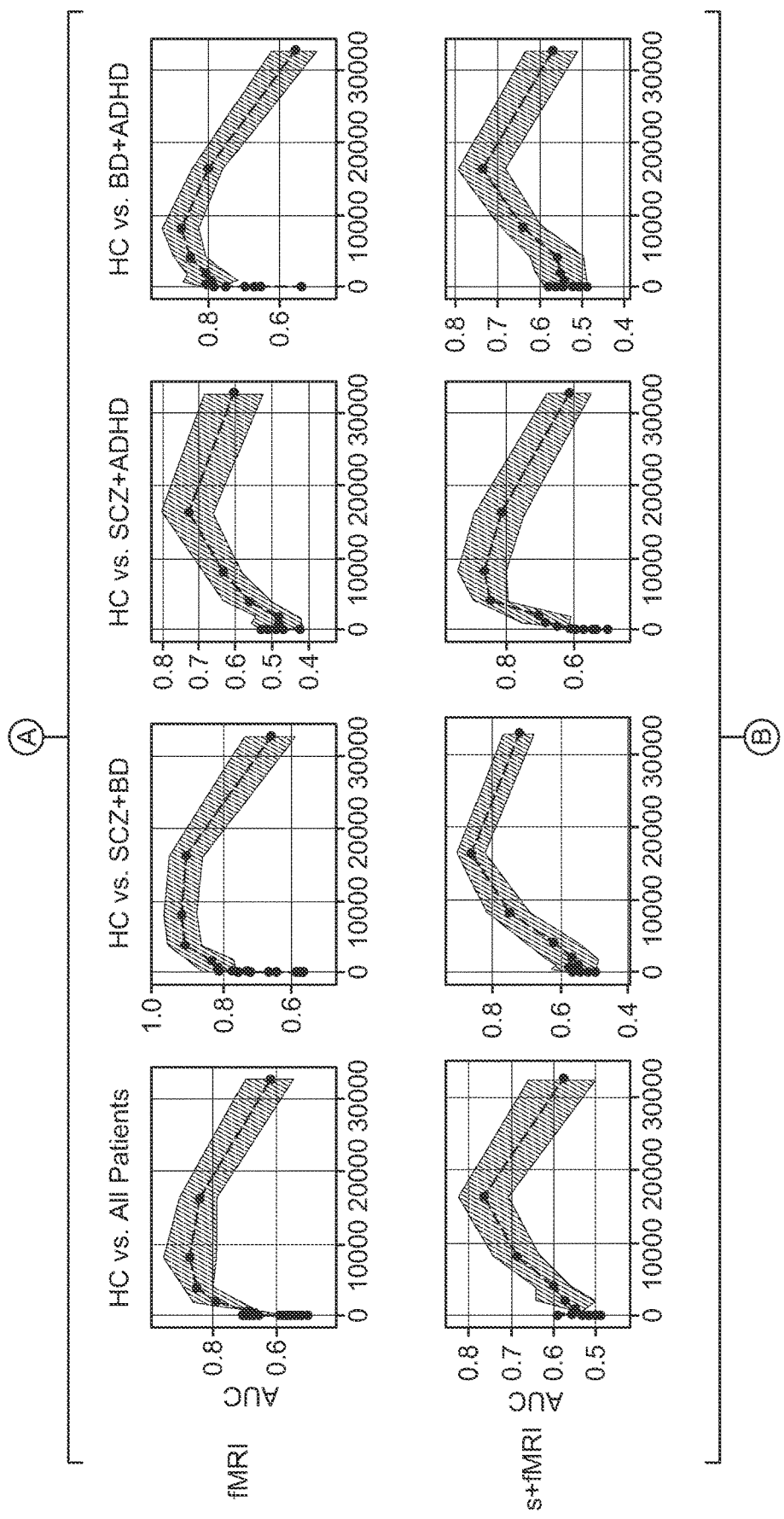
Figure 6C:
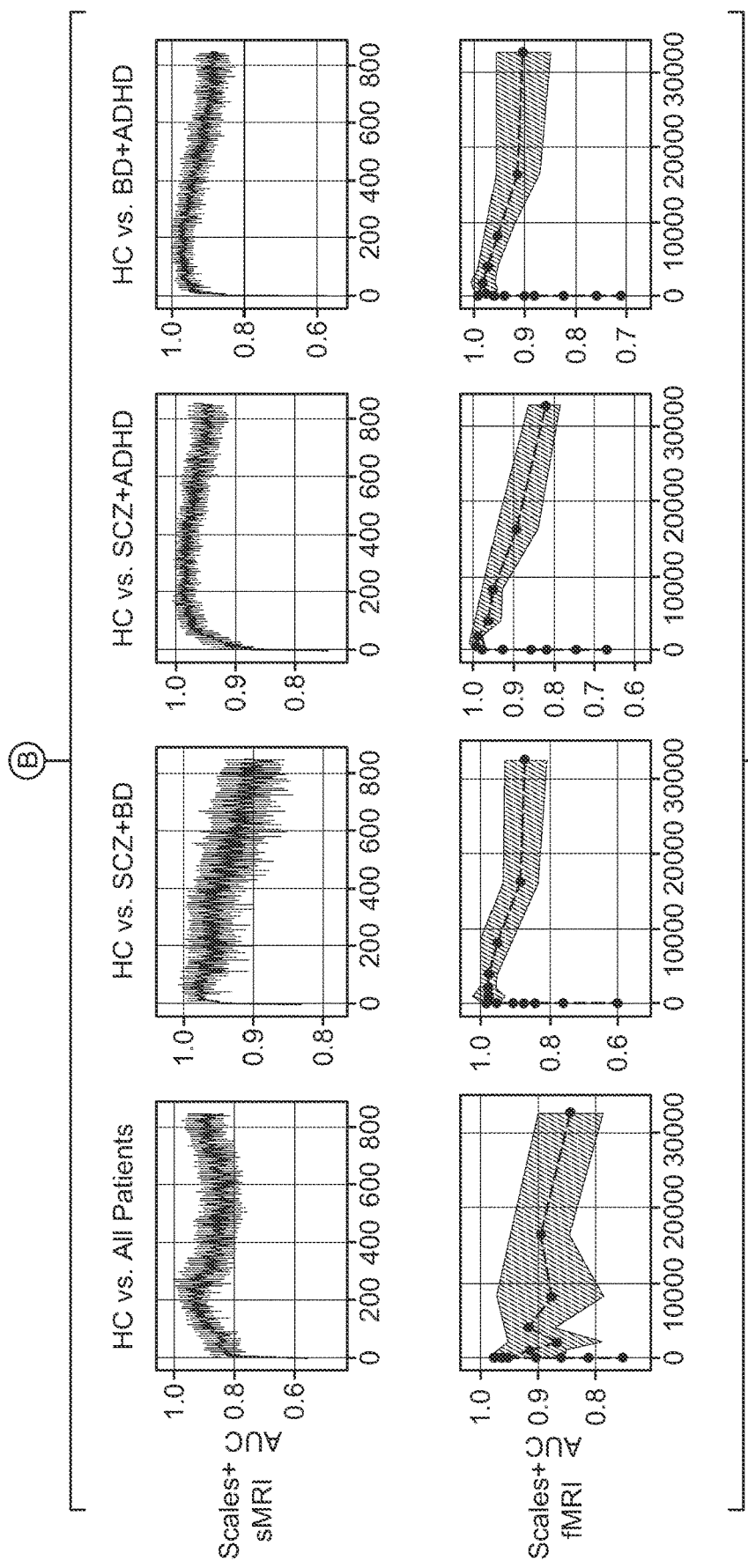
Figure 6D:
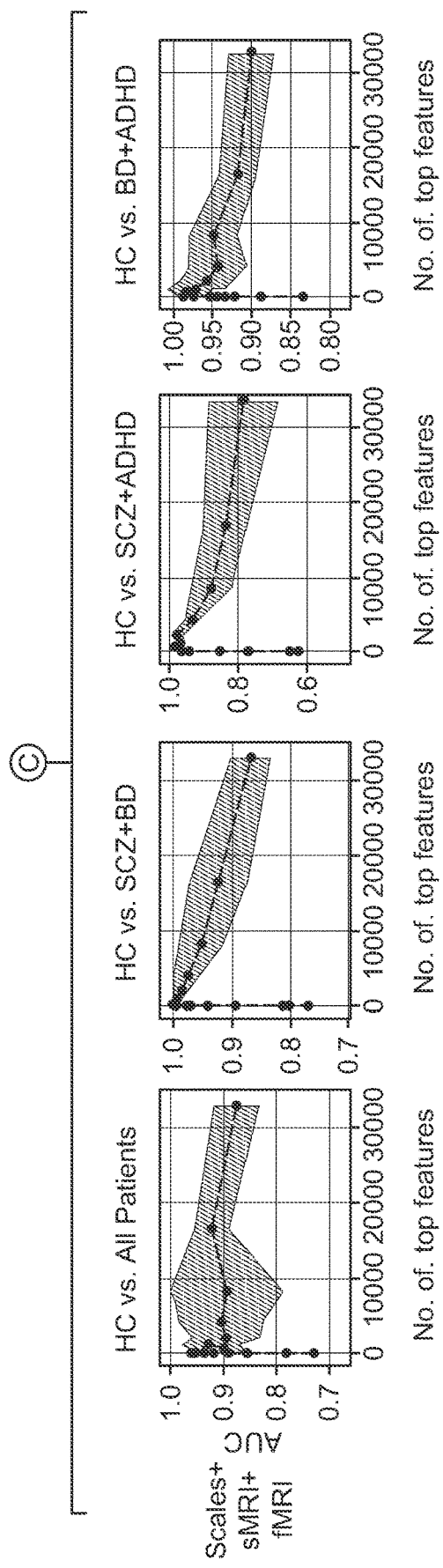
Figure 7A:
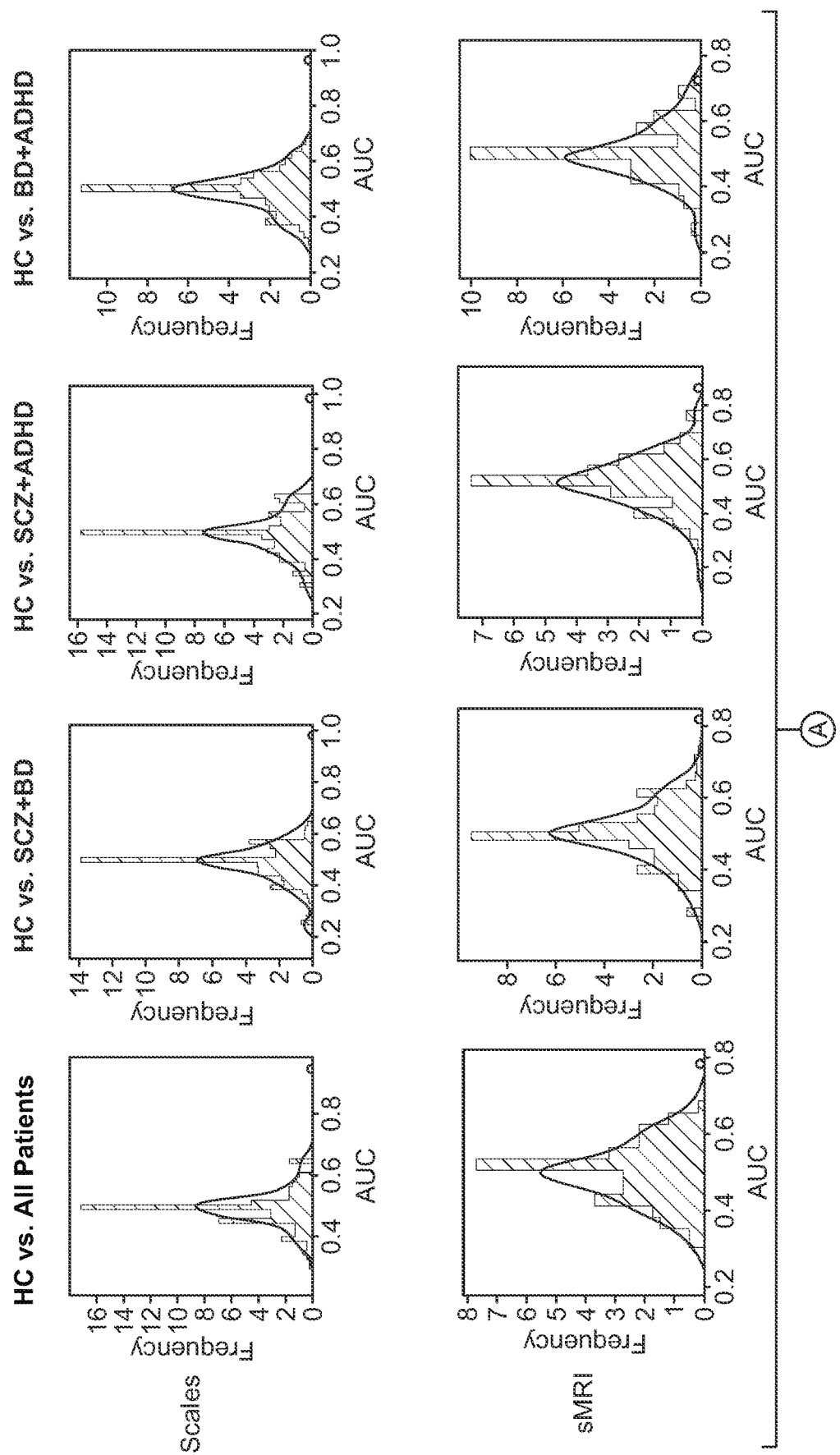
FIGS. 7A-7D illustrates actual AUC's versus the distribution of AUC's from classifiers trained and tested on randomly permuted class labels, according to some implementations of the present disclosure.
Figure 7B:
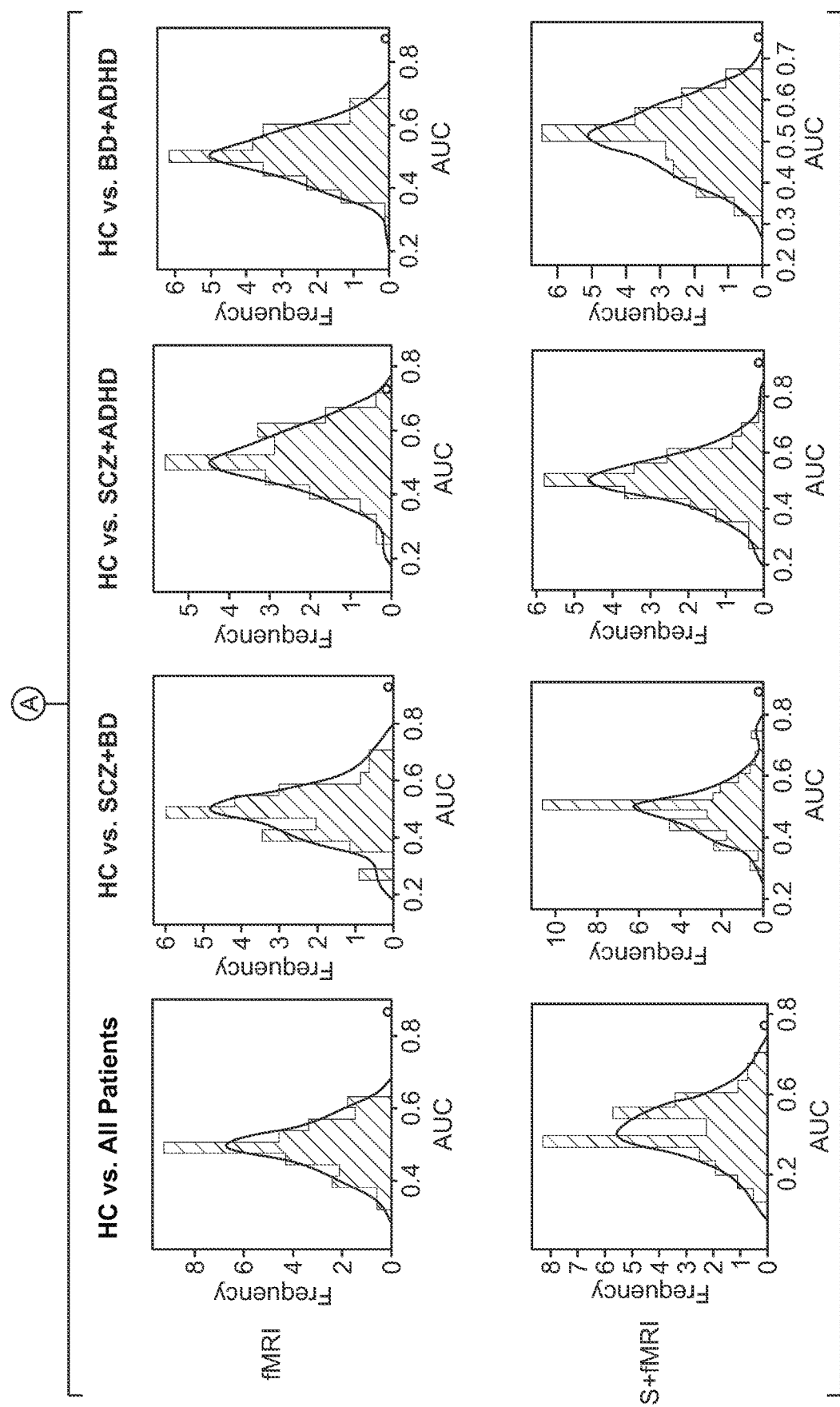
Figure 7C:
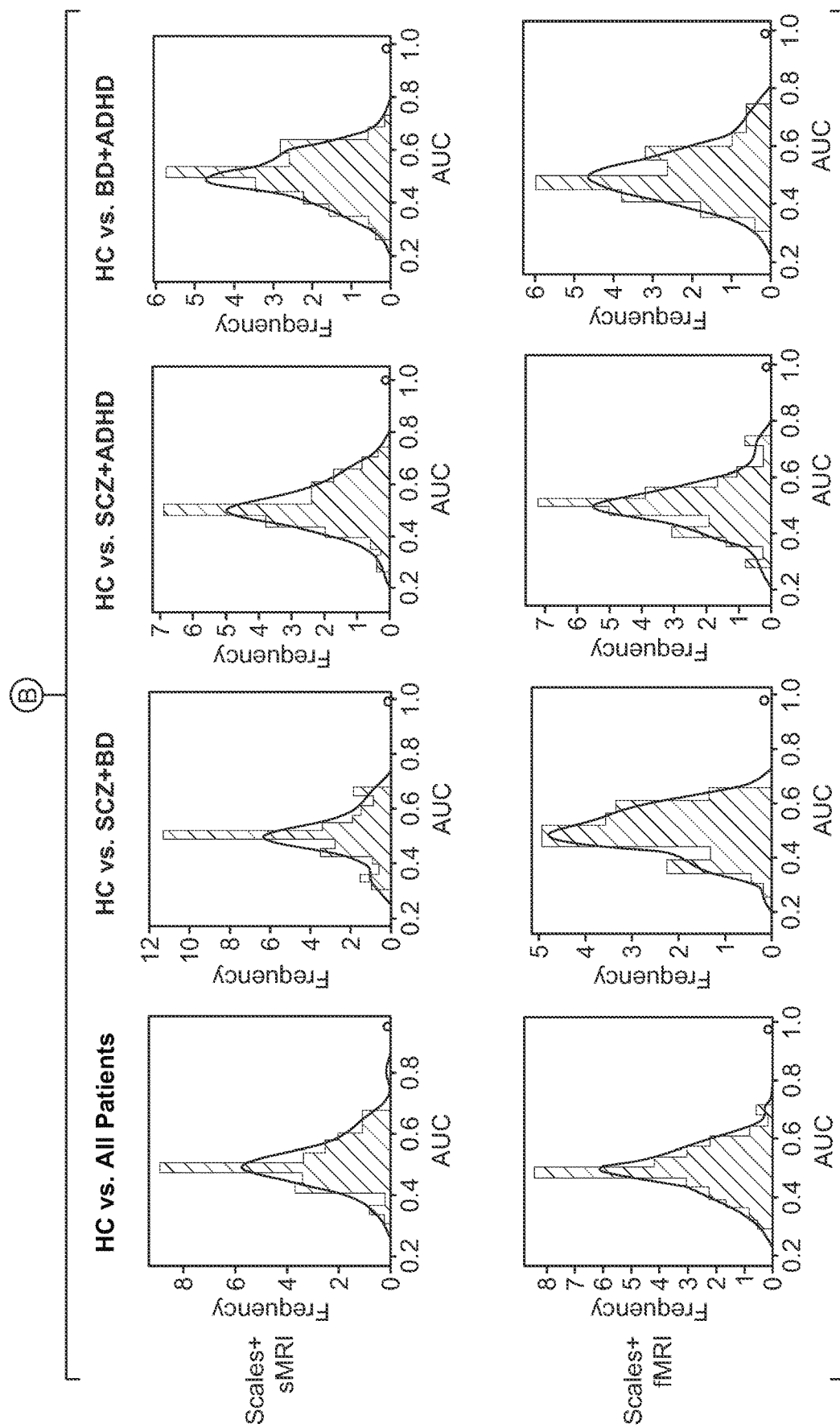
Figure 7D:
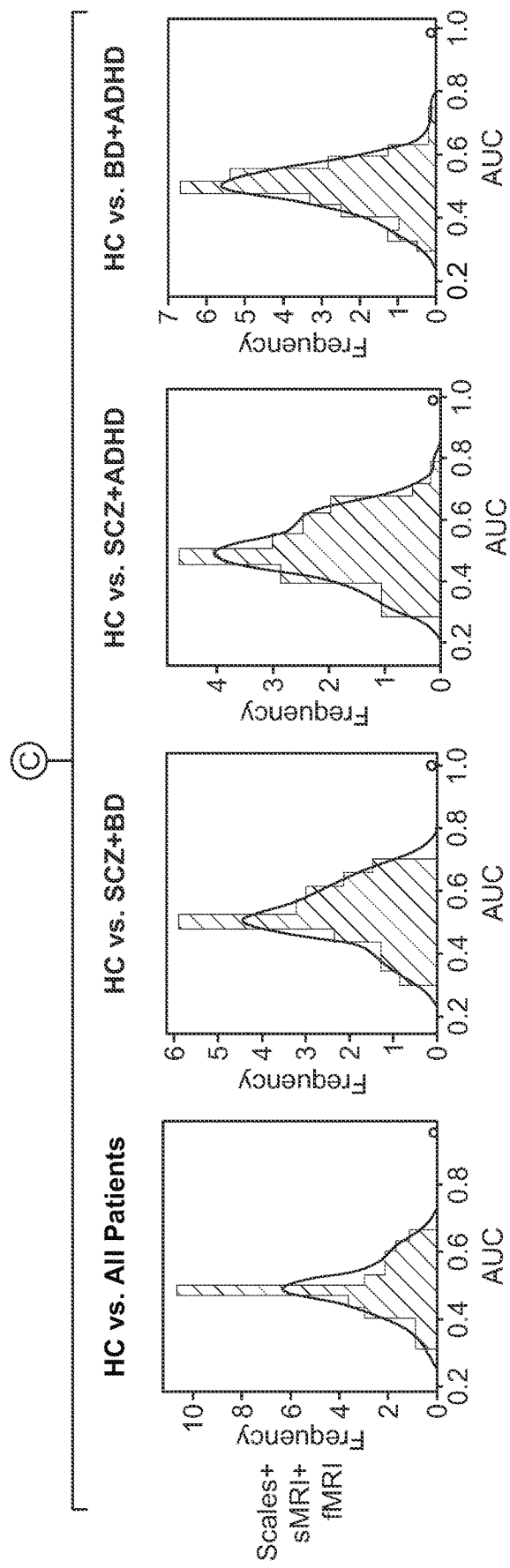

FIG. 4 illustrates the percentage of questions from each of the thirteen (13) questionnaires among the set of most predictive questions producing the highest AUC. "Barratt" represents Barratt impulsiveness scale; "bipolari" represents Scale for Traits that Increase Risk for Bipolar II Disorder; "chaphypo" represents Hypomanic Personality Scale; "chapper" represents Chapman Perceptual Aberration Scale; "chapphy" represents Chapman Physical Anhedonia Scale; "chapsoc" represents Chapman Social Anhedonia Scale; "dick" represents Dickman Functional & Dysfunctional Impulsivity Scale; "Eysenck" represents Eysenck Impulsiveness, Venturesomeness & Empathy Scale; "asrs" represents Adult ADHD Self-Report Scale v1.1 Screener; "golden" represents Golden and Meehl's 7 MMPI Items; "Hopkins" represents Hopkins Symptom Checklist; "mpq" represents Multidimensional Personality Questionnaire—Control Subscale; and "tci" represents Temperament and Character Inventory.

To investigate these shared phenotypical features, the proportion of questionnaire items from each clinical scale selected to be among the top set of features by the best truncated model (having the highest AUC) are shown in FIG. 4. For all four (4) transdiagnostic classifiers, items from all 13 instruments were selected to be among the top features by the classifiers, which suggests that patient populations share a wide range of phenotypes that are distinct from healthy controls. These instruments cover broad phenotypes and symptom domains encompassing personality and traits, positive and negative effects (reward, fear, and anxiety), cognition (attention, response inhibition/impulsivity), sensory processing (perceptual disturbances), and social processing.

FIGS. 5A-5D illustrate comparing the count of items from each questionnaire among the actual set of most predictive questions with those from randomly ordered lists of questions. While all questions included among the top features are highly predictive of patients from healthy controls, the instruments having the largest proportions among the top questions from all 4 transdiagnostic classifiers are the temperament and character inventory, the hypomanic personality scale, and Eysenck's impulsivity inventory. To examine whether particular instruments have significantly higher number of items among top questions (reaching highest AUC) than chance, the list of questions 100 times is shuffled and compared the number of top questions from each instrument obtained from the shuffled lists with the actual counts (see FIGS. 5A-5D).

These items from such instruments may indicate traits and symptom dimensions strongly represented across specific patient populations. For Healthy vs. Patients classifier, the temperament and character inventory had significantly higher count than chance. The individual items overall covered aspects of temperament pertaining to harm avoidance, novelty seeking, persistence, and reward dependence. For Healthy vs. SCZ & BD classifier, both the hypomanic personality scale and the Golden and Meehl's Seven MMPI items had significantly higher count than chance. For Healthy vs. SCZ & ADHD classifier, again the hypomanic personality scale had significantly higher count than chance. For Healthy vs. BD & ADHD classifier, the ADHD self-report scale v1.1 screener had significantly higher count than chance.

Additional Information

In this disclosure, robust transdiagnostic classifiers is built based on phenotype data obtained from clinical instruments and MRI data to distinguish SCZ, BD, and ADHD patients from healthy controls. The feature importance-guided forward model selection approach adopted in this disclosure was shown to 1) produce transdiagnostic classifiers having outstanding performance and 2) identify the set of most predictive features shared across the patient populations. The classifiers based on phenotype data from clinical instruments reliably predicted patients from healthy controls. Interestingly, combining the phenotype data with MRI data did not significantly improve the results, suggesting that a robust set of features shared across patient populations can be found in phenotype data alone. Further investigation of the shared phenotypical features revealed that patient populations share a broad range of abnormal psychopathological dimensions spanning personality and traits, positive and negative affect, cognition, sensory and social processing. Overall, a data-driven approach is presented, which does not rely on a-priori hypotheses to build robust transdiagnostic classifiers and to mine the shared psychopathological dimensions across patient populations.

The use of machine learning tools in psychiatry to systematically search for consistent patterns in clinical data across disease categories defined in DSM is an emerging trend. A substantial body of prior studies have focused on patient subtyping within a given. The present disclosure includes machine learning methods to develop transdiagnostic perspectives on the symptom dimensions and psychopathology. The machine learning approaches can include classification, regression, dimensionality reduction, and clustering to mine the transdiagnostic symptom dimensions underlying various psychiatric disorders.

Some machine learning approaches either adopted a hypothesis-driven approach wherein a subset of measures (e.g., phenotype data from a given instrument and/or neuroimaging measures from a set of brain regions) were preselected based on a priori knowledge, or used the full set of input features without considering their relative importance in terms of predictive ability. Such approaches may not be ideal since neither of them lets the algorithm to be trained on the optimal set of features. This disclosure uses feature importance to guide forward model selection while building transdiagnostic classifiers to identify shared psychopathological features across multiple disease categories. The superb performance of the truncated models selected via this model selection approach demonstrate the robustness of the identified features.

A broad set of phenotypes from the self-report clinical instruments were identified by the transdiagnostic classifiers to be shared across the patient populations. The phenotypes are distributed across all 13 self-reported clinical instruments and covers symptom domains encompassing personality and traits, positive and negative effects, cognition, sensory and social processing. There are shared symptom domains across SCZ, BD, and ADHD. In addition, these three disorders are significantly correlated risk factors for heritability. For SCZ and BD, shared features are identified both in terms of symptoms and the underlying psychopathology and biology. Similarly, shared symptoms and biology are identified between SCZ and ADHD. In addition, shared features are identified between BD and ADHD, along with high levels of comorbidity between them. Thus, this disclosure provides a data-driven confirmation on the shared phenotypes and symptoms across the three disease categories.

An interesting finding is that in all four transdiagnostic classifiers, the temperament and character inventory had the largest proportion of questions among the set of most predictive questions determined by the classifier. The personality traits and characters defined in the TCI are associated with various mood disorders. Specifically, for disorders in the CNP dataset, positive association can be found between personality dimensions characterized in TCI and overall ADHD symptom as well as subtypes of ADHD. For SCZ, links are identified between positive and negative symptom dimensions and TCI factors. Among BD patients, personality profiles are identified that are distinct from healthy controls, and these profiles were further found to be shared with MDD.

Further, this disclosure establishes the usefulness of personality traits as a set of robust transdiagnostic features. The fact that the TCI had the highest number of questions among top features in all four transdiagnostic classifiers suggests a broad domain of shared personality traits across these three patient categories.

While the transdiagnostic classifiers selected questions from all 13 self-reported questionnaires, statistical tests between the actual count of questions from each questionnaire and those from a randomly shuffled importance ordering revealed subtle differences between the classifiers for different combinations of patient populations. These differences may in particular reflect clustered personality traits and symptom dimensions across specific patient populations. For the HC vs. SCZ & BD case, the elevated item count from the hypomanic personality scale is consistent with the results obtained in the original paper by Eckblad and Chapman where high scorers on the hypomanic personality scale reported more schizotypical features in addition to increased hypomanic and depressive episodes. A 13-year follow-up of these high scorers showed that they had more mood and psychotic-like symptoms compared to healthy controls. Therefore, the items from the hypomanic personality scale may capture these clustered symptom domains.

Additionally, the elevated item count from the Golden and Meehl's 7 MMPI items may reflect clustered phenotypes from the so-called "schizotypy" dimension within SCZ and BD patients. For HC vs. SCZ & ADHD case, the hypomanic personality scale again had elevated item count. Symptom overlaps are identified, as well as genetic links between ADHD and schizophrenia and other psychosis disorders. Specifically, off-springs of SCZ patients are found to be more likely to have higher ratings of hyperactivity, which encompasses symptoms including increased activity, impulsivity, distractibility, and low tolerance for frustration. Such externalizing and attention problems are shared between ADHD and psychosis among adolescents. Therefore, the selected items from the hypomanic personality scale may reflect the shared hyperactivity domains across SCZ and ADHD patients. Finally, for the HC vs. BD & ADHD case, the elevated item count from ADHD self-report scale v1.1 screener may indicate the similar aspects between hyperactivity and manic symptoms as well as other shared symptoms such as inattention between BD and ADHD patients.

Experimental Method and Additional Details—Part II

An experimental methodology is disclosed further herein which provides additional examples of methodologies 2900 and 3000, as would be readily apparent to one skilled in the art. The experimental methodology includes experimental results which verify additional aspects of the disclosed systems and methods; the experimental results further verify additional benefits of the present disclosure as compared against conventional systems and methods.

Participants

Four groups of subjects were included in the sample which was drawn from adults ages 21-50: healthy controls (HC, n=130), Schizophrenia patients (SZ, n=50), Bipolar Disorder patient (BD, n=49), and Attention Deficit and Hyperactivity Disorder (ADHD, n=43). Stable medications were permitted for participants. Diagnoses were based on the Structured Clinical Interview for DSM-IV (SCID) and supplemented with the Adult ADHD Interview. Out of all subjects, one had incomplete clinical phenotype data from the clinical scales used, 10 had missing structural MRI (sMRI) data, and 10 had missing resting-state functional MRI (fMRI) data. Fifty-five subjects had an aliasing artifact in their sMRI data, whereas 22 subjects had errors in the structural-functional alignment step during MRI preprocessing. These subjects were excluded from the corresponding modeling analyses performed.

The participant numbers and demographics information are given in Table 5. In Table 5, the demographic information is based on initial number of subjects. The number of subjects with sMRI data excludes subjects with aliasing artifacts. The number of subjects with fMIR data excludes subjects with misaligned structural-function imaging data.

TABLE 5

Participant Demographics

|  | HC | SCZ | BD | ADHD |
|---|---|---|---|---|
| No. of subjects | 130 | 50 | 49 | 43 |
| With complete phenotype data | 130 | 50 | 48 | 43 |
| With sMRI data | 98 | 30 | 44 | 34 |
| With fMRI data | 104 | 47 | 41 | 37 |
| Age |  |  |  |  |
| Mean age | 31.26 | 36.46 | 35.15 | 33.09 |
| SD age | 8.74 | 8.88 | 9.07 | 10.76 |
| Range age | 21-50 | 22-49 | 21-50 | 21-50 |
| Gender |  |  |  |  |
| No. of female subjects | 62 | 12 | 21 | 22 |
| Percent female subjects | 47.69% | 24.00% | 42.86% | 51.16% |
| Race |  |  |  |  |
| American Indian or Alaskan Native | 19.23% | 22.00% | 6.25% | 0% |
| Asian | 15.38% | 2.00% | 0% | 2.33% |
| Black/African American | 0.77% | 4.00% | 2.08% | 2.33% |
| White | 78.46% | 66.00% | 77.08% | 88.37% |
| More than one race | 0% | 2.00% | 14.58% | 6.98% |

TABLE 5-continued

Participant Demographics

|  | HC | SCZ | BD | ADHD |
|---|---|---|---|---|
| Education |  |  |  |  |
| No high school | 1.54% | 18.00% | 2.08% | 0% |
| High school | 12.31% | 44.00% | 29.17% | 23.26 |
| Some college | 20.77% | 18.00% | 25.00% | 30.23% |
| Associate's degree | 7.69% | 4.00% | 6.25% | 6.98% |
| Bachelor's degree | 50.00% | 10.00% | 29.17% | 32.56% |
| Graduate degree | 6.92% | 0% | 4.17% | 2.33% |
| Other | 0.77% | 4.00% | 4.17% | 4.65% |

CNP Dataset

Of the extensive behavioral testing that participants underwent, results were analyzed from tests of their symptoms and traits, either clinician-administered or self-reported. The self-reported tests used in our analysis include Chapman social anhedonia scale (chapsoc), Chapman physical anhedonia scale (chapphy), Chapman perceptual aberrations scale (chapper), Chapman hypomanic personality scale, Hopkins symptom checklist (hopkins), Temperament and character inventory (tci), Adult ADHD self-report scale v1.1 screener (asrs), Barratt impulsiveness scale (barratt), Dickman functional and dysfunctional impulsivity scale (dickman), Multidimensional personality questionnaire—control sub scale (mpq), Eysenck's impulsivity inventory (eysenck), Scale for traits that increase risk for bipolar II disorder (bipolarii), and Golden and Meehl's Seven MMPI items selected by taxonomic method (Golden). The clinician-administered scales used in our analysis include Hamilton rating scale for depression (hamd), the Brief psychiatric rating scale (bprs), and Scale for the assessment of negative symptoms (sans).

All participants used in this sample also underwent magnetic resonance imaging sessions with T1 scans (structural MRI) and T2* scans of blood-oxygen-level-dependent (BOLD) resting-state functional-MRI and several tasks. The sMRI and resting-state fMRI data (304 seconds in length) were utilized. Resting-state fMRI data were analyzed. The resting-state fMRI data provided a fine-grained, data-driven set of functional connectivity features that exhibit meaningful individual differences that relate to symptoms.

Preprocessing Data into Features

All responses to individual questions were used, from the 13 self-report scales as input features for a total of 578 questions. Subjects who had missing values for any scales used in a particular model were not included in that model. Outcome variables for modeling depression, anxiety, anhedonia, and related negative symptoms were also selected from clinical scales, either self-report or clinician-administered.

sMRI

Preprocessing of sMRI was performed using Freesurfer's recon-all processing pipeline. Briefly, the T1-weighted structural image from each subject was intensity normalized and skull-stripped. The subcortical structures, white matter, and ventricles were segmented and labeled according to the algorithm described in. The pial and white matter surfaces were then extracted and tessellated, and cortical parcellation was obtained on the surfaces according to a gyral-based anatomical atlas which partitions each hemisphere into 34 regions.

Preprocessing of fMRI was performed using AFNI. Preprocessing of each subject's echo planar image (EPI) data included several steps: removal of the first 3 volumes (before the scanner reached equilibrium magnetization), de-spiking, registration of all volumes to the now first volume, spatial smoothing with a 6 mm full-width half-maximum Gaussian filter, and normalization of all EPI volumes by the mean signal to represent data as percent signal change. Anatomical data also underwent several steps: deobliquing of the T1 data, uniformization of the T1 to remove shading artifacts, skull-stripping of the T1, spatial alignment of the T1 and Freesurfer-segmented and -parceled anatomy to the first volume of the EPI data, and resampling of the Freesurfer anatomy to the resolution of the EPI data. Subsequently, the ANATICOR procedure was used for nuisance tissue regression. White matter and ventricle masks were created and used to extract the BOLD signals (before spatially-smoothing the BOLD signal). A 25 mm-radius sphere at each voxel of the white matter mask was used to get averaged local white matter signal estimates while the average ventricle signal was calculated from the whole ventricle mask. Time series for the motion estimates, and the BOLD signals in the ventricles and white matter were detrended with a 4th order polynomial. To clean the BOLD signal, the nuisance tissue regressors and the six motion estimate parameters were regressed out. Cleaned data residuals were used for all subsequent analysis.

Both the preprocessed T1 scan and the cleaned residuals of the EPI scan were warped to MNI space and resampled to 2 mm isotropic voxels. The time series of the cleaned residual data was extracted from each of 264 regions of interest (ROIs) as delineated by the Power atlas. At each ROI, the signals from the voxels within a 5 mm radius sphere were averaged. Pearson's correlations were then calculated between the averaged time series from all ROIs yielding 34716 unique edges in the functional connectivity graph (upper triangle of the full correlation matrix). Quality control (QC) for MRI preprocessing was performed individually on the whole dataset, and rejection decisions were made for each participant's sMRI and fMRI data, respectively. Discrepancies were resolved in order to create a final rejection list of participants.

Input features for each subject came from the three preprocessed datasets: raw scores on the 578 individual items of 13 self-report clinical scales, Freesurfer-calculated structural measurements (including subcortical volume, cortical volume, cortical area, cortical thickness), and AFNI-calculated functional connectivity scores between individual ROIs. Subsets of these input features were used as predictor variables in subsequent modeling as explained below. Output variables that were modeled included those which indexed depression, anxiety, anhedonia, or other negative symptoms. A mix of total scores, sub-scale sum or average scores, and individual question scores as each has their advantages.

These scores include the 28-question versions of the total HAMD score ('hamd'), the HAMD subscore for questions 1, 7, and 8 ('hamd178', indexes a melancholic-type of symptom), the HAMD item score for question 7 ('hamd7', indexes lack of interest or anhedonia), the Chapman Social Anhedonia total score ('chapsoc'), the Chapman Physical Anhedonia total score ('chapphy'), BPRS negative subscore ('bprs_negative', the average of negative symptom questions 13, 16, 17, and 18), BPRS depression-anxiety subscore ('bprs_depanx', the average of depression and anxiety symptom questions 2, 3, 4, and 5), Hopkins anxiety score ('hopkins_anxiety', the average of anxiety symptom questions 2, 17, 23, 33, 39, and 50), Hopkins depression score ('hopkins_depression', the average of depression symptom questions 5, 15, 19, 20, 22, 26, 29, 30, 31, 32, and 54), Bipolar ii mood score ('bipolarii_mood', the sum of mood questions 1-9), Bipolar ii anxiety score ('bipolar_anxiety', the sum of anxiety questions 24-31), SANS anhedonia factor score ('sans_factor_anhedonia', the average of anhedonia questions 17, 18, 19, and 20), SANS anhedonia global score ('sans_global_anhedonia', questions 21 which is the clinician's overall anhedonia assessment score), SANS avolition factor score ('sans_factor_avolition', the average of avolition items 12, 13, 14, and 15), SANS avolition global score ('sans_globals_avolition', question 16 which is the clinician's overall avolition assessment score), SANS blunt affect factor score ('sans_factor_bluntaffect', the average of affective flattening items 1, 2, 3, 4, 5, and 6), SANS blunt affect global score ('sans_global_bluntaffect', question 7 which is the clinician's overall blunt affect assessment score), SANS alogia factor score ('sans_factor_alogia', the average of alogia items 8, 9, and 10), SANS alogia global score ('sans_global_alogia', question 11 which is the clinician's overall alogia assessment score), SANS attention factor score ('sans_factor_attention', the average of attention items 22 and 23), and SANS attention global score ('sans_global_attention', question 24 which is the clinician's overall attention assessment score).

Sum scores are commonly accepted by the FDA regarding positive efficacy results, but using only sum scores may obfuscate brain-behavior relationships at more fine-grained levels of symptoms. Subjects with missing values ("n/a") for any input or output variables or who did not pass MRI QC were removed from the input set. As different input feature sets were used, different models had different sample sizes. The availability of clinical scores for particular clinical scales taken only by certain subsets of patients also affected the final sample size for each model. The samples sizes resulting from these factors are listed in Table 6.

TABLE 6

Sample size for each model

| Predicted Scores | Scales | sMRI | fMRI | Scales_ sMRI | sMRI_ fMRI | Scales_ fMRI | Scales_ sMRI_ fMRI |
|---|---|---|---|---|---|---|---|
| Chapman Social Anhedonia | 271 | 206 | 147 | 205 | 117 | 146 | 116 |
| Chapman Physical Anhedonia | 271 | 206 | 147 | 205 | 117 | 146 | 116 |
| HAMD, total score | 141 | 108 | 82 | 107 | 63 | 81 | 62 |
| HAMD, q1, 7, 8 sum score | 140 | 108 | 82 | 107 | 63 | 81 | 62 |
| HAMD, q7 | 140 | 108 | 82 | 107 | 63 | 81 | 62 |
| BPRS, negative score | 141 | 108 | 82 | 107 | 63 | 81 | 62 |

TABLE 6-continued

Sample size for each model

| Predicted Scores | Scales | sMRI | fMRI | Scales_sMRI | sMRI_fMRI | Scales_fMRI | Scales_sMRI_fMRI |
|---|---|---|---|---|---|---|---|
| BPRS, depression-anxiety score | 141 | 108 | 82 | 107 | 63 | 81 | 62 |
| Hopkins, anxiety score | 271 | 206 | 147 | 205 | 117 | 146 | 116 |
| Hopkins, depression score | 271 | 206 | 147 | 205 | 117 | 146 | 116 |
| Bipolar II, depression score | 271 | 206 | 147 | 205 | 117 | 146 | 116 |
| Bipolar II, anxiety score | 271 | 206 | 147 | 205 | 117 | 146 | 116 |
| SANS, anhedonia factor score | 99 | 75 | 54 | 74 | 40 | 53 | 39 |
| SANS, avolition factor score | 99 | 75 | 54 | 74 | 40 | 53 | 39 |
| SANS, blunt affect factor score | 99 | 75 | 54 | 74 | 40 | 53 | 39 |
| SANS, alogia factor score | 99 | 75 | 54 | 74 | 40 | 53 | 39 |
| SANS, attention factor score | 99 | 75 | 54 | 74 | 40 | 53 | 39 |
| SANS, anhedonia global score | 98 | 75 | 54 | 74 | 40 | 53 | 39 |
| SANS, avolition global score | 99 | 75 | 54 | 74 | 40 | 53 | 39 |
| SANS, blunt affect global score | 99 | 75 | 54 | 74 | 40 | 53 | 39 |
| SANS, alogia global score | 99 | 75 | 54 | 74 | 40 | 53 | 39 |
| SANS, attention global score | 99 | 75 | 54 | 74 | 40 | 53 | 39 |

Regression Modeling

All regression modeling was performed with a combination of custom python code and the python toolbox scikit-learn. Twenty-one (21) different sum, sub-, or individual item scores were modeled across the clinical scales. For each of the 21 models, seven combinations of feature types were used as the inputs to be able to evaluate performance of single- and multi-modal feature sets. These included clinical scales only, sMRI only, fMRI only, scales+sMRI, scales+fMRI, sMRI+fMRI, and scales+sMRI+fMRI.

As input features varied in their mean values and regularized models require normally-distributed data, scaled each input feature was scaled separately to have zero mean and unit variance. For each scale output and feature set input, used two regularized general linear model regression algorithms were used—Lasso and Elastic Net—and one non-linear regression model algorithm—Random Forest—for the modeling. These methods improve prediction accuracy and interpretability over regular regression methods using ordinary least squares.

The Lasso approach uses regularization by imposing an $L_1$-penalty parameter to force some coefficients to zero; this step introduces model parsimony that benefits interpretability and predictive performance. If predictor variables are correlated, however, the Lasso approach will arbitrarily force only a subset of them to zero which makes interpretation of specific features more difficult. The Elastic Net algorithm uses both $L_1$- and $L_2$-penalty parameters to better be able to retain groups of correlated predictor variables; this improves interpretability as highly predictive features will not randomly be set to zero thereby diminishing their importance to the model. It is also better suited in cases when the number of predictor variables is much greater than the number of samples (p>>n). The non-linear regression algorithm Random Forest was also chosen for comparison purposes.

Thus, 441 (21×7×3) sets of models were built. For each of these sets of models, hyperparameters were tuned using 5-fold cross-validated grid-search on a training set of data (80% of data), and selected hyperparameters were used on a separate evaluation set of data (20% held-out sample). The hyperparameter range for Lasso was alpha=[0.01 0.03 and 0.1] (three samples through the log space of [0.01:0.1]). Hyperparameter ranges for Elastic Net were alpha=[0.01 0.03 and 0.1] and l1_ratio=[0.1 0.5 0.9]. And hyperparameter ranges for Random Forest included number of estimators=[10 100] and minimum samples at a leaf=[1 5 10]. The best hyperparameters were chosen from the model that maximized the $r^2$ score (coefficient of determination) across the 5-fold cross-validation procedure in the training set. All subsequent models were built using the best hyperparameters for that set.

Figure 8A:
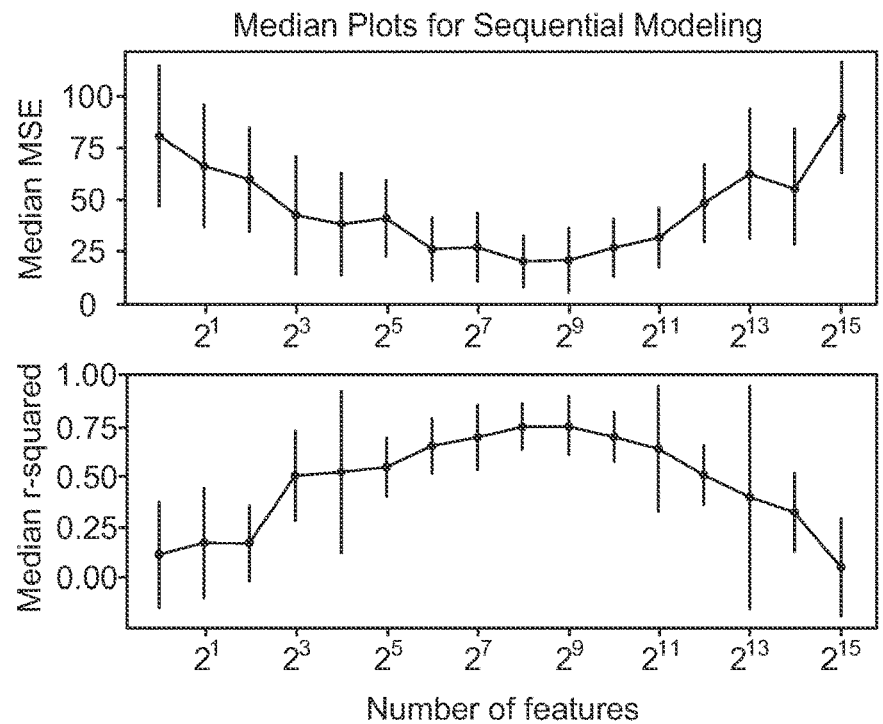
FIG. 8A illustrates X-Y plots of number of features versus predicted outcome scores, according to some implementations of the present disclosure.
Figure 8B:
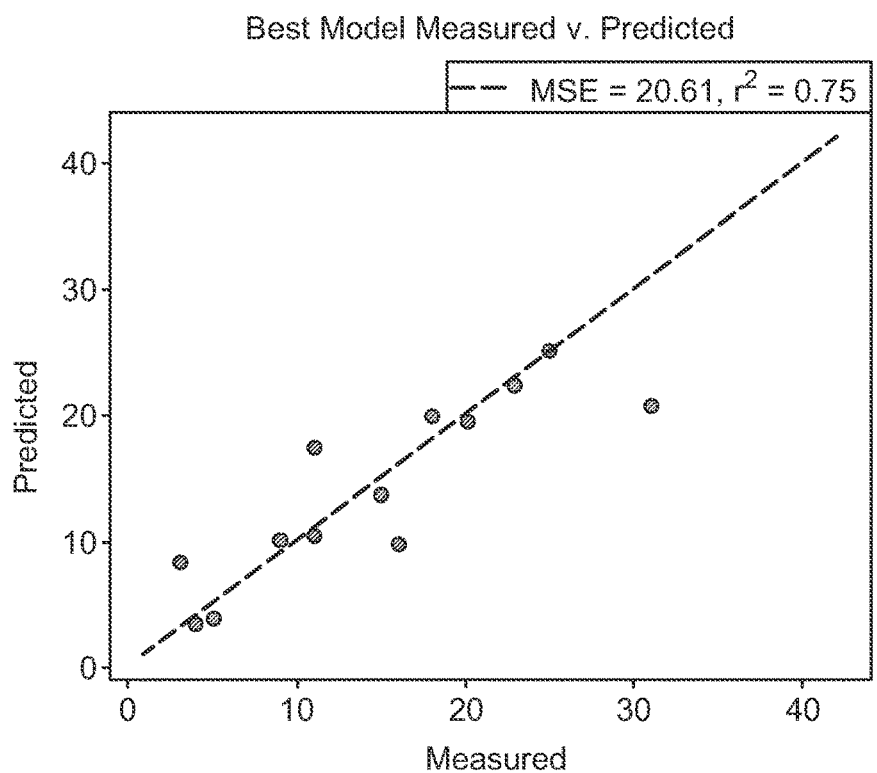
FIG. 8B illustrates a comparison of measured outcome scores and predicted outcome scores, according to some implementations of the present disclosure.

FIG. 8A illustrates X-Y plots of number of features versus predicted outcome scores. For example, predicting the total HAMD score using Elastic Net and scales+sMRI+fMRI as input illustrates how median MSE (left, top) and median $r^2$ (left, bottom) varies with each feature subset, each with standard deviation bars. FIG. 8B illustrates a comparison of measured outcome scores and predicted outcome scores. For example, measured versus predicted outcome scores (right) illustrate how closely the model predictions are to actual outcome scores for individuals in the held-out sample.

Referring generally to FIGS. 8A-9B, for each of the 441 sets of models, an importance-weighted, forward selection approach was used to regression modeling, which involves the following steps: (1) an initial rank-ordering step for ordering features by importance, (2) a forward-selection search step for building a series of models utilizing subsets of ordered features selected from the first step, and (3) an evaluation step for evaluating each of these models using these candidate subsets according to a pre-specified criterion to find the optimal model. This approach thus integrates feature selection into modeling.

Each step utilized the grid-search procedure to optimize hyperparameters as explained above. First, the feature rank-ordering step uses the full feature set (either scale only, sMRI only, etc.) as the input to the model algorithms which returns not only predicted values for the evaluation dataset but also the importance of each feature for the resulting model. Feature importance was assessed from the regression coefficients with ordering (most important to least important) based on the absolute value of the coefficient. Ordering by absolute value reflects that features with the largest magnitude influence the symptom severity scores the most.

Feature ordering was performed separately for Lasso and Elastic Net models, but as feature importance is harder to assess for the Random Forest algorithm, the ordering from the Elastic Net models was used as input for the subsequent steps of Random Forest modeling instead.

Second, the forward-selection search step systematically searches through subsets of the rank-ordered features for the subset that leads to the best model. Since having more features than samples increases the risk of overfitting and uninformative features add noise which decreases model performance, a data-driven method of searching the ordered feature space was selected for an optimal subset of features. A series of regressions was run on subsets of the ordered features with subsets chosen in powers of 2 (e.g., inputting the top feature only, the top 2 features only, the top 4 features only, etc.) up to $2^{15}$ features. In order to generate descriptive statistics for this step, twenty-five (25) iterations of modeling for each feature subset were used to get median and standard deviation metric scores. The metrics chosen for the final step of evaluation were mean squared error (MSE) and $r^2$. The median $r^2$ and standard deviation of $r^2$ were found for each subset.

Figure 9A:
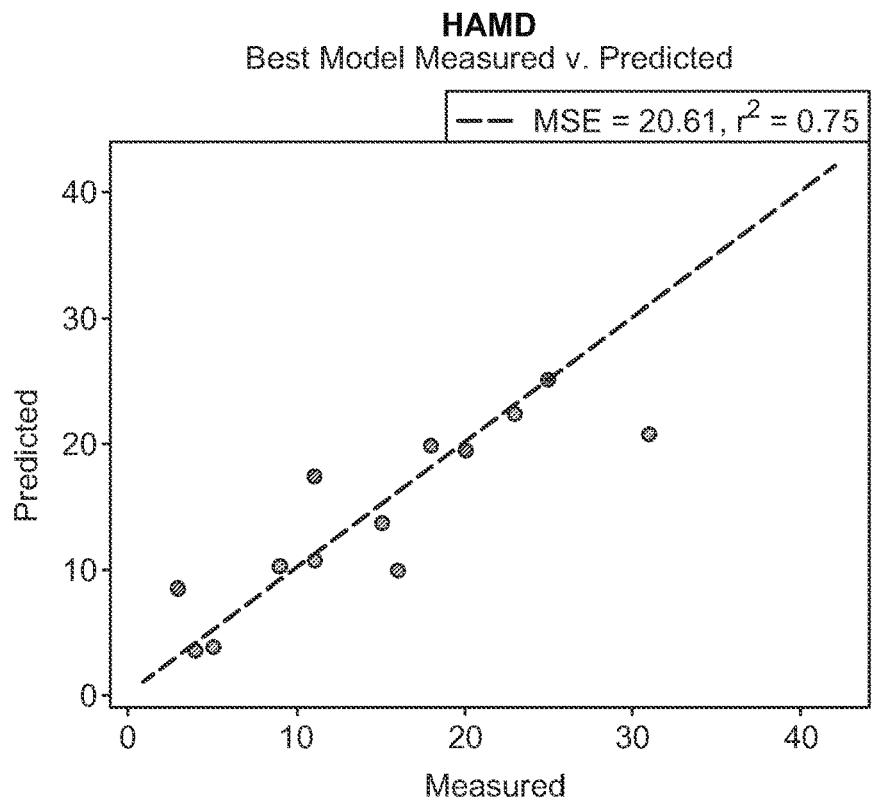
FIGS. 9A-9F illustrate measured versus predicted values for best models for depression or depressed mood, according to some implementations of the present disclosure.
Figure 9B:
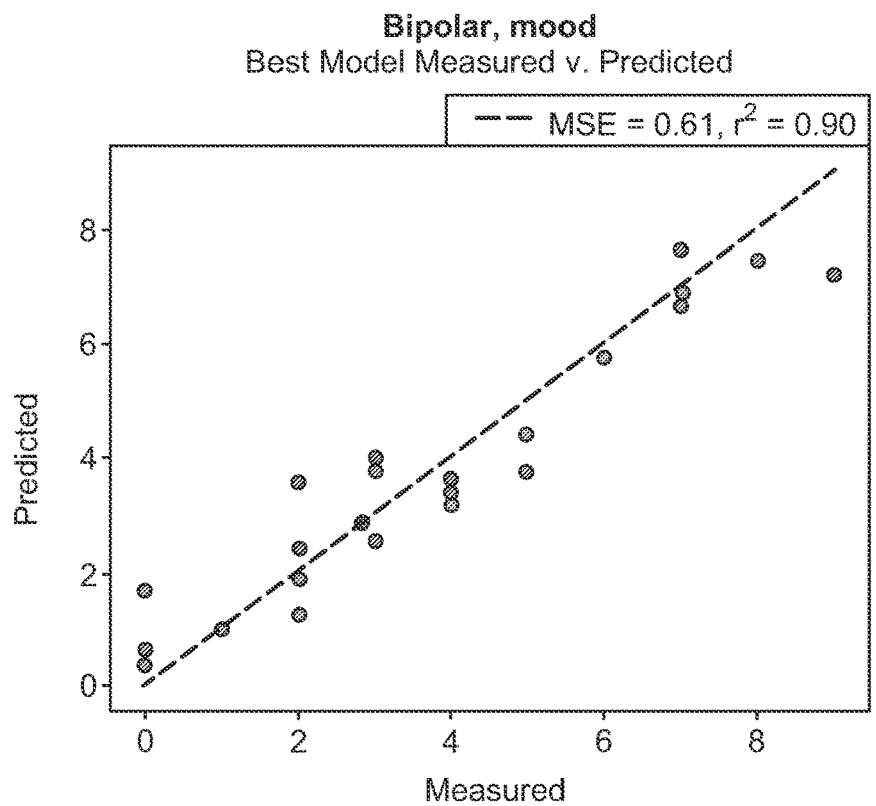
Figure 9C:
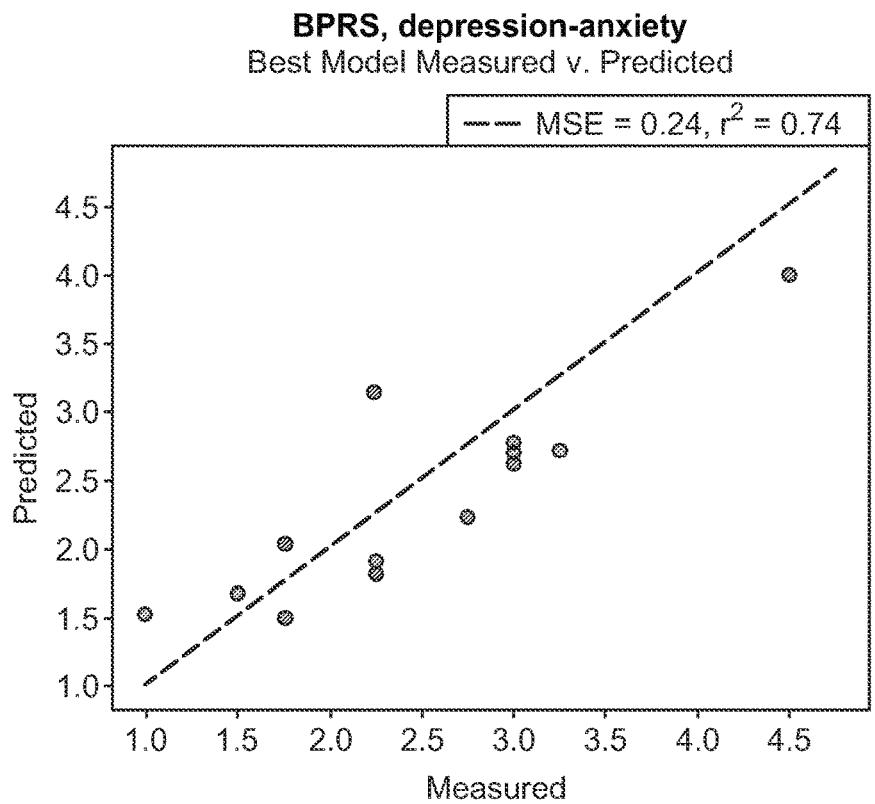
Figure 9D:
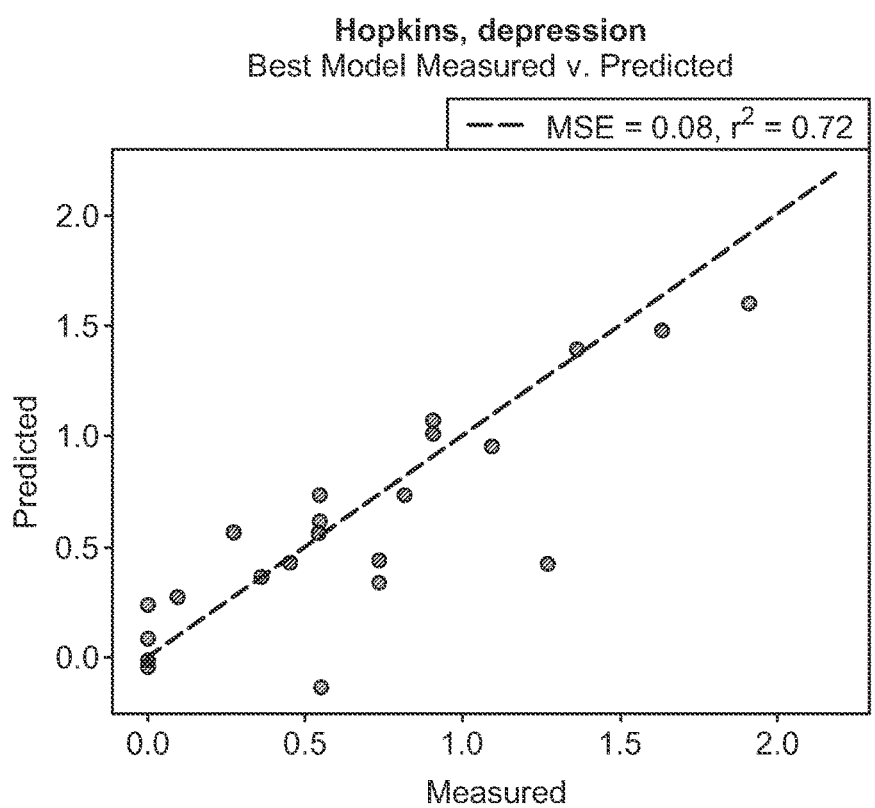
Figure 9E:
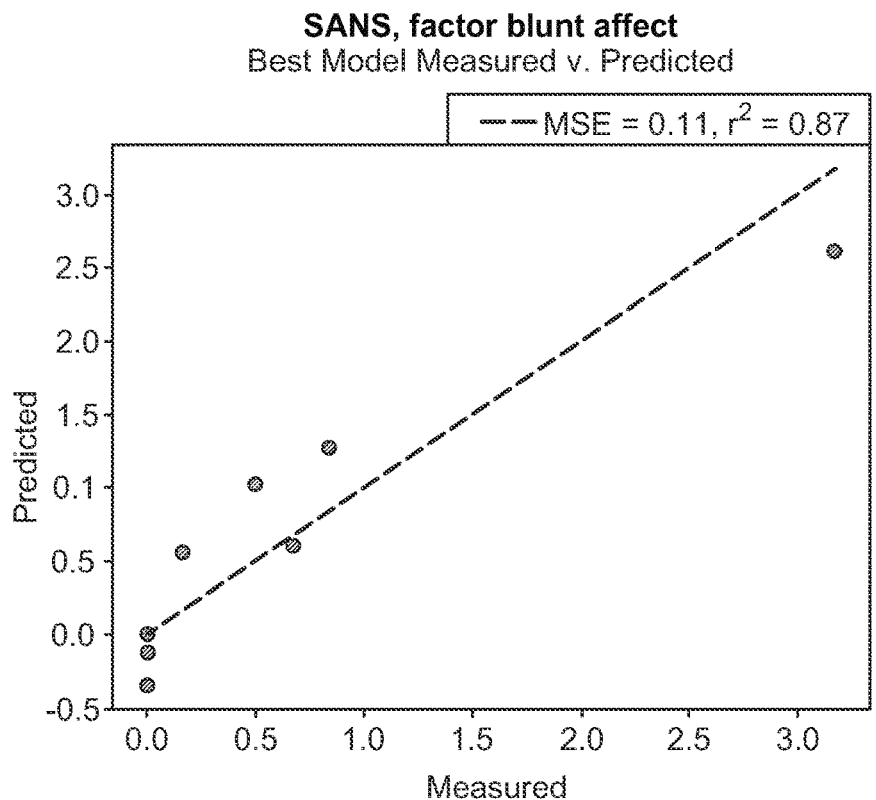
Figure 9F:
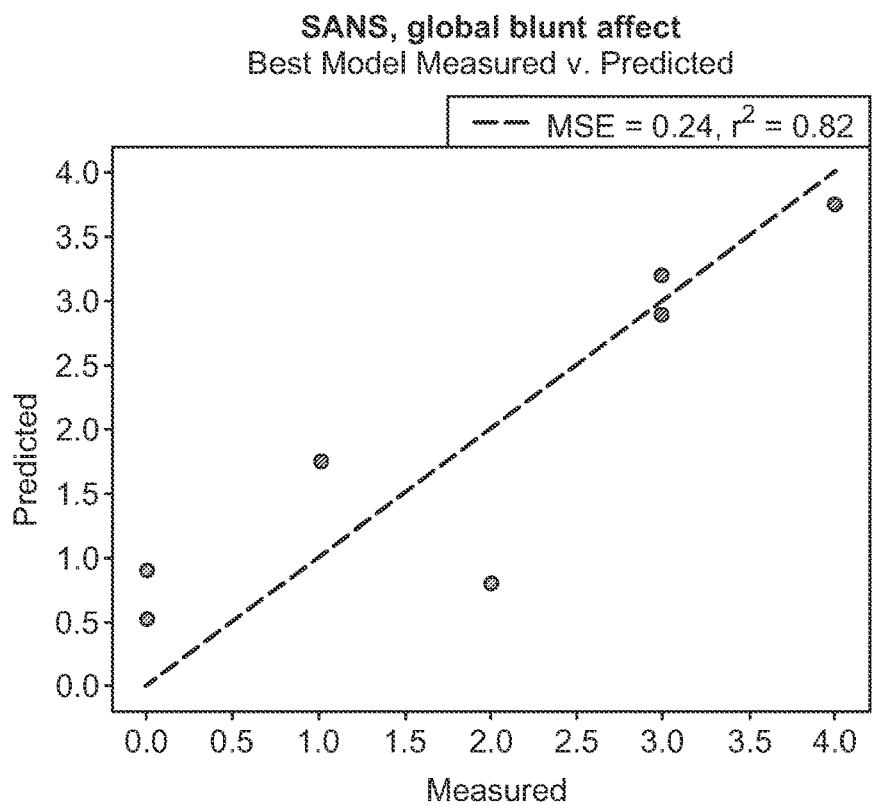
Figure 10A:
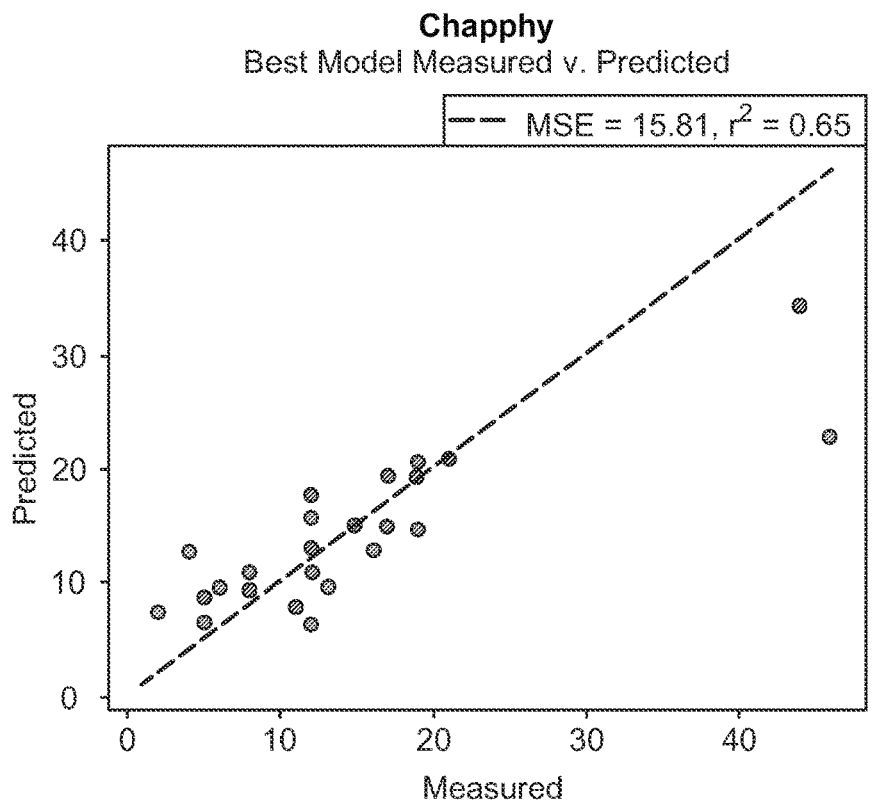
FIGS. 10A-10E illustrate measured versus predicted values for best models for anhedonia, according to some implementations of the present disclosure.
Figure 10B:
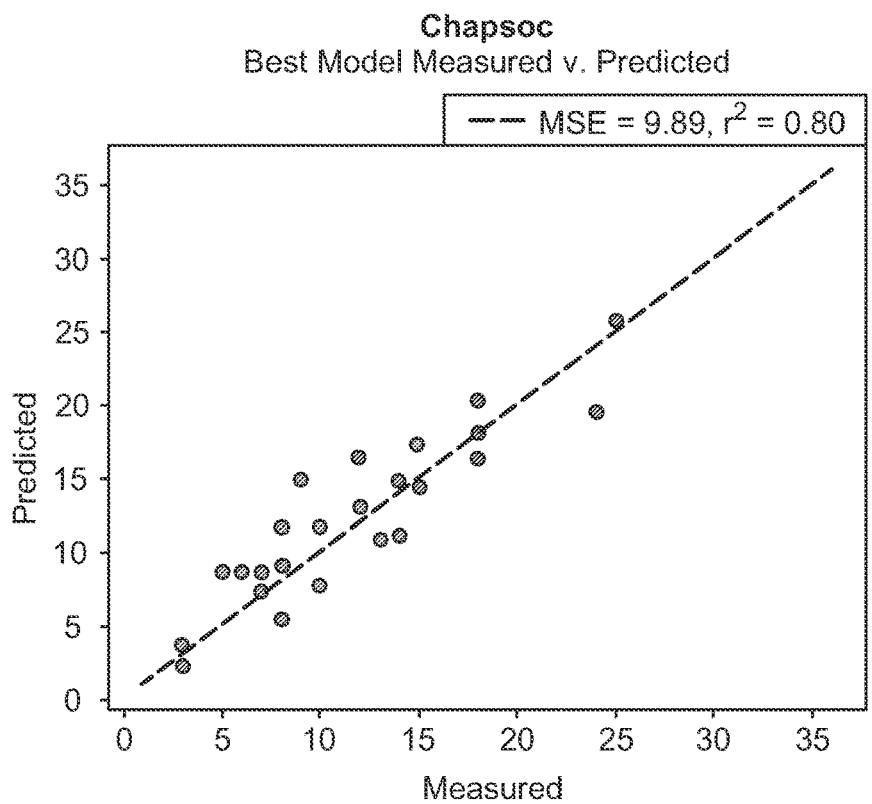
Figure 10C:
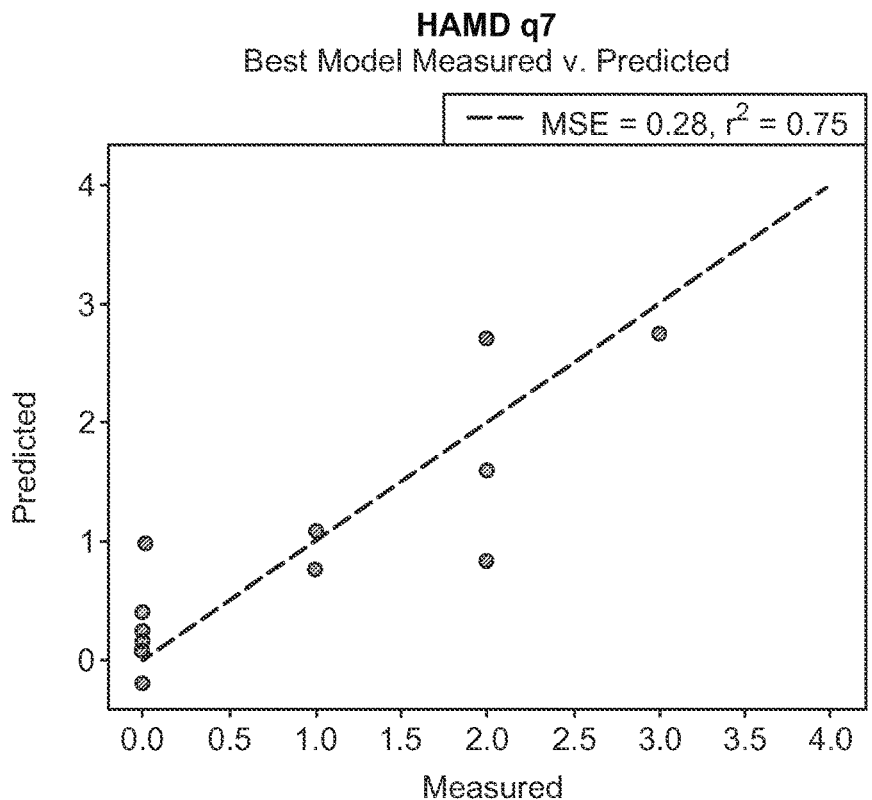
Figure 10D:
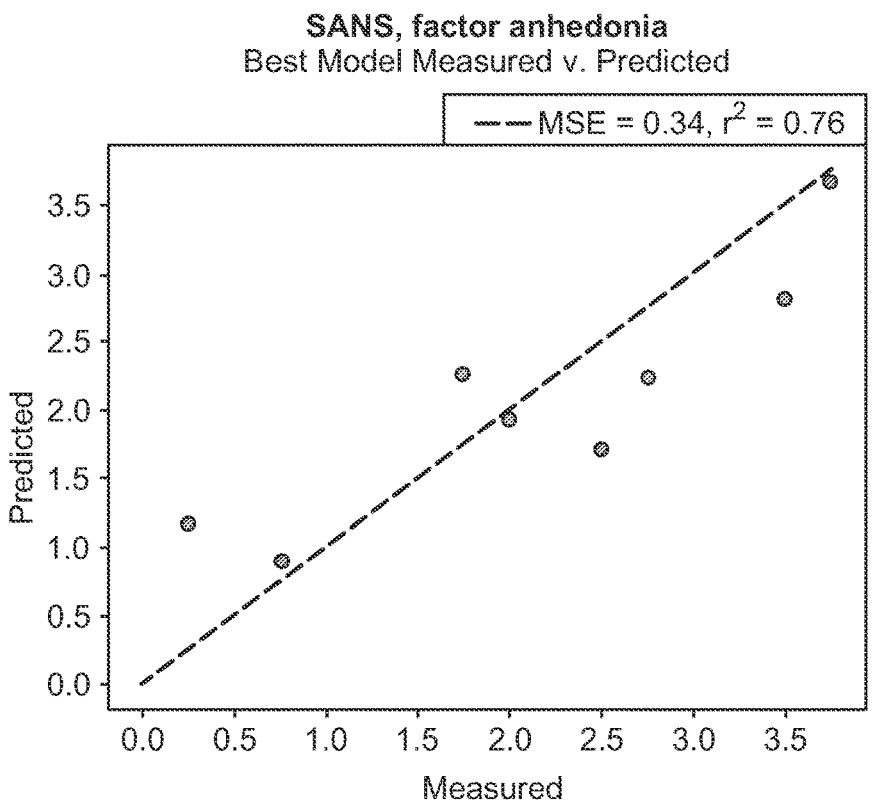
Figure 10E:
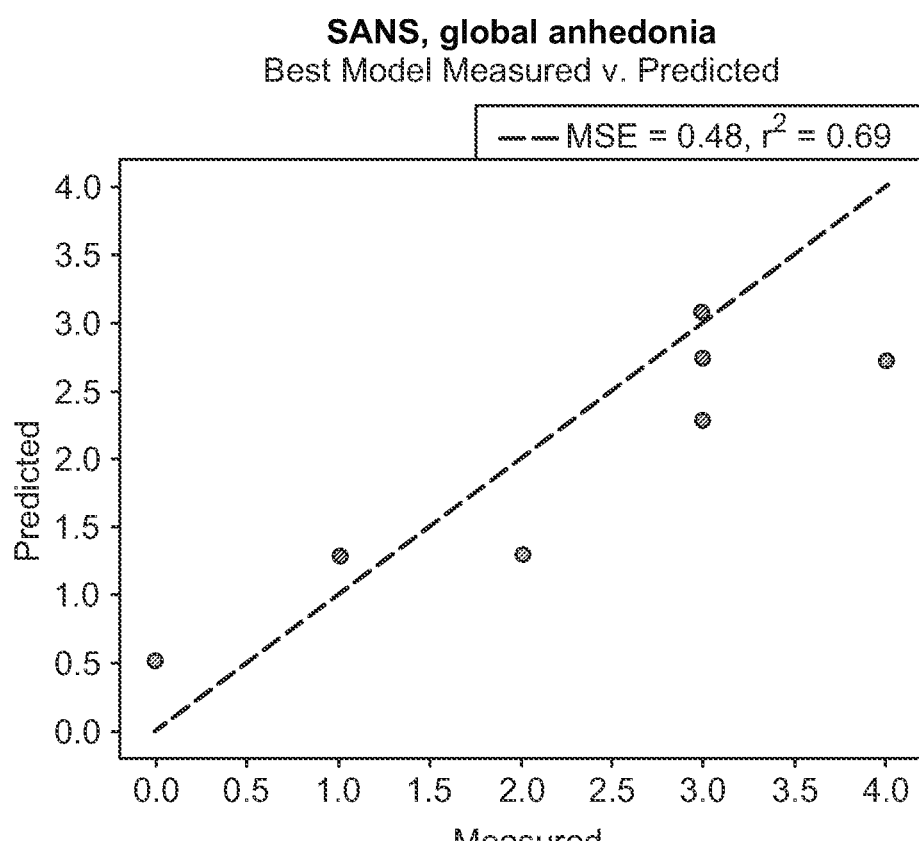
Figure 11A:
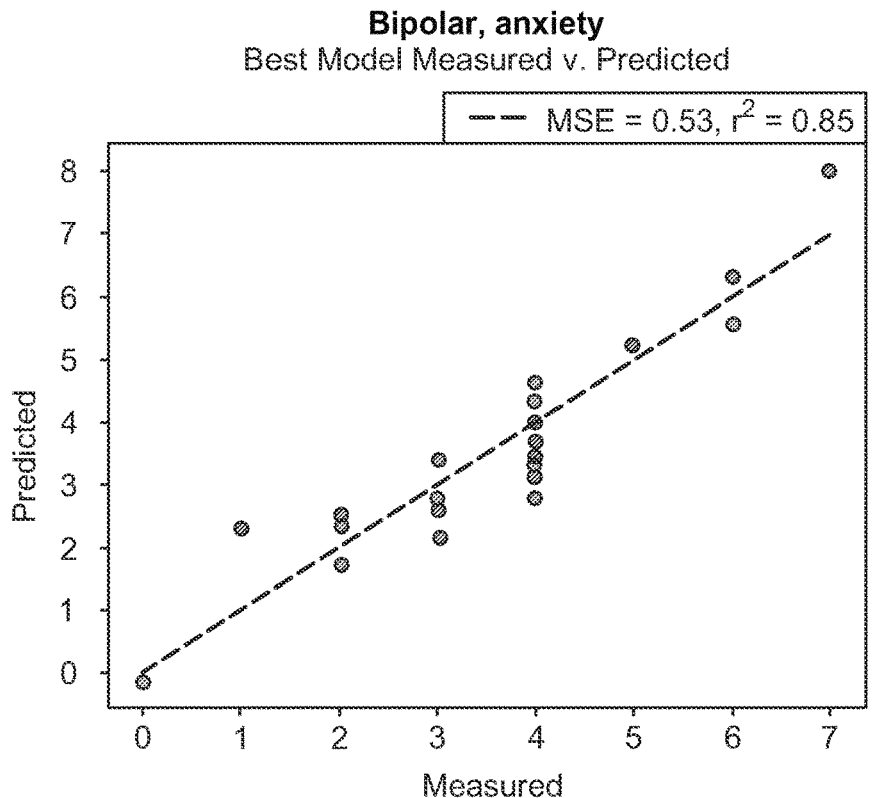
FIG. 11A-11B illustrate measured versus predicted values for best models for anxiety, according to some implementations of the present disclosure.
Figure 11B:
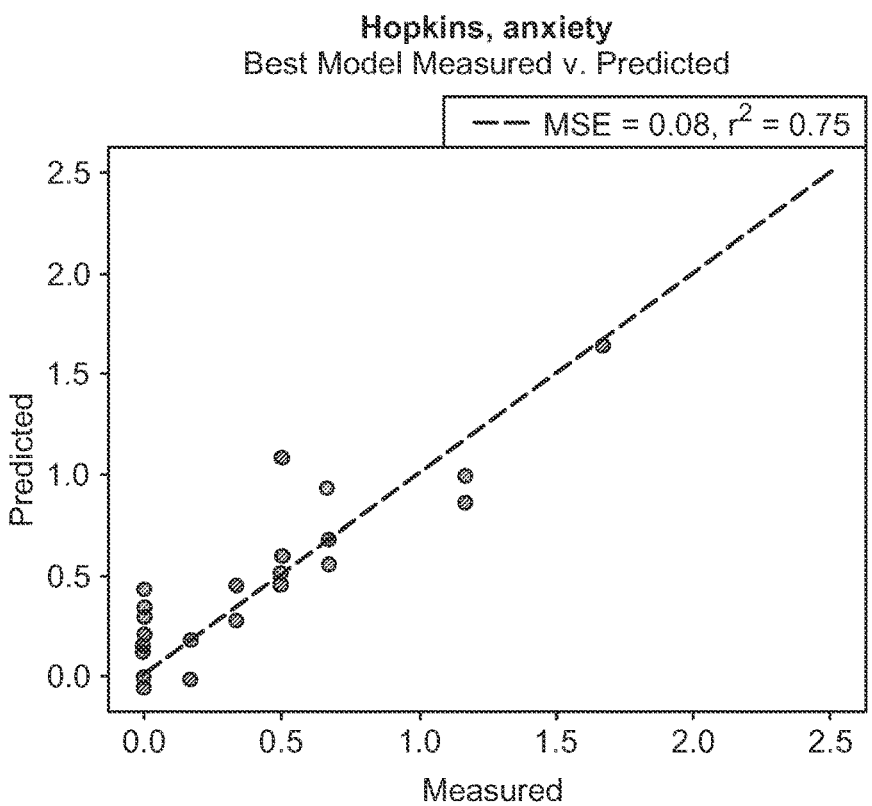
Figure 12A:
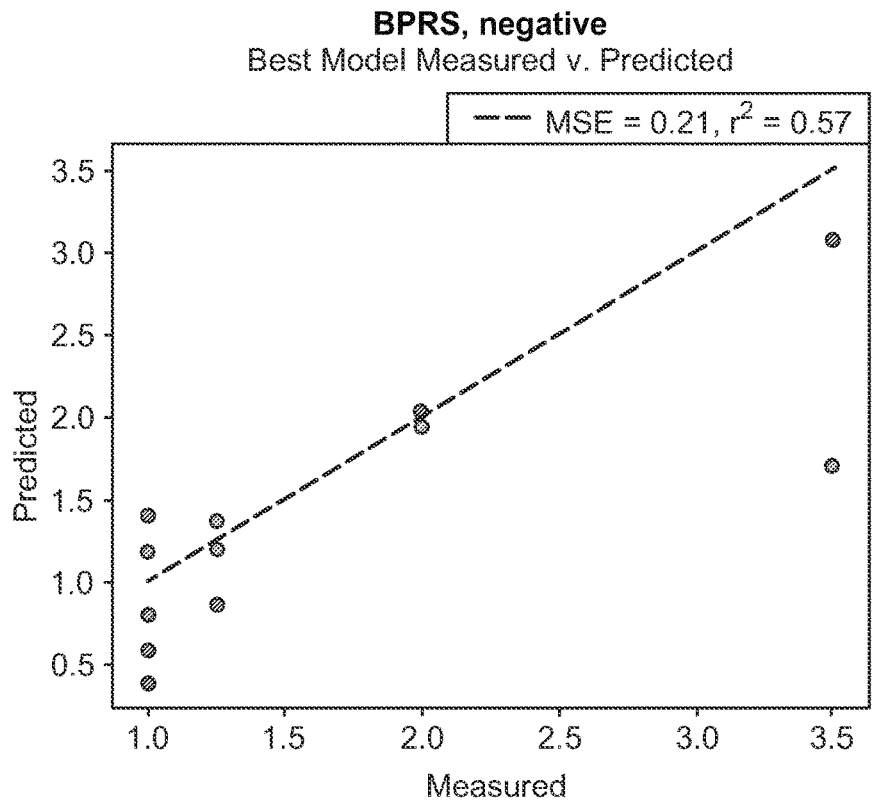
FIGS. 12A-12H illustrate measured versus predicted values for best models for negative symptoms, according to some implementations of the present disclosure.
Figure 12B:
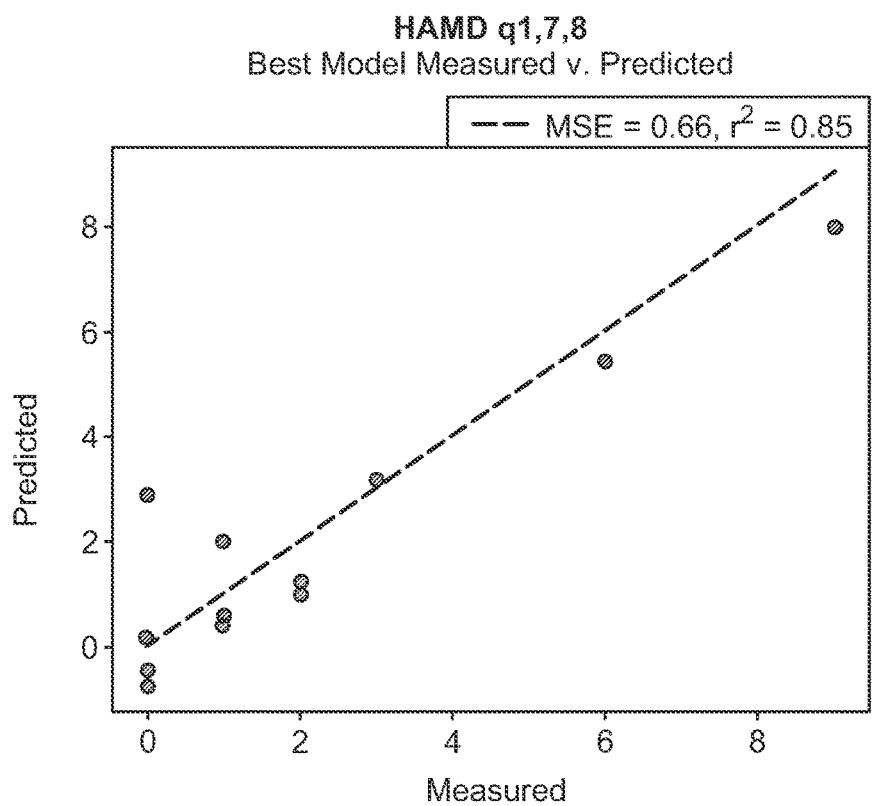
Figure 12C:
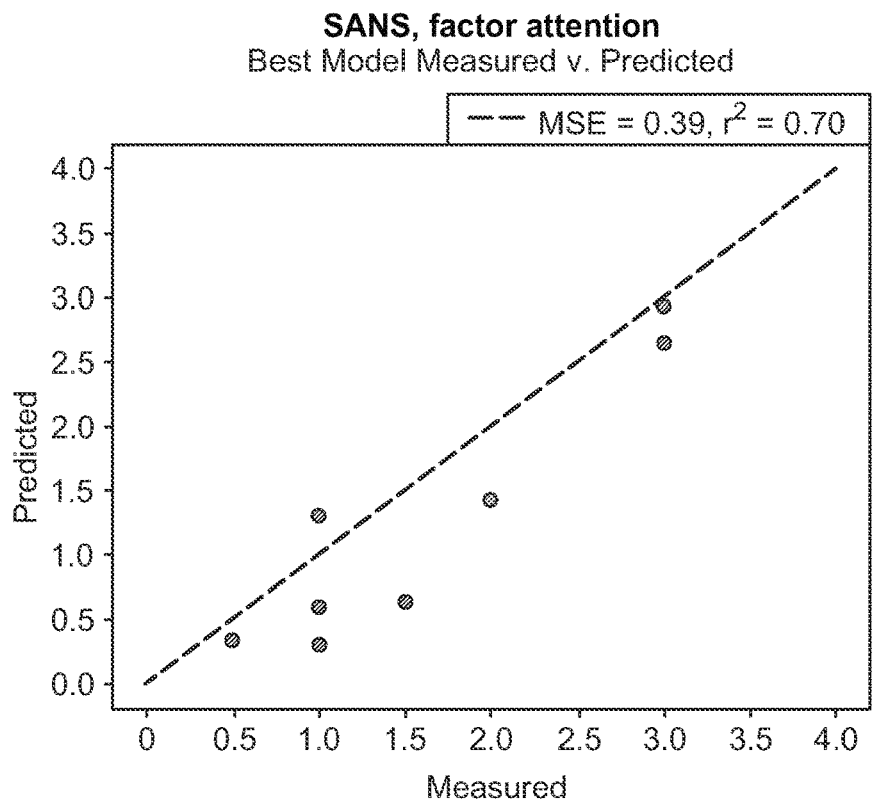
Figure 12D:
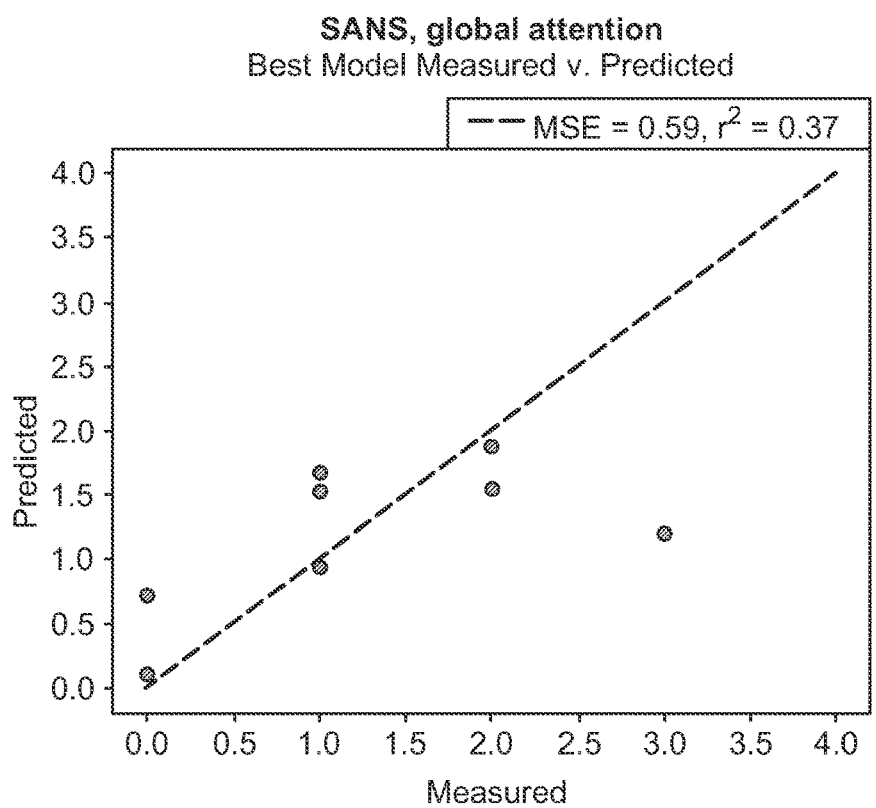
Figure 12E:
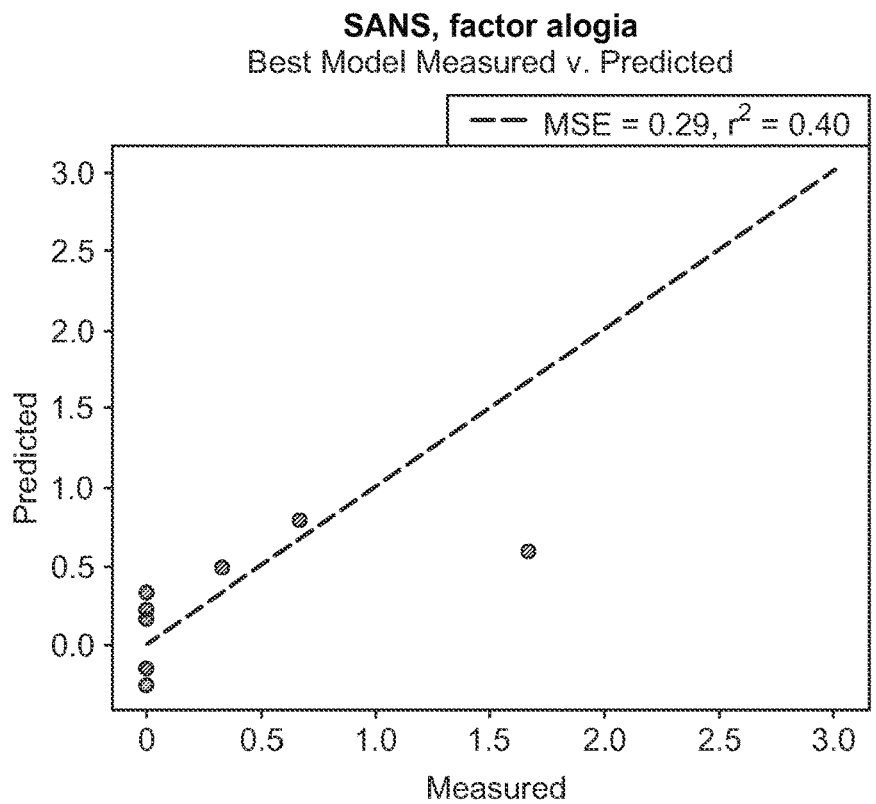
Figure 12F:
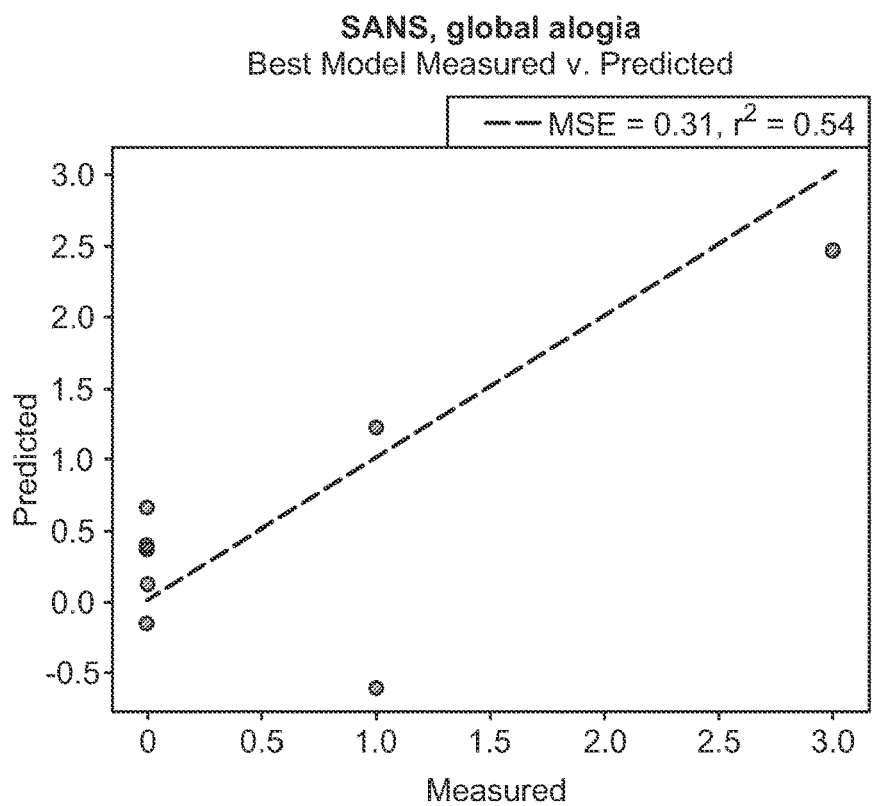
Figure 12G:
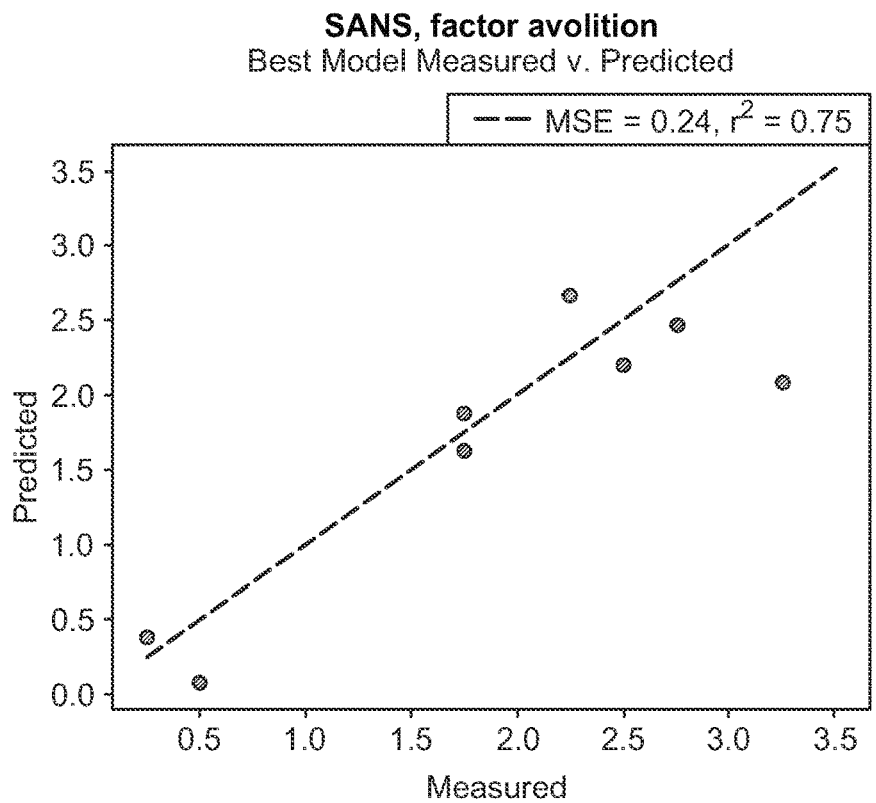
Figure 12H:
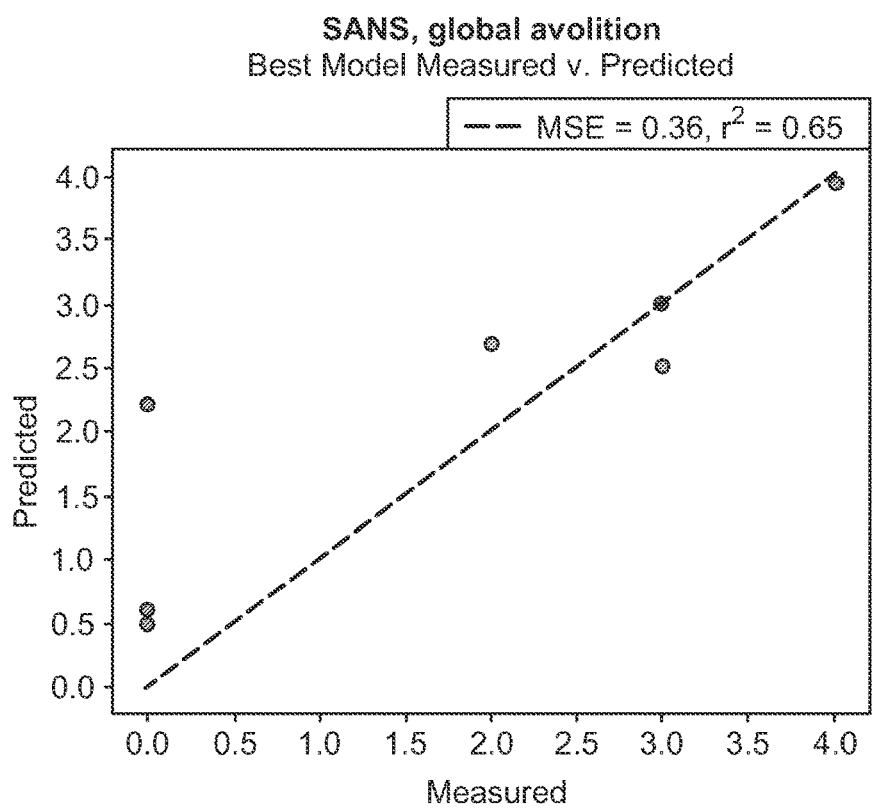

The best model overall was selected by finding the maximum median $r^2$ value over all feature subsets and selecting the model that corresponded to that max median $r^2$ value (FIGS. 9A-9B). All subsequent follow up is on the 441 best models for each combination of input x model type x output. To find which input feature set (clinical scales only, sMRI only, fMRI only, scales+sMRI, scales+fMRI, sMRI+fMRI, and scales+sMRI+fMR) and which model type (Lasso, Elastic Net, Random Forest) lead to the best biomarkers, subsequent comparisons were also made based on the $r^2$ of the best models. The $r^2$ is a standardized measurement of explained variance while the MSE values are not standardized across the different models making it less appropriate to use MSE for comparison.

Experimental Results

Within a multi-modal dataset, the best biomarkers were found for symptom severity. Of the 441 sets of models created, the best median MSE, $r^2$, and number of features chosen for the best model are listed by input type in Tables 7-15.

TABLE 7

Models with scales as Input Feature Set

| Predicted Scores | Metric | Lasso | ElasticNet | RandomForest |
| --- | --- | --- | --- | --- |
| Chapman Social Anhedonia | median MSE | 11.1271192 | 12.5102035 | 18.52422909 |
|  | median $r^2$ | 0.79553146 | 12.5102035 | 0.663112391 |
|  | p | 60 | 126 | n/a |
| Chapman Physical Anhedonia | median MSE | 22.1445803 | 19.66968 | 29.07554113 |
|  | median $r^2$ | 0.62740091 | 0.64236923 | 0.390169303 |
|  | p | 30 | 240 | n/a |
| HAMD, total score | median MSE | 43.793948 | 39.5487303 | 55.91616365 |
|  | median $r^2$ | 0.64032781 | 0.68561252 | 0.52124878 |
|  | p | 31 | 30 | n/a |
| HAMD, q1, 7, 8 sum score | median MSE | 2.01814843 | 1.66515201 | 2.259603571 |
|  | median $r^2$ | 0.57873064 | 0.62740408 | 0.450071051 |
|  | p | 30 | 111 | n/a |
| HAMD, q7 | median MSE | 0.62723587 | 0.64544389 | 0.728892857 |
|  | median $r^2$ | 0.53344986 | 0.50668328 | 0.358667497 |
|  | p | 31 | 31 | n/a |
| BPRS, negative score | median MSE | 0.26698062 | 0.25566474 | 0.265797419 |
|  | median $r^2$ | 0.31461782 | 0.31801616 | 0.322618632 |
|  | p | 15 | 16 | n/a |
| BPRS, depression-anxiety score | median MSE | 0.41526043 | 0.49462448 | 0.645597869 |
|  | median $r^2$ | 0.69385756 | 0.63793659 | 0.506121615 |
|  | p | 29 | 15 | n/a |
| Hopkins, anxiety score | median MSE | 0.12342578 | 0.13413996 | 0.132160047 |
|  | median $r^2$ | 0.56143153 | 0.5247619 | 0.514104345 |
|  | p | 16 | 54 | n/a |
| Hopkins, depression score | median MSE | 0.12009199 | 0.14761639 | 0.157354172 |
|  | median $r^2$ | 0.55009395 | 0.52978675 | 0.487804566 |
|  | p | 30 | 50 | n/a |
| Bipolar II, depression score | median MSE | 1.48573552 | 1.48573552 | 1.48573552 |
|  | median $r^2$ | 0.79140084 | 0.79140084 | 0.79140084 |
|  | p | 53 | 53 | 53 |
| Bipolar II, anxiety score | median MSE | 1.14386984 | 1.25201497 | 1.432082609 |
|  | median $r^2$ | 0.60840301 | 0.61587207 | 0.527387046 |
|  | p | 55 | 62 | n/a |
| SANS, anhedonia factor score | median MSE | 0.83876628 | 0.59576226 | 0.956182813 |
|  | median $r^2$ | 0.47594879 | 0.54907114 | 0.35565793 |
|  | p | 8 | 31 | n/a |
| SANS, avolition factor score | median MSE | 0.75904172 | 0.53277714 | 0.842343438 |
|  | median $r^2$ | 0.37282752 | 0.52685866 | 0.277248843 |
|  | p | 16 | 95 | n/a |
| SANS, blunt affect factor score | median MSE | 0.35110694 | 0.29422649 | 0.467130979 |
|  | median $r^2$ | 0.50744677 | 0.63150632 | 0.404207334 |
|  | p | 27 | 30 | n/a |
| SANS, alogia factor score | median MSE | 0.30051278 | 0.28023609 | 0.261009716 |
|  | median $r^2$ | 0.47299533 | 0.45477607 | 0.347271029 |
|  | p | 16 | 21 | n/a |
| SANS, attention factor score | median MSE | 0.86509729 | 0.51250215 | 0.83855625 |
|  | median $r^2$ | 0.19195497 | 0.55007444 | 0.306327586 |
|  | p | 23 | 31 | n/a |

TABLE 7-continued

Models with scales as Input Feature Set

| Predicted Scores | Metric | Lasso | ElasticNet | RandomForest |
|---|---|---|---|---|
| SANS, anhedonia global score | median MSE | 0.97997004 | 0.77234958 | 1.3385 |
|  | median r² | 0.48838999 | 0.51134602 | 0.280770186 |
|  | p | 30 | 97 | n/a |
| SANS, avolition global score | median MSE | SANS, avolition global score | SANS, avolition global score | SANS, avolition global score |
|  | median r² | SANS, avolition global score | SANS, avolition global score | SANS, avolition global score |
|  | p | SANS, avolition global score | SANS, avolition global score | SANS, avolition global score |
| SANS, blunt affect global score | median MSE | 0.7771112 | 0.73140944 | 1.117416344 |
|  | median r² | 0.51491093 | 0.51498925 | 0.279459854 |
|  | p | 28 | 16 | n/a |
| SANS, alogia global score | median MSE | 0.47215453 | 0.38144655 | 0.7015 |
|  | median r² | 0.52195716 | 0.56271799 | 0.175649402 |
|  | p | 48 | 54 | n/a |
| SANS, attention global score | median MSE | 1.0888059 | 1.14883735 | 1.33584404 |
|  | median r² | 0.36828624 | 0.37581968 | 0.207184361 |
|  | p | 16 | 23 | n/a |

TABLE 8

Models with sMRI as Input Feature Set

| Predicted Scores | Metric | Lasso | ElasticNet | RandomForest |
|---|---|---|---|---|
| Chapman Social Anhedonia | median MSE | 46.6436876 | 43.8925147 | 56.19190933 |
|  | median r² | 0.13059127 | 0.06492086 | 0.018169833 |
|  | p | 32 | 32 | n/a |
| Chapman Physical Anhedonia | median MSE | 45.608347 | 42.8346492 | 51.84063311 |
|  | median r² | 0.08315395 | 0.1578689 | 0.051603031 |
|  | p | 29 | 61 | n/a |
| HAMD, total score | median MSE | 106.7787 | 126.52325 | 148.4359545 |
|  | median r² | 0.18545856 | 0.13091374 | −0.028624069 |
|  | p | 30 | 63 | n/a |
| HAMD, q1, 7, 8 sum score | median MSE | 3.91992524 | 3.6155941 | 4.89586655 |
|  | median r² | 0.24368153 | 0.41216092 | 0.029851586 |
|  | p | 12 | 32 | n/a |
| HAMD, q7 | median MSE | 1.09102119 | 1.03588134 | 1.235452088 |
|  | median r² | 0.233324 | 0.25076498 | 0.094440028 |
|  | p | 12 | 8 | n/a |
| BPRS, negative score | median MSE | 0.39982436 | 0.32335276 | 0.402057778 |
|  | median r² | 0.00824425 | −0.0155099 | −0.007323061 |
|  | p | 4 | 0 | n/a |
| BPRS, depression-anxiety score | median MSE | 1.15920977 | 0.95818565 | 1.451526015 |
|  | median r² | 0.17862626 | 0.28621436 | 0.054920555 |
|  | p | 16 | 16 | n/a |
| Hopkins, anxiety score | median MSE | 0.26190654 | 0.25999248 | 0.305197627 |
|  | median r² | 0.0345918 | 0.04196626 | −0.024837299 |
|  | p | 3 | 6 | n/a |
| Hopkins, depression score | median MSE | 0.28184369 | 0.29874141 | 0.312998029 |
|  | median r² | 0.02605857 | 0.01897287 | 0.013456599 |
|  | p | 4 | 3 | n/a |
| Bipolar II, mood score | median MSE | 6.60397522 | 6.40784263 | 6.606565127 |
|  | median r² | 0.04096752 | 0.12327275 | 0.000331189 |
|  | p | 15 | 22 | n/a |
| Bipolar II, anxiety score | median MSE | 2.96567459 | 2.86508927 | 3.207035714 |
|  | median r² | 0.0553218 | 0.12103751 | −0.038229814 |
|  | p | 15 | 16 | n/a |
| SANS, anhedonia factor score | median MSE | 1.2865302 | 1.37559255 | 1.500729847 |
|  | median r² | 0.07116012 | 0.0838163 | 0.049659227 |
|  | p | 1 | 7 | n/a |
| SANS, avolition factor score | median MSE | 0.84434359 | 0.68288494 | 1.226599689 |
|  | median r² | 0.06990071 | 0.25025035 | −0.055433989 |
|  | p | 8 | 16 | n/a |
| SANS, blunt affect factor score | median MSE | 1.02091208 | 0.73699746 | 0.860400744 |
|  | median r² | −0.0397132 | 0.17453646 | −0.048103458 |
|  | p | 6 | 8 | n/a |
| SANS, alogia factor score | median MSE | 0.48120689 | 0.42570429 | 0.45733438 |
|  | median r² | 0.13644323 | 0.14511349 | 0.125931485 |
|  | p | 2 | 4 | n/a |
| SANS, attention factor score | median MSE | 1.1922749 | 1.10667518 | 1.225370598 |
|  | median r² | 0.05745299 | 0.07908587 | 0.022559648 |
|  | p | 2 | 10 | n/a |

TABLE 8-continued

Models with sMRI as Input Feature Set

| Predicted Scores | Metric | Lasso | ElasticNet | RandomForest |
|---|---|---|---|---|
| SANS, anhedonia global score | median MSE | 1.69045647 | 1.31358016 | 2.053971977 |
| | median $r^2$ | 0.11891888 | 0.26245368 | 0.008426596 |
| | p | 7 | 16 | n/a |
| SANS, avolition global score | median MSE | 1.33022003 | 1.81957272 | 1.972625302 |
| | median $r^2$ | 0.24852834 | 0.11766409 | −0.052500711 |
| | p | 15 | 8 | n/a |
| SANS, blunt affect global score | median MSE | 1.70285398 | 1.28177902 | 1.779535383 |
| | median $r^2$ | −0.0107927 | 0.21717229 | −0.0705761 |
| | p | 20 | 30 | n/a |
| SANS, alogia global score | median MSE | 1.0508356 | 0.69226706 | 1.125291206 |
| | median $r^2$ | −0.0546058 | 0.12641629 | −0.046307774 |
| | p | 2 | 16 | n/a |
| SANS, attention global score | median MSE | 1.39313125 | 1.23859557 | 1.600134651 |
| | median $r^2$ | 0.05351207 | 0.18494907 | 0.018476896 |
| | p | 15 | 8 | n/a |

TABLE 9

Models with fMRI as Input Feature Set

| Predicted Scores | Metric | Lasso | ElasticNet | RandomForest |
|---|---|---|---|---|
| Chapman Social Anhedonia | median MSE | 24.1366711 | 13.2464801 | 35.74676667 |
| | median $r^2$ | 0.5908661 | 0.7319229 | 0.258061818 |
| | p | 75 | 345 | n/a |
| Chapman Physical Anhedonia | median MSE | 30.901329 | 21.4057029 | 39.74679883 |
| | median $r^2$ | 0.61525222 | 0.65566807 | 0.247477881 |
| | p | 76 | 358 | n/a |
| HAMD, total score | median MSE | 33.2005788 | 38.9725415 | 71.34669412 |
| | median $r^2$ | 0.66777371 | 0.59569346 | 0.207388274 |
| | p | 16 | 500 | n/a |
| HAMD, q1, 7, 8 sum score | median MSE | 0.95578396 | 0.91593487 | 2.650023529 |
| | median $r^2$ | 0.79179955 | 0.74061902 | 0.332485876 |
| | p | 28 | 191 | n/a |
| HAMD, q7 | median MSE | 0.31201916 | 0.37790437 | 0.808070588 |
| | median $r^2$ | 0.73200199 | 0.69881084 | 0.356340961 |
| | p | 38 | 54 | n/a |
| BPRS, negative score | median MSE | 0.18757938 | 0.1506109 | 0.241262868 |
| | median $r^2$ | 0.58051551 | 0.57369558 | 0.279867098 |
| | p | 15 | 131 | n/a |
| BPRS, depression-anxiety score | median MSE | 0.48898993 | 0.38228361 | 0.69174958 |
| | median $r^2$ | 0.51218225 | 0.54291803 | 0.343333691 |
| | p | 23 | 36 | n/a |
| Hopkins, anxiety score | median MSE | 0.16332994 | 0.10991548 | 0.250750368 |
| | median $r^2$ | 0.4518252 | 0.65341477 | 0.307182751 |
| | p | 24 | 85 | n/a |
| Hopkins, depression score | median MSE | 0.14661675 | 0.1591489 | 0.206618425 |
| | median $r^2$ | 0.48845674 | 0.45016098 | 0.280274072 |
| | p | 31 | 29 | n/a |
| Bipolar II, depression score | median MSE | 2.2093303 | 2.53026198 | 4.058693333 |
| | median $r^2$ | 0.64341678 | 0.62534857 | 0.323775594 |
| | p | 50 | 255 | n/a |
| Bipolar II, anxiety score | median MSE | 1.74502231 | 0.98772213 | 2.523746667 |
| | median $r^2$ | 0.48106 | 0.6442545 | 0.304516018 |
| | p | 43 | 153 | n/a |
| SANS, anhedonia factor score | median MSE | 0.57249993 | 0.44668826 | 0.671989773 |
| | median $r^2$ | 0.54341834 | 0.72603119 | 0.476297105 |
| | p | 16 | 66 | n/a |
| SANS, avolition factor score | median MSE | 0.38427335 | 0.41349887 | 0.523188636 |
| | median $r^2$ | 0.60922858 | 0.68171714 | 0.393902033 |
| | p | 20 | 63 | n/a |
| SANS, blunt affect factor score | median MSE | 0.35097663 | 0.13853868 | 0.319771716 |
| | median $r^2$ | 0.36340364 | 0.81112876 | 0.421756359 |
| | p | 22 | 29 | n/a |
| SANS, attention factor score | median MSE | 0.5114133 | 0.5450171 | 0.863740909 |
| | median $r^2$ | 0.58044727 | 0.55803846 | 0.351176332 |
| | p | 11 | 16 | n/a |
| SANS, anhedonia global score | median MSE | 0.6479366 | 0.653431 | 0.703936364 |
| | median $r^2$ | 0.57849286 | 0.5910022 | 0.567246117 |
| | p | 13 | 22 | n/a |
| SANS, avolition global score | median MSE | 0.65626457 | 0.45879379 | 1.112490909 |
| | median $r^2$ | 0.65501818 | 0.7356483 | 0.41697963 |
| | p | 8 | 126 | n/a |

TABLE 9-continued

Models with fMRI as Input Feature Set

| Predicted Scores | Metric | Lasso | ElasticNet | RandomForest |
| --- | --- | --- | --- | --- |
| SANS, blunt affect global score | median MSE | 0.76806032 | 0.40498193 | 0.725527273 |
| | median r² | 0.5075324 | 0.67717999 | 0.438660494 |
| | p | 20 | 18 | n/a |
| SANS, alogia global score | median MSE | 0.18058636 | 0.25612571 | 0.360454545 |
| | median r² | 0.71239653 | 0.44974554 | 0.20472973 |
| | p | 12 | 21 | n/a |
| SANS, attention global score | median MSE | 0.82370349 | 0.84473842 | 1.018854545 |
| | median r² | 0.53408014 | 0.55862342 | 0.381446429 |
| | p | 8 | 70 | n/a |

TABLE 10

Models with sMRI + fMRI as Input Feature Set

| Predicted Scores | Metric | Lasso | ElasticNet | RandomForest |
| --- | --- | --- | --- | --- |
| Chapman Social Anhedonia | median MSE | 20.3800964 | 14.682152 | 34.56825833 |
| | median r² | 0.61287335 | 0.67729341 | 0.271666677 |
| | p | 30 | 559 | n/a |
| Chapman Physical Anhedonia | median MSE | 29.5944321 | 14.4191528 | 39.64058054 |
| | median r² | 0.47730737 | 0.73988389 | 0.270972364 |
| | p | 72 | 211 | n/a |
| HAMD, total score | median MSE | 40.444502 | 27.0655892 | 65.45605995 |
| | median r² | 0.46827069 | 0.61111933 | 0.317391988 |
| | p | 13 | 448 | n/a |
| HAMD, q1, 7, 8 sum score | median MSE | 2.36930173 | 1.3053619 | 2.42418007 |
| | median r² | 0.57469992 | 0.78027275 | 0.415661799 |
| | p | 21 | 78 | n/a |
| HAMD, q7 | median MSE | 0.48427727 | 0.44843705 | 0.733507692 |
| | median r² | 0.51760748 | 0.62850068 | 0.374694444 |
| | p | 4 | 95 | n/a |
| BPRS, negative score | median MSE | 0.10894905 | 0.20808541 | 0.228798077 |
| | median r² | 0.58309527 | 0.48416688 | 0.339701299 |
| | p | 10 | 12 | n/a |
| BPRS, depression-anxiety score | median MSE | 0.74672192 | 0.4527803 | 0.745567681 |
| | median r² | 0.34811518 | 0.59421236 | 0.305609826 |
| | p | 15 | 119 | n/a |
| Hopkins, anxiety score | median MSE | 0.12090694 | 0.09822079 | 0.189571301 |
| | median r² | 0.55139531 | 0.65036656 | 0.303938076 |
| | p | 8 | 29 | n/a |
| Hopkins, depression score | median MSE | 0.17540687 | 0.1383836 | 0.199493796 |
| | median r² | 0.38018872 | 0.4151432 | 0.199243267 |
| | p | 21 | 16 | n/a |
| Bipolar II, depression score | median MSE | 3.58417568 | 1.86722182 | 4.104375843 |
| | median r² | 0.45476109 | 0.71921058 | 0.297745091 |
| | p | 48 | 241 | n/a |
| Bipolar II, anxiety score | median MSE | 1.28026365 | 0.70325067 | 2.257191667 |
| | median r² | 0.60209066 | 0.78935698 | 0.32304625 |
| | p | 25 | 161 | n/a |
| SANS, anhedonia factor score | median MSE | 0.40512803 | 0.35700521 | 0.63381875 |
| | median r² | 0.71570239 | 0.77152059 | 0.552279155 |
| | p | 8 | 48 | n/a |
| SANS, avolition factor score | median MSE | 0.18738998 | 0.11302804 | 0.45203125 |
| | median r² | 0.67281 | 0.84257768 | 0.519285076 |
| | p | 7 | 41 | n/a |
| SANS, blunt affect factor score | median MSE | 0.1055558 | 0.16598636 | 0.406562166 |
| | median r² | 0.7535557 | 0.76532171 | 0.476367098 |
| | p | 24 | 65 | n/a |
| SANS, attention factor score | median MSE | 0.40859079 | 0.11637806 | 0.236031927 |
| | median r² | 0.29255013 | 0.7725277 | 0.559877681 |
| | p | 7 | 77 | n/a |
| SANS, anhedonia global score | median MSE | 0.88823187 | 0.57576394 | 1.095494073 |
| | median r² | 0.40161221 | 0.63872035 | 0.319304654 |
| | p | 17 | 107 | n/a |
| SANS, avolition global score | median MSE | 0.55331606 | 0.21081588 | 0.7125 |
| | median r² | 0.56105366 | 0.82726123 | 0.5096 |
| | p | 6 | 67 | n/a |
| SANS, blunt affect global score | median MSE | 0.76193885 | 0.26705401 | 0.75875 |
| | median r² | 0.5411395 | 0.84012485 | 0.526436782 |
| | p | 11 | 41 | n/a |
| SANS, alogia global score | median MSE | 0.52887025 | 0.25762776 | 0.3487375 |
| | median r² | 0.31534639 | 0.65101623 | 0.320888889 |
| | p | 8 | 26 | n/a |

TABLE 10-continued

| | Models with sMRI + fMRI as Input Feature Set | | | |
|---|---|---|---|---|
| Predicted Scores | Metric | Lasso | ElasticNet | RandomForest |
| SANS, attention global score | median MSE | 0.35172813 | 0.28886716 | 0.5875 |
| | median $r^2$ | 0.70380789 | 0.75674345 | 0.5975 |
| | p | 8 | 13 | n/a |

TABLE 11

| | Models with Scales + sMRI as Input Feature Set | | | |
|---|---|---|---|---|
| Predicted Scores | Metric | Lasso | ElasticNet | RandomForest |
| Chapman Social Anhedonia | median MSE | 10.1872913 | 10.8473571 | 23.01353415 |
| | median $r^2$ | 0.8189687 | 0.79591289 | 0.599748178 |
| | p | 59 | 63 | n/a |
| Chapman Physical Anhedonia | median MSE | 15.1648738 | 15.1775051 | 31.00075366 |
| | median $r^2$ | 0.6745091 | 0.69034822 | 0.429974564 |
| | p | 92 | 123 | n/a |
| HAMD, total score | median MSE | 44.8743169 | 21.4111889 | 51.17416788 |
| | median $r^2$ | 0.62386495 | 0.80822534 | 0.600713723 |
| | p | 31 | 123 | n/a |
| HAMD, q1, 7, 8 sum score | median MSE | 2.04269051 | 1.25720156 | 2.447818182 |
| | median $r^2$ | 0.59849127 | 0.76841313 | 0.474861019 |
| | p | 38 | 110 | n/a |
| HAMD, q7 | median MSE | 0.5660152 | 0.37695234 | 0.771495455 |
| | median $r^2$ | 0.60961318 | 0.73435387 | 0.407349419 |
| | p | 28 | 58 | n/a |
| BPRS, negative score | median MSE | 0.22947823 | 0.11052677 | 0.223487784 |
| | median $r^2$ | 0.3567901 | 0.68800207 | 0.426280069 |
| | p | 12 | 54 | n/a |
| BPRS, depression-anxiety score | median MSE | 0.47774909 | 0.37200915 | 0.716768024 |
| | median $r^2$ | 0.6784626 | 0.76758706 | 0.520999457 |
| | p | 39 | 58 | n/a |
| Hopkins, anxiety score | median MSE | 0.15278469 | 0.14505891 | 0.147720373 |
| | median $r^2$ | 0.46629576 | 0.47103414 | 0.475010058 |
| | p | 14 | 49 | n/a |
| Hopkins, depression score | median MSE | 0.13015768 | 0.10560835 | 0.148762648 |
| | median $r^2$ | 0.58405287 | 0.67747487 | 0.516387069 |
| | p | 15 | 102 | n/a |
| Bipolar II, depression score | median MSE | 1.11473489 | 1.02057729 | 1.722802026 |
| | median $r^2$ | 0.84118256 | 0.86421896 | 0.745336441 |
| | p | 32 | 114 | n/a |
| Bipolar II, anxiety score | median MSE | 0.81608355 | 0.79832926 | 1.565412195 |
| | median $r^2$ | 0.7409768 | 0.73479011 | 0.523792469 |
| | p | 30 | 58 | n/a |
| SANS, anhedonia factor score | median MSE | 0.80659301 | 0.8876104 | 1.02542 |
| | median $r^2$ | 0.4847042 | 0.43714204 | 0.251376657 |
| | p | 24 | 13 | n/a |
| SAMS avolition factor score | median MSE | 0.35767455 | 0.29545236 | 0.76713875 |
| | median $r^2$ | 0.64133778 | 0.69348871 | 0.252067852 |
| | p | 30 | 54 | n/a |
| SANS, blunt affect global score | median MSE | 0.29046712 | 0.35398284 | 0.555033335 |
| | median $r^2$ | 0.65317772 | 0.57650195 | 0.346361453 |
| | p | 15 | 29 | n/a |
| SANS, alogia global score | median MSE | 0.27355305 | 0.22486147 | 0.370562213 |
| | median $r^2$ | 0.43984006 | 0.45944781 | 0.260900092 |
| | p | 16 | 22 | n/a |
| SANS, attention factor score | median MSE | 0.61391724 | 0.52919515 | 0.840366667 |
| | median $r^2$ | 0.42634181 | 0.56616671 | 0.26694625 |
| | p | 15 | 90 | n/a |
| SANS, anhedonia global score | median MSE | 0.82696728 | 0.91638191 | 1.31 |
| | median $r^2$ | 0.52922904 | 0.52124193 | 0.349258197 |
| | p | 16 | 57 | n/a |
| SANS, avolition global score | median MSE | 1.0735851 | 0.96201314 | 1.69874 |
| | median $r^2$ | 0.48944093 | 0.4703767 | 0.186773404 |
| | p | 15 | 92 | n/a |
| SANS, blunt affect global score | median MSE | 0.47919468 | 0.64615998 | 0.941919557 |
| | median $r^2$ | 0.56575973 | 0.5970739 | 0.403780513 |
| | p | 16 | 89 | n/a |

TABLE 11-continued

| | Models with Scales + sMRI as Input Feature Set | | | |
|---|---|---|---|---|
| Predicted Scores | Metric | Lasso | ElasticNet | RandomForest |
| SANS, alogia global score | median MSE | 0.42319702 | 0.51674167 | 0.709333333 |
| | median $r^2$ | 0.41947137 | 0.43807514 | 0.181628238 |
| | p | 15 | 16 | n/a |
| SANS, attention global score | median MSE | 0.5766073 | 0.87984786 | 1.165269856 |
| | median $r^2$ | 0.53935525 | 0.37445084 | 0.141182351 |
| | p | 23 | 56 | n/a |

TABLE 12

| | Models with Scales + fMRI as Input Feature Set | | | |
|---|---|---|---|---|
| Predicted Scores | Metric | Lasso | ElasticNet | RandomForest |
| Chapman Social Anhedonia | median MSE | 7.54857525 | 8.62749906 | 15.861 |
| | median $r^2$ | 0.85696606 | 0.82923337 | 0.624779485 |
| | p | 47 | 31 | n/a |
| Chapman Physical Anhedonia | median MSE | 11.4387261 | 9.64819292 | 30.3415 |
| | median $r^2$ | 0.80523296 | 0.84146325 | 0.46116541 |
| | p | 46 | 211 | n/a |
| HAMD, total score | median MSE | 30.0928229 | 18.4018727 | 56.24705882 |
| | median $r^2$ | 0.68185562 | 0.75611578 | 0.409766837 |
| | p | 64 | 500 | n/a |
| HAMD, q1, 7, 8 sum score | median MSE | 0.78599809 | 1.39375053 | 2.453211765 |
| | median $r^2$ | 0.8139221 | 0.66728025 | 0.351087925 |
| | p | 26 | 38 | n/a |
| HAMD, q7 | median MSE | 0.50886936 | 0.2839172 | 0.698394118 |
| | median $r^2$ | 0.56050644 | 0.74835288 | 0.35008427 |
| | p | 14 | 71 | n/a |
| BPRS, negative score | median MSE | 0.12890998 | 0.10125789 | 0.263854412 |
| | median $r^2$ | 0.6985185 | 0.72757156 | 0.365523303 |
| | p | 15 | 77 | n/a |
| BPRS, depression-anxiety score | median MSE | 0.38343051 | 0.3666505 | 0.614460907 |
| | median $r^2$ | 0.60430968 | 0.6324356 | 0.400634204 |
| | p | 10 | 126 | n/a |
| Hopkins, anxiety score | median MSE | 0.15000759 | 0.09454587 | 0.182484719 |
| | median $r^2$ | 0.59683759 | 0.70395432 | 0.494827971 |
| | p | 27 | 127 | n/a |
| Hopkins, depression score | median MSE | 0.07745056 | 0.109673 | 0.166952453 |
| | median $r^2$ | 0.70911272 | 0.61049809 | 0.487824855 |
| | p | 16 | 26 | n/a |
| Bipolar II, depression score | median MSE | 0.8612683 | 0.81444012 | 1.874116667 |
| | median $r^2$ | 0.86949418 | 0.87448985 | 0.716193323 |
| | p | 50 | 236 | n/a |
| Bipolar II, anxiety score | median MSE | 0.92825662 | 0.5885091 | 1.4777 |
| | median $r^2$ | 0.72875618 | 0.82518059 | 0.545020104 |
| | p | 31 | 32 | n/a |
| SANS, anhedonia factor score | median MSE | 0.75319007 | 0.40312956 | 0.602954545 |
| | median $r^2$ | 0.45645379 | 0.69809318 | 0.4687 |
| | p | 20 | 113 | n/a |
| SANS, avolition factor score | median MSE | 0.44983495 | 0.23568128 | 0.523295022 |
| | median $r^2$ | 0.54295816 | 0.75660524 | 0.482050744 |
| | p | 4 | 104 | n/a |
| SANS, blunt affect factor score | median MSE | 0.59539547 | 0.15419775 | 0.651515161 |
| | median $r^2$ | 0.11155579 | 0.74503811 | 0.238753545 |
| | p | 18 | 66 | n/a |
| SANS, alogia factor score | median MSE | 0.20516943 | 0.18387234 | 0.251717177 |
| | median $r^2$ | 0.27467066 | 0.25771316 | 0.141923298 |
| | p | 15 | 44 | n/a |
| SANS, attention factor score | median MSE | 0.62059488 | 0.67939691 | 0.932954545 |
| | median $r^2$ | 0.5322245 | 0.55054858 | 0.260303398 |
| | p | 8 | 21 | n/a |
| SANS, anhedonia global score | median MSE | 1.03514893 | 0.51331319 | 0.843345455 |
| | median $r^2$ | 0.37662089 | 0.71666415 | 0.526349083 |
| | p | 38 | 94 | n/a |
| SANS, avolition global score | median MSE | 0.69546127 | 0.31666292 | 0.8424 |
| | median $r^2$ | 0.5712837 | 0.7831869 | 0.423196371 |
| | p | 32 | 76 | n/a |
| SANS, blunt affect global score | median MSE | 0.53970926 | 0.24419898 | 0.918772727 |
| | median $r^2$ | 0.63412804 | 0.8621164 | 0.286820238 |
| | p | 7 | 104 | n/a |
| SANS, alogia global score | median MSE | 0.23416101 | 0.1346341 | 0.459032293 |
| | median $r^2$ | 0.63027204 | 0.76082807 | 0.337482692 |
| | p | 16 | 79 | n/a |

TABLE 12-continued

Models with Scales + fMRI as Input Feature Set

| Predicted Scores | Metric | Lasso | ElasticNet | RandomForest |
|---|---|---|---|---|
| SANS, attention global score | median MSE | 0.67038649 | 0.3496769 | 0.864181818 |
| | median $r^2$ | 0.60670155 | 0.72306165 | 0.405159722 |
| | p | 34 | 49 | n/a |

TABLE 13

Models with Scales + sMRI + fMRI as Input Feature Set

| Predicted Scores | Metric | Lasso | ElasticNet | RandomForest |
|---|---|---|---|---|
| Chapman Social Anhedonia | median MSE | 7.02713487 | 9.88649254 | 19.15130417 |
| | median $r^2$ | 0.82179475 | 0.80395702 | 0.574399043 |
| | p | 30 | 106 | n/a |
| Chapman Physical Anhedonia | median MSE | 23.103581 | 15.813689 | 24.33652917 |
| | median $r^2$ | 0.62015743 | 0.65207517 | 0.427901305 |
| | p | 48 | 32 | n/a |
| HAMD, total score | median MSE | 53.9003365 | 20.609113 | 56.87493846 |
| | median $r^2$ | 0.40119528 | 0.74613682 | 0.382350302 |
| | p | 45 | 287 | n/a |
| HAMD, q1, 7, 8 sum score | median MSE | 0.83612067 | 0.66395437 | 1.736653846 |
| | median $r^2$ | 0.74556212 | 0.84561512 | 0.4934095 |
| | p | 22 | 15 | n/a |
| HAMD, q7 | median MSE | 0.37916308 | 0.27904854 | 0.592908763 |
| | median $r^2$ | 0.68283541 | 0.74596354 | 0.456458962 |
| | p | 24 | 41 | n/a |
| BPRS, negative score | median MSE | 0.12270201 | 0.21086621 | 0.238864423 |
| | median $r^2$ | 0.67420458 | 0.56848126 | 0.393594454 |
| | p | 20 | 59 | n/a |
| BPRS, depression-anxiety score | median MSE | 0.43485082 | 0.23737832 | 0.5453289 |
| | median $r^2$ | 0.62338118 | 0.73608677 | 0.465149531 |
| | p | 16 | 101 | n/a |
| Hopkins, anxiety score | median MSE | 0.08598748 | 0.07735448 | 0.155089002 |
| | median $r^2$ | 0.68432645 | 0.75087675 | 0.472547865 |
| | p | 27 | 47 | n/a |
| Hopkins, depression score | median MSE | 0.13237647 | 0.07568423 | 0.128395595 |
| | median $r^2$ | 0.51367615 | 0.72075418 | 0.551525829 |
| | p | 8 | 28 | n/a |
| Bipolar II, depression score | median MSE | 0.72420064 | 0.61353445 | 1.800416667 |
| | median $r^2$ | 0.87359605 | 0.90430728 | 0.707705862 |
| | p | 31 | 93 | n/a |
| Bipolar II, anxiety score | median MSE | 0.52050357 | 0.53484936 | 1.415204167 |
| | median $r^2$ | 0.83781236 | 0.84698368 | 0.541076495 |
| | p | 72 | 31 | n/a |
| SANS, anhedonia factor score | median MSE | 0.3853509 | 0.34019896 | 0.741640625 |
| | median $r^2$ | 0.66868235 | 0.76398652 | 0.479339276 |
| | p | 25 | 96 | n/a |
| SANS, avolition factor score | median MSE | 0.11339753 | 0.24172352 | 0.337739063 |
| | median $r^2$ | 0.87833197 | 0.75047895 | 0.54596125 |
| | p | 15 | 37 | n/a |
| SANS, blunt affect factor score | median MSE | 0.28002122 | 0.10988582 | 0.373347216 |
| | median $r^2$ | 0.62139163 | 0.86521702 | 0.504200316 |
| | p | 12 | 48 | n/a |
| SANS, alogia factor score | median MSE | 0.18371445 | 0.28849662 | 0.245543402 |
| | median $r^2$ | 0.56331434 | 0.39736881 | 0.370516386 |
| | p | 4 | 11 | n/a |
| SANS, attention factor score | median MSE | 0.33208967 | 0.38759467 | 0.5703125 |
| | median $r^2$ | 0.76203213 | 0.69803375 | 0.388411538 |
| | p | 14 | 75 | n/a |
| SANS, anhedonia global score | median MSE | 0.31323163 | 0.48323333 | 0.9457375 |
| | median $r^2$ | 0.77081433 | 0.69441199 | 0.416995804 |
| | p | 10 | 100 | n/a |
| SANS, avolition global score | median MSE | 0.40052226 | 0.35670872 | 0.61165 |
| | median $r^2$ | 0.68969915 | 0.65259748 | 0.437284034 |
| | p | 20 | 8 | n/a |
| SANS, blunt affect global score | median MSE | 0.77088686 | 0.24344448 | 0.6033125 |
| | median $r^2$ | 0.4716052 | 0.81951831 | 0.669752381 |
| | p | 12 | 60 | n/a |

TABLE 13-continued

| Models with Scales + sMRI + fMRI as Input Feature Set | | | | |
|---|---|---|---|---|
| Predicted Scores | Metric | Lasso | ElasticNet | RandomForest |
| SANS, alogia global score | median MSE | 0.29111249 | 0.30605891 | 0.434708622 |
| | median $r^2$ | 0.3509162 | 0.54233936 | 0.377058065 |
| | p | 12 | 13 | n/a |
| SANS, attention global score | median MSE | 0.62341815 | 0.59315255 | 0.7232875 |
| | median $r^2$ | 0.39958268 | 0.36730395 | 0.333212632 |
| | p | 8 | 57 | n/a |

TABLE 14

Comparison of all Elastic Net Models using Truncated Feature Sets Returned by Forward Selection Approach

| Predicted Scores | Metric | Scales | sMRI | fMRI | Scales_ sMRI | sMRI_ fMRI | Scales_ fMRI | Scales_ sMRI_ fMRI |
|---|---|---|---|---|---|---|---|---|
| Chapman Social Anhedonia | median MSE | 12.510 | 43.893 | 13.246 | 10.847 | 14.682 | 8.627 | 9.886 |
| | median $r^2$ | 0.782 | 0.065 | 0.732 | 0.796 | 0.677 | 0.829 | 0.804 |
| | p | 126 | 32 | 345 | 63 | 559 | 31 | 106 |
| Chapman Physical Anhedonia | median MSE | 19.670 | 42.835 | 21.406 | 15.178 | 14.419 | 9.648 | 15.814 |
| | median $r^2$ | 0.642 | 0.158 | 0.656 | 0.690 | 0.740 | 0.841 | 0.652 |
| | p | 240 | 61 | 358 | 123 | 211 | 211 | 32 |
| HAMD, total score | median MSE | 39.549 | 126.523 | 38.973 | 21.411 | 27.066 | 18.402 | 20.609 |
| | median $r^2$ | 0.686 | 0.131 | 0.596 | 0.808 | 0.611 | 0.756 | 0.746 |
| | p | 30 | 63 | 500 | 123 | 448 | 500 | 287 |
| HAMD, q1, 7, 8 sum score | median MSE | 1.665 | 3.616 | 0.916 | 1.257 | 1.305 | 1.394 | 0.664 |
| | median $r^2$ | 0.627 | 0.412 | 0.741 | 0.768 | 0.780 | 0.667 | 0.846 |
| | p | 111 | 32 | 191 | 110 | 78 | 38 | 15 |
| HAMD, q7 | median MSE | 0.645 | 1.036 | 0.378 | 0.377 | 0.448 | 0.284 | 0.279 |
| | median $r^2$ | 0.507 | 0.251 | 0.699 | 0.734 | 0.629 | 0.748 | 0.746 |
| | p | 31 | 8 | 54 | 58 | 95 | 71 | 41 |
| BPRS, negative score | median MSE | 0.256 | 0.323 | 0.151 | 0.111 | 0.208 | 0.101 | 0.211 |
| | median $r^2$ | 0.318 | −0.016 | 0.574 | 0.688 | 0.484 | 0.728 | 0.568 |
| | p | 16 | 0 | 131 | 54 | 12 | 77 | 59 |
| BPRS, depression-anxiety score | median MSE | 0.495 | 0.958 | 0.382 | 0.372 | 0.453 | 0.367 | 0.237 |
| | median $r^2$ | 0.638 | 0.286 | 0.543 | 0.768 | 0.594 | 0.632 | 0.736 |
| | p | 15 | 16 | 36 | 58 | 119 | 126 | 101 |
| Hopkins, anxiety score | median MSE | 0.134 | 0.260 | 0.110 | 0.145 | 0.098 | 0.095 | 0.077 |
| | median $r^2$ | 0.525 | 0.042 | 0.653 | 0.471 | 0.650 | 0.704 | 0.751 |
| | p | 54 | 6 | 85 | 49 | 29 | 127 | 47 |
| Hopkins, depression score | median MSE | 0.148 | 0.299 | 0.159 | 0.106 | 0.138 | 0.110 | 0.076 |
| | median $r^2$ | 0.530 | 0.019 | 0.450 | 0.677 | 0.415 | 0.610 | 0.721 |
| | p | 50 | 3 | 29 | 102 | 16 | 26 | 28 |
| Bipolar II, mood score | median MSE | 1.183 | 6.408 | 2.530 | 1.021 | 1.867 | 0.814 | 0.614 |
| | median $r^2$ | 0.836 | 0.123 | 0.625 | 0.864 | 0.719 | 0.874 | 0.904 |
| | p | 112 | 22 | 255 | 114 | 241 | 236 | 93 |
| Bipolar II, anxiety score | median MSE | 1.252 | 2.865 | 0.988 | 0.798 | 0.703 | 0.589 | 0.535 |
| | median $r^2$ | 0.616 | 0.121 | 0.644 | 0.735 | 0.789 | 0.825 | 0.847 |
| | p | 62 | 16 | 153 | 58 | 161 | 32 | 31 |
| SANS, anhedonia factor score | median MSE | 0.596 | 1.376 | 0.447 | 0.888 | 0.357 | 0.403 | 0.340 |
| | median $r^2$ | 0.549 | 0.084 | 0.726 | 0.437 | 0.772 | 0.698 | 0.764 |
| | p | 31 | 7 | 66 | 13 | 48 | 113 | 96 |
| SANS, avolition factor score | median MSE | 0.533 | 0.683 | 0.413 | 0.295 | 0.113 | 0.236 | 0.242 |
| | median $r^2$ | 0.527 | 0.250 | 0.682 | 0.693 | 0.843 | 0.757 | 0.750 |
| | p | 95 | 16 | 63 | 54 | 41 | 104 | 37 |
| SANS, blunt affect factor score | median MSE | 0.294 | 0.737 | 0.139 | 0.354 | 0.166 | 0.154 | 0.110 |
| | median $r^2$ | 0.632 | 0.175 | 0.811 | 0.577 | 0.765 | 0.745 | 0.865 |
| | p | 30 | 8 | 29 | 29 | 65 | 66 | 48 |
| SANS, alogia factor score | median MSE | 0.280 | 0.426 | 0.092 | 0.225 | 0.116 | 0.184 | 0.288 |
| | median $r^2$ | 0.455 | 0.145 | 0.783 | 0.459 | 0.773 | 0.258 | 0.397 |
| | p | 21 | 4 | 37 | 22 | 77 | 44 | 11 |
| SANS, attention factor score | median MSE | 0.513 | 1.107 | 0.545 | 0.529 | 0.436 | 0.679 | 0.388 |
| | median $r^2$ | 0.550 | 0.079 | 0.558 | 0.566 | 0.607 | 0.551 | 0.698 |
| | p | 31 | 10 | 16 | 90 | 93 | 21 | 75 |
| SANS, anhedonia global score | median MSE | 0.772 | 1.314 | 0.653 | 0.916 | 0.576 | 0.513 | 0.483 |
| | median $r^2$ | 0.511 | 0.262 | 0.591 | 0.521 | 0.639 | 0.717 | 0.694 |
| | p | 97 | 16 | 22 | 57 | 107 | 94 | 100 |
| SANS, avolition global score | median MSE | 1.175 | 1.820 | 0.459 | 0.962 | 0.211 | 0.317 | 0.357 |
| | median $r^2$ | 0.514 | 0.118 | 0.736 | 0.470 | 0.827 | 0.783 | 0.653 |
| | p | 41 | 8 | 126 | 92 | 67 | 76 | 8 |
| SANS, blunt affect global score | median MSE | 0.731 | 1.282 | 0.405 | 0.646 | 0.267 | 0.244 | 0.243 |
| | median $r^2$ | 0.515 | 0.217 | 0.677 | 0.597 | 0.840 | 0.862 | 0.820 |
| | p | 16 | 30 | 18 | 89 | 41 | 104 | 60 |

TABLE 14-continued

Comparison of all Elastic Net Models using Truncated
Feature Sets Returned by Forward Selection Approach

| Predicted Scores | Metric | Scales | sMRI | fMRI | Scales_sMRI | sMRI_fMRI | Scales_fMRI | Scales_sMRI_fMRI |
|---|---|---|---|---|---|---|---|---|
| SANS, alogia global score | median MSE | 0.381 | 0.692 | 0.256 | 0.517 | 0.258 | 0.135 | 0.306 |
| | median $r^2$ | 0.563 | 0.126 | 0.450 | 0.438 | 0.651 | 0.761 | 0.542 |
| | p | 54 | 16 | 21 | 16 | 26 | 79 | 13 |
| SANS, attention global score | median MSE | 1.149 | 1.239 | 0.845 | 0.880 | 0.289 | 0.350 | 0.593 |
| | median $r^2$ | 0.376 | 0.185 | 0.559 | 0.374 | 0.757 | 0.723 | 0.367 |
| | p | 23 | 8 | 70 | 56 | 13 | 49 | 57 |

TABLE 15

Comparison of all Elastic Net Models using Full Feature Sets

| Predicted Scores | Metric | Scales | sMRI | fMRI | Scales_sMRI | sMRI_fMRI | Scales_fMRI | Scales_sMRI_fMRI |
|---|---|---|---|---|---|---|---|---|
| Chapman Social Anhedonia | MSE | 23.597 | 118.983 | 60.536 | 21.494 | 39.454 | 25.938 | 25.641 |
| | $r^2$ | 0.539 | −0.941 | −0.255 | 0.597 | −0.443 | 0.565 | 0.293 |
| Chapman Physical Anhedonia | MSE | 48.835 | 69.992 | 64.141 | 36.425 | 65.951 | 25.679 | 59.355 |
| | $r^2$ | 0.249 | −1.046 | −0.156 | 0.052 | −0.537 | 0.435 | 0.247 |
| HAMD, total score | MSE | 77.891 | 282.184 | 164.331 | 46.766 | 161.696 | 69.011 | 86.035 |
| | $r^2$ | 0.474 | −0.369 | −0.110 | 0.640 | −0.235 | 0.143 | 0.210 |
| HAMD, q1, 7, 8 sum score | MSE | 4.178 | 3.786 | 4.760 | 3.286 | 3.250 | 4.631 | 2.246 |
| | $r^2$ | 0.320 | 0.242 | −0.448 | 0.637 | −0.140 | 0.244 | 0.350 |
| HAMD, q7 | MSE | 1.198 | 1.945 | 1.179 | 1.052 | 2.082 | 1.430 | 1.439 |
| | $r^2$ | −0.053 | −0.409 | −1.543 | 0.224 | −0.407 | −0.023 | 0.162 |
| BPRS, negative score | MSE | 0.504 | 0.764 | 0.678 | 0.207 | 0.461 | 0.345 | 0.632 |
| | $r^2$ | 0.037 | −0.361 | −0.564 | 0.024 | −0.104 | −1.803 | 0.219 |
| BPRS, depression-anxiety score | MSE | 0.992 | 1.606 | 1.301 | 0.610 | 1.091 | 0.929 | 0.850 |
| | $r^2$ | 0.146 | 0.060 | −0.283 | 0.580 | −1.005 | −0.164 | −0.347 |
| Hopkins, anxiety score | MSE | 0.105 | 0.328 | 0.343 | 0.130 | 0.261 | 0.253 | 0.213 |
| | $r^2$ | 0.324 | −0.028 | −0.110 | 0.322 | 0.031 | −0.097 | −0.510 |
| Hopkins, depression score | MSE | 0.196 | 0.310 | 0.276 | 0.208 | 0.348 | 0.224 | 0.103 |
| | $r^2$ | 0.373 | 0.019 | −0.595 | 0.229 | −0.157 | 0.290 | 0.238 |
| Bipolar II, mood score | MSE | 2.172 | 11.538 | 7.683 | 1.809 | 6.379 | 2.426 | 2.099 |
| | $r^2$ | 0.670 | −0.282 | −0.140 | 0.676 | −0.255 | 0.579 | 0.658 |
| Bipolar II, anxiety score | MSE | 1.831 | 3.432 | 3.634 | 1.815 | 2.762 | 1.200 | 1.108 |
| | $r^2$ | 0.183 | −0.115 | 0.003 | 0.624 | −0.072 | 0.473 | 0.387 |
| SANS, anhedonia factor score | MSE | 2.195 | 2.619 | 1.974 | 1.724 | 0.975 | 1.499 | 1.464 |
| | $r^2$ | −0.328 | −1.457 | −0.254 | −0.092 | 0.053 | −0.039 | 0.154 |
| SANS, avolition factor score | MSE | 1.446 | 1.203 | 1.682 | 1.023 | 0.646 | 0.935 | 0.585 |
| | $r^2$ | 0.007 | −0.326 | −0.490 | −0.097 | −0.292 | −0.238 | 0.354 |
| SANS, blunt affect factor score | MSE | 0.564 | 1.736 | 0.396 | 0.809 | 0.472 | 0.997 | 0.381 |
| | $r^2$ | −0.666 | −0.339 | −0.896 | 0.256 | −0.249 | −0.204 | −2.057 |
| SANS, alogia factor score | MSE | 0.552 | 0.285 | 0.365 | 0.483 | 0.242 | 1.137 | 0.505 |
| | $r^2$ | 0.009 | −0.088 | −0.591 | −0.005 | −1.901 | −0.517 | −0.014 |
| SANS, attention factor score | MSE | 1.343 | 1.985 | 1.573 | 1.282 | 2.240 | 2.140 | 1.794 |
| | $r^2$ | −0.094 | −0.502 | −0.244 | −0.431 | −0.327 | −0.850 | −0.305 |
| SANS, anhedonia global score | MSE | 2.081 | 2.232 | 2.138 | 2.234 | 2.147 | 2.496 | 1.920 |
| | $r^2$ | 0.022 | −0.395 | −0.244 | −0.018 | −0.227 | −0.697 | 0.122 |
| SANS, avolition global score | MSE | 2.720 | 2.947 | 1.774 | 2.670 | 0.923 | 1.217 | 1.698 |
| | $r^2$ | −0.441 | −0.326 | 0.050 | −0.318 | 0.222 | −0.753 | −0.132 |
| SANS, blunt affect global score | MSE | 1.611 | 2.108 | 1.737 | 1.064 | 0.810 | 1.251 | 0.629 |
| | $r^2$ | −0.184 | −1.010 | −0.083 | 0.288 | −0.672 | 0.243 | 0.085 |
| SANS, alogia global score | MSE | 0.790 | 1.879 | 1.408 | 1.154 | 0.746 | 0.789 | 0.901 |
| | $r^2$ | −0.926 | −0.566 | −0.469 | −0.273 | −0.541 | −0.325 | −0.802 |
| SANS, attention global score | MSE | 3.080 | 1.995 | 2.191 | 1.911 | 1.207 | 1.045 | 2.996 |
| | $r^2$ | −0.721 | −0.163 | −0.287 | −0.250 | −0.016 | −0.129 | −1.084 |

Weaker models were filtered out by first examining which model algorithm gave the best $r^2$ metric across the outcome variables for each predictor variable. Not only did Elastic Net perform the best according to this criteria (73% won), but it also returns the most interpretable features (for methodological reasons as discussed herein). Then for each outcome variable the $r^2$ across different predictor variable sets were compared (e.g., Table 14). Overall, both scales+fMRI and scales+sMRI+fMRI input sets had the majority of, but an equal number of, winning models based on $r^2$ (seven winning models each). All other models performed relatively well except sMRI-only models. For comparison with the modeling results using the full feature sets (not the truncated sets returned by the forward modeling approach), as shown in Table 15. These were suboptimal to the forward modeling approach. The features returned for one of the winning sets were further examined. Those models used all three features types as input.

Referring to FIGS. 9A-12H, for the 21 models with Scales+sMRI+fMRI input feature set, model performance was evaluated on the held-out test set with measured versus predicted plots. FIGS. 9A-9F illustrate measured versus predicted values for best models for depression or depressed mood, according to some implementations of the present disclosure. The measured versus predicted outcome scores (right) illustrate how closely the model predictions are to actual outcome scores for individuals in the held-out sample for this set of models. Held-out sample sizes differ between models since some scales were not given to all participants (e.g., the SANS scale was only given to BD and SZ patients). Similar to FIG. 9A-9F, FIGS. 10A-10E illustrate measured versus predicted values for best models for anhedonia; FIG. 11A-11B illustrate measured versus predicted values for best models for anxiety; and FIGS. 12A-12H illustrate measured versus predicted values for best models for negative symptoms.

Figure 13:
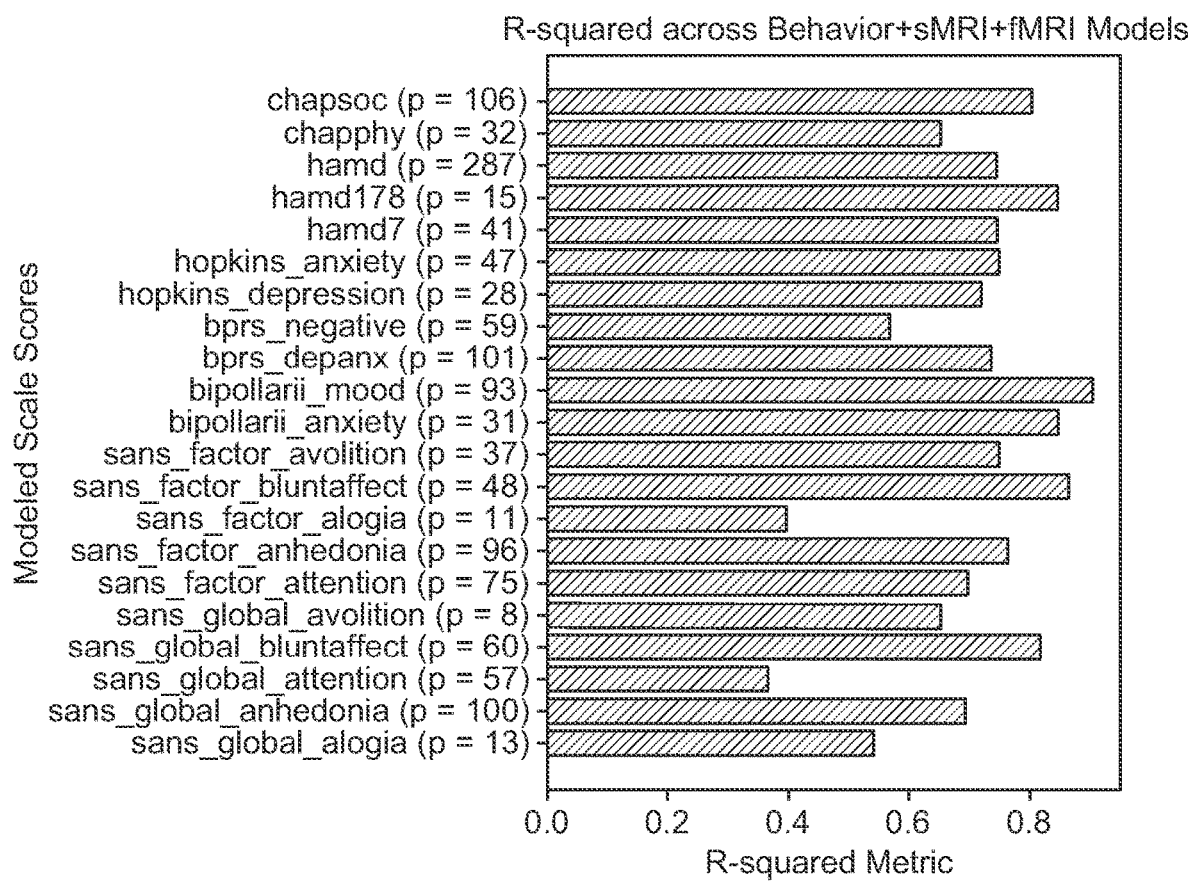
FIG. 13 illustrates best median $r^2$ for the best models for each outcome variable, according to some implementations of the present disclosure.

Referring to FIG. 13, for the 21 models with Scales+sMRI+fMRI input feature set, model performance was evaluated on the held-out test set with $r^2$ values across models for different outcome variables (see Table 14—last column). FIG. 13 illustrates best median $r^2$ for the best models for each outcome variable. Models selected were using Scales+sMRI+fMRI as the input feature set and Elastic Net. Next to each outcome variable, the corresponding number of non-zero features (p) returned by the model appears.

Figure 14A:
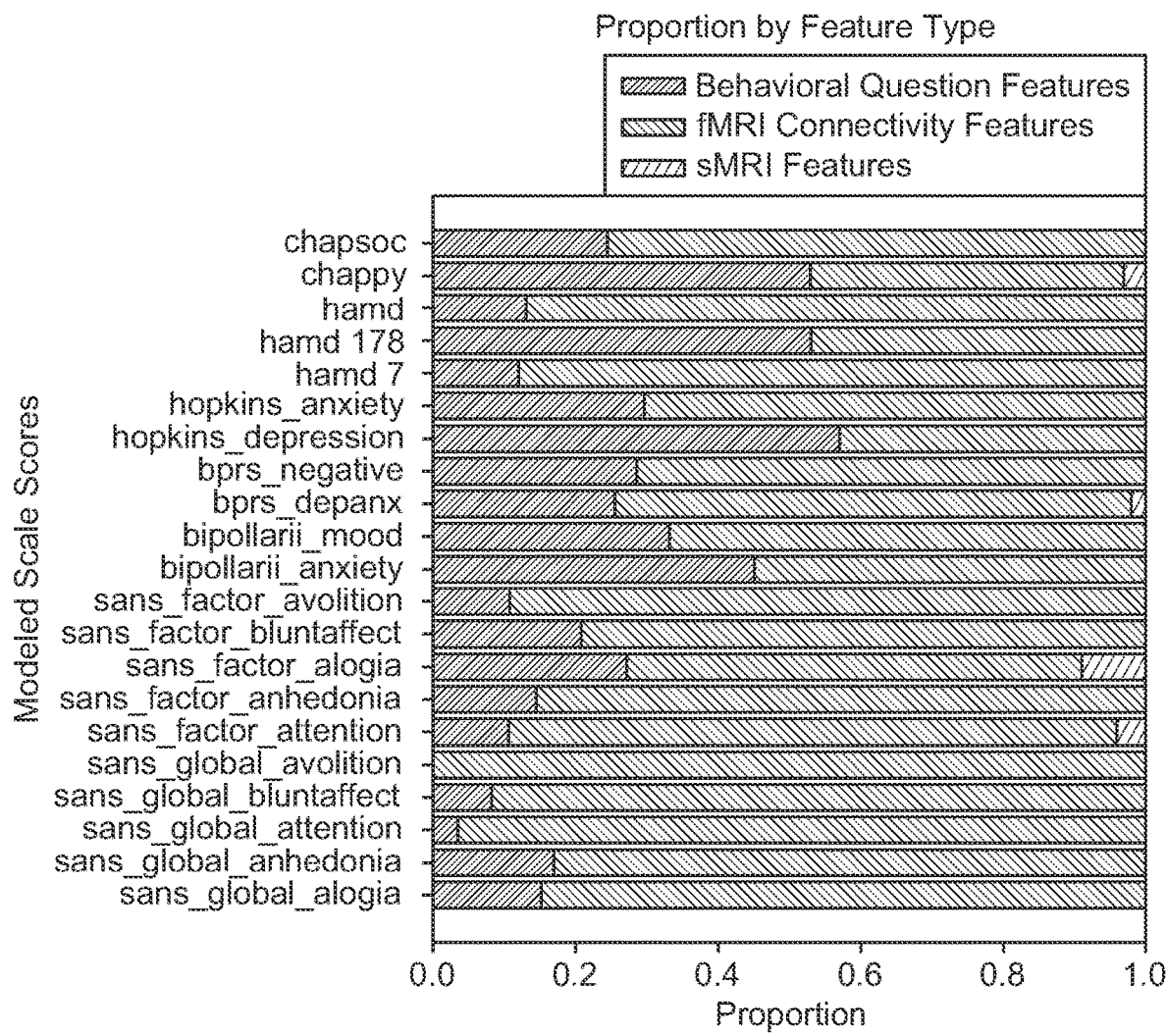
FIGS. 14A-14B illustrate proportions of feature types in best models, according to some implementations of the present disclosure.
Figure 14B:
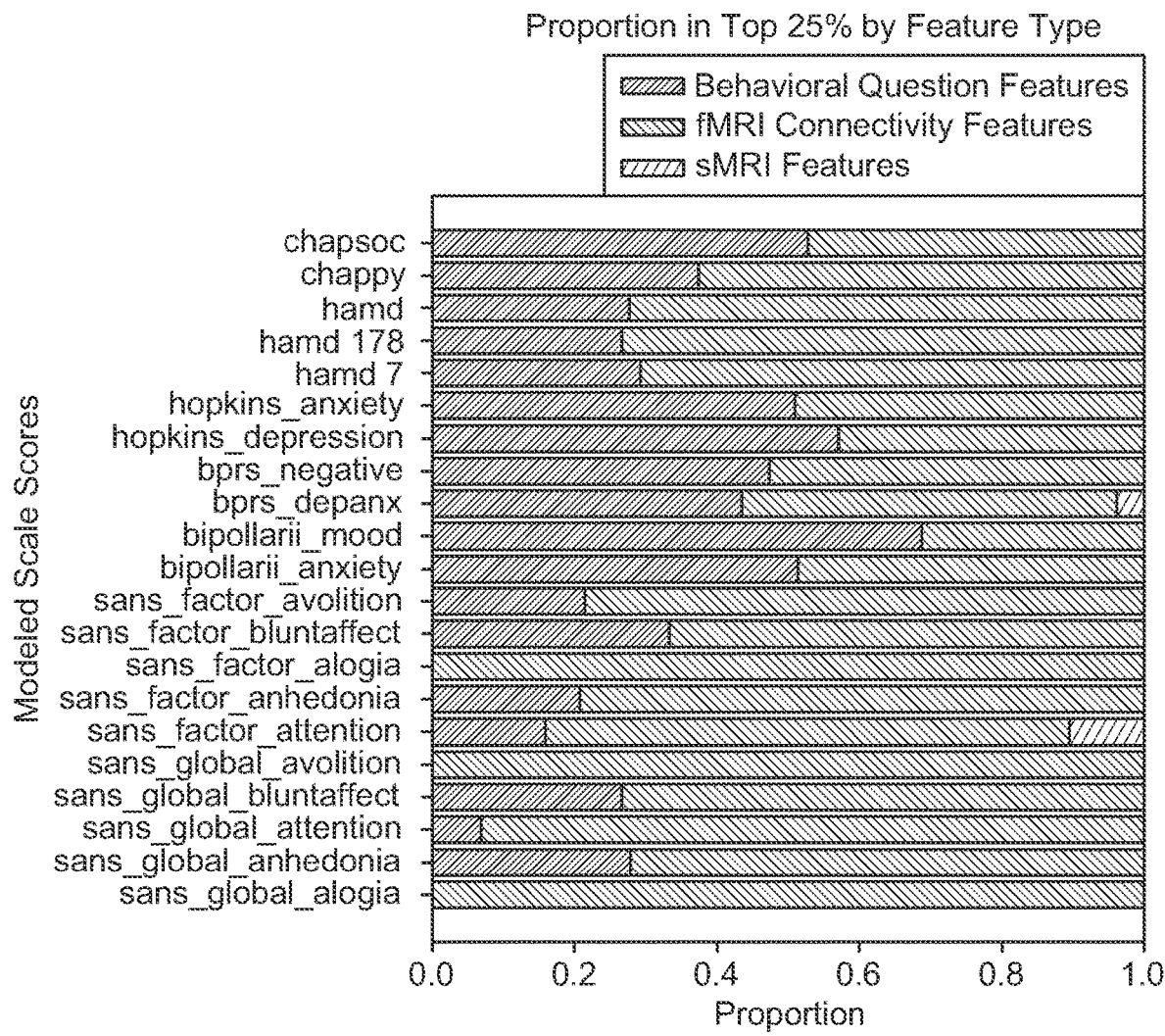
Figure 15A:
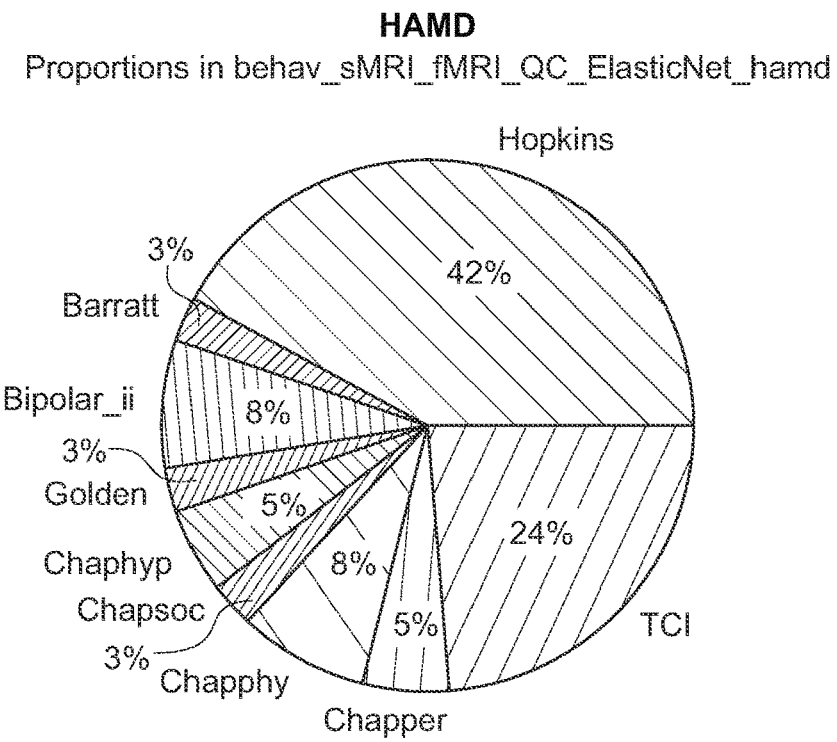
FIGS. 15A-15F illustrate proportions of features from each scale for best model predicting depression or depressed mood, according to some implementations of the present disclosure.
Figure 15B:
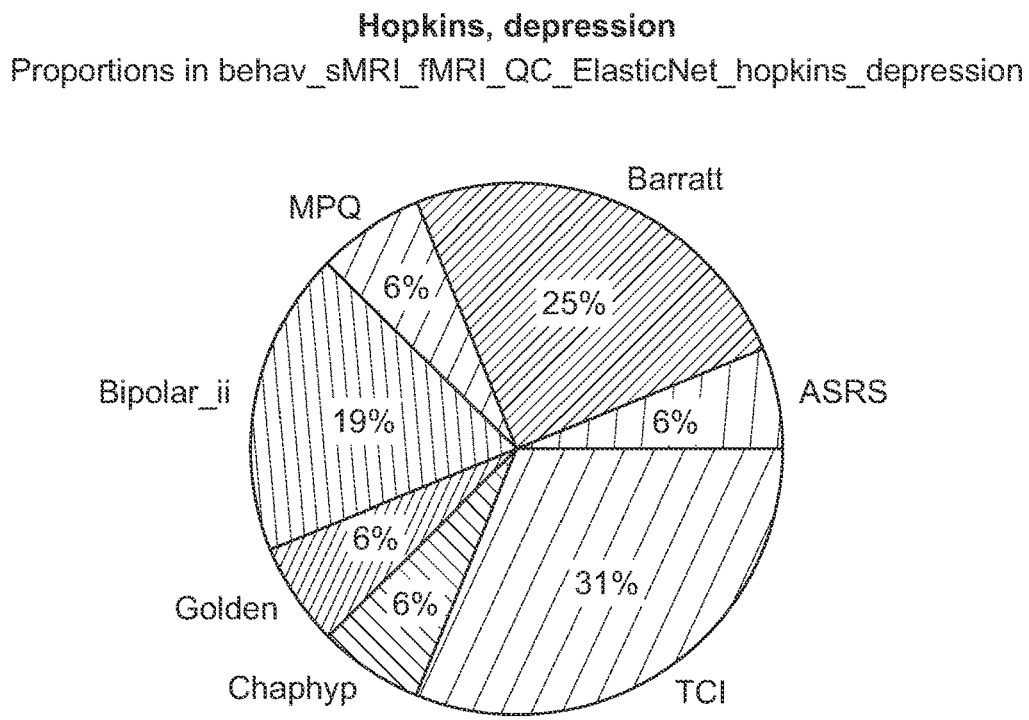
Figure 15C:
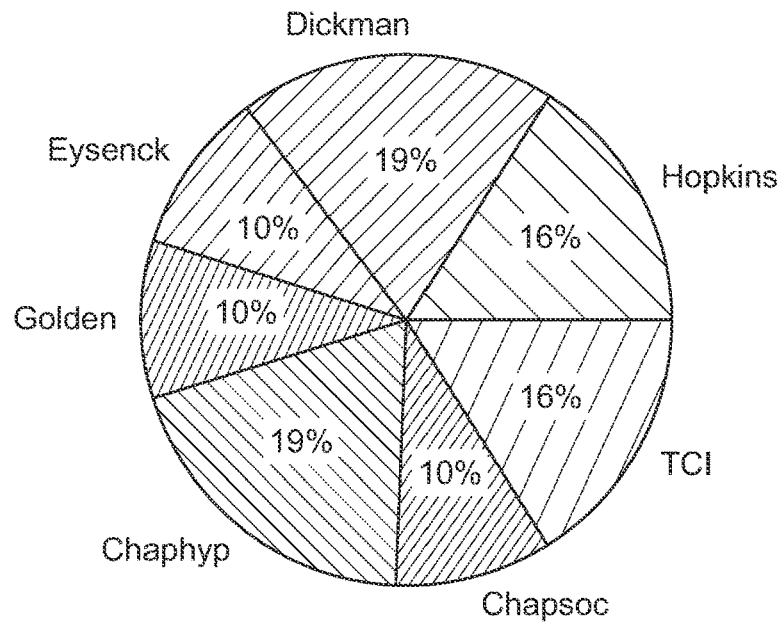
Figure 15D:
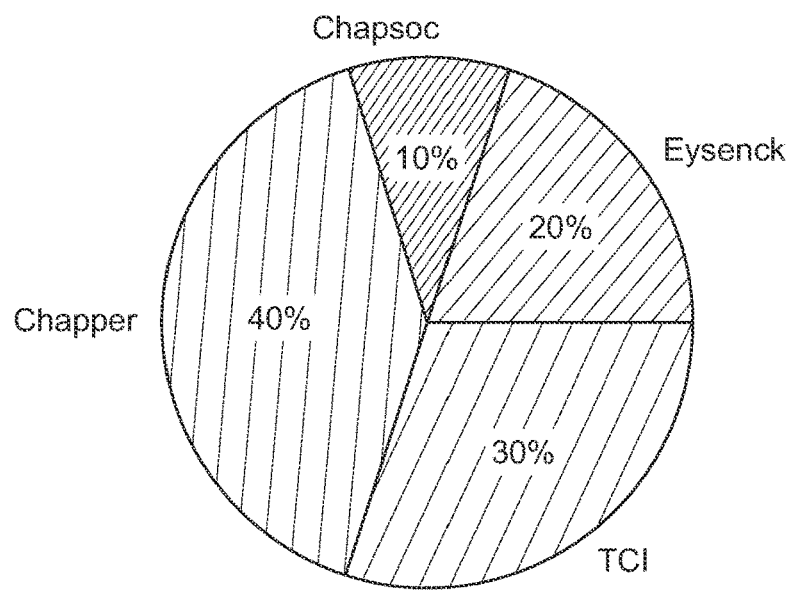
Figure 15E:
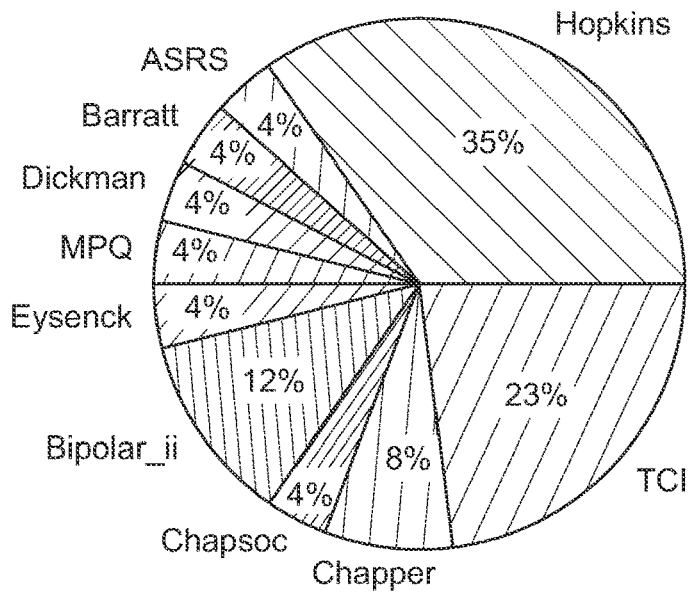
Figure 15F:
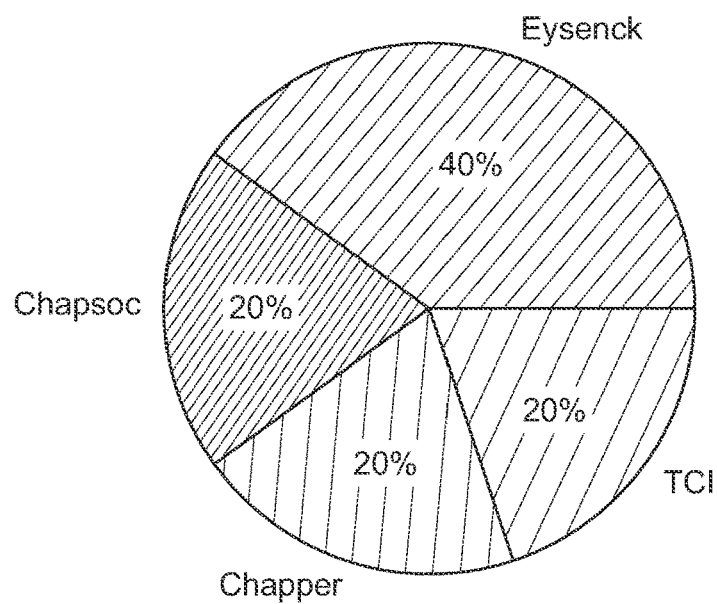
Figure 16A:
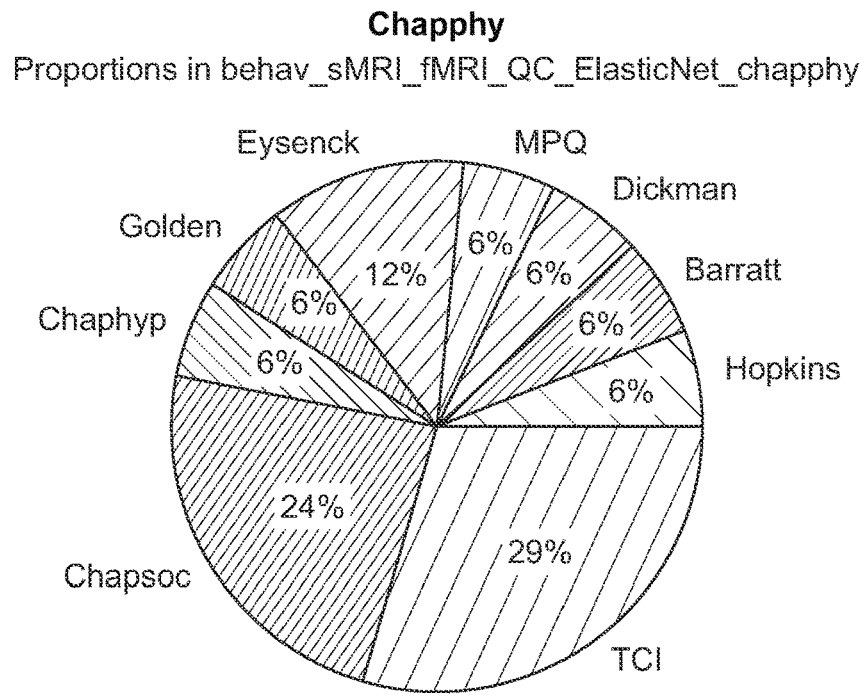
FIGS. 16A-16E illustrate proportions of features from each scale for best model predicting anhedonia, according to some implementations of the present disclosure.
Figure 16B:
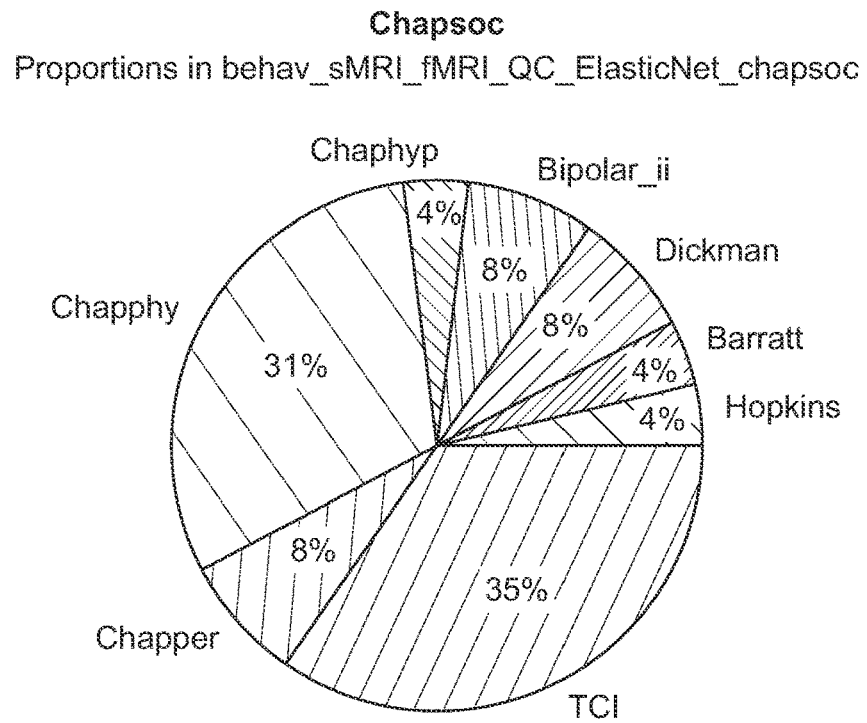
Figure 16C:
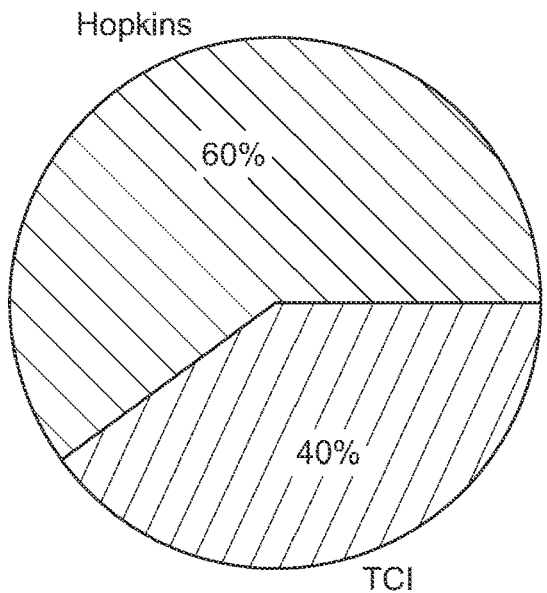
Figure 16D:
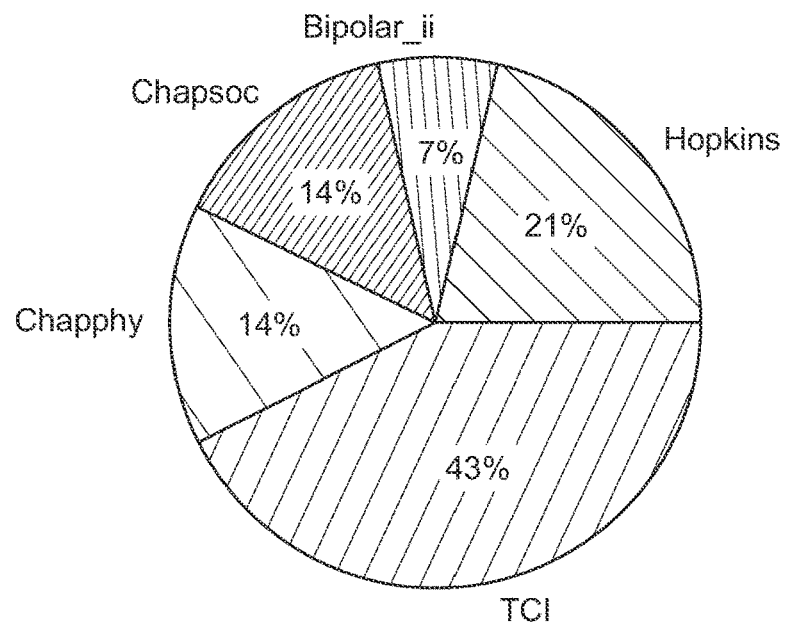
Figure 16E:
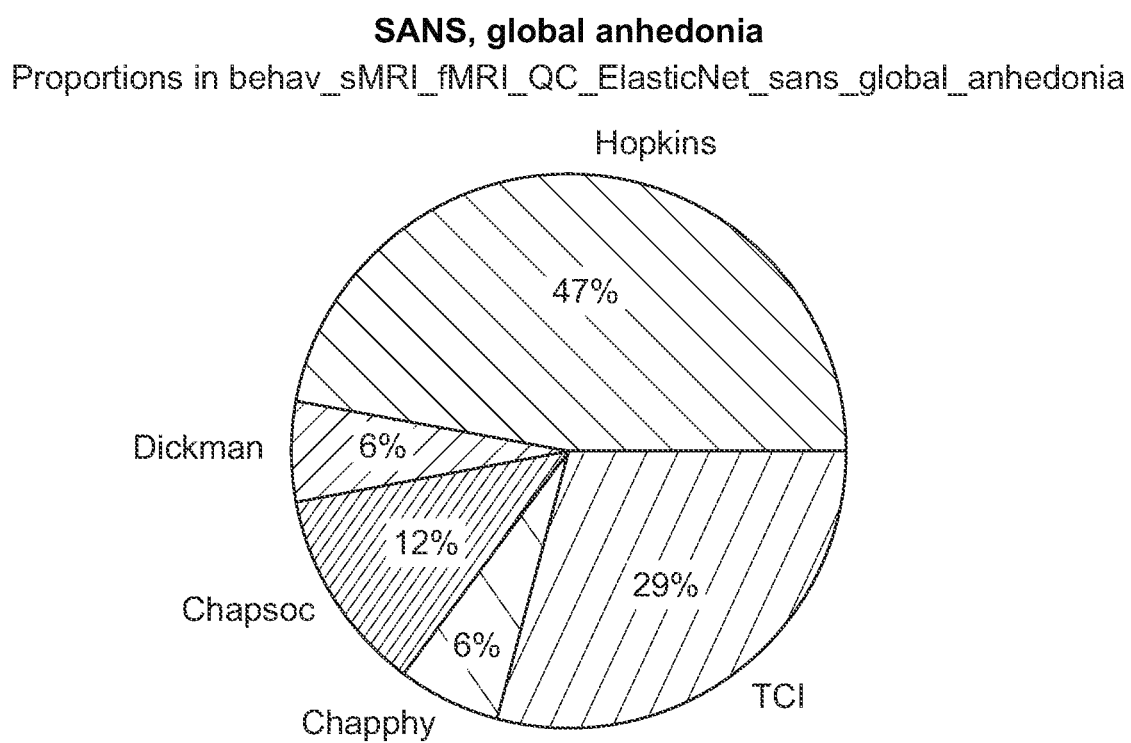

Next, turning to FIGS. 14A-14B, proportions of features derived from scale, fMRI, and sMRI feature sets were compared, for the best model for each outcome variable, both among the whole feature set and the top 25% of features. FIGS. 14A-14B illustrate proportions of feature types in best models. More specifically, FIG. 14A illustrates proportion of all features returned by the model. The densest hatching plots proportion of features from scales; the hatching with medium density plots proportion from fMRI connectivity measures; and the least dense hatching plots proportion from sMRI measures. FIG. 14B illustrates proportion of feature types in the top 25% of features returned by the model. Thus, FIG. 14B demonstrates that for many outcome variables there is a disproportionate number of scale features in the top features though there are more fMRI features overall in the models (see FIG. 14A).

There is a paucity of sMRI features in both the whole feature set and the top quarter of features. Groupings of the scale-based features were further examined. The groups were sorted by proportion of the scales from which they are derived. For each model, grouped by symptom type of the outcome variable, the scale features for the best model are proportionately selected from the scales shown in FIGS. 15A-18G. The TCI scale in particular is often represented among the top scales by proportion.

Figure 17A:
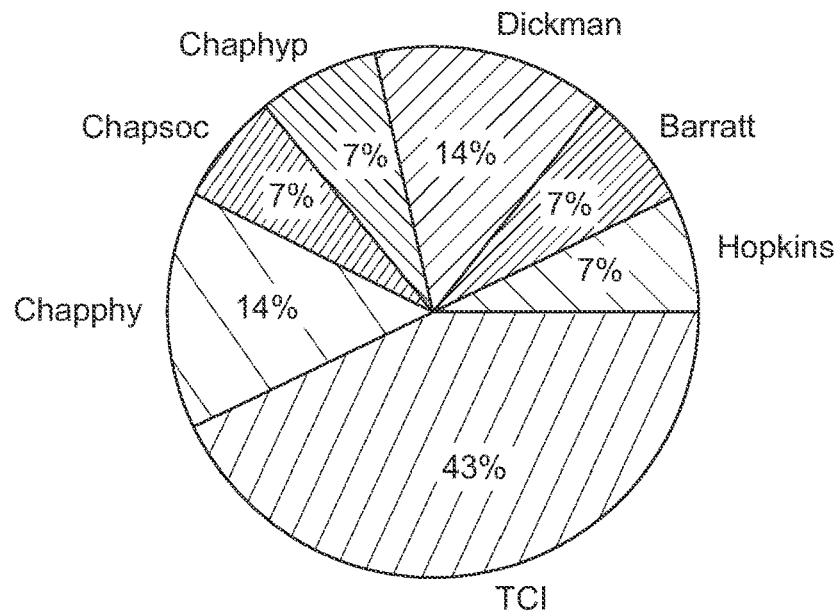
FIGS. 17A-17B illustrate proportions of features from each scale for best model predicting anxiety, according to some implementations of the present disclosure.
Figure 17B:
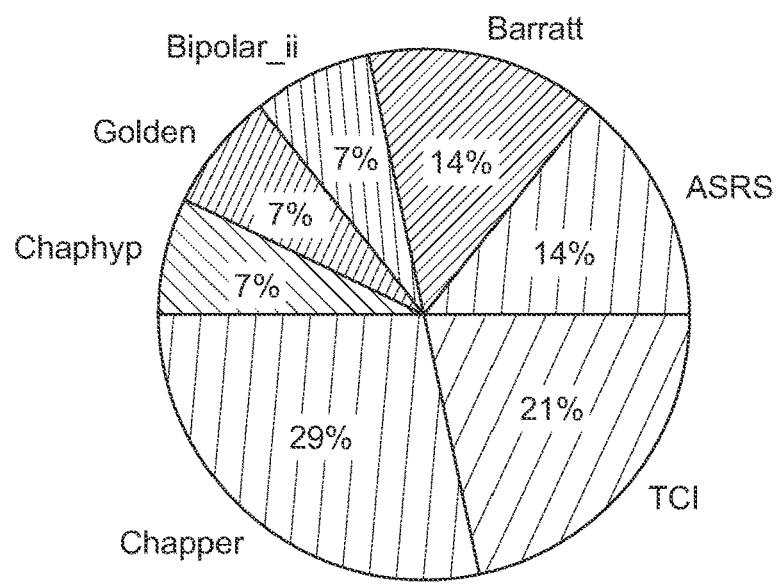
Figure 18A:
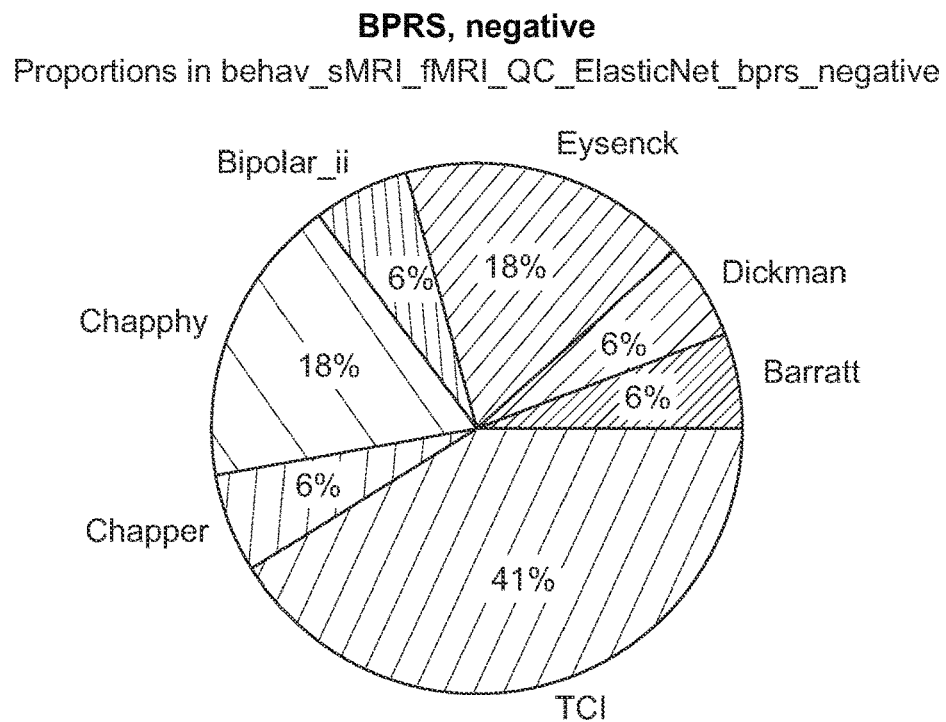
FIGS. 18A-18G illustrate proportion of features from each scale for best model predicting negative symptoms, according to some implementations of the present disclosure.
Figure 18B:
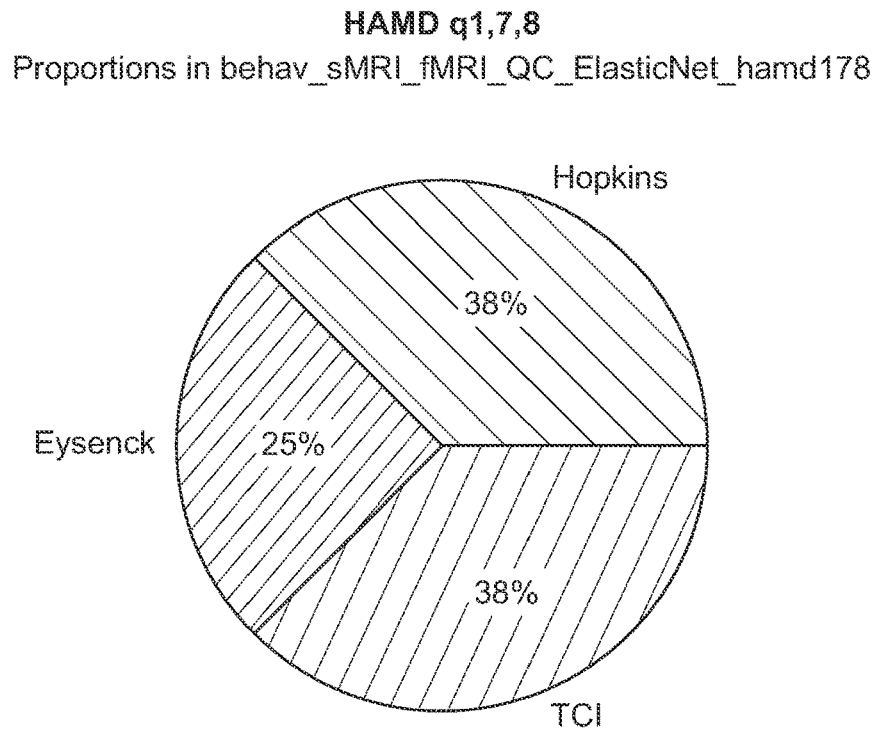
Figure 18C:
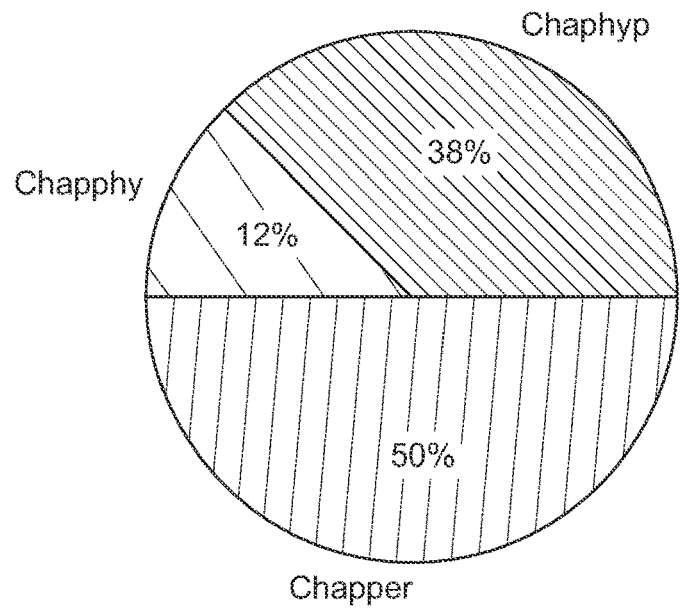
Figure 18D:
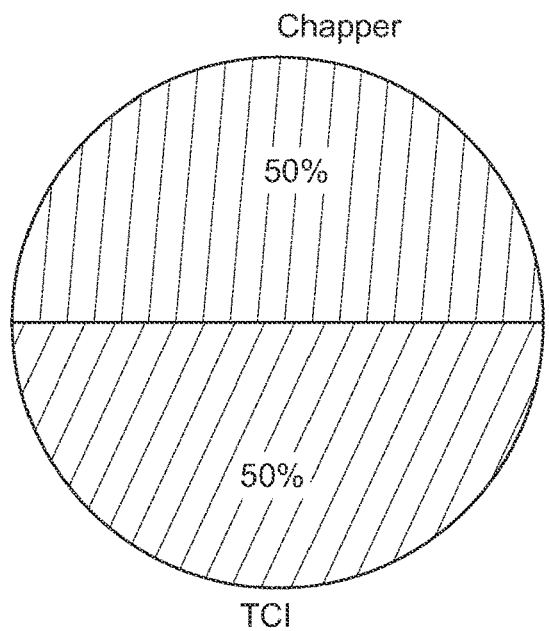
Figure 18E:
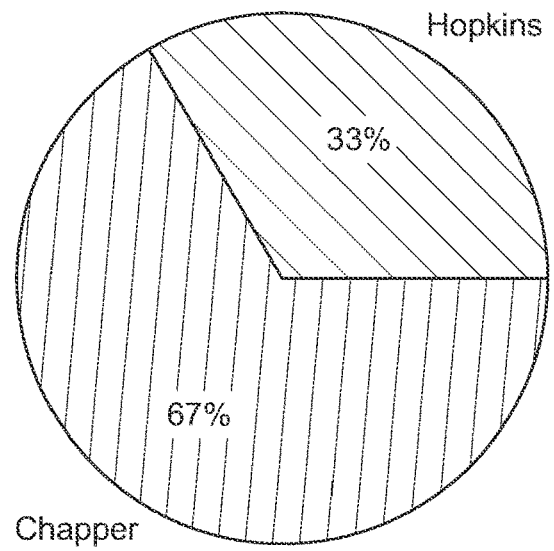
Figure 18F:
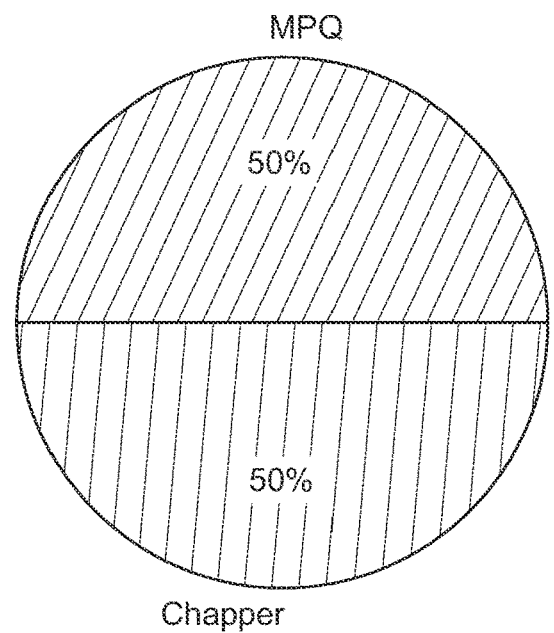
Figure 18G:
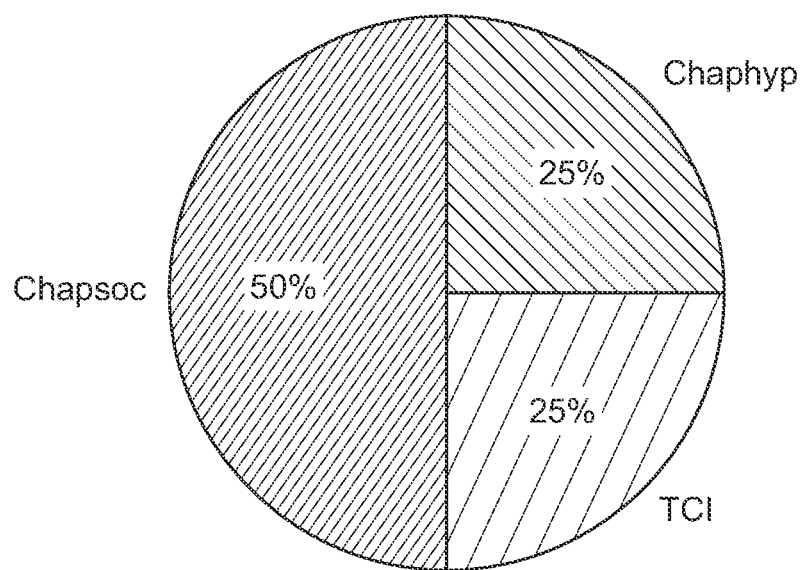
Figure 19A:
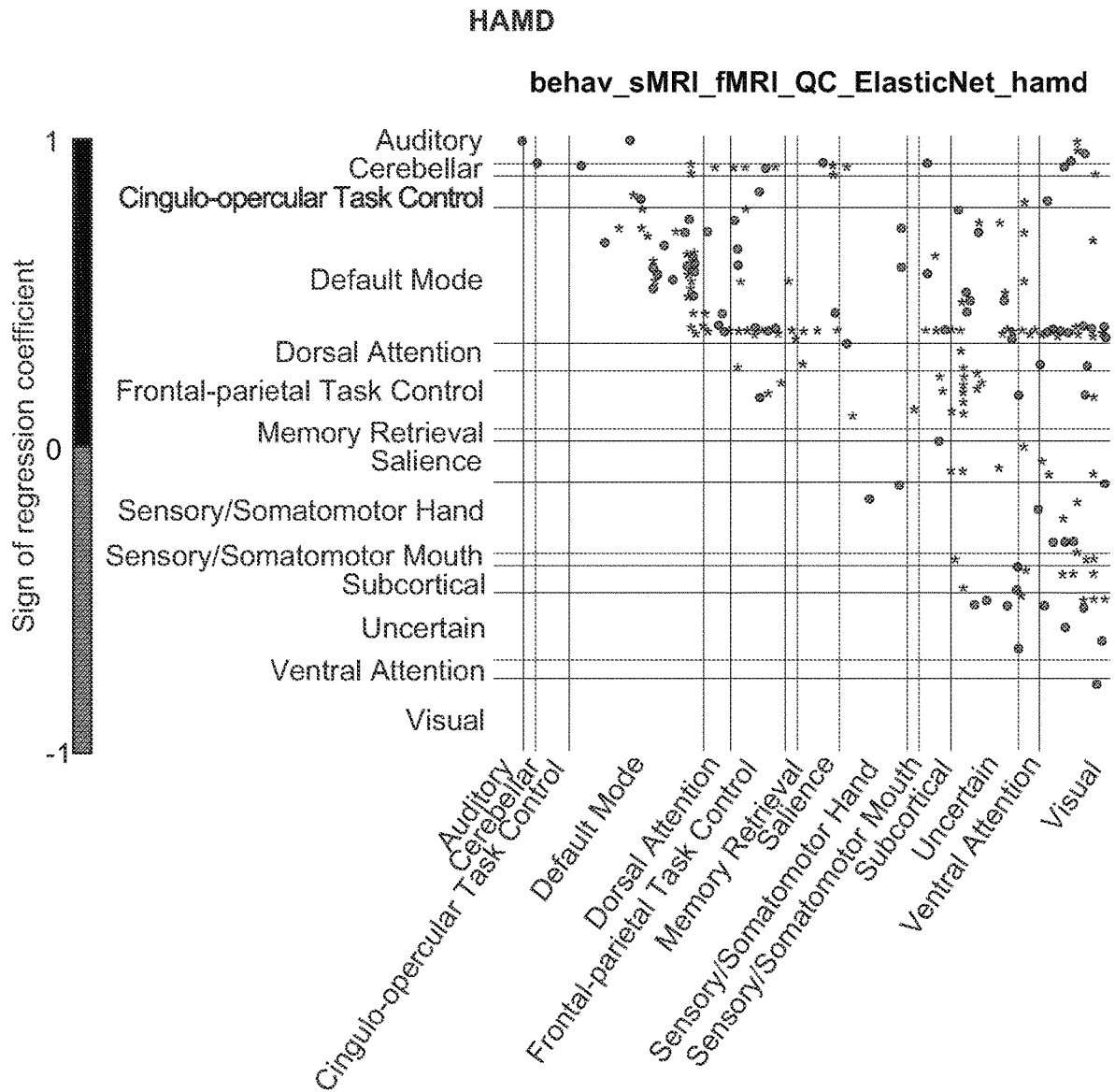
FIGS. 19A-19F illustrate binary heat maps for fMRI connectivity features of best model predicting depression or depressed mood, according to some implementations of the present disclosure.
Figure 19B:
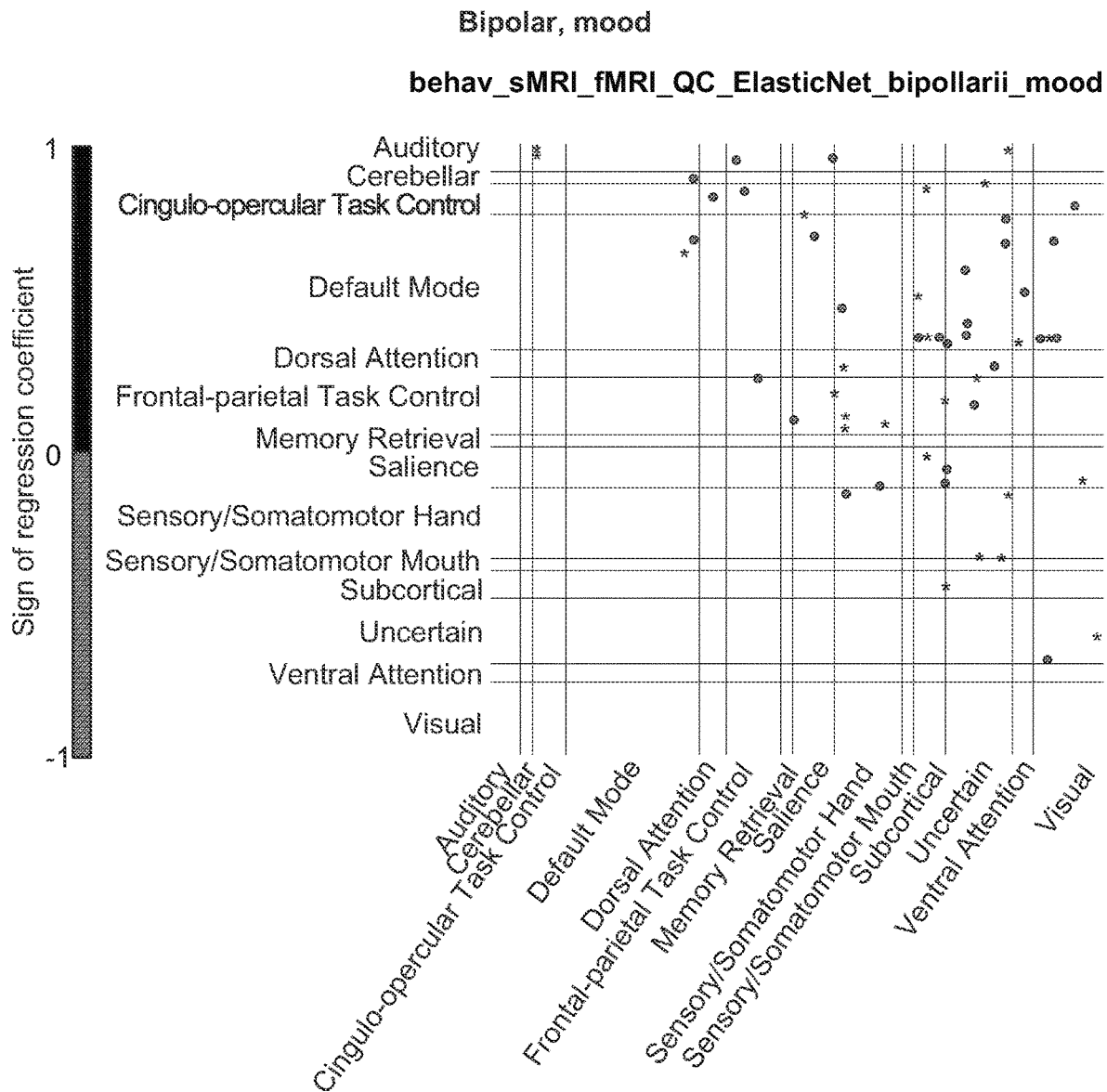
Figure 19C:
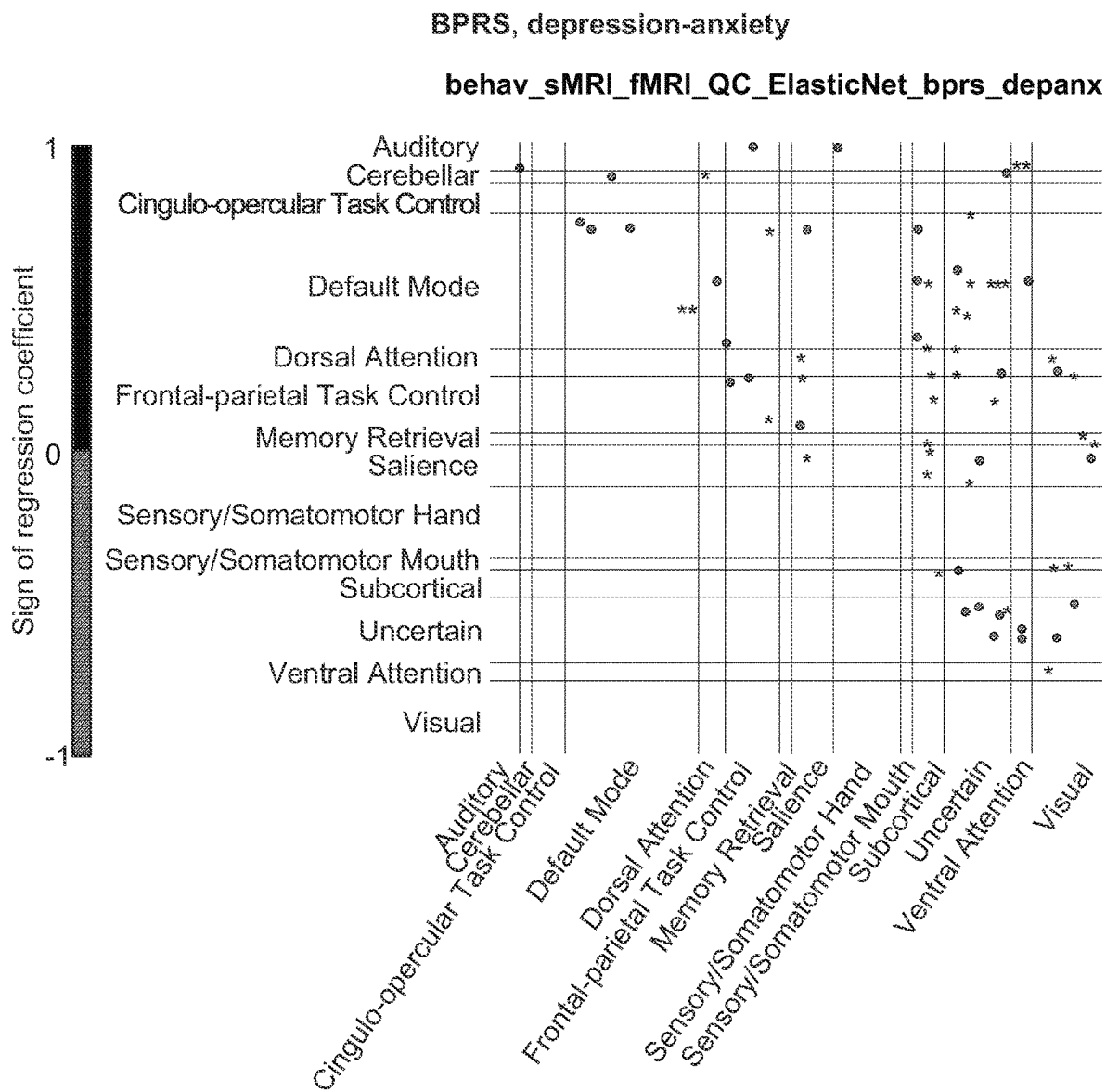
Figure 19D:
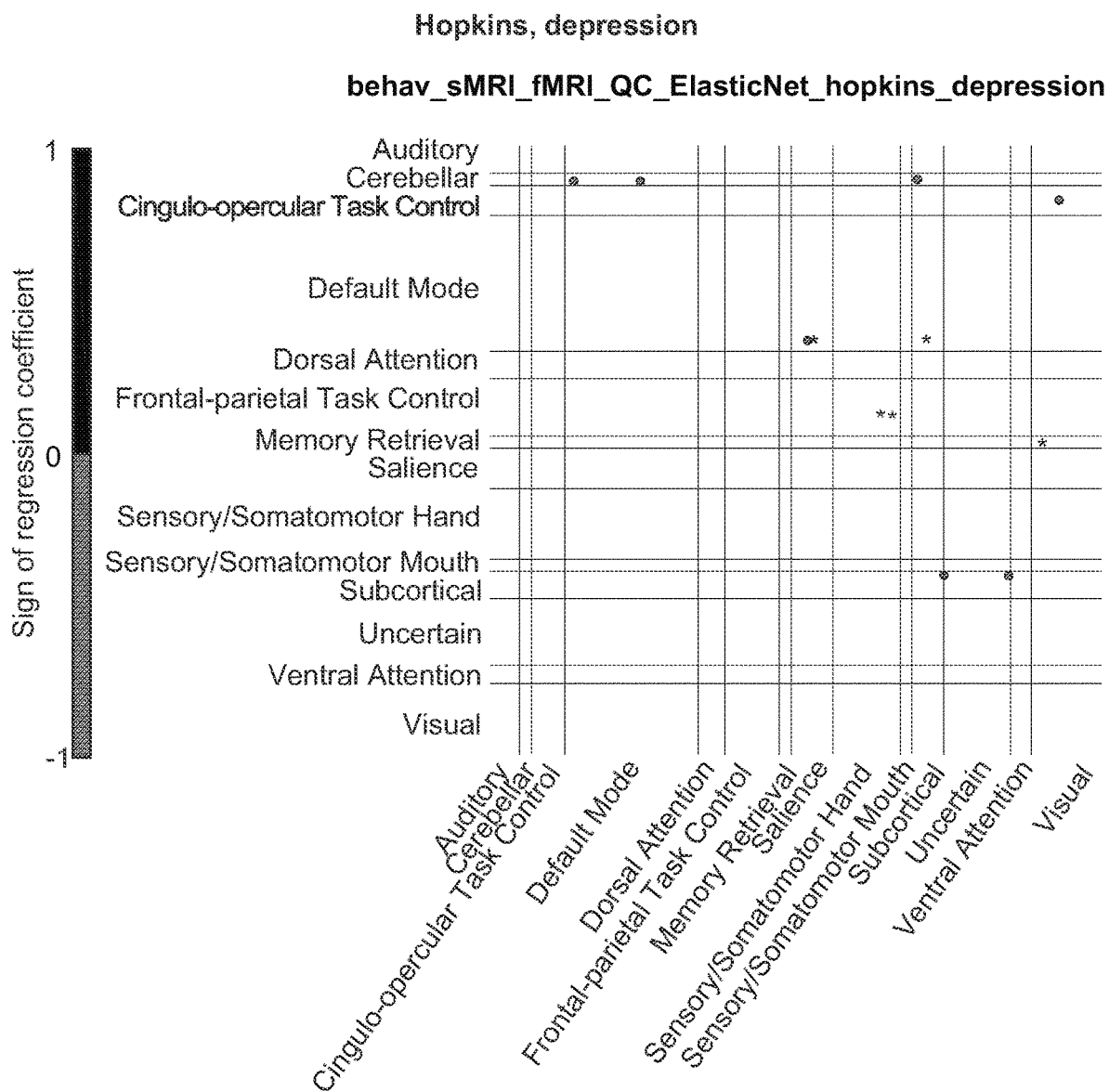
Figure 19E:
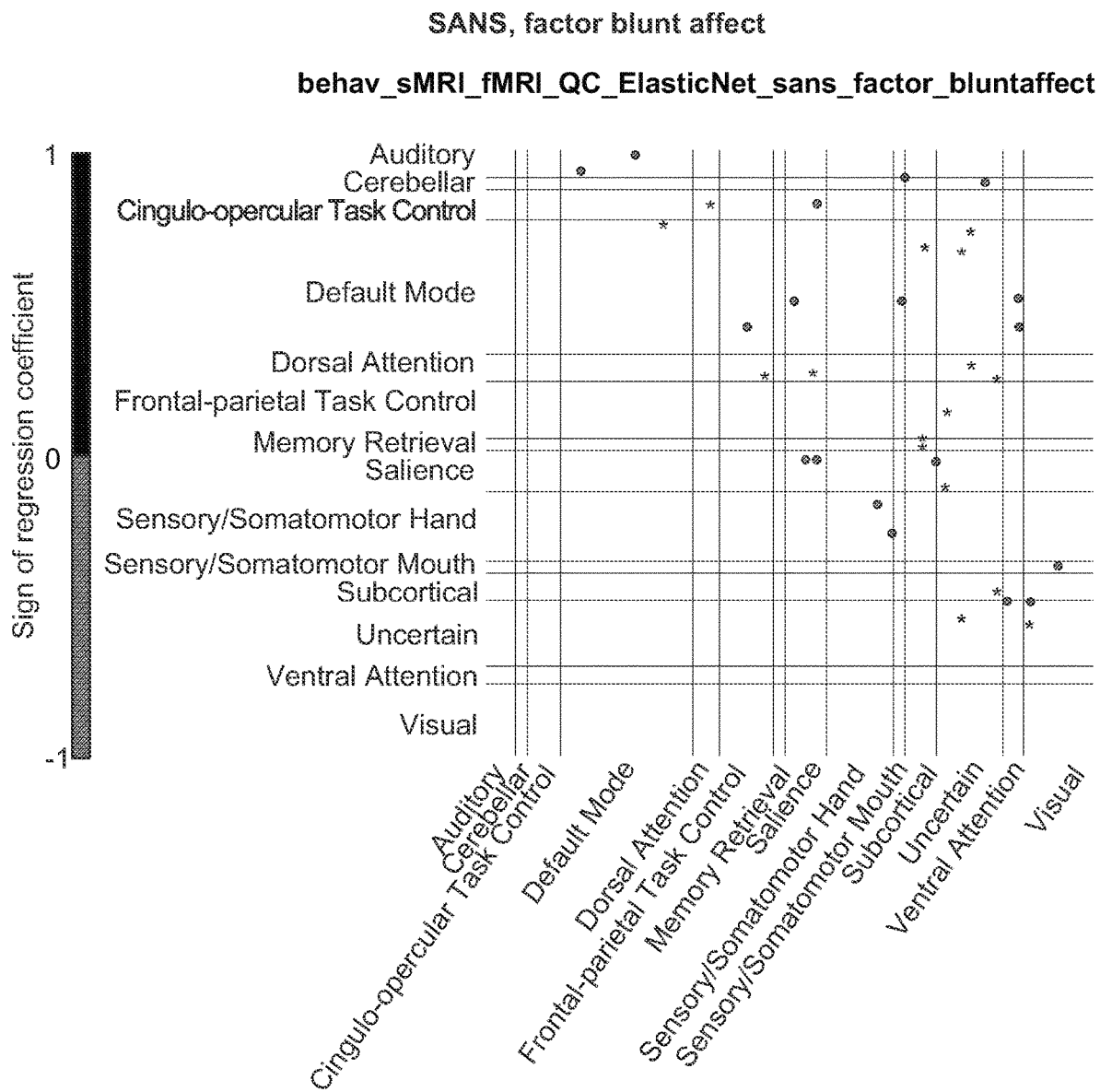
Figure 19F:
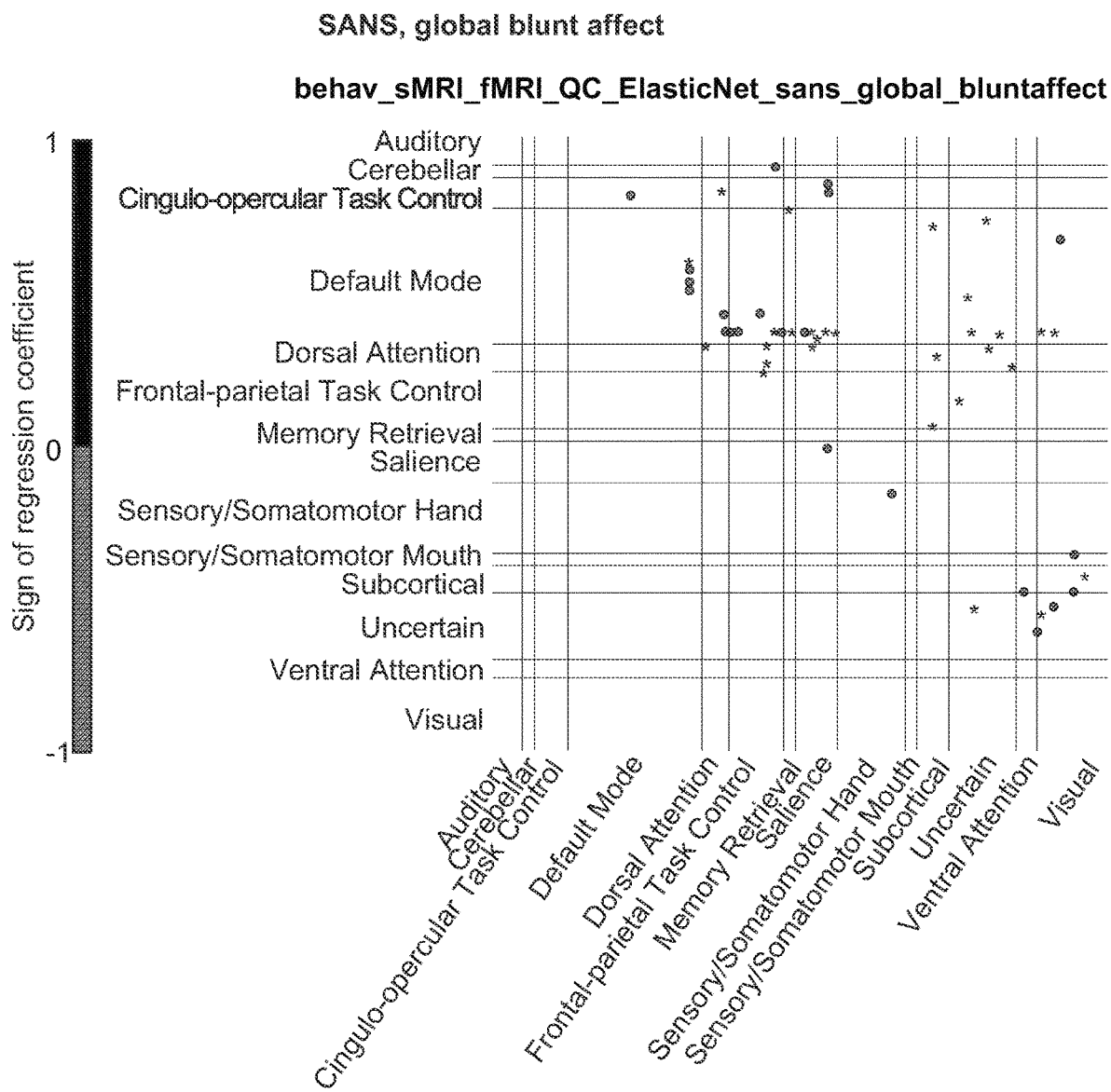
Figure 20A:
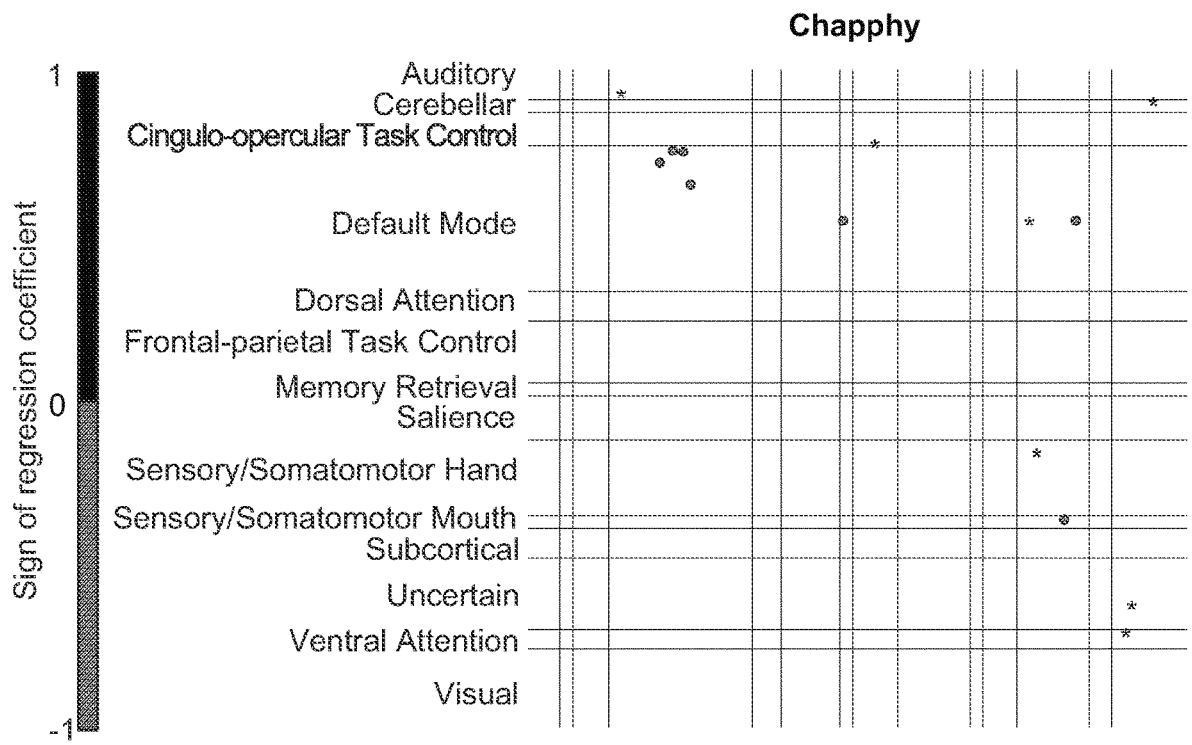
FIGS. 20A-20E illustrate binary heat maps for fMRI connectivity features of best model predicting anhedonia, according to some implementations of the present disclosure.
Figure 20B:
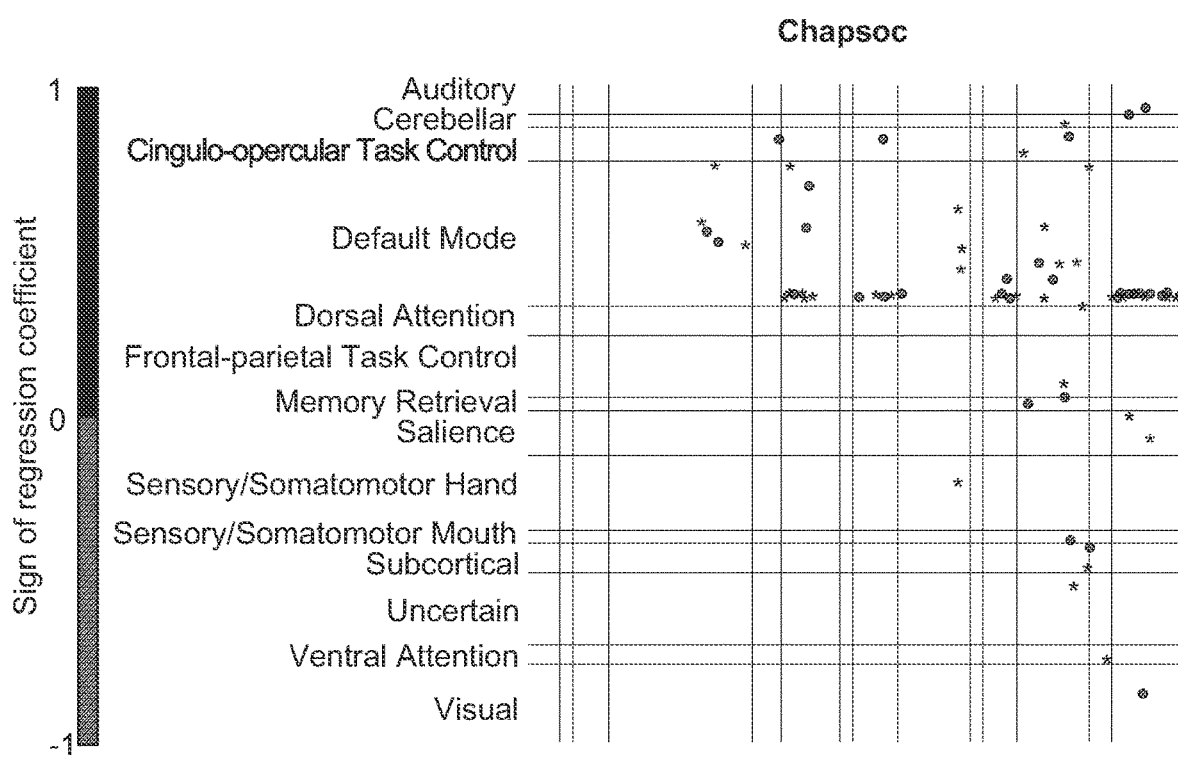
Figure 20C:
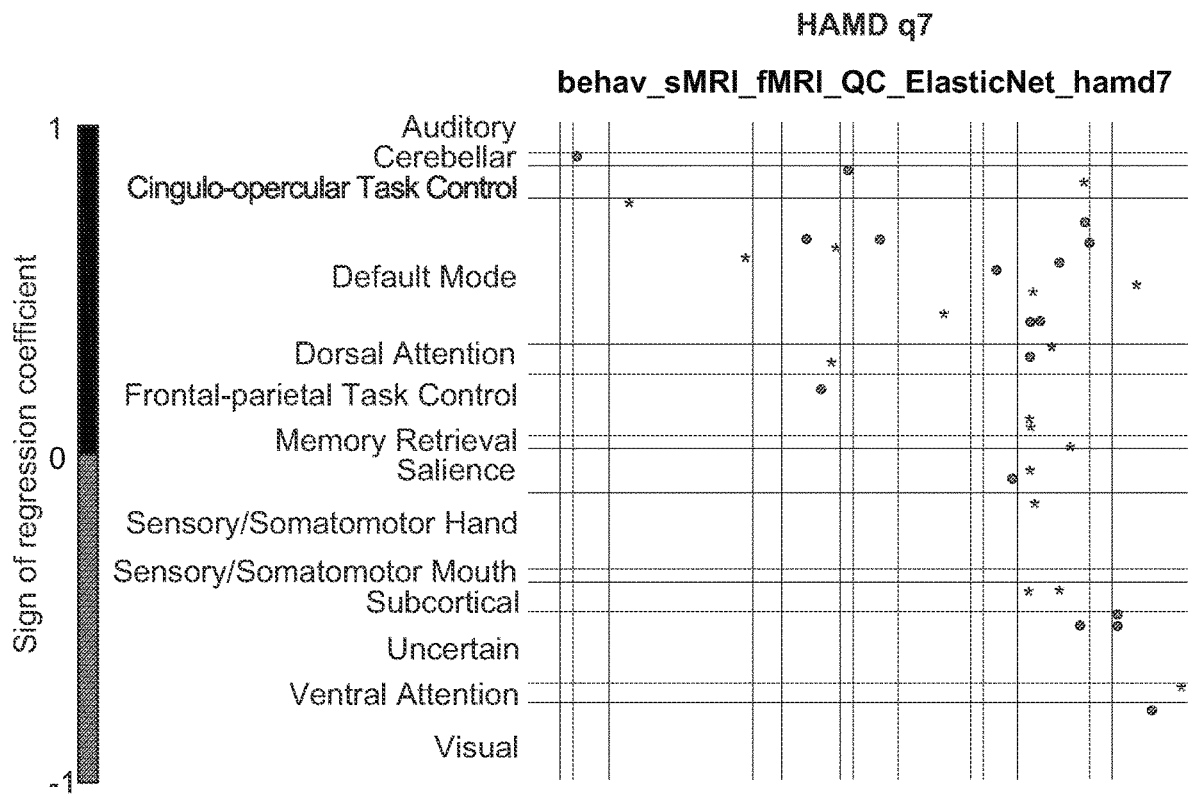
Figure 20D:
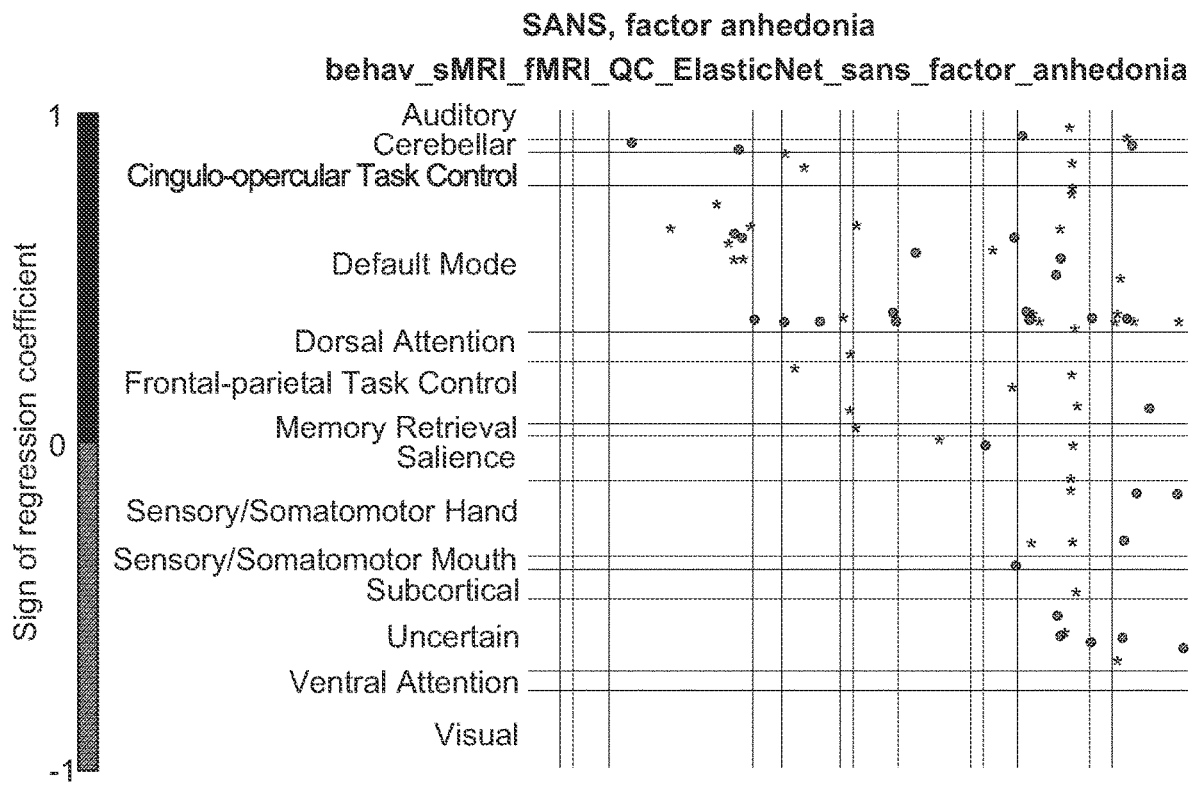
Figure 20E:
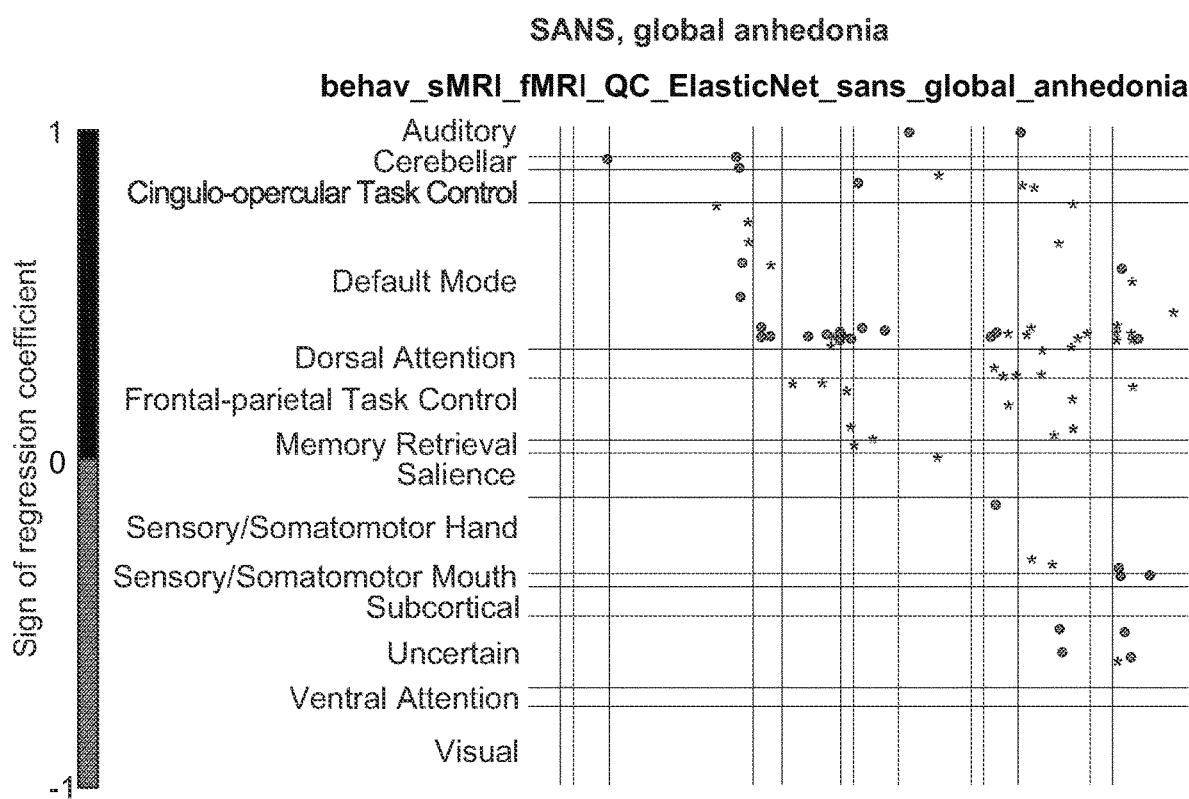
Figure 21A:
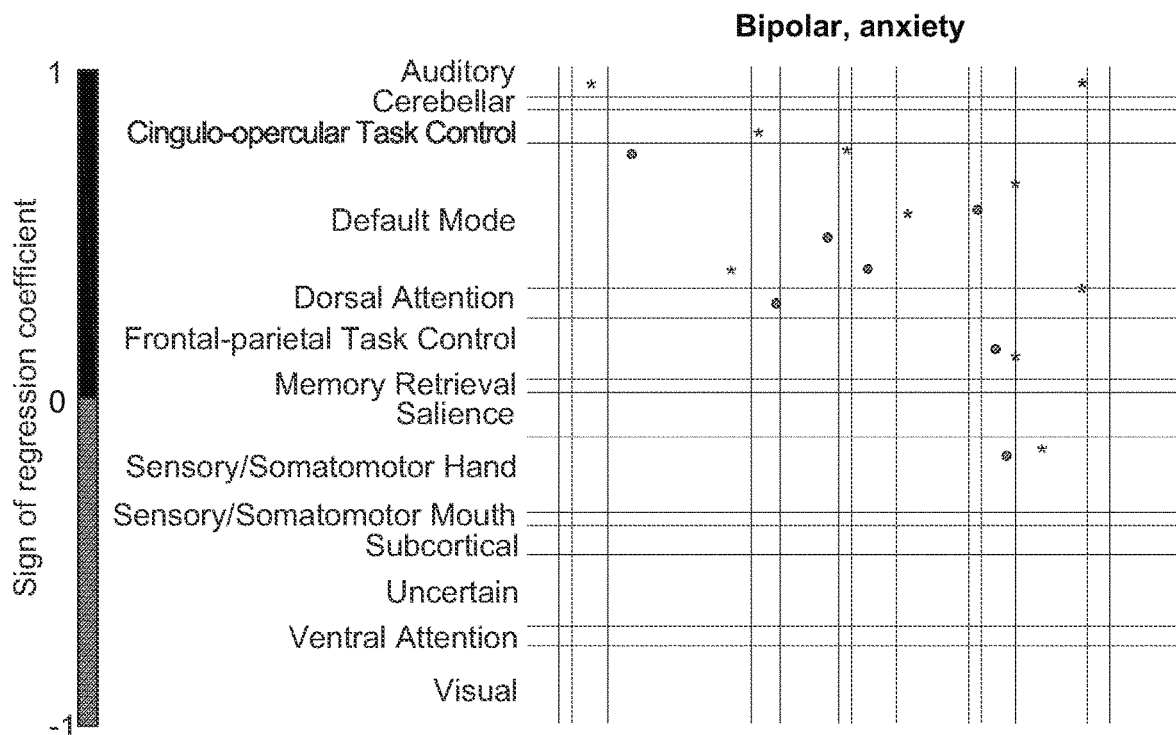
FIGS. 21A-21B illustrate binary heat maps for fMRI connectivity features of best model predicting anxiety, according to some implementations of the present disclosure.
Figure 21B:
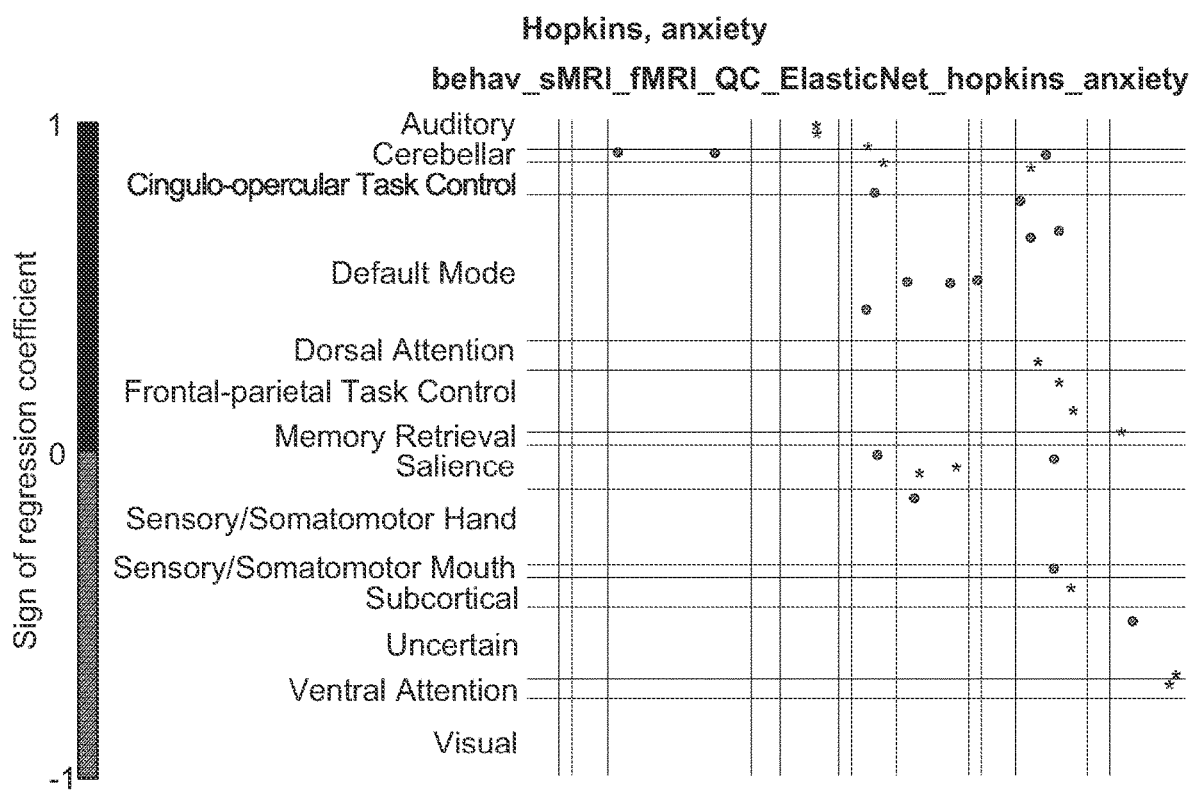
Figure 22A:
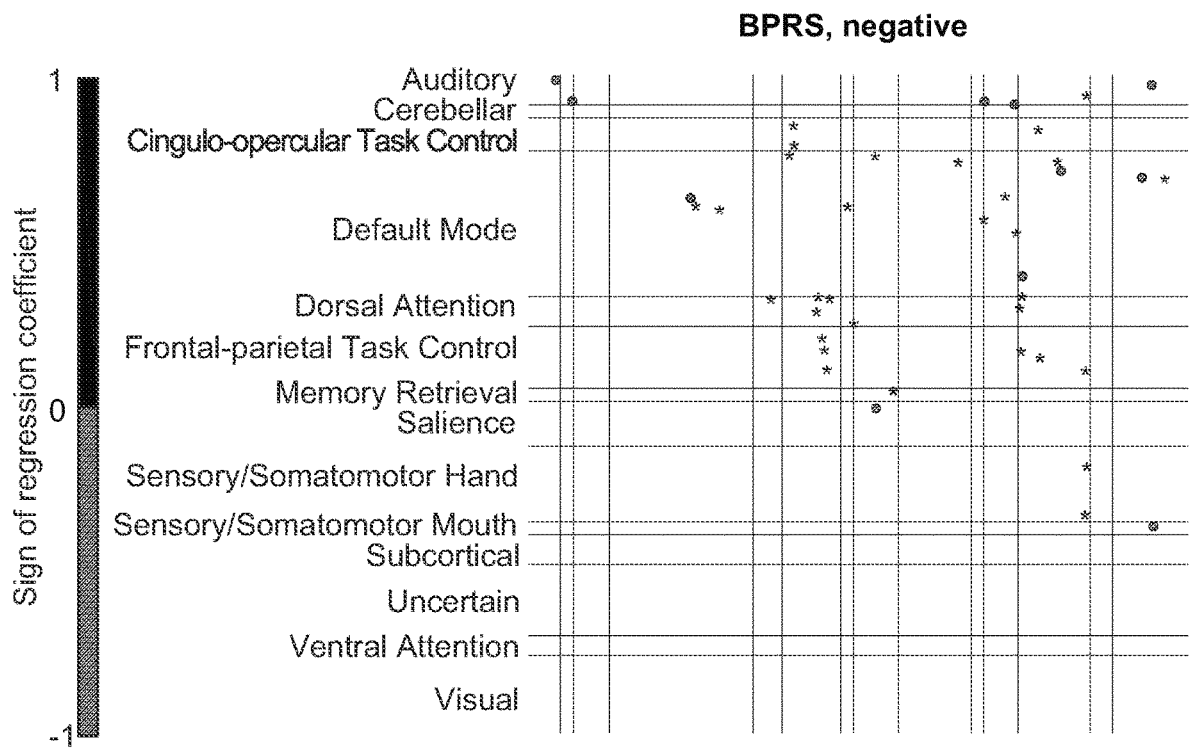
FIGS. 22A-22H illustrate binary heat maps for fMRI connectivity features of best model predicting negative symptoms, according to some implementations of the present disclosure.
Figure 22B:
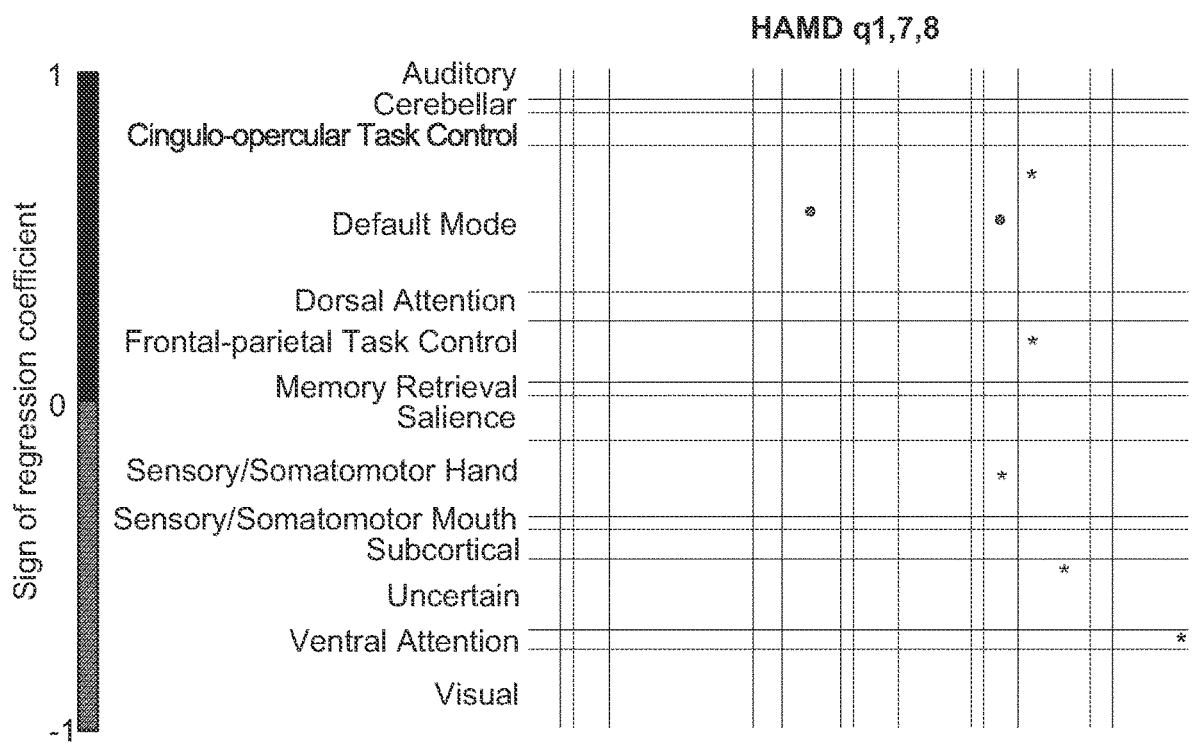
Figure 22C:
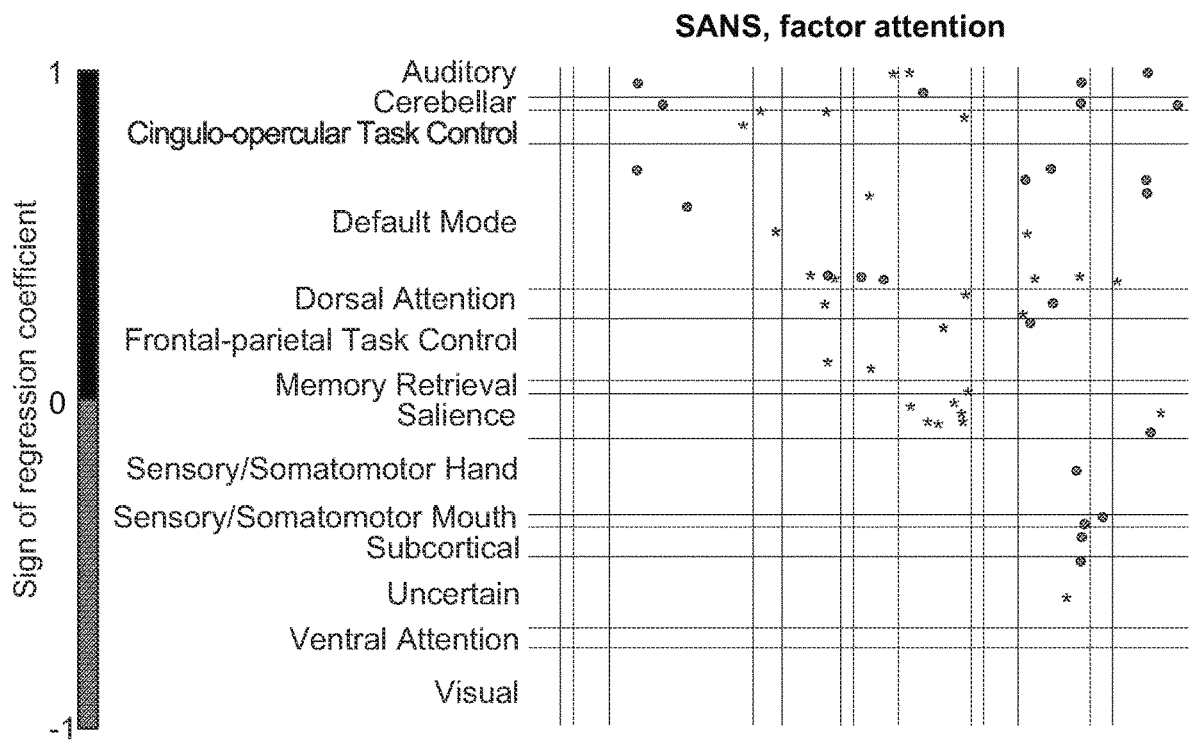
Figure 22D:
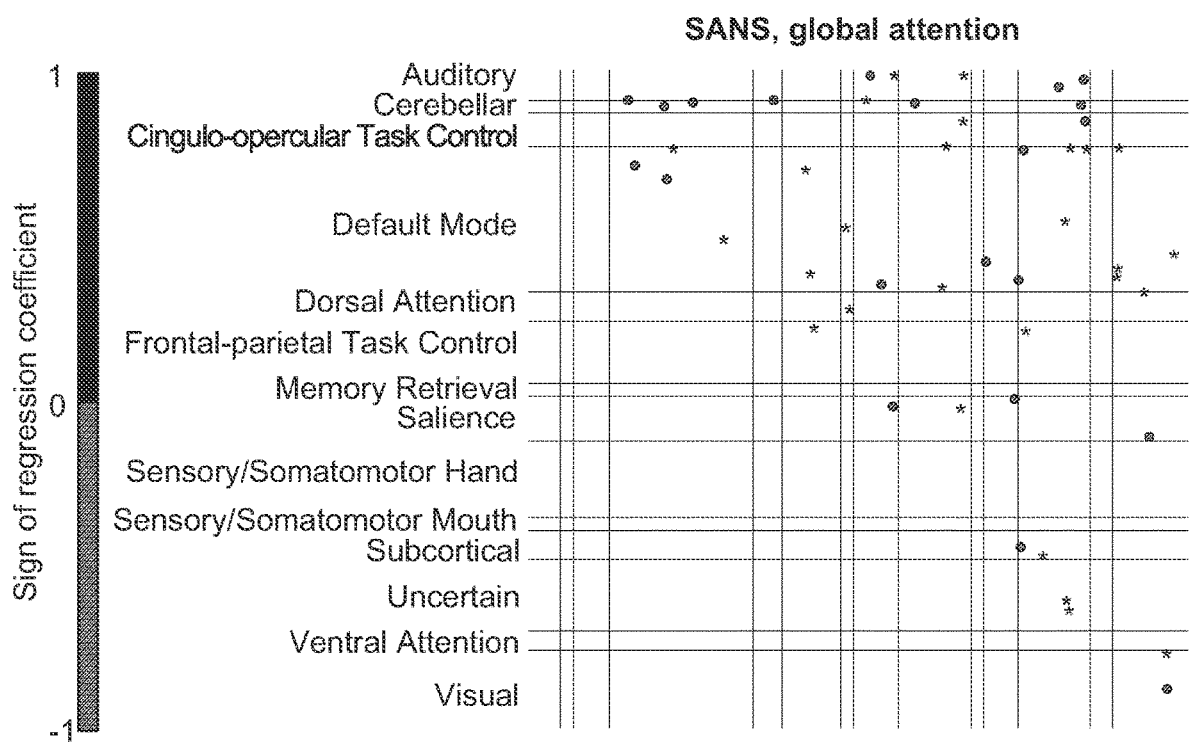
Figure 22E:
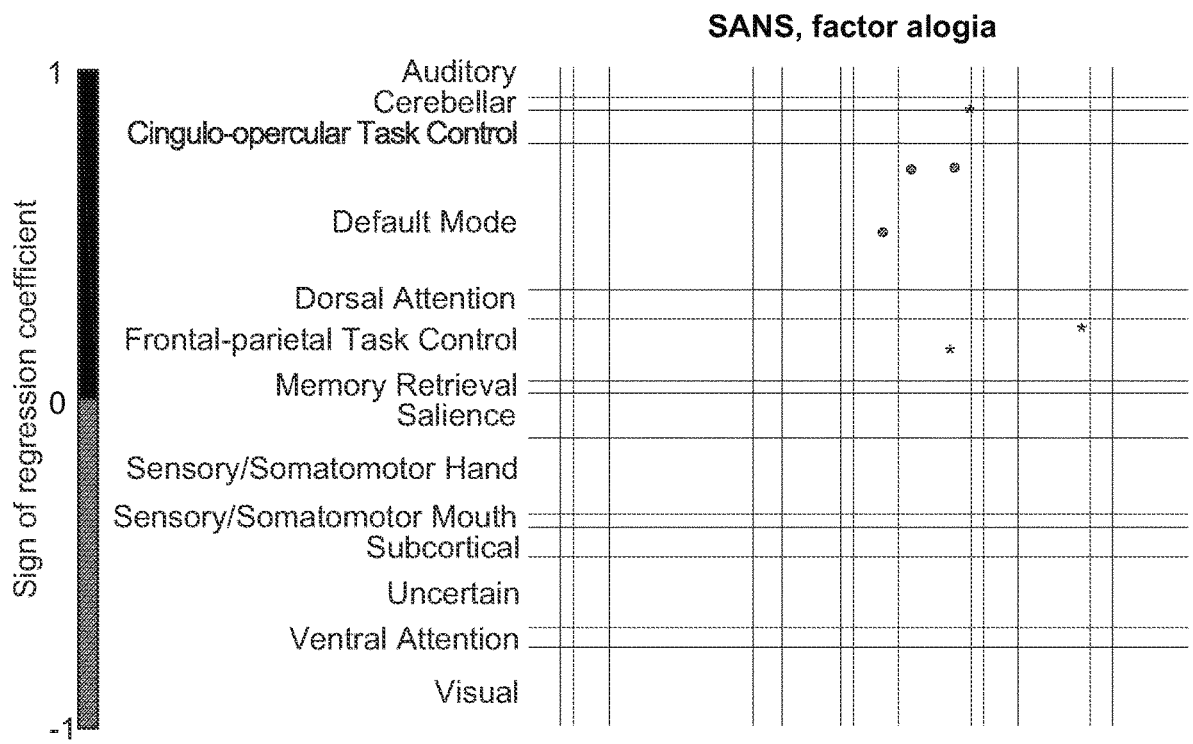
Figure 22F:
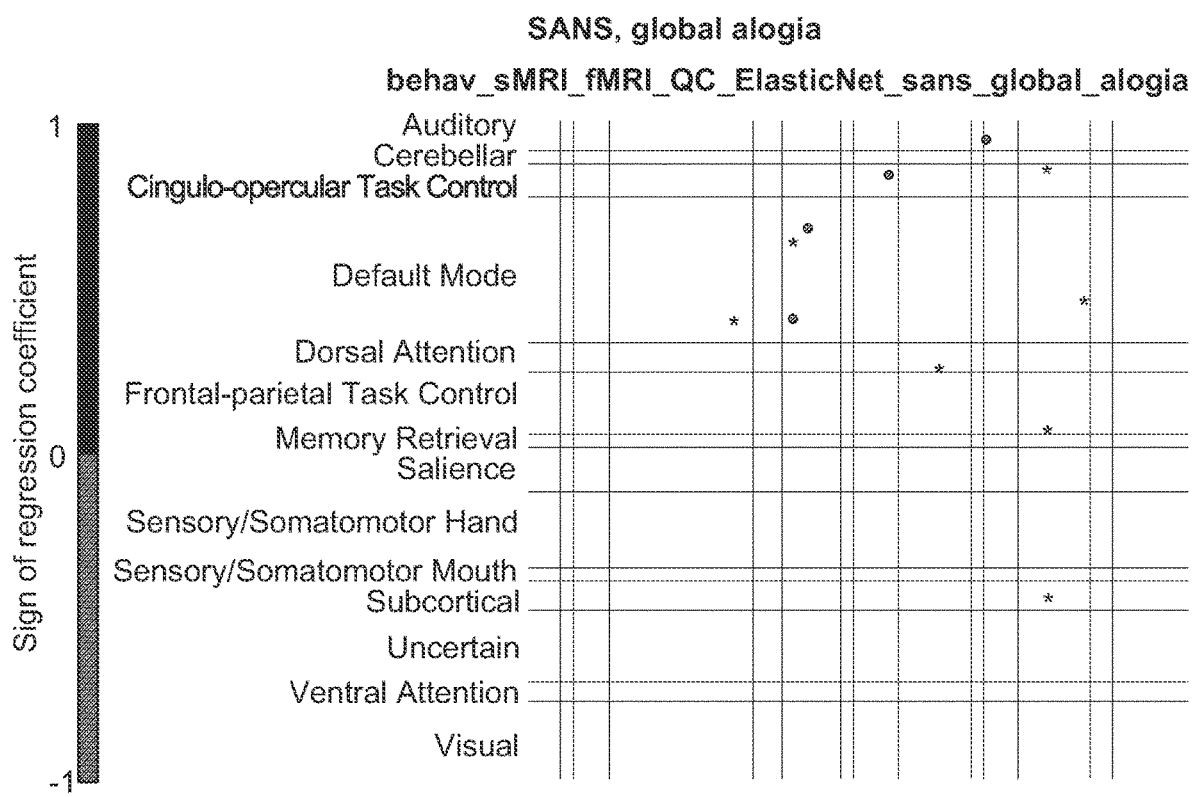
Figure 22G:
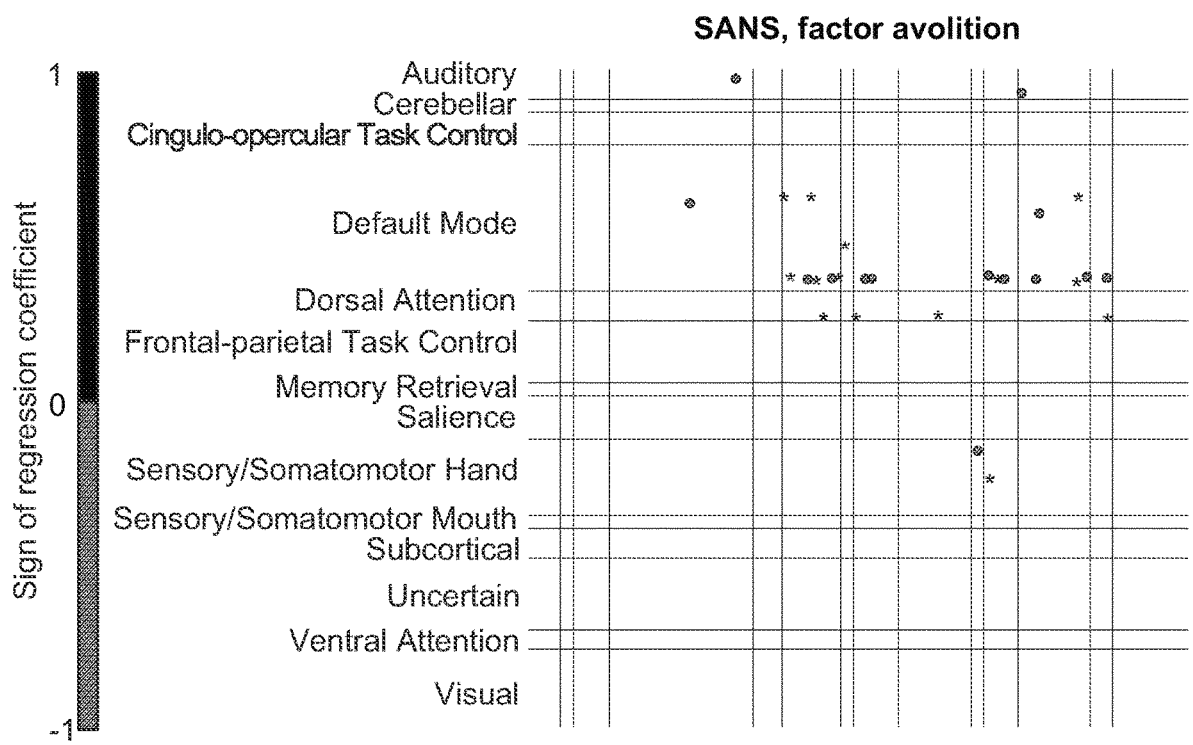
Figure 22H:
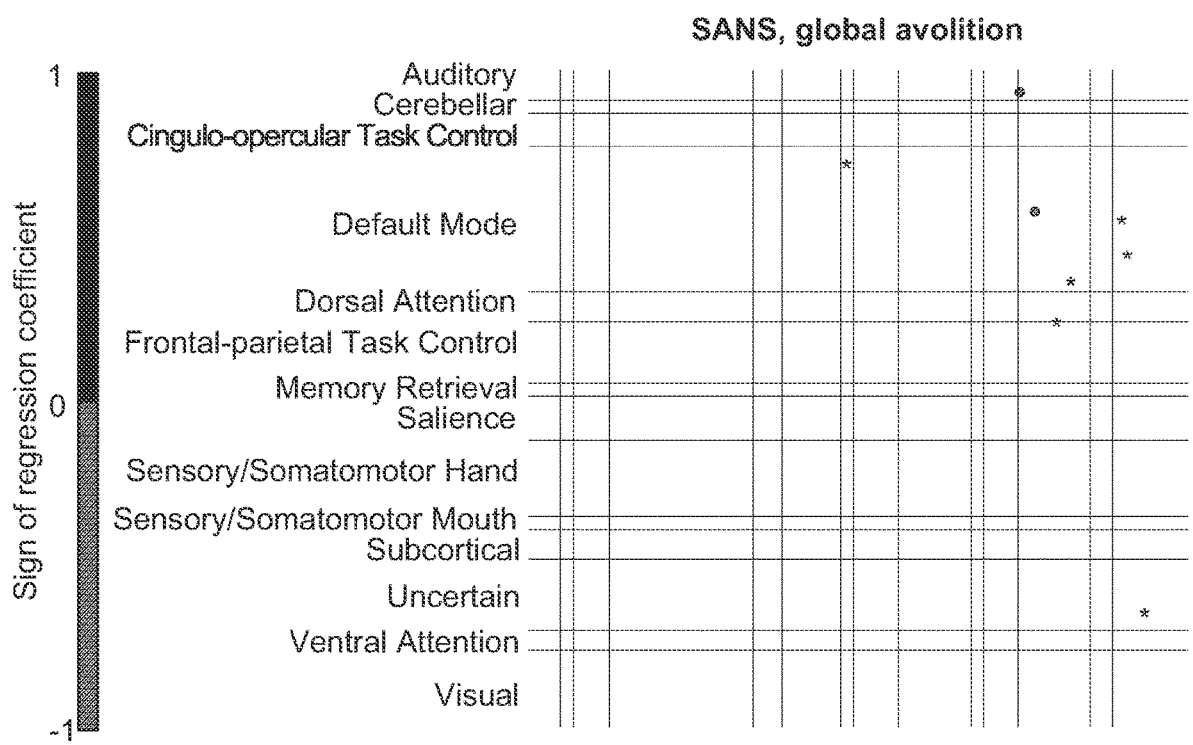

Referring now to FIGS. 15A-15F, proportions of features from each scale are illustrated, for best model predicting depression or depressed mood. Of the features returned by the best model that were scale items, each pie chart illustrates the proportion of those items that were from the corresponding scales for the model for each outcome variable. For example, for the SANS, global blunt affect model, 20% of the scale items were from the TCI scale, 20% from the chapper scale, 20% from the chapsoc scale, and 40% from the Eysenck scale. Similar to FIGS. 15A-15F, FIGS. 16A-16E illustrate proportions of features from each scale for best model predicting anhedonia; FIGS. 17A-17B illustrate proportions of features from each scale for best model predicting anxiety; and FIGS. 18A-18G illustrate proportion of features from each scale for best model predicting negative symptoms.

Turning generally to FIGS. 19A-22H, the fMRI features can also be grouped by suggested canonical resting-state networks from the Power atlas and are shown in the connectivity matrices, according to some implementations of the present disclosure. More specifically, FIGS. 19A-19F illustrate binary heat maps for fMRI connectivity features of best model predicting depression or depressed mood. For all non-zero fMRI connectivity features returned by the respective model, the regression coefficients for each individual edge between two nodes is plotted in the connectivity matrix for that model. Each row and column represents a single ROI from the Power atlas, ordered consistently in both directions. Coefficients have been binarized (positive plotted as stars, negative as circles) for easier viewing of sparse matrices. Upper and lower triangles illustrate redundant information, so only upper triangles are plotted. Lines delineate canonical resting state networks for easier visualization of network category for each feature. Similar to FIGS. 19A-22H, FIGS. 20A-20E illustrate binary heat maps for fMRI connectivity features of best model predicting anhedonia; FIGS. 21A-21B illustrate binary heat maps for fMRI connectivity features of best model predicting anxiety; and FIGS. 22A-22H illustrate binary heat maps for fMRI connectivity features of best model predicting negative symptoms.

Binarized versions of the regression coefficients (pos->1, neg->−1) are plotted for better visualization of the location of features across the networks. Connectivity matrices have the same ROIs and networks listed on both axes, and the lower left triangle is redundant to the upper right triangle. Thus data is only plotted in the upper triangle. The predictive fMRI connectivity features appear mostly distributed across multiple networks rather than selective to a few particular networks. The exception for a few outcome variables ('hamd,' 'sans_global_bluntaffect,' 'chapsoc,' 'sans_global_anhedonia,' and 'sans_factor_avolition') is in connectivity between the DMN and other networks. In particular, the predictive edges between the DMN and other networks mostly originate from the anterior cingulate and/or the medial orbitofrontal lobe.

Figure 23A:
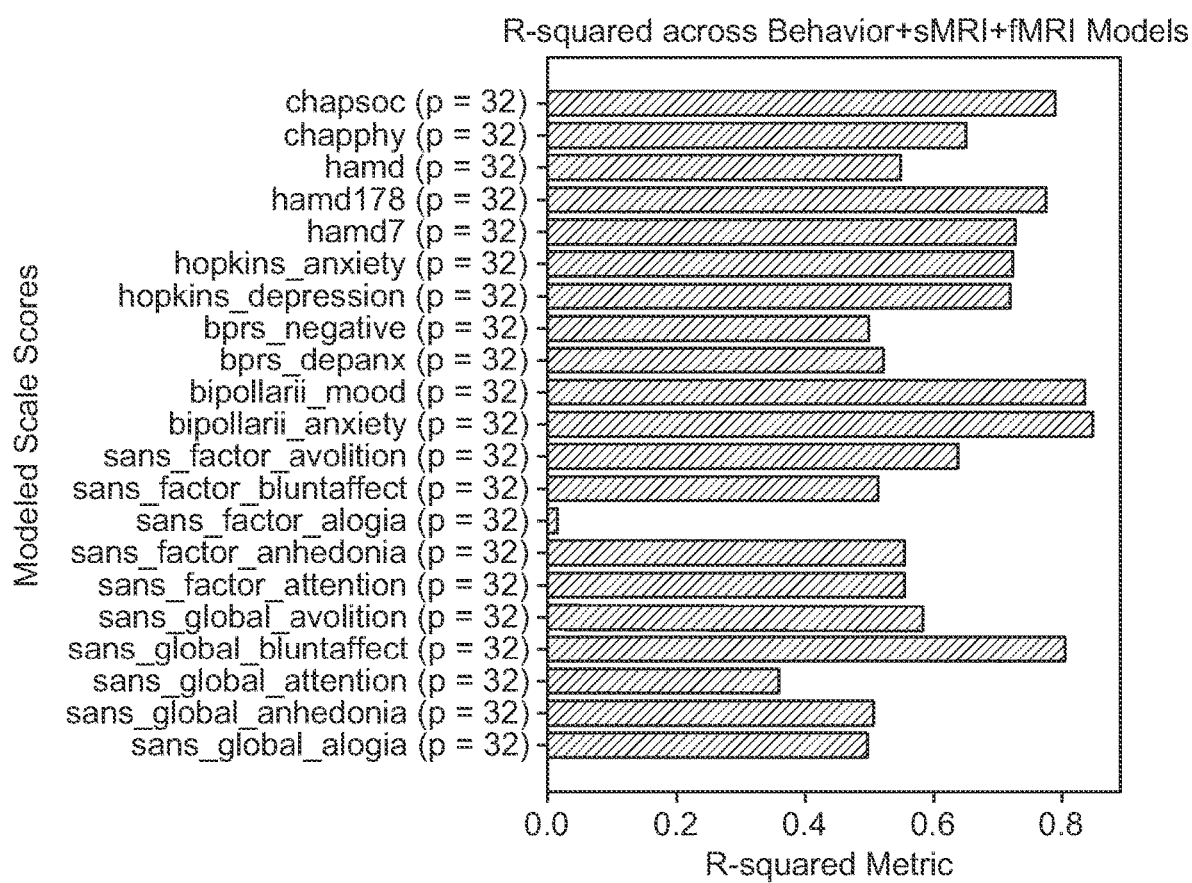
FIGS. 23A-23B illustrate median $r^2$ for models with specific number of features, according to some implementations of the present disclosure.
Figure 23B:
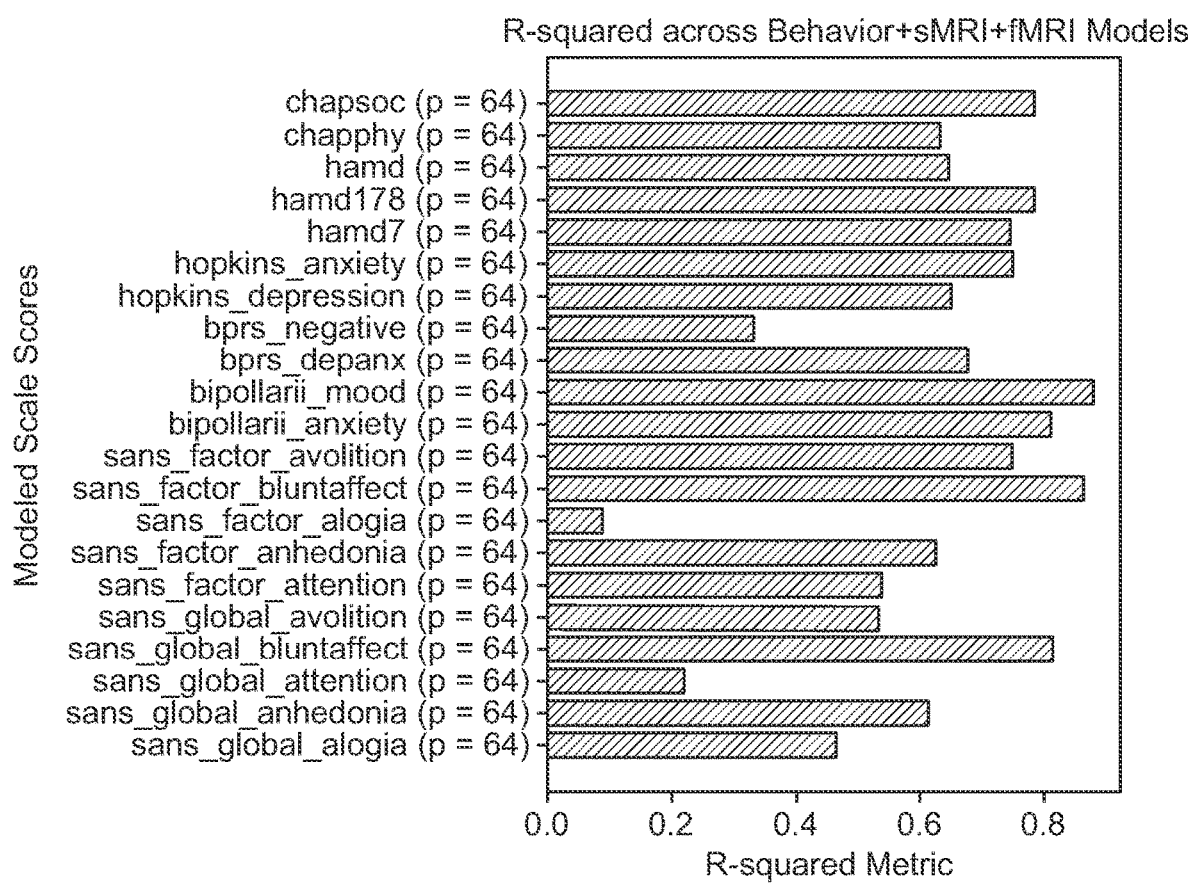
Figure 24A:
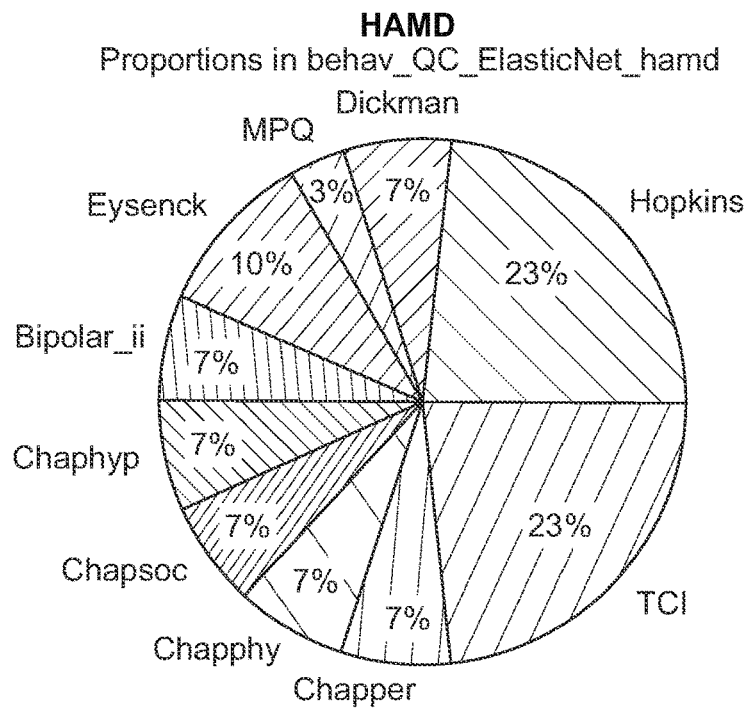
FIGS. 24A-24F illustrate proportions of features from each scale for the scales-only model predicting depression or depressed mood according to some implementations of the present disclosure.
Figure 24B:
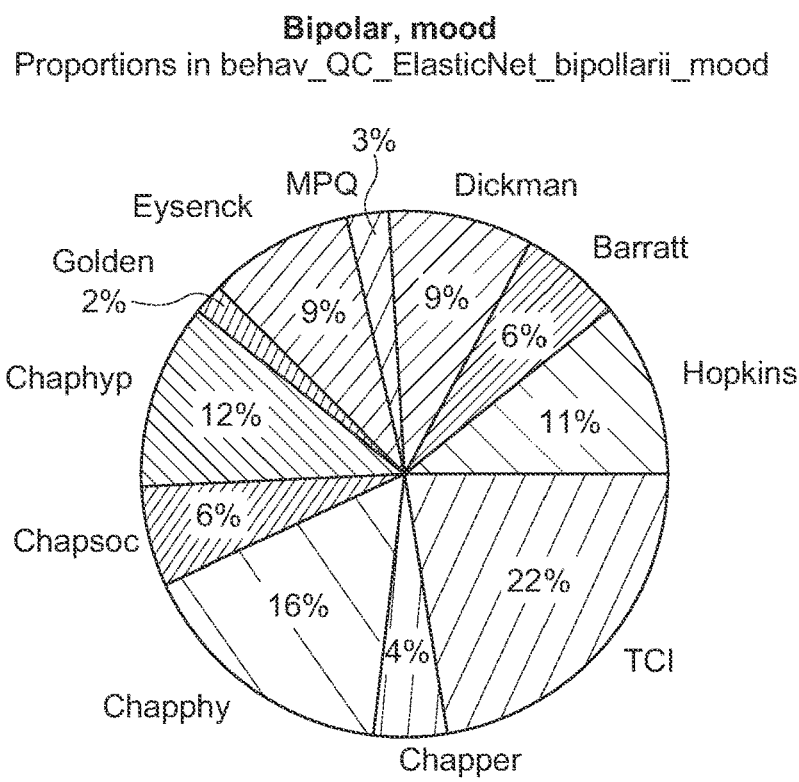
Figure 24C:
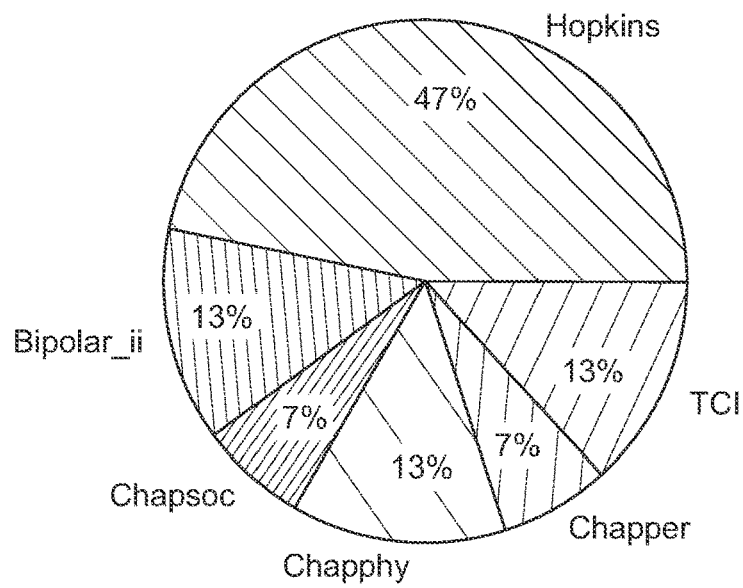
Figure 24D:
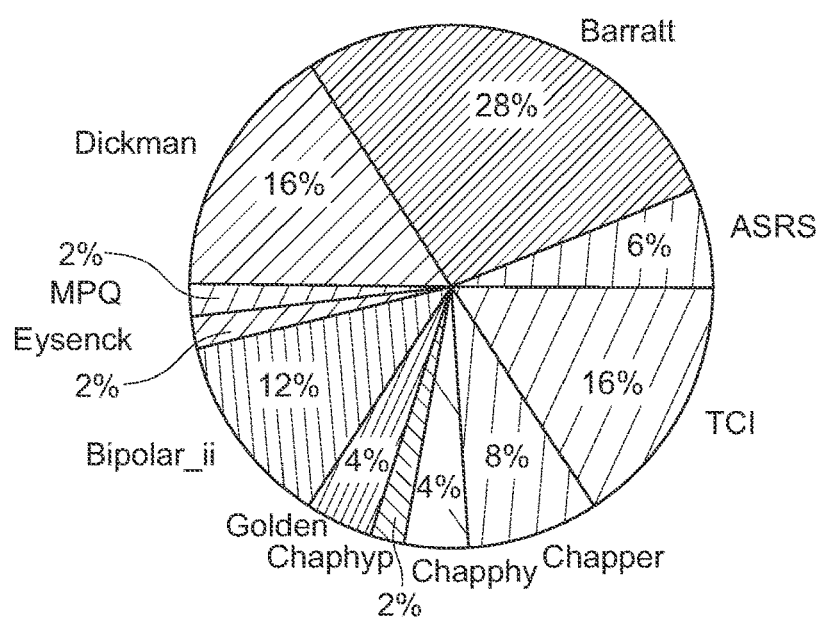
Figure 24E:
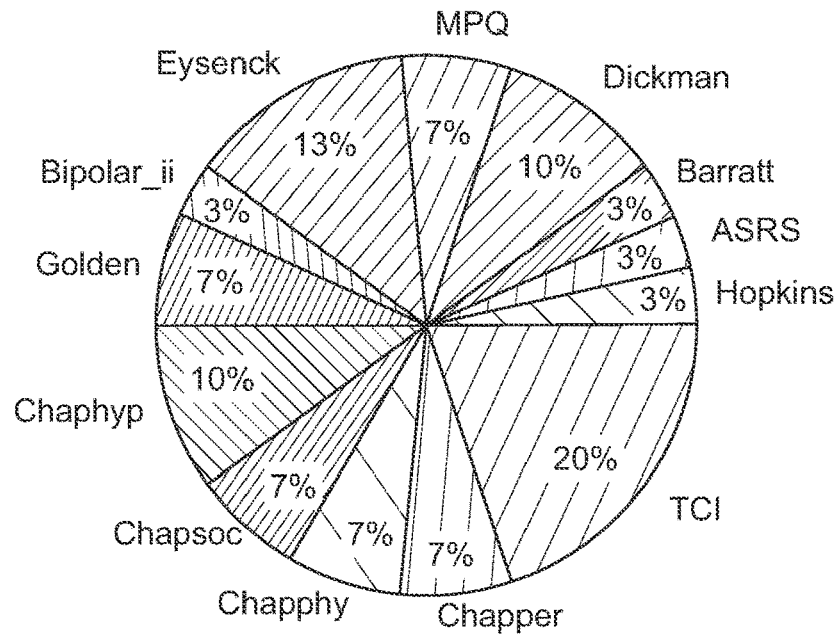
Figure 24F:
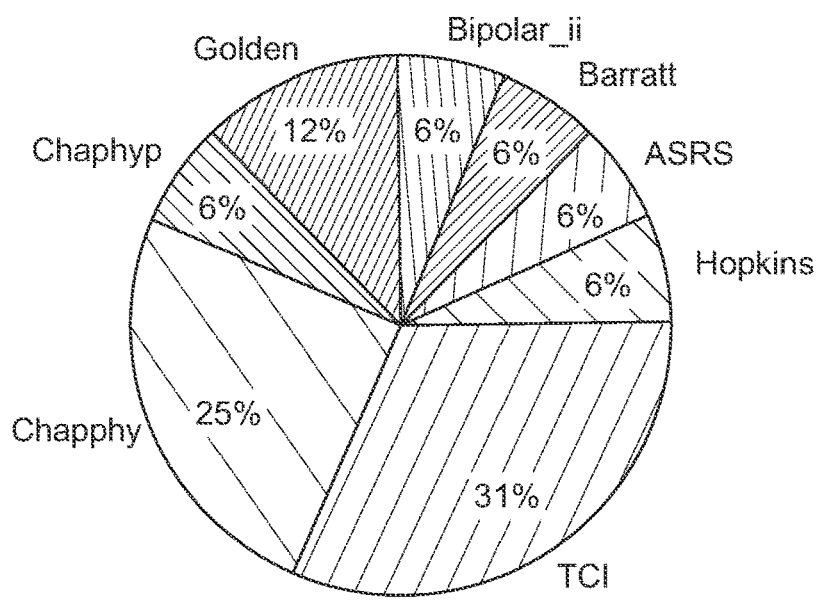
Figure 25A:
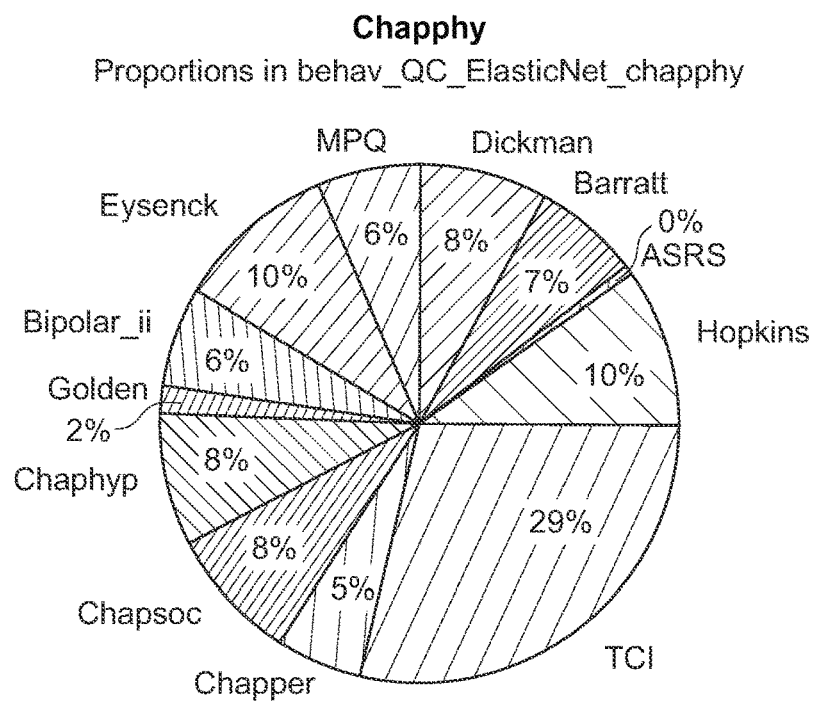
FIGS. 25A-25E illustrate proportions of features from each scale for scales-only model predicting anhedonia, according to some implementations of the present disclosure.
Figure 25B:
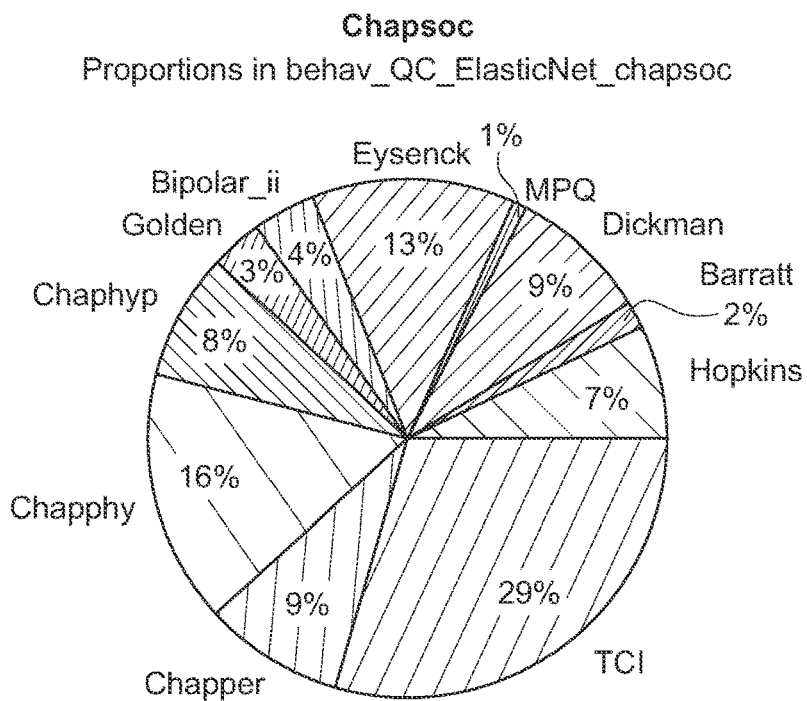
Figure 25C:
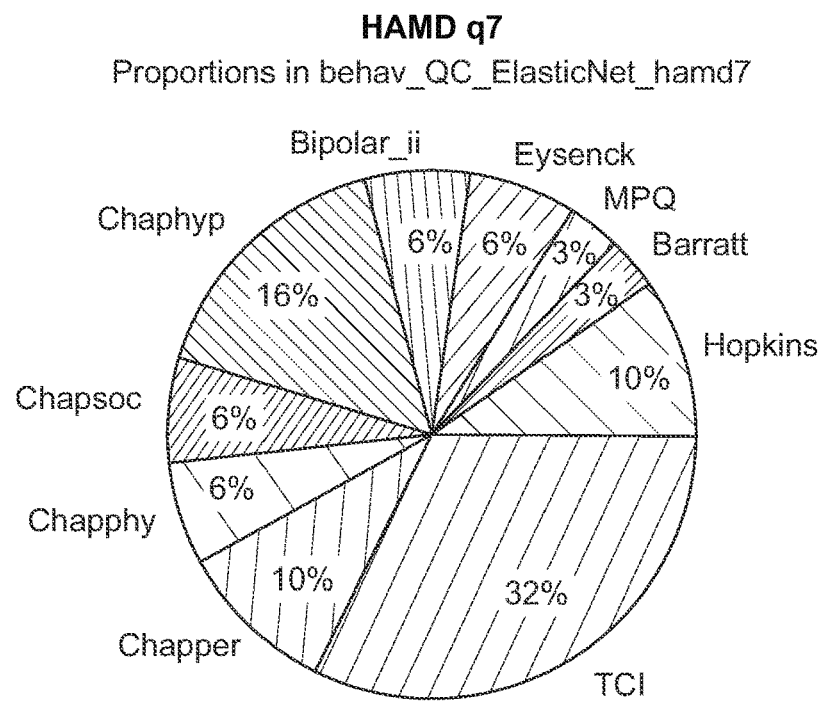
Figure 25D:
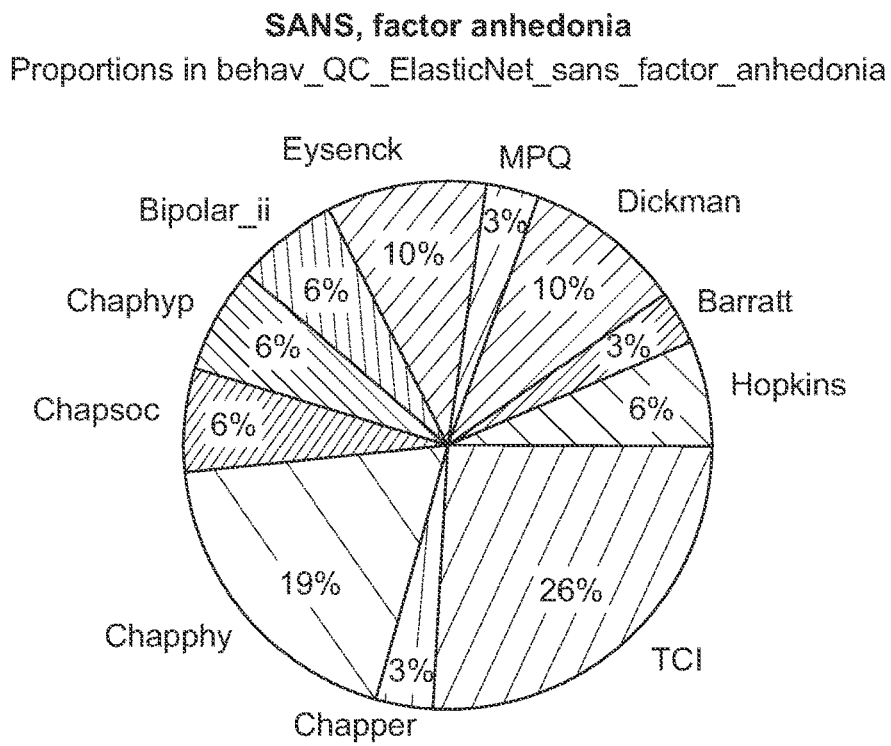
Figure 25E:
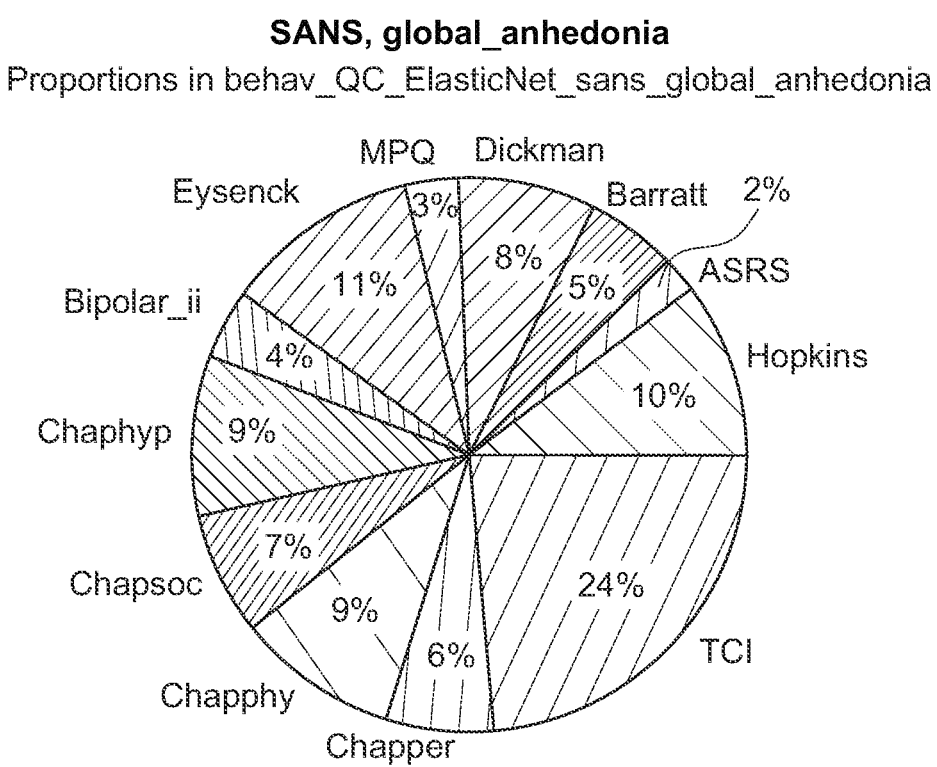

Since the number of samples used in each model varied based on the number of subjects who completed a particular scale and the number of dropped subjects due to poor quality (did not pass QC), some models were built with as few as n=38 subjects (the SANS models with all three input types). To examine if the results could be due to overfitting, $r^2$ was further compared for just p=32 and 64 features to look at cases where overfitting is less likely (p<n), such as shown in FIGS. 23A-23B. To constrain the number of features used by the model to less than the sample size, median $r^2$ values for models were plotted, where p<n for all models (left) or p<n for about half of the models (right) since n=38 or 39 for the SANS models when using scales+sMRI+fMRI inputs (see Table 6). These plots illustrate that most $r^2$ values are >0.5 suggesting that overfitting is not the major contributor to the high predictability of these models. Thus, predictive value was still largely high with $r^2$ values mostly >0.5 for these models, suggesting that performance in the best models is likely not solely due to overfitting.

In addition, according to some implementations of the present disclosure, the models with the least complexity are scales-only models. Results for this set of models is shown in FIGS. 24A-27H. (See Table 14 for metrics of scales-only models). More specifically, FIGS. 24A-24F illustrate proportions of features from each scale for the scales-only model predicting depression or depressed mood The model using Elastic Net with the median $r^2$ value was chosen for this further examination.

Figure 26A:
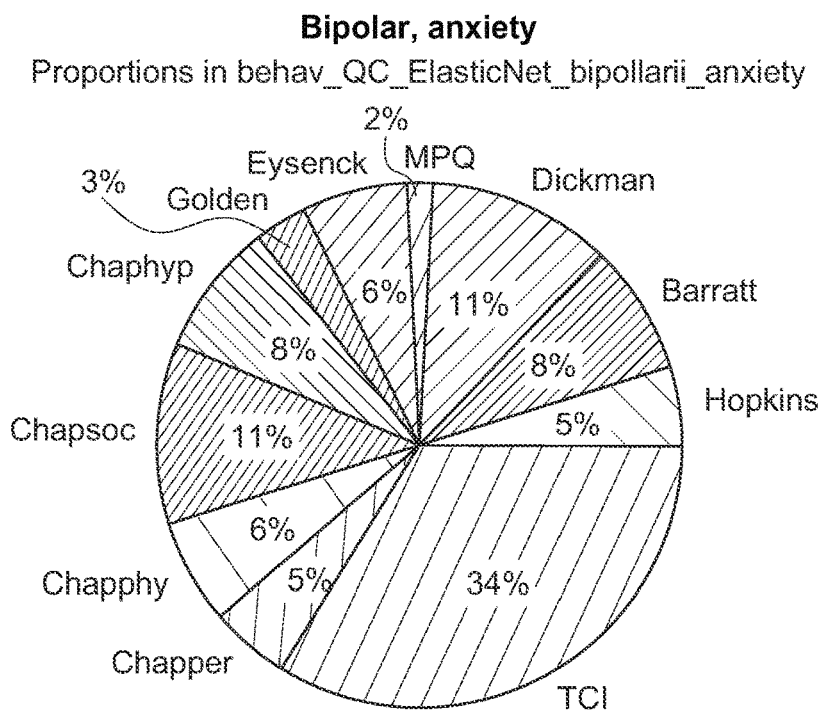
FIGS. 26A-26B illustrate proportions of features from each scale for scales-only model predicting anxiety, according to some implementations of the present disclosure.
Figure 26B:
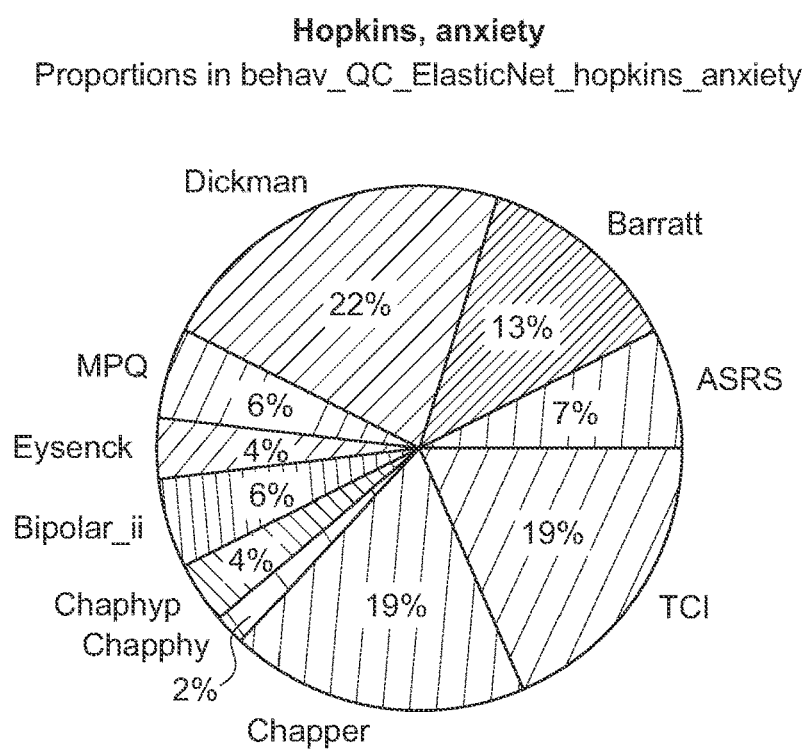
Figure 27A:
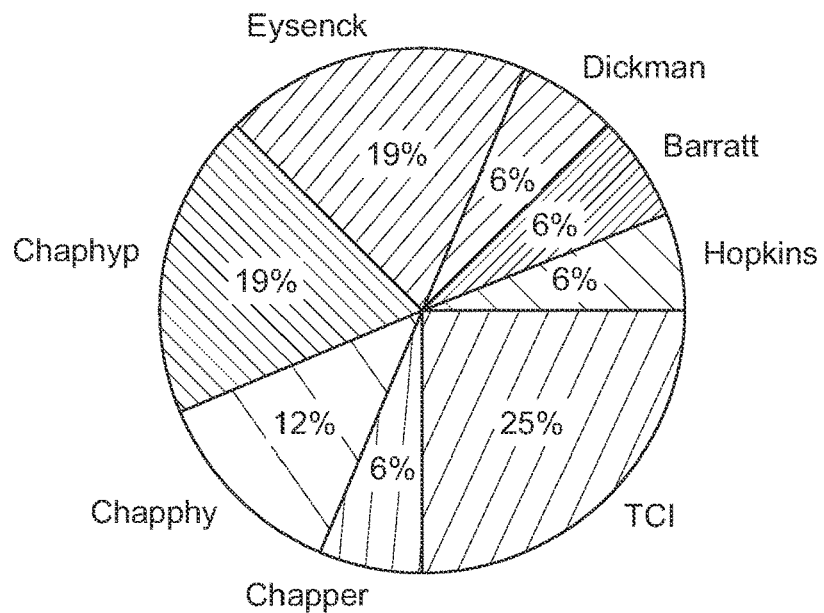
FIGS. 27A-27H illustrate proportions of features from each scale for scales-only model predicting negative symptoms, according to some implementations of the present disclosure.
Figure 27B:
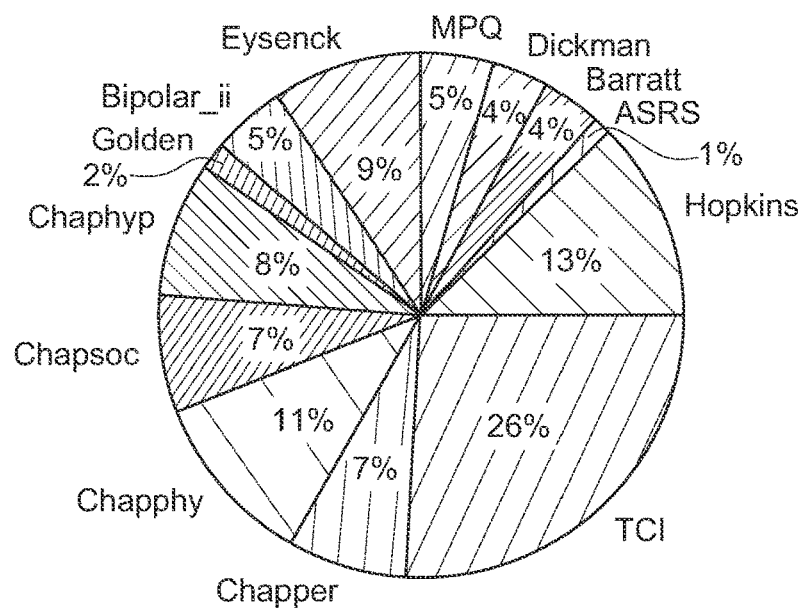
Figure 27C:
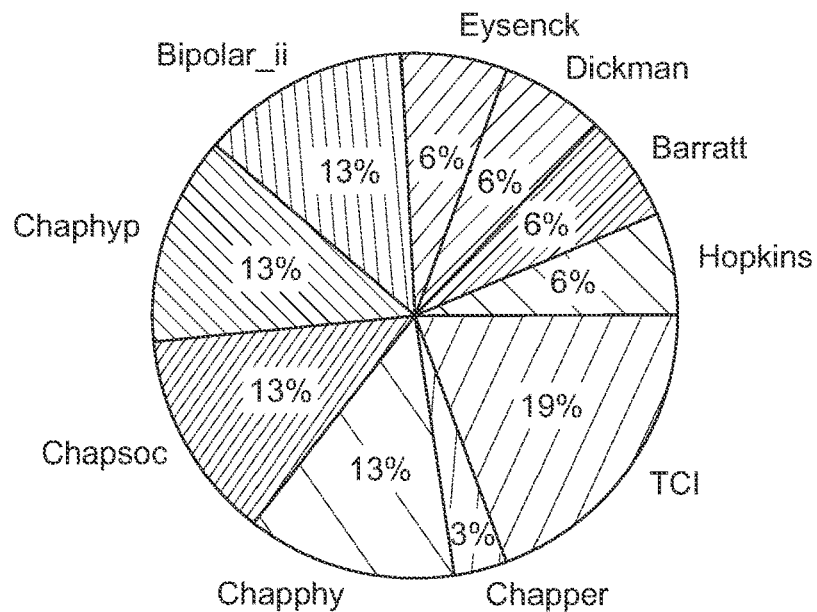
Figure 27D:
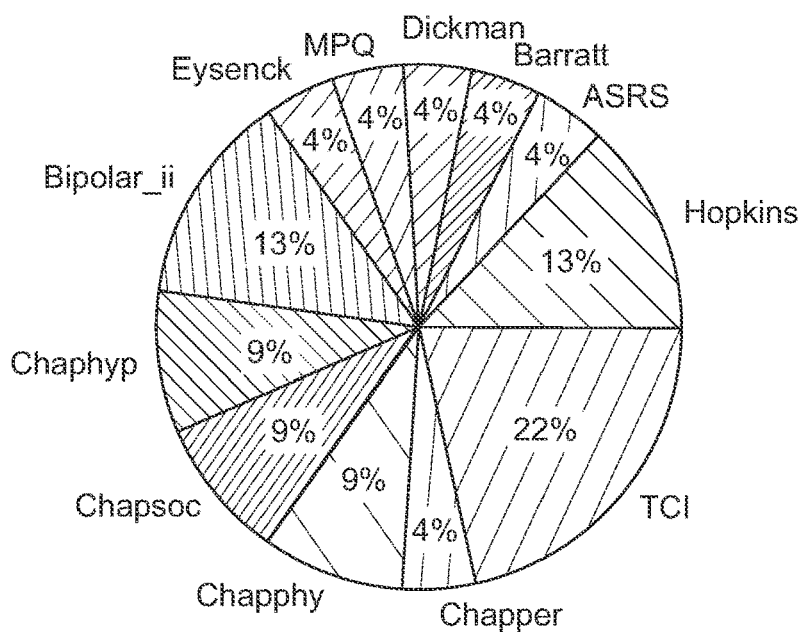
Figure 27E:
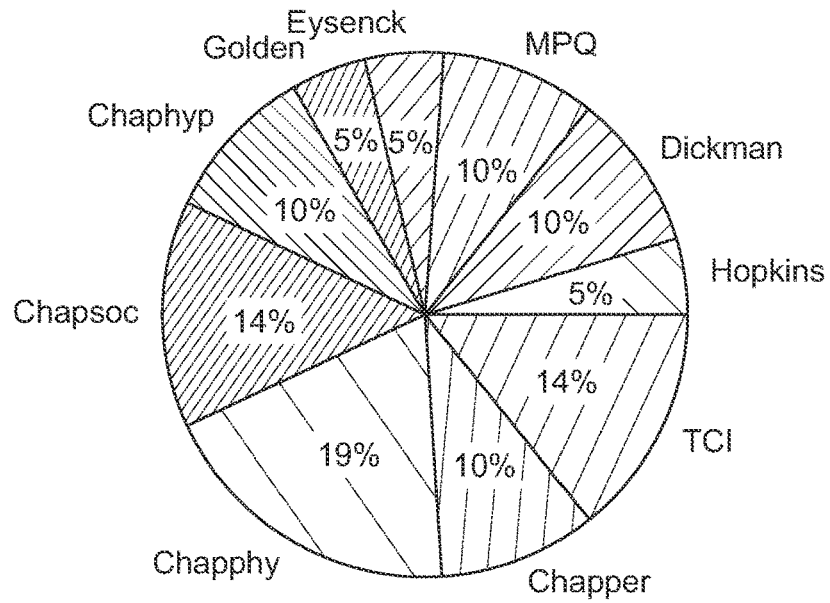
Figure 27F:
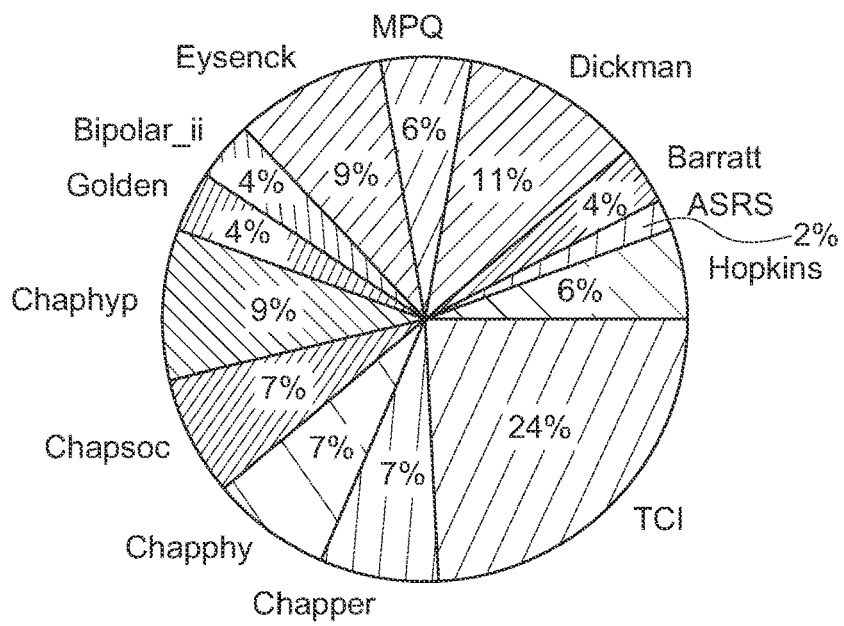
Figure 27G:
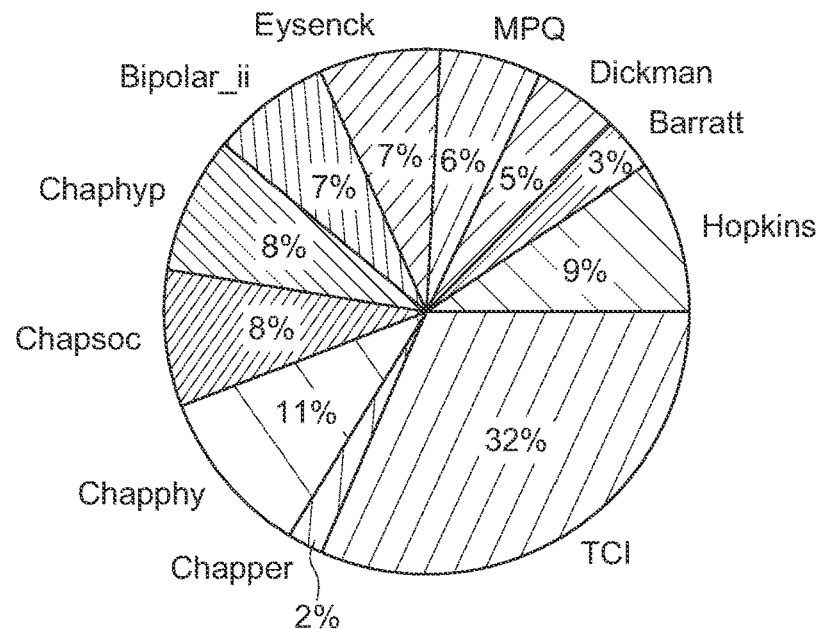
Figure 27H:
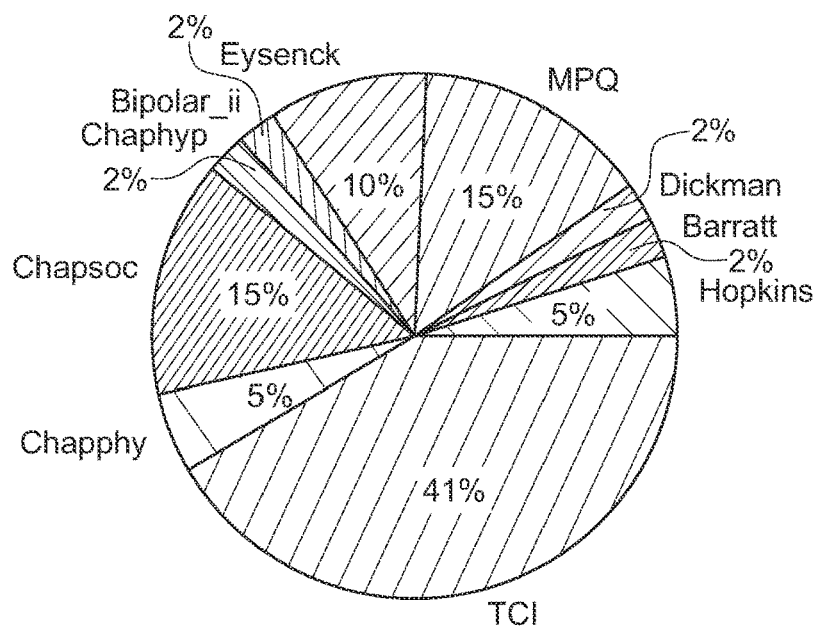

FIGS. 25A-25E illustrate proportions of features from each scale for scales-only model predicting anhedonia, according to some implementations of the present disclosure;

FIGS. 26A-26B illustrate proportions of features from each scale for scales-only model predicting anxiety, according to some implementations of the present disclosure;

FIGS. 27A-27H illustrate proportions of features from each scale for scales-only model predicting negative symptoms, according to some implementations of the present disclosure;

Additional Information

According to some implementations of the present disclosure, biomarkers were explored for severity of various psychiatric symptoms including depression, anxiety, anhedonia, and other negative symptoms in a transdiagnostic sample. An importance-ranked, forward selection modeling approach was applied to search for the most predictive input features from a set of clinical scale measures, structural MRI measures, and functional MRI measures and to evaluate several different modeling algorithms. Notably, this data-driven methods of selecting feature subsets additionally improved model predictability over models using the whole feature set. Overall, Elastic Net regression with multi-modal inputs, either all three input feature types or a combination of scale scores and fMRI connectivity measures, preformed the best. These models explained the most variance in the outcome measures which were a range of total scores of a scale, scores from a subset of questions from a scale, or individual question scores from a scale for the symptoms evaluated.

Elastic Net regression returns regression coefficients which can be examined for further interpretation of biomarkers. The magnitude of the non-zero coefficients included in the best models were evaluated to parse out the features. Overall, the individual, edge-level fMRI connectivity measures between specific network nodes dominated in nearly all of the regression models for different symptom measures, but responses to individual questions in self-report clinical scales were also highly predictive. sMRI measures were not well-represented among the essential features in our models. Scale features also tended to be more highly represented in the top 25% of features than in the whole set of features returned by the models, though this was not the case for every outcome variable. Thus, their relative importance may be higher than fMRI features, though clearly the multi-modal models performed better than scales-only models suggesting an additive effect to the multi-modal models. Therefore, a comparison of different feature types in transdiagnostic was disclosed, along with identifying a community-based symptom severity biomarker.

The categorical origins of the clinical scale features and fMRI features for these models were further investigated. Within each symptom grouping (depression/mood, anxiety, anhedonia, negative symptoms.) of the outcome variables, there was also some similarity in the scales from which they were drawn as many included items from the TCI scale, Hopkins Symptom Checklist, and several Chapman scales. The TCI scale in particular was consistently among the top three scales in predicting all but one outcome variable for depression, anxiety, and anhedonia. This scale measures temperaments such as harm avoidance and novelty seeking which are associated with depression and anxiety.

The number of scales from which predictor variables were drawn also seemed to correspond to how broad the outcome variable was. For example, 'hamd,' 'chapphy,' and 'chapsoc' outcome variables were all total scores from their respective scales, and their models drew features from more scales than models predicting sub-scores or individual item scores (such as 'sans_factor_bluntaffect' or 'hamd7'). This may suggest that predicting more narrowly-defined outcome scores utilizes less scales and may require administration of few scales to patients for optimal modeling at least within multi-modal datasets.

Assessing the categorical groupings of importance-ranked fMRI connectivity features for each model was done according to canonical resting-state networks of the Power atlas. This analysis demonstrated that these highly-predictive features are distributed across many networks in many of our models. This may have the implication that it is useful for examining connections between individual nodes when creating models instead of relying solely upon summary metrics of networks such as graph theory metrics.

In several models ('hamd,' 'sans_global_bluntaffect, ''chapsoc,' 'sans_global_anhedonia,' and 'sans_factor_avolition'), some pattern of connectivity between the default mode network (DMN) and other networks did emerge as an important set of predictor variables. In particular, the predictive edges between the DMN and other networks mostly originate from the anterior cingulate and/or the medial orbitofrontal lobe, regions that have previously been implicated in anhedonia. In addition, DMN connectivity is associated with depressive and negative symptoms. DMN variability increases in SZ patients with depression and correlates with this symptom score. Additionally, hypoconnectivity in the DMN is found in patients with SZ and psychotic bipolar disorder where connectivity was negatively correlated with negative. DMN within- and between-network connectivity is also altered in mood and psychotic disorders and tied to reduced reward responsiveness (a proxy for anhedonia).

The present disclosure includes a data-driven method to search for improved biomarkers and to show the representation of the most predictive features at a high level. Other high-dimensional datasets, such as genetic expression data, may also benefit from an importance-weighted forward modeling approach to find which genes are most predictive of which symptoms. Clustering methods can provide one way to reduce the dimensionality by grouping genes by similarity. Feature selection may also benefit from grouping or selecting variables by predictability rather than similarity. While cross-validation on held-out test sets is meant to minimize overfitting, some models returned p>n and thus may still be susceptible to overfitting. But models which perform feature selection such as Elastic Net are designed to work on problems where p>>n and may help to reduce overfitting.

Additional Embodiments

Further aspects of the present disclosure include the following method: Clinical scale data, resting-state functional-MRI data, and structural-MRI scans are received for multiple patients with schizophrenia, bipolar disorder, attention deficit and hyperactivity disorder ("ADHD"), or healthy controls. The received data are preprocessed. At least one logistic regression model of features in the received data is generated. A set of predictive phenotypic features in the received data is generated based on weights generated from the at least one logistic regression model.

Additional aspects of the present disclosure include the following computing system: A computer system includes at least one database, a memory, and a processor. The at least one database stores clinical scale data, resting-state functional-MRI data, and structural-MRI scans for multiple patients with schizophrenia, bipolar disorder, ADHD, or healthy controls. The memory stores computer instructions. The processor is configured to execute the computer instructions to preprocess the data stored in the at least one database. At least one logistic regression model of features in the received data is generated. A set of predictive phenotypic features in the received data is generated based on weights generated from the at least one logistic regression model.

Still further aspects of the present disclosure include a system for evaluating a patient for mental health issues. The system includes a display, a user interface, a memory, and a control system. The memory contains machine readable medium. The machine readable medium includes machine executable code storing instructions for performing a method. The control system is coupled to the memory, and includes one or more processors. The control system is configured to execute the machine executable code to cause the control system to perform the method: On the display, a series of questions is displayed. The series of questions is from mental health questionnaires. The series of questions includes text and answers for each question. From the user interface, a selection of answers is received from a patient of each of the series of questions. A set of MRI data output is received after scanning the patient's brain using magnetic resonance imaging. Using a machine learning model, the selection of answers and the set of MRI data are processed to output an indication of the mental health of the patient. In some aspects, the mental health includes neuropsychiatric disorders, schizophrenia, and bi-polar disorder.

Still additional aspects of the present disclosure include a machine learning based approach to build robust data-driven transdiagnostic classifiers to distinguish SCZ, BD, and ADHD patients from healthy controls (HCs) based on the openly available CNP dataset is described. Multiple data modalities are utilized, including clinical behavioral/symptom phenotypes and neuroimaging data (sMRI and fMRI) to obtain the optimal transdiagnostic models. Specifically, feature-importance guided sequential model selection approach is adopted in which classifiers were first built based on full sets of features to extract the feature importance and then from which a series of truncated models were built and evaluated to obtain the model producing the best performance. All transdiagnostic classifiers achieved very high performance in classifying various patient cohorts from healthy controls. More importantly, this feature and model selection approach not only allowed for the finding of the most robust transdiagnostic classifier but also identify the corresponding subset of most predictive features shared commonly across SCZ, BD, and ADHD patients. These shared features are reported and the identified latent abnormal psychopathological structure across these psychiatric disorders is discussed.

Although the present disclosure provides for models trained on the CNP database, the present disclosure contemplates that any database comprising clinical scales data and MRI data can be used to produce models, as would be readily contemplated by one skilled in the art.

The disclosed models selected as informative the features which trend in the same direction for all participants. The present disclosure contemplates that brain activity can be examined which diverges between patient groups; such an approach can yield other features.

Although the present disclosure discusses input primarily in terms of fMRI data and sMRI data, other embodiments can provide for receiving rs-fMRI.

Altogether, the present disclosure provides a data-driven way to improve biomarker development for predicting symptom severity transdiagnostically and can be used in a personalized medicine approach in diagnosing and treating behavioral disorders.

Machine Learning Implementation

Various aspects of the present disclosure can be performed by a machine-learning algorithm, as readily understood by a person skilled in the art. In some examples, step 2940 of FIG. 29 and methodology 3000 of FIG. 30 can be performed by a supervised or unsupervised algorithm. For instance, the system may utilize more basic machine learning tools including 1) decision trees ("DT"), (2) Bayesian networks ("BN"), (3) artificial neural network ("ANN"), or (4) support vector machines ("SVM"). In other examples, deep learning algorithms or other more sophisticated machine learning algorithms, e.g., convolutional neural networks ("CNN"), or capsule networks ("CapsNet") may be used.

DT are classification graphs that match input data to questions asked at each consecutive step in a decision tree. The DT program moves down the "branches" of the tree based on the answers to the questions (e.g., First branch: Did the clinical scales data include certain input? yes or no. Branch two: Did the MRI data include certain features? yes or no, etc.).

Bayesian networks ("BN") are based on likelihood something is true based on given independent variables and are modeled based on probabilistic relationships. BN are based purely on probabilistic relationships that determine the likelihood of one variable based on another or others. For example, BN can model the relationships between MRI data, clinical scales data, and any other information as contemplated by the present disclosure. Particularly, if a question type and particular features of the patient's MRI data are known, a BN can be used to compute a symptom severity indicator. Thus, using an efficient BN algorithm, an inference can be made based on the input data.

Artificial neural networks ("ANN") are computational models inspired by an animal's central nervous system. They map inputs to outputs through a network of nodes. However, unlike BN, in ANN the nodes do not necessarily represent any actual variable. Accordingly, ANN may have a hidden layer of nodes that are not represented by a known variable to an observer. ANNs are capable of pattern recognition. Their computing methods make it easier to understand a complex and unclear process that might go on during determining a symptom severity indicator based on a variety of input data.

Support vector machines ("SVM") came about from a framework utilizing of machine learning statistics and vector spaces (linear algebra concept that signifies the number of dimensions in linear space) equipped with some kind of limit-related structure. In some cases, they may determine a new coordinate system that easily separates inputs into two classifications. For example, a SVM could identify a line that separates two sets of points originating from different classifications of events.

Deep neural networks (DNN) have developed recently and are capable of modeling very complex relationships that have a lot of variation. Various architectures of DNN have been proposed to tackle the problems associated with algorithms such as ANN by many researchers during the last few decades. These types of DNN are CNN (Convolutional Neural Network), RBM (Restricted Boltzmann Machine), LSTM (Long Short Term Memory) etc. They are all based on the theory of ANN. They demonstrate a better performance by overcoming the back-propagation error diminishing problem associated with ANN.

Machine learning models require training data to identify the features of interest that they are designed to detect. For instance, various methods may be utilized to form the machine learning models, including applying randomly assigned initial weights for the network and applying gradient descent using back propagation for deep learning algorithms. In other examples, a neural network with one or two hidden layers can be used without training using this technique.

In some examples, the machine learning model can be trained using labeled data, or data that represents certain user input. In other examples, the data will only be labeled with the outcome and the various relevant data may be input to train the machine learning algorithm.

For instance, to determine whether particular mental health disorder fits the input data, various machine learning models may be utilized that input various data disclosed herein. In some examples, the input data will be labeled by having an expert in the field label the relevant regulations according to the particular situation. Accordingly, the input to the machine learning algorithm for training data identifies various data as from a healthy control or from a patient.

Exemplary NMR System

Figure 31A:
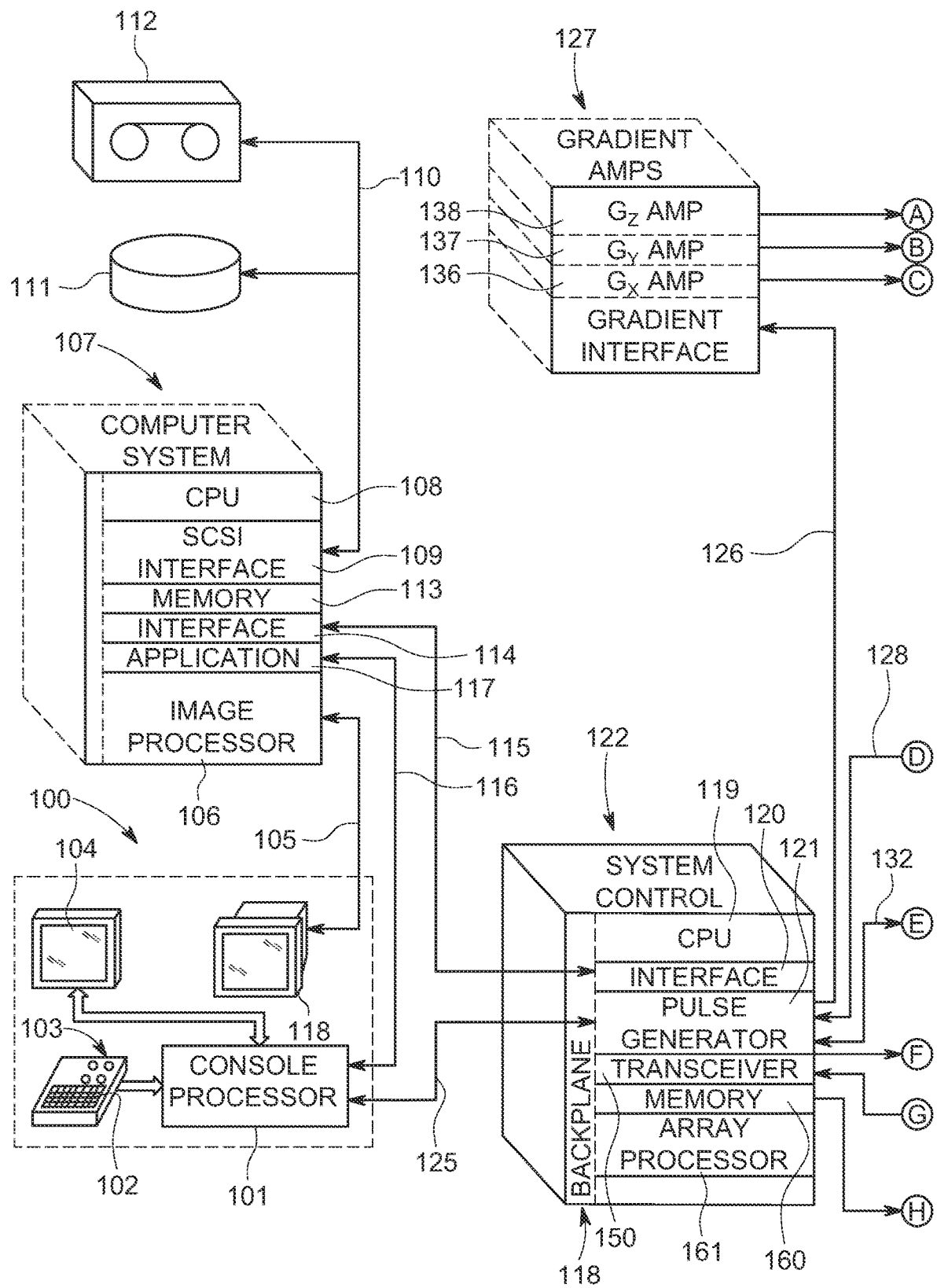
FIGS. 31A-31B illustrates a block diagram of an MRI system used to acquire NMR data, according to some implementations of the present disclosure.
Figure 31B:
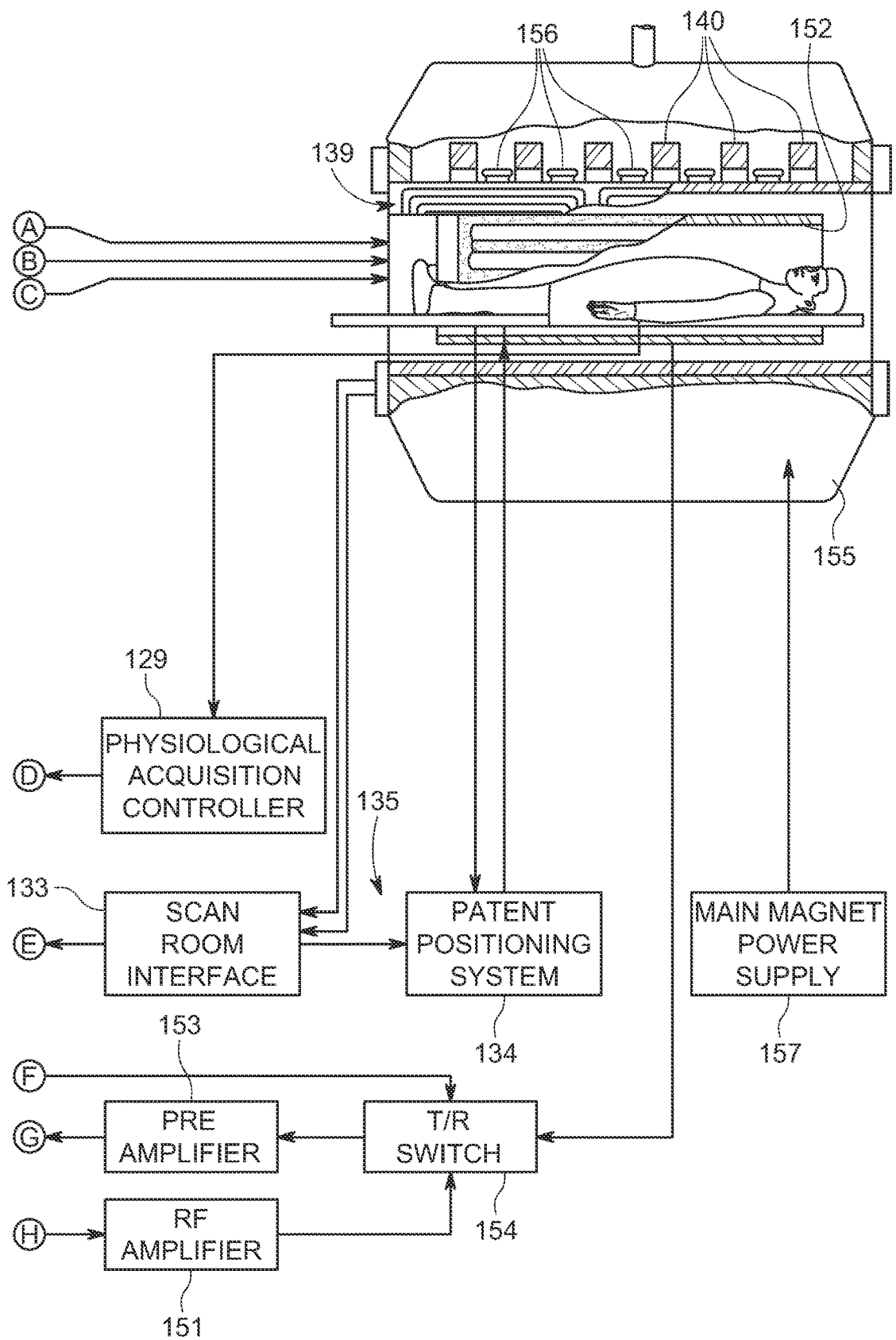
Figure 32:
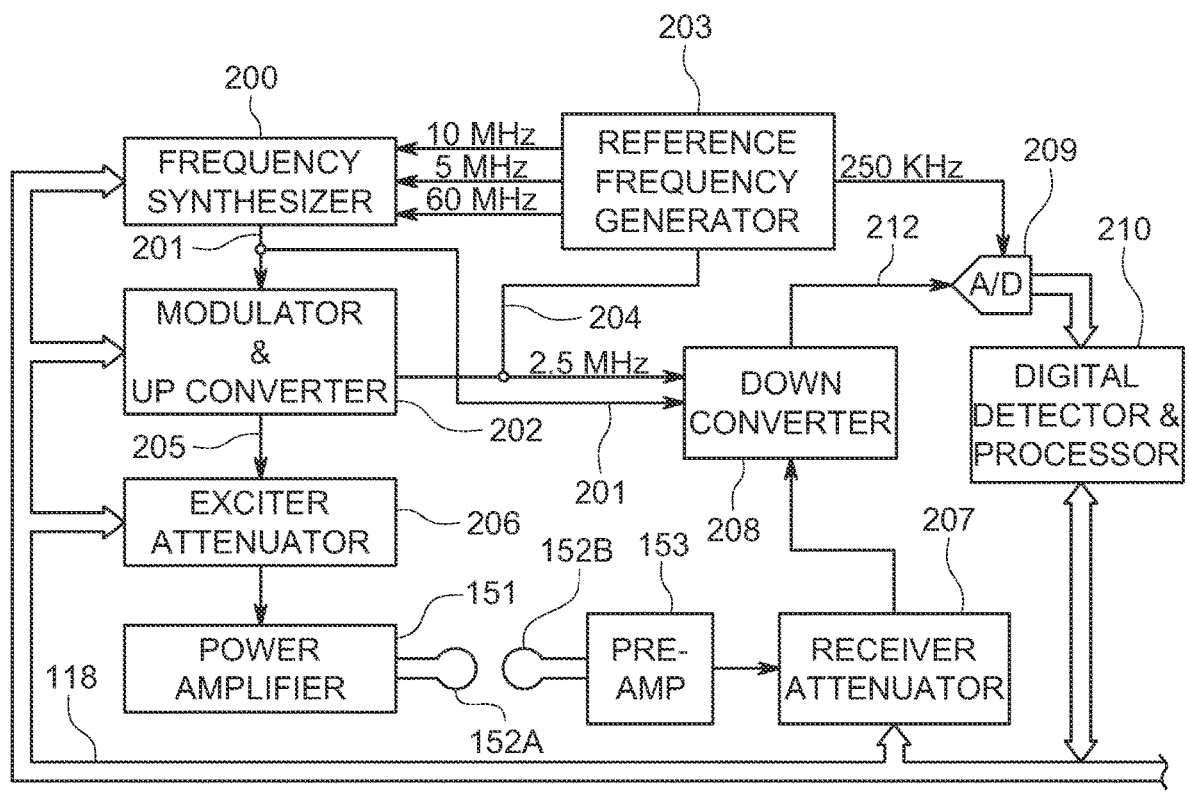
FIG. 32 illustrates a block diagram of a transceiver which forms part of the MRI system of FIG. 31A, according to some implementations of the present disclosure.

Referring now to FIGS. 31A-32, the methods and embodiments of the present disclosure can be performed on an exemplary nuclear magnetic resonance ("NMR system"). As a person of ordinary skill in the art understands, NMR commonly refers to the hardware used to generate different types of scans, including MRI scans. Referring now to FIGS. 31A-32, there is shown the major components of an NMR system which can be used to carry out the methods of the various embodiments. FIG. 32 shows the components of an exemplary transceiver for the NMR system of FIGS. 31A-31B. It should be noted that the methods of the various embodiments can also be carried out using other NMR systems.

The operation of the system of FIGS. 31A-32 is controlled from an operator console 100 which includes a console processor 101 that scans a keyboard 102 and receives inputs from a human operator through a control panel 103 and a plasma display/touch screen 104. The console processor 101 communicates through a communications link 116 with an applications interface module 117 in a separate computer system 107. Through the keyboard 102 and controls 103, an operator controls the production and display of images by an image processor 106 in the computer system 107, which connects directly to a video display 118 on the console 100 through a video cable 105.

The computer system 107 is formed about a backplane bus which conforms with the VME standards, and it includes a number of modules which communicate with each other through this backplane. In addition to the application interface 117 and the image processor 106, these include a CPU module 108 that controls the VME backplane, and an SCSI interface module 109 that connects the computer system 107 through a bus 110 to a set of peripheral devices, including disk storage 111 and tape drive 112. The computer system 107 also includes a memory module 113, known in the art as a frame buffer for storing image data arrays, and a serial interface module 114 that links the computer system 107 through a high speed serial link 115 to a system interface module 120 located in a separate system control cabinet 122.

The system control 122 includes a series of modules which are connected together by a common backplane 118. The backplane 118 is comprised of a number of bus structures, including a bus structure which is controlled by a CPU module 119. The serial interface module 120 connects this backplane 118 to the high speed serial link 115, and pulse generator module 121 connects the backplane 118 to the operator console 100 through a serial link 125. It is through this link 125 that the system control 122 receives commands from the operator which indicate the scan sequence that is to be performed.

The pulse generator module 121 operates the system components to carry out the desired scan sequence. It produces data which indicates the timing, strength and shape of the RF pulses which are to be produced, and the timing of and length of the data acquisition window. The pulse generator module 121 also connects through serial link 126 to a set of gradient amplifiers 127, and it conveys data thereto which indicates the timing and shape of the gradient pulses that are to be produced during the scan. The pulse generator module 121 also receives patient data through a serial link 128 from a physiological acquisition controller 129. The physiological acquisition control 129 can receive a signal from a number of different sensors connected to the patient. For example, it may receive ECG signals from electrodes or respiratory signals from a bellows and produce pulses for the pulse generator module 121 that synchronizes the scan with the patient's cardiac cycle or respiratory cycle. And finally, the pulse generator module 121 connects through a serial link 132 to scan room interface circuit 133 which receives signals at inputs 135 from various sensors associated with the position and condition of the patient and the magnet system. It is also through the scan room interface circuit 133 that a patient positioning system 134 receives commands which move the patient cradle and transport the patient to the desired position for the scan.

The gradient waveforms produced by the pulse generator module 121 are applied to a gradient amplifier system 127 comprised of Gx, Gy, and Gz amplifiers 136, 137 and 138, respectively. Each amplifier 136, 137, and 138 is utilized to excite a corresponding gradient coil in an assembly generally designated 139. The gradient coil assembly 139 forms part of a magnet assembly 155 which includes a polarizing magnet 140 that produces a 1.5 Tesla polarizing field that extends horizontally through a bore. The gradient coils 139 encircle the bore, and when energized, they generate magnetic fields in the same direction as the main polarizing magnetic field, but with gradients Gx, Gy and Gz directed in the orthogonal x-, y- and z-axis directions of a Cartesian coordinate system. That is, if the magnetic field generated by the main magnet 140 is directed in the z direction and is termed BO, and the total magnetic field in the z direction is referred to as Bz, then Gx∂Bz/∂x, Gy=∂Bz/∂y and Gz=∂Bz/∂z, and the magnetic field at any point (x,y,z) in the bore of the magnet assembly 141 is given by B(x,y,z)=Bo+Gxx+GyyGzz. The gradient magnetic fields are utilized to encode spatial information into the NMR signals emanating from the patient being scanned. Because the gradient fields are switched at a very high speed when an EPI sequence is used to practice the preferred embodiment of the invention, local gradient coils are employed in place of the whole-body gradient coils 139. These local gradient coils are designed for the head and are in close proximity thereto. This enables the inductance of the local gradient coils to be reduced and the gradient switching rates increased as required for the EPI pulse sequence. For a description of these local gradient coils which is incorporated herein by reference, see U.S. Pat. No. 5,372,137 issued on Dec. 13, 1994, and entitled "NMR Local Coil for Brain Imaging".

Located within the bore 142 is a circular cylindrical whole-body RF coil 152. This coil 152 produces a circularly polarized RF field in response to RF pulses provided by a transceiver module 150 in the system control cabinet 122. These pulses are amplified by an RF amplifier 151 and coupled to the RF coil 152 by a transmit/receive switch 154 which forms an integral part of the RF coil assembly. Waveforms and control signals are provided by the pulse generator module 121 and utilized by the transceiver module 150 for RF carrier modulation and mode control. The resulting NMR signals radiated by the excited nuclei in the patient may be sensed by the same RF coil 152 and coupled through the transmit/receive switch 154 to a preamplifier 153. The amplified NMR signals are demodulated, filtered, and digitized in the receiver section of the transceiver 150.

The transmit/receive switch 154 is controlled by a signal from the pulse generator module 121 to electrically connect the RF amplifier 151 to the coil 152 during the transmit mode and to connect the preamplifier 153 during the receive mode. The transmit/receive switch 154 also enables a separate local RF head coil to be used in the transmit and receive mode to improve the signal-to-noise ratio of the received NMR signals. With currently available NMR systems such a local RF coil is preferred in order to detect small variations in NMR signal. Reference is made to the above cited U.S. Pat. No. 5,372,137 for a description of the preferred local RF coil.

In addition to supporting the polarizing magnet 140 and the gradient coils 139 and RF coil 152, the main magnet assembly 141 also supports a set of shim coils 156 associated with the main magnet 140 and used to correct inhomogeneities in the polarizing magnet field. The main power supply 157 is utilized to bring the polarizing field produced by the superconductive main magnet 140 to the proper operating strength and is then removed.

The NMR signals picked up by the RF coil are digitized by the transceiver module 150 and transferred to a memory module 160 which is also part of the system control 122. When the scan is completed and an entire array of data has been acquired in the memory modules 160, an array processor 161 operates to Fourier transform the data into an array of image data. This image data is conveyed through the serial link 115 to the computer system 107 where it is stored in the disk memory 111. In response to commands received from the operator console 100, this image data may be archived on the tape drive 112, or it may be further processed by the image processor 106 and conveyed to the operator console 100 and presented on the video display 118 as will be described in more detail hereinafter.

Referring particularly to FIG. 32, the transceiver 150 includes components which produce the RF excitation field B1 through power amplifier 151 at a coil 152A and components which receive the resulting NMR signal induced in a coil 152B. As indicated above, the coils 152A and B may be a single whole-body coil, but the best results are achieved with a single local RF coil specially designed for the head. The base or carrier frequency of the RF excitation field is produced under control of a frequency synthesizer 200 which receives a set of digital signals (CF) through the backplane 118 from the CPU module 119 and pulse generator module 121. These digital signals indicate the frequency and phase of the RF carrier signal, which is produced at an output 201. The commanded RF carrier is applied to a modulator and up converter 202 where its amplitude is modulated in response to a signal R(t) also received through the backplane 118 from the pulse generator module 121. The signal R(t) defines the envelope, and therefore the bandwidth, of the RF excitation pulse to be produced. It is produced in the module 121 by sequentially reading out a series of stored digital values that represent the; desired envelope. These stored digital values may, in turn, be changed from the operator console 100 to enable any desired RF pulse envelope to be produced. The modulator and up converter 202 produces an RF pulse at the desired Larmor frequency at an output 205. The magnitude of the RF excitation pulse output through line 205 is attenuated by an exciter attenuator circuit 206 which receives a digital command, TA, from the backplane 118. The attenuated RF excitation pulses are applied to the power amplifier 151 that drives the RF coil 152A. For a more detailed description of this portion of the transceiver 122, reference is made to U.S. Pat. No. 4,952,877, which is incorporated herein by reference.

Referring still to FIGS. 31A-32, the NMR signal produced by the subject is picked up by the receiver coil 152B and applied through the preamplifier 153 to the input of a receiver attenuator 207. The receiver attenuator 207 further amplifies the NMR signal, and this is attenuated by an amount determined by a digital attenuation signal (RA) received from the backplane 118. The receive attenuator 207 is also turned on and off by a signal from the pulse generator module 121 such that it is not overloaded during RF excitation. The received NMR signal is at or around the Larmor frequency, which in the preferred embodiment is around 63.86 MHz for 1.5 Tesla. This high-frequency signal is down-converted in a two-step process by a down converter 208 which first mixes the NMR signal with the carrier signal on line 201 and then mixes the resulting difference signal with the 2.5 MHz reference signal on line 204. The resulting down-converted NMR signal on line 212 has a maximum bandwidth of 125 kHz, and it is centered at a frequency of 187.5 kHz. The down-converted NMR signal is applied to the input of an analog-to-digital (A/D) converter 209, which samples and digitizes the analog signal at a rate of 250 kHz. The output of the A/D converter 209 is applied to a digital detector, and signal processor 210 which produce 16-bit in-phase (I) values and 16-bit quadrature (Q) values corresponding to the received digital signal. The resulting stream of digitized I and Q values of the received NMR signal is output through backplane 118 to the memory module 160 where they are employed to reconstruct an image.

To preserve the phase information contained in the received NMR signal, both the modulator and up converter 202 in the exciter section and the down converter 208 in the receiver section are operated with common signals. More particularly, the carrier signal at the output 201 of the frequency synthesizer 200 and the 2.5 MHz reference signal at the output 204 of the reference frequency generator 203 are employed in both frequency conversion processes. Phase consistency is thus maintained, and phase changes in the detected NMR signal accurately indicate phase changes produced by the excited spins. The 2.5 MHz reference signal as well as 5, 10 and 60 MHz reference signals are produced by the reference frequency generator 203 from a common 20 MHz master clock signal. The latter three reference signals are employed by the frequency synthesizer 200 to produce the carrier signal on output 201. For a more detailed description of the receiver, reference is made to U.S. Pat. No. 4,992,736, which is incorporated herein by reference.

Computer & Hardware Implementation of Disclosure

It should initially be understood that the disclosure herein may be implemented with any type of hardware and/or software, and may be a pre-programmed general purpose computing device. For example, the system may be implemented using a server, a personal computer, a portable computer, a thin client, or any suitable device or devices. The disclosure and/or components thereof may be a single device at a single location, or multiple devices at a single, or multiple, locations that are connected together using any appropriate communication protocols over any communication medium such as electric cable, fiber optic cable, or in a wireless manner.

It should also be noted that the disclosure is illustrated and discussed herein as having a plurality of modules which perform particular functions. It should be understood that these modules are merely schematically illustrated based on their function for clarity purposes only, and do not necessary represent specific hardware or software. In this regard, these modules may be hardware and/or software implemented to substantially perform the particular functions discussed. Moreover, the modules may be combined together within the disclosure, or divided into additional modules based on the particular function desired. Thus, the disclosure should not be construed to limit the present invention, but merely be understood to illustrate one example implementation thereof.

The computing system can include clients and servers. A client and server are generally remote from each other and typically interact through a communication network. The relationship of client and server arises by virtue of computer programs running on the respective computers and having a client-server relationship to each other. In some implementations, a server transmits data (e.g., an HTML page) to a client device (e.g., for purposes of displaying data to and receiving user input from a user interacting with the client device). Data generated at the client device (e.g., a result of the user interaction) can be received from the client device at the server.

Implementations of the subject matter described in this specification can be implemented in a computing system that includes a back-end component (e.g., as a data server) or a middleware component (e.g., an application server) or a front-end component (e.g., a client computer having a graphical user interface or a Web browser through which a user can interact with an implementation of the subject matter described in this specification) or any combination of one or more such back-end, middleware, or front-end components. The components of the system can be interconnected by any form or medium of digital data communication (e.g., a communication network). Examples of communication networks include a local area network ("LAN") and a wide area network ("WAN"), an internetwork (e.g., the Internet), and peer-to-peer networks (e.g., ad hoc peer-to-peer networks).

Implementations of the subject matter and the operations described in this specification can be implemented in digital electronic circuitry, or in computer software, firmware, or hardware, including the structures disclosed in this specification and their structural equivalents, or in combinations of one or more of them. Implementations of the subject matter described in this specification can be implemented as one or more computer programs (e.g., one or more modules of computer program instructions) encoded on computer storage medium for execution by, or to control the operation of, data processing apparatus. Alternatively or in addition, the program instructions can be encoded on an artificially-generated propagated signal (e.g., a machine-generated electrical, optical, or electromagnetic signal) that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate physical components or media (e.g., multiple CDs, disks, or other storage devices).

The operations described in this specification can be implemented as operations performed by a "data processing apparatus" on data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, or combinations, of the foregoing The apparatus can include special purpose logic circuitry (e.g., an FPGA (field-programmable gate array) or an ASIC (application-specific integrated circuit)). The apparatus can also include, in addition to hardware, code that creates an execution environment for the computer program in question (e.g., code that constitutes processor firmware, a protocol stack, a database management system, an operating system, a cross-platform runtime environment, a virtual machine, or a combination of one or more of them). The apparatus and execution environment can realize various different computing model infrastructures, such as web services, distributed computing, and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry (e.g., an FPGA (field-programmable gate array) or an ASIC (application-specific integrated circuit)).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data (e.g., magnetic, magneto-optical disks, or optical disks). However, a computer need not have such devices. Moreover, a computer can be embedded in another device (e.g., a mobile telephone, a personal digital assistant (PDA), a mobile audio or video player, a game console, a Global Positioning System (GPS) receiver, or a portable storage device (e.g., a universal serial bus (USB) flash drive), to name just a few). Devices suitable for storing computer program instructions and data include all forms of non-volatile memory, media and memory devices, including by way of example semiconductor memory devices (e.g., EPROM, EEPROM, and flash memory devices; magnetic disks, e.g., internal hard disks or removable disks; magneto-optical disks; and CD-ROM and DVD-ROM disks). The processor and the memory can be supplemented by, or incorporated in, special purpose logic circuitry.

CONCLUSION

The various methods and techniques described above provide a number of ways to carry out the invention. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features, and steps discussed above, as well as other known equivalents for each such element, feature or step, can be employed in various combinations by one of ordinary skill in this art to perform methods in accordance with the principles described herein.

Among the various elements, features, and steps, some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Certain embodiments of this application are described herein. Variations on those embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

Particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

While various examples of the present disclosure have been described above, it should be understood that they have been presented by way of example only, and not limitation. Numerous changes to the disclosed examples can be made in accordance with the disclosure herein without departing from the spirit or scope of the disclosure. Thus, the breadth and scope of the present disclosure should not be limited by any of the above described examples. Rather, the scope of the disclosure should be defined in accordance with the following claims and their equivalents.

Although the disclosure has been illustrated and described with respect to one or more implementations, equivalent alterations and modifications will occur to others skilled in the art upon the reading and understanding of this specification and the annexed drawings. In addition, while a particular feature of the disclosure may have been disclosed with respect to only one of several implementations, such feature may be combined with one or more other features of the other implementations as may be desired and advantageous for any given or particular application.

The terminology used herein is for the purpose of describing particular examples only and is not intended to be limiting of the disclosure. As used herein, the singular forms "a," "an," and "the" are intended to include the plural forms as well, unless the context clearly indicates otherwise. Furthermore, to the extent that the terms "including," "includes," "having," "has," "with," or variants thereof, are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art to which this disclosure belongs. Furthermore, terms, such as those defined in commonly used dictionaries, should be interpreted as having a meaning that is consistent with their meaning in the context of the relevant art, and will not be interpreted in an idealized or overly formal sense unless expressly so defined herein.

REFERENCES

1. Anckarsäter H, Stahlberg O, Larson T, Hakansson C, Jutblad S-B, Niklasson L, Nydén A, Wentz E, Westergren S, Cloninger C R, Gillberg C, Rastam M (2006) The Impact of ADHD and Autism Spectrum Disorders on Temperament, Character, and Personality Development. Am J Psychiat 163:1239-1244.
2. Anttila V et al. (2017) Analysis of shared heritability in common disorders of the brain. Biorxiv 360:048991.
3. Biswal, B. B., Mennes, M., Zuo, X.-N., Gohel, S., Kelly, C., Smith, S. M., . . . Milham, M. P. (2010). Toward discovery science of human brain function. *Proceedings of the National Academy of Sciences*, 107(10), 4734-4739. https://doi.org/10.1073/pnas.0911855107 (Original work published)
4. Breiman, L. (2001). Random Forests. *Machine Learning*, 45(1), 5-32. https://doi.org/10.1023/a:1010933404324 (Original work published)
5. Brodersen K H, Deserno L, Schlagenhauf F, Lin Z, Penny W D, Buhmann J M, Stephan K E (2014) Dissecting psychiatric spectrum disorders by generative embedding. Neuroimage Clin 4:98-111.
6. Bzdok D, Meyer-Lindenberg A (2017) Machine Learning for Precision Psychiatry: Opportunities and Challenges. Biological Psychiatry Cognitive Neurosci Neuroimaging.
7. Celikel, F., Kose, S., Cumurcu, B., Erkorkmaz, U., Sayar, K., Borckardt, J. J., & Cloninger, R. C. (2009). Cloninger's temperament and character dimensions of personality in patients with major depressive disorder. *Comprehensive Psychiatry*, 50(6), 556-561. https://doi.org/10.1016/j.comppsych.2008.11.012 (Original work published)
8. Cenik, B., Cenik, C., Snyder, M. P., & Brown, S. E. (2017). Plasma sterols and depressive symptom severity in a population-based cohort. *PLOS ONE*, 12(9), e0184382. https://doi.org/10.1371/journal.pone.0184382 (Original work published)
9. Clementz B A, Sweeney J A, Hamm J P, Ivleva E I, Ethridge L E, Pearlson G D, Keshavan M S, Tamminga C A (2016) Identification of Distinct Psychosis Biotypes Using Brain-Based Biomarkers. Am J Psychiat 173:373-384.
10. Cloninger C R, Bayon C, rakic D (1998) Measurement of temperament and character in mood disorders: a model of fundamental states as personality types. J Affect Disorders 51:21-32.
11. Cloninger, R. C., Svrakic, D. M., & Przybeck, T. R. (1993). A Psychobiological Model of Temperament and Character. *Archives of General Psychiatry*, 50(12), 975-990. https://doi.org/10.1001/archpsyc.1993.01820240059008 (Original work published)
12. Consortium B et al. (2018) Genomic Dissection of Bipolar Disorder and Schizophrenia, Including 28 Subphenotypes. Cell 173:1705-1715.e16.
13. Consortium C-D (2013) Identification of risk loci with shared effects on five major psychiatric disorders: a genome-wide analysis. Lancet 381:1371-1379.
14. Consortium, T., Anttila, V., Bulik-Sullivan, B., Finucane, H. K., Walters, R. K., Bras, J., . . . Neale, B. M. (2018). Analysis of shared heritability in common disorders of the brain. *Science*, 360(6395), eaap8757. https://doi.org/10.1126/science.aap8757 (Original work published)
15. Cox, R. W. (1996). AFNI: Software for Analysis and Visualization of Functional Magnetic Resonance Neuroimages. *Computers and Biomedical Research*, 29(3), 162-173. https://doi.org/10.1006/cbmr.1996.0014 (Original work published)
16. Desikan R S, Ségonne F, Fischl B, Quinn B T, Dickerson B C, Blacker D, Buckner R L, Dale A M, Maguire P R, Hyman B T, Albert M S, Killiany R J (2006) An automated labeling system for subdividing the human cerebral cortex on MRI scans into gyral based regions of interest. Neuroimage 31:968-980. https://doi.org/10.1016/j.neuroimage.2006.01.021 (Original work published)
17. Dias T G, Iyer S P, Carpenter S D, Cary R P, Wilson V B, Mitchell S H, Nigg J T, Fair D A (2015) Characterizing heterogeneity in children with and without ADHD based on reward system connectivity. Dev Cogn Neurosci 11:155-174.
18. Doshi-Velez F, Ge Y, Kohane I (2014) Comorbidity Clusters in Autism Spectrum Disorders: An Electronic Health Record Time-Series Analysis. Pediatrics 133:e54-e63.
19. Drevets, W. C., Price, J. L., & Furey, M. L. (2008). Brain structural and functional abnormalities in mood disorders:

implications for neurocircuitry models of depression. *Brain Structure and Function,* 213(1-2), 93-118. https://doi.org/10.1007/s00429-008-0189-x (Original work published)
20. Drysdale A T et al. (2016) Resting-state connectivity biomarkers define neurophysiological subtypes of depression. Nat Med.
21. Dubois, J., & Adolphs, R. (2016). Building a Science of Individual Differences from fMRI. *Trends in Cognitive Sciences,* 20(6), 425-443. https://doi.org/10.1016/j.tics.2016.03.014 (Original work published)
22. Eckblad M, Chapman L J (1986) Development and validation of a scale for hypomanic personality. J Abnorm Psychol 95:214.
23. Elliott M L, Romer A L, Knodt A R, Hariri A R (2018) A Connectome Wide Functional Signature of Transdiagnostic Risk for Mental Illness. Biorxiv:196220.
24. ETTINGER U, JOOBER R, GUZMAN R D, O'DRISCOLL G A (2006) Schizotypy, attention deficit hyperactivity disorder, and dopamine genes. Psychiat Clin Neuros 60:764-767.
25. Fischl B, Liu A, Dale A M (2001) Automated Manifold Surgery: Constructing Geometrically Accurate and Topologically Correct Models of the Human Cerebral Cortex. Ieee T Med Imaging 20:70.
26. Fischl B, Salat D H, Busa E, Albert M, Dieterich M, Haselgrove C, van der Kouwe A, Killiany R, Kennedy D, Klaveness S, Montillo A, Makris N, Rosen B, Dale A M (2002) Whole Brain Segmentation Automated Labeling of Neuroanatomical Structures in the Human Brain. Neuron 33:341-355. https://doi.org/10.1016/s0896-6273(02)00569-x (Original work published)
27. Fried, E. I., & Nesse, R. M. (2015). Depression sumscores don't add up: why analyzing specific depression symptoms is essential. *BMC Medicine,* 13(1). https://doi.org/10.1186/s12916-015-0325-4 (Original work published)
28. Gandal M J, Haney J R, Parikshak N N, Leppa V, Ramaswami G, Hartl C, Schork A J, Appadurai V, Buil A, Werge T M, Liu C, White K P, Consortium C, Consortium P, Group iPSYCH-B, Horvath S, Geschwind D H (2018) Shared molecular neuropathology across major psychiatric disorders parallels polygenic overlap. Science 359: 693-697.
29. Geisler D, Walton E, Naylor M, Roessner V, Lim K O, Schulz C S, Gollub R L, Calhoun V D, Sponheim S R, Ehrlich S (2015) Brain structure and function correlates of cognitive subtypes in schizophrenia. Psychiatry Res Neuroimaging 234:74-83.
30. Georgiades S, Szatmari P, Boyle M, Hanna S, Duku E, Zwaigenbaum L, Bryson S, Fombonne E, Volden J, Mirenda P, Smith I, Roberts W, Vaillancourt T, Waddell C, Bennett T, Thompson A, in Team P (2013) Investigating phenotypic heterogeneity in children with autism spectrum disorder: a factor mixture modeling approach. J Child Psychol Psyc 54:206-215.
31. Getz, G., Levine, E., & Domany, E. (2000). Coupled two-way clustering analysis of gene microarray data. *Proceedings of the National Academy of Sciences,* 97(22), 12079-12084. https://doi.org/10.1073/pnas.210134797 (Original work published)
32. Gheiratmand M, Rish I, Cecchi G A, Brown M R, Greiner R, Polosecki P I, Bashivan P, Greenshaw A J, Ramasubbu R, Dursun S M (2017) Learning stable and predictive network-based patterns of schizophrenia and its clinical symptoms. Npj Schizophrenia 3:22. https://doi.org/10.1038/s41537-017-0022-8 (Original work published)
33. Golden R R, Meehl P E (1979) Detection of the schizoid taxon with MMPI indicators. J Abnorm Psychol 88:217.
34. Gotts, S. J., Simmons, K. W., Milbury, L. A., Wallace, G. L., Cox, R. W., & Martin, A. (2012). Fractionation of social brain circuits in autism spectrum disorders. *Brain,* 135(9), 2711-2725. https://doi.org/10.1093/brain/aws160 (Original work published)
35. Grisanzio K A, Goldstein-Piekarski A N, Wang M, Ahmed A P, Samara Z, Williams L M (2017) Transdiagnostic Symptom Clusters and Associations With Brain, Behavior, and Daily Function in Mood, Anxiety, and Trauma Disorders. Jama Psychiatry. https://doi.org/10.1001/jamapsychiatry.2017.3951 (Original work published)
36. Grucza R A, Przybeck T R, Spitznagel E L, Cloninger C R (2003) Personality and depressive symptoms: a multidimensional analysis. J Affect Disorders 74:123-130.
37. Guillem F, Bicu M, Semkovska M, Debruille J B (2002) The dimensional symptom structure of schizophrenia and its association with temperament and character. Schizophr Res 56:137-147.
38. Hajirezaei S, Mohammadi A, Soleimani M, Rahiminezhad F, Mohammadi M, Cloninger R C (2017) Comparing the Profile of Temperament and Character Dimensions in Patients with Major Depressive Disorder and Bipolar Mood Disorder with a Control Group. Iranian J Psychiatry 12:147-153.
39. Hamshere M L, Stergiakouli E, Langley K, Martin J, Holmans P, Kent L, Owen M J, Gill M, Thapar A, O& #39; Donovan M, Craddock N (2013) Shared polygenic contribution between childhood attention-deficit hyperactivity disorder and adult schizophrenia. Br J Psychiatry 203:107-111.
40. Harvey, P.-O., Pruessner, J., Czechowska, Y., & Lepage, M. (2007). Individual differences in trait anhedonia: a structural and functional magnetic resonance imaging study in non-clinical subjects. *Molecular Psychiatry,* 12(8), 4002021. https://doi.org/10.1038/sj.mp 0.4002021 (Original work published)
41. Hastie, T., Tibshirani, R., & Friedman, J. (2009). *The elements of statistical learning: data mining, inference, and prediction* (2nd ed.). New York: Springer. (Original work published)
42. Hori H, Noguchi H, Hashimoto R, Nakabayashi T, Saitoh O, Murray R M, Okabe S, Kunugi H (2008) Personality in schizophrenia assessed with the Temperament and Character Inventory (TCI). Psychiat Res 160: 175-183.
43. Insel, T. R., & Cuthbert, B. N. (2015). Brain disorders? Precisely. *Science,* 348(6234), 499-500. https://doi.org/10.1126/science.aab2358 (Original work published)
44. Jo H, Saad Z S, Simmons K W, Milbury L A, Cox R W (2010) Mapping sources of correlation in resting state FMRI, with artifact detection and removal. Neuroimage 52:571-582. https://doi.org/10.1016/j.neuroimage.2010.04.246 (Original work published)
45. Joyce, D. W., Kehagia, A. A., Tracy, D. K., Proctor, J., & Shergill, S. S. (2017). Realising stratified psychiatry using multidimensional signatures and trajectories. *Journal of Translational Medicine,* 15(1), 15. https://doi.org/10.1186/s12967-016-1116-1 (Original work published)
46. Kanth Ryali, Chen T, Supekar K, Menon V (2012) Estimation of functional connectivity in fMRI data using stability selection-based sparse partial correlation with elastic net penalty. Neuroimage 59:3852-3861.
47. Kapur, S., Phillips, A., & Insel, T. (2012). Why has it taken so long for biological psychiatry to develop clinical tests and what to do about it? *Molecular Psychiatry*, 17(12), 1174. https://doi.org/10.1038/mp.2012.105 (Original work published)
48. Keedwell, P. A., Andrew, C., Williams, S., Brammer, M. J., & Phillips, M. L. (2005). The Neural Correlates of Anhedonia in Major Depressive Disorder. *Biological Psychiatry*, 58(11), 843-853. https://doi.org/10.1016/j.biopsych.2005.05.019 (Original work published)
49. Keshavan M S, Sujata M, Mehra A, Montrose D M, Sweeney J A (2003) Psychosis proneness and ADHD in young relatives of schizophrenia patients. Schizophr Res 59:85-92.
50. Kessler R, Gruber M, Hettema J, Hwang I, Sampson N, Yonkers K (2007) Co-morbid major depression and generalized anxiety disorders in the National Comorbidity Survey follow-up. Psychol Med 38:365-374.
51. Klassen L J, Katzman M A, Chokka P (2010) Adult ADHD and its comorbidities, with a focus on bipolar disorder. J Affect Disorders 124:1-8.
52. Kwapil T R, Miller M B, Zinser M C, Chapman L J, Chapman J, Eckblad M (2000) A longitudinal study of high scorers on the Hypomanic Personality Scale. J Abnorm Psychol 109:222.
53. Lamers F, Burstein M, He J, Avenevoli S, Angst J, Merikangas K R (2012) Structure of major depressive disorder in adolescents and adults in the US general population. Br J Psychiatry 201:143-150.
54. Larsson H, Rydén E, Boman M, Långström N, Lichtenstein P, Landén M (2013) Risk of bipolar disorder and schizophrenia in relatives of people with attention-deficit hyperactivity disorder. Br J Psychiatry 203:103-106.
55. Lewandowski K, Sperry S, Cohen B, Öngür D (2014) Cognitive variability in psychotic disorders: a cross-diagnostic cluster analysis. Psychol Med 44:3239-3248.
56. Lo, A., Chernoff, H., Zheng, T., & Lo, S.-H. (2015). Why significant variables aren't automatically good predictors. *Proceedings of the National Academy of Sciences*, 112 (45), 13892-13897. https://doi.org/10.1073/pnas.1518285112 (Original work published)
57. Loo H M et al. (2014) MAJOR DEPRESSIVE DISORDER SUBTYPES TO PREDICT LONG-TERM COURSE. Depress Anxiety 31:765-777.
58. Lotan, A., Fenckova, M., Bralten, J., Alttoa, A., Dixson, L., Williams, R. W., & van der Voet, M. (2014). Neuroinformatic analyses of common and distinct genetic components associated with major neuropsychiatric disorders. *Frontiers in Neuroscience*, 8, 331. https://doi.org/10.3389/fnins.2014.00331 (Original work published)
59. Lynn D E, Lubke G, Yang M, McCracken J T, McGough J J, Ishii J, Loo S K, Nelson S F, Smalley S L (2005) Temperament and Character Profiles and the Dopamine D4 Receptor Gene in ADHD. Am J Psychiat 162:906-913.
60. Martino, M., Magioncalda, P., Huang, Z., Conio, B., Piaggio, N., Duncan, N. W., . . . Northoff, G. (2016). Contrasting variability patterns in the default mode and sensorimotor networks balance in bipolar depression and mania. *Proceedings of the National Academy of Sciences*, 113(17), 4824-4829. https://doi.org/10.1073/pnas.1517558113 (Original work published)
61. Mayberg, H. S., Liotti, M., Brannan, S. K., McGinnis, S., Mahurin, R. K., Jerabek, P. A., . . . Fox, P. T. (1999). Reciprocal Limbic-Cortical Function and Negative Mood: Converging PET Findings in Depression and Normal Sadness. *American Journal of Psychiatry*, 156(5), 675-682. https://doi.org/10.1176/ajp.156.5.675 (Original work published)
62. Meda, S. A., Ruaño, G., Windemuth, A., O'Neil, K., Berwise, C., Dunn, S. M., . . . Pearlson, G. D. (2014). Multivariate analysis reveals genetic associations of the resting default mode network in psychotic bipolar disorder and schizophrenia. *Proceedings of the National Academy of Sciences*, 111(19), E2066-E2075. https://doi.org/10.1073/pnas.1313093111 (Original work published)
63. Mostert J C, Hoogman M, Onnink M A, van Rooij D, von Rhein D, van Hulzen K J, Dammers J, Kan C C, Buitelaar J K, Norris D G, Franke B (2018) Similar Subgroups Based on Cognitive Performance Parse Heterogeneity in Adults With ADHD and Healthy Controls. J Atten Disord 22:281-292.
64. Nagel, M., Jansen, P. R., Stringer, S., Watanabe, K., de Leeuw, C. A., Bryois, J., . . . Posthuma, D. (2018). Meta-analysis of genome-wide association studies for neuroticism in 449,484 individuals identifies novel genetic loci and pathways. *Nature Genetics*, 50(7), 920-927. https://doi.org/10.1038/s41588-018-0151-7 (Original work published)
65. Nierenberg A A, Miyahara S, Spencer T, Wisniewski S R, Otto M W, Simon N, Pollack M H, Ostacher M J, Yan L, Siegel R, Sachs G S, Investigators S-B (2005) Clinical and Diagnostic Implications of Lifetime Attention-Deficit/Hyperactivity Disorder Comorbidity in Adults with Bipolar Disorder: Data from the First 1000 STEP-BD Participants. Biol Psychiat 57:1467-1473.
66. Öngür, D., Farabaugh, A., Iosifescu, D. V., Perlis, R., & Fava, M. (2005). Tridimensional Personality Questionnaire Factors in Major Depressive Disorder: Relationship to Anxiety Disorder Comorbidity and Age of Onset. *Psychotherapy and Psychosomatics*, 74(3), 173-178. https://doi.org/10.1159/000084002 (Original work published)
67. Pallanti S, Salerno L (2015) Raising attention to attention deficit hyperactivity disorder in schizophrenia. World J Psychiatry 5:47-55.
68. Pan, P., Sato, J. R., Salum, G. A., Rohde, L. A., Gadelha, A., Zugman, A., . . . Stringaris, A. (2017). Ventral Striatum Functional Connectivity as a Predictor of Adolescent Depressive Disorder in a Longitudinal Community-Based Sample. *American Journal of Psychiatry*, 174(11), 1112-1119. https://doi.org/10.1176/appi.ajp.2017.17040430 (Original work published)
69. Park M M, Raznahan A, Shaw P, Gogtay N, Lerch J P, Chakravarty M M (2018) Neuroanatomical phenotypes in mental illness: identifying convergent and divergent cortical phenotypes across autism, ADHD and schizophrenia. J Psychiatry Neurosci Jpn 43:201-212.
70. Pearlson G D (2015) Etiologic, Phenomenologic, and Endophenotypic Overlap of Schizophrenia and Bipolar Disorder. Annu Rev Clin Psycho 11:1-31.
71. Peralta V, de Jalón E, Campos M S, Zandio M, Sanchez-Torres A, Cuesta M J (2011) The meaning of childhood attention-deficit hyperactivity symptoms in patients with a first-episode of schizophrenia-spectrum psychosis. Schizophr Res 126:28-35.
72. Philippi, C. L., Motzkin, J. C., Pujara, M. S., & Koenigs, M. (2015). Subclinical depression severity is associated with distinct patterns of functional connectivity for sub-regions of anterior cingulate cortex. *Journal of Psychiatric Research*, 71, 103-111. https://doi.org/10.1016/j.jpsychires.2015.10.005 (Original work published)

73. Poldrack R A, Congdon E, Triplett W, Gorgolewski K J, Karlsgodt K H, Mumford J A, Sabb F W, Freimer N B, London E D, Cannon T D, Bilder R M (2016) A phenome-wide examination of neural and cognitive function. Scientific Data, 3, 160110. https://doi.org/10.1038/sdata.2016.110 (Original work published)

74. Power J D, Cohen A L, Nelson S M, Wig G S, Barnes K, Church J A, Vogel A C, Laumann T O, Miezin F M, Schlaggar B L, Petersen S E (2011) Functional Network Organization of the Human Brain. Neuron 72:665-678.

75. Power, J. D., Cohen, A. L., Nelson, S. M., Wig, G. S., Barnes, K., Church, J. A., . . . Petersen, S. E. (2011). Functional Network Organization of the Human Brain. Neuron, 72(4), 665-678. https://doi.org/10.1016/j.neuron.2011.09.006 (Original work published)

76. Purcell S M et al. (2009) Common polygenic variation contributes to risk of schizophrenia and bipolar disorder. Nature 460:748.

77. Rhebergen D, Lamers F, Spijker J, de Graaf R, Beekman A, Penninx B (2011) Course trajectories of unipolar depressive disorders identified by latent class growth analysis. Psychol Med 42:1383-1396.

78. Rieder R O, Nichols P L (1979) Offspring of Schizophrenics III: Hyperactivity and Neurological Soft Signs. Arch Gen Psychiat 36:665-674.

79. Salgado C A I, Bau C H D, Grevet E H, Fischer A G, Victor M M, Kalil K L S, Sousa N O, Garcia C R, Belmonte-de-Abreu P (2009) Inattention and Hyperactivity Dimensions of ADHD Are Associated with Different Personality Profiles. Psychopathology 42:108-112.

80. Sharma, A., Wolf, D. H., Ciric, R., Kable, J. W., Moore, T. M., Vandekar, S. N., . . . Satterthwaite, T. D. (2017). Common Dimensional Reward Deficits Across Mood and Psychotic Disorders: A Connectome-Wide Association Study. American Journal of Psychiatry, 174(7), 657-666. https://doi.org/10.1176/appi.ajp.2016.16070774 (Original work published)

81. Shen, X., Finn, E. S., Scheinost, D., Rosenberg, M. D., Chun, M. M., Papademetris, X., & Constable, T. R. (2017). Using connectome-based predictive modeling to predict individual behavior from brain connectivity. Nature Protocols, 12(3), 506-518. https://doi.org/10.1038/nprot.2016.178 (Original work published)

82. Sun H, Lui S, Yao L, Deng W, Xiao Y, Zhang W, Huang X, Hu J, Bi F, Li T, Sweeney J A, Gong Q (2015) Two Patterns of White Matter Abnormalities in Medication-Naive Patients With First-Episode Schizophrenia Revealed by Diffusion Tensor Imaging and Cluster Analysis. Jama Psychiatry 72:678-686.

83. Tibshirani, R. (1996). Regression shrinkage and selection via the lasso. Journal of the Royal Statistical Society, Series B, 58(1), 267-288. (Original work published)

84. van Hulst B, de Zeeuw P, Durston S (2014) Distinct neuropsychological profiles within ADHD: a latent class analysis of cognitive control, reward sensitivity and timing. Psychol Med 45:735-745.

85. van Hulzen K, Scholz C J, Franke B, Ripke S, Klein M, McQuillin A, Sonuga-Barke E J, Group P, Kelsoe J R, Landén M, Andreassen O A, Group P, Lesch K-P, Weber H, Faraone S V, Arias-Vasquez A, Reif A (2017) Genetic Overlap Between Attention-Deficit/Hyperactivity Disorder and Bipolar Disorder: Evidence From Genome-wide Association Study Meta-analysis. Biol Psychiat 82:634-641.

86. van Loo H M, de Jonge P, Romeijn J-W, Kessler R C, Schoevers R A (2012) Data-driven subtypes of major depressive disorder: a systematic review. Bmc Med 10:1-12.

87. Veatch O, Veenstra-VanderWeele J, Potter M, Pericak-Vance M, Haines J (2014) Genetically meaninngful phenotypic subgroups in autism spectrum disorders. Genes Brain Behav 13:276-285.

88. Wacker, J., Dillon, D. G., & Pizzagalli, D. A. (2009). The role of the nucleus accumbens and rostral anterior cingulate cortex in anhedonia: Integration of resting EEG, fMRI, and volumetric techniques. NeuroImage, 46(1), 327-337. https://doi.org/10.1016/j.neuroimage.2009 0.01.058 (Original work published)

89. Wang H, Jung Y-E, Chung S-K, Hong J, Kang N, Kim M-D, Bahk W-M (2017) Prevalence and correlates of bipolar spectrum disorder comorbid with ADHD features in nonclinical young adults. J Affect Disorders 207:175-180.

90. WILLIAM B (2001) Schizophrenia and Attention Deficit Disorder. Ann Ny Acad Sci 931:239-250.

91. Woo, C.-W., Chang, L. J., Lindquist, M. A., & Wager, T. D. (2017). Building better biomarkers: brain models in translational neuroimaging. Nature Neuroscience, 20(3), 365-377. https://doi.org/10.1038/nn.4478 (Original work published)

92. Xia, C., Ma, Z., Ciric, R., Gu, S., Betzel, R. F., Kaczkurkin, A. N., . . . Satterthwaite, T. D. (2018). Linked dimensions of psychopathology and connectivity in functional brain networks. Nature Communications, 9(1), 3003. https://doi.org/10.1038/s41467-018-05317-y (Original work published)

93. Yarkoni, T., & Westfall, J. (2017). Choosing Prediction Over Explanation in Psychology: Lessons From Machine Learning. Perspectives on Psychological Science, 12(6), 1100-1122. https://doi.org/10.1177/1745691617693393 (Original work published)

94. Zou H, Hastie T (2005) Regularization and variable selection via the elastic net. Journal of the Royal Statistical Society: Series B (Statistical Methodology), 67(2), 301-320. https://doi.org/10.1111/j.1467-9868.2005.00503.x (Original work published)

What is claimed is:

1. A system for evaluating a patient for mental health issues, the system comprising:
   a user interface;
   a memory containing machine readable medium comprising machine executable code having stored thereon instructions for performing a method; and
   a control system coupled to the memory comprising one or more processors, the control system configured to execute the machine executable code to cause the control system to:
     receive, from the user interface, a selection of answers from a patient, the selection of answers corresponding to each question in a series of questions from mental health questionnaires;
     receive, unprocessed MM data associated with the patient; and
     process, using a machine learning model, the selection of answers and the unprocessed MRI data to output a mental health indication of the patient, wherein the machine learning model was generated by:
receiving training data corresponding to a plurality of individuals, the training data comprising:
MRI data; and
a selection of answers to the series of questions;
determining a plurality of features from the training data;
extracting importance measures for each of the plurality of features;
generating a plurality of subset machine learning models based on the extracted importance measures for the plurality of features; and
selecting at least one of the subset machine learning models as the machine learning model.

2. The system of claim 1, wherein the unprocessed MM data corresponds to MRI data for a brain of the patient, wherein the training data is labeled training data corresponding to the plurality of individuals, the labeled training data indicating whether each of the plurality of individuals has one or more mental health disorders.

3. The system of claim 1, wherein the unprocessed MRI data comprises at least one of: functional MM data, resting-state functional MM data, structural MRI data, and any combination thereof.

4. The system of claim 1, wherein the control system is further configured to preprocess the unprocessed MRI data to identify a plurality of MRI features, wherein the machine learning model was further generated by training an initial machine learning model in a supervised manner using the plurality of features, wherein the extracting the importance measures for each of the plurality of features is based on the training of the initial machine learning model.

5. The system of claim 1, wherein the machine learning model is at least one of: a generalized linear model, a regression model, a logistical regression model, a supervised regression method, random forest model, LASSO model, a supervised machine-learning model, and an elastic net model.

6. The system of claim 1, wherein the selecting at least one of the subset machine learning models as the machine learning model includes evaluating a classification performance of the generated plurality of subset machine learning models.

7. The system of claim 1, wherein the mental health indication is categorical, wherein the mental health indication comprises a determination that the processed selection of answers and the processed MM data includes indications of at least one of: a neuropsychiatric disorder, schizophrenia, a bi-polar disorder, and any combination thereof.

8. The system of claim 1, wherein outputting the mental health indication further comprises determining that the processed selection of answers and the processed MRI data identifies features corresponding to a mental disorder.

9. A system for evaluating mental health of patients, the system comprising:
a memory containing machine readable medium comprising machine executable code having stored thereon instructions for performing a method; and
a control system coupled to the memory comprising one or more processors, the control system configured to execute the machine executable code to cause the control system to:
receive a selection of answers associated with a patient, the selection of answers corresponding to each question in a series of questions from mental health questionnaires;
receive, unprocessed MRI data associated with the patient;
and process, using a machine learning model, the selection of answers, and the set of MRI features, to output a mental health indication of the patient,
wherein the machine learning model was generated by:
receiving labeled training data corresponding to a plurality of individuals indicating whether each of the plurality of individuals has one or more mental health disorders, the labeled training data comprising:
MRI data; and
a selection of answers to the series of questions;
determining a plurality of features from the labeled training data;
training an initial machine learning model in a supervised manner, based on the plurality of features;
extracting importance measures for each of the plurality of features, based on the training of the initial machine learning model; and
generating the machine learning model based on the extracted importance measures for the plurality of features.

10. The system of claim 9, wherein the unprocessed MM data corresponds to MM data for a brain of the patient.

11. The system of claim 9, wherein the unprocessed MRI data comprises at least one of: functional MM data, resting-state functional MM data, structural MRI data, and any combination thereof.

12. The system of claim 9, wherein the control system is further configured to preprocess the unprocessed MM data to identify a plurality of MRI features.

13. The system of claim 9, wherein the machine learning model is at least one of: a generalized linear model, a regression model, a logistical regression model, a supervised regression method, random forest model, LASSO model, a supervised machine-learning model, and an elastic net model.

14. The system of claim 9, the mental health indication comprises a determination that the processed selection of answers and the processed MRI data includes indications of at least one of: a neuropsychiatric disorder, schizophrenia, a bi-polar disorder, and any combination thereof.

15. The system of claim 9, wherein outputting the mental health indication further comprises determining that the processed selection of answers and the processed MRI data identifies features corresponding to a mental disorder.

16. A computer-implemented method, comprising:
displaying a series of questions on a display device, the series of questions being from mental health questionnaires comprising text and answers for each question;
receive, from the user interface, a selection of answers from a patient, the selection of answers corresponding to the series of questions;
receive, unprocessed MM data associated with the patient; and
process, using a machine learning model, the selection of answers and the unprocessed MRI data to output a mental health indication of the patient,
wherein the machine learning model was generated by:
receiving training data corresponding to a plurality of individuals, the training data comprising:
MRI data; and
a selection of answers to the series of questions;
determining a plurality of features from the training data;

training an initial machine learning model based on the plurality of features;

using the initial machine learning model to extract importance measures for each of the plurality of features;

generating a plurality of subset machine learning models based on the extracted importance measures for the plurality of features; and selecting at least one of the subset machine learning models as the machine learning model.

17. The computer-implemented method of claim 16, wherein the unprocessed MRI data corresponds to MM data for a brain of the patient, wherein the training data is labeled training data corresponding to the plurality of individuals, the labeled training data indicating whether each of the plurality of individuals has one or more mental health disorders.

18. The computer-implemented method of claim 16, wherein the unprocessed MM data comprises at least one of: functional MRI data, resting-state functional MM data, structural MRI data, and any combination thereof.

19. The computer-implemented method of claim 16, wherein the control system is further configured to preprocess the unprocessed MRI data to identify a plurality of MRI features, wherein the machine learning model was further generated by training an initial machine learning model in a supervised manner using the plurality of features, wherein the extracting the importance measures for each of the plurality of features is based on the training of the initial machine learning model.

20. The computer-implemented method of claim 16, wherein the selecting at least one of the subset machine learning models as the machine learning model includes evaluating a classification performance of the generated plurality of subset machine learning models.

* * * * *